US007897730B2

(12) United States Patent
Yu et al.

(10) Patent No.: US 7,897,730 B2
(45) Date of Patent: Mar. 1, 2011

(54) TRAIL RECEPTOR-BINDING AGENTS AND USES OF THE SAME

(75) Inventors: Zheng Yu, Beijing (CN); Min Zhou, Beijing (CN); Enyun Shen, Beijing (CN); Xianzhao Jia, Beijing (CN); Yang Song, Beijing (CN)

(73) Assignee: Beijing Cotimes Biotech Ltd., Beijing (CN)

( * ) Notice: Subject to any disclaimer, the term of this patent is extended or adjusted under 35 U.S.C. 154(b) by 36 days.

(21) Appl. No.: 12/298,001

(22) PCT Filed: Apr. 29, 2007

(86) PCT No.: PCT/CN2007/001453
§ 371 (c)(1),
(2), (4) Date: Oct. 21, 2008

(87) PCT Pub. No.: WO2007/128321
PCT Pub. Date: Nov. 15, 2007

(65) Prior Publication Data
US 2009/0136503 A1    May 28, 2009

(30) Foreign Application Priority Data
Apr. 30, 2006  (CN) ........................ 2006 1 0079301
Mar. 6, 2007  (CN) ........................ 2006 1 0109138

(51) Int. Cl.
C07K 16/00 (2006.01)
C07K 17/00 (2006.01)
C07K 17/14 (2006.01)
C12P 21/08 (2006.01)
A61K 39/395 (2006.01)
A61K 39/00 (2006.01)

(52) U.S. Cl. .............. 530/387.1; 530/387.7; 530/387.9; 530/391.1; 530/391.7; 424/130.1; 424/138.1; 424/139.1; 424/178.1

(58) Field of Classification Search ........................ None
See application file for complete search history.

(56) References Cited

U.S. PATENT DOCUMENTS

| 5,057,313 | A | 10/1991 | Shih et al. |
| 7,115,717 | B2 | 10/2006 | Mori et al. |
| 2002/0153509 | A1 | 10/2002 | Lynch |
| 2004/0214235 | A1* | 10/2004 | Mori et al. ............... 435/7.2 |
| 2005/0249729 | A1* | 11/2005 | Mori et al. ............. 424/143.1 |
| 2005/0282230 | A1 | 12/2005 | Ashkenazi et al. |

FOREIGN PATENT DOCUMENTS

WO  WO 99/37684       7/1999
WO  WO 2004085478 A2 * 10/2004

OTHER PUBLICATIONS

Burgess, Shaheen, Ravera, Jaye, Donohue, and Winkles. Possible dissociation of the heparin binding and mitogenic activities of heparin-binding (acidic fibroblast) growth factor-1 from its receptor binding activities by site directed mutagenesis of a single lysine residue. Journal of Cell Biology, 1990. vol. 111, pp. 2129-2138.*

Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*

Rudikoff, Giusti, Cook and Scharff. Single amino acid substitution altering antigen-binding specificity. Proceedings of the National Academy of Sciences, 1982. vol. 79, pp. 1979-1983.*

Mac Callum, Martin, and Thornton. Antibody-antigen interactions: contact analysis and binding site topography. Journal of Molecular Biology, 1996. vol. 262, pp. 732-745.*

De Pascalis, Iwahashi, Tamura, Padlan, Gonzales, Santos, Giuliano, Schuck, Schlom, and Kashmiri. Grafting of abbreviated complementarity-determining regions containing specificity determining residues essential for ligand contact to engineer a less immunogenic humanized monoclonal antibody. Journal of Immunology, 2002. vol. 169, pp. 3076-3084.*

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

Vajdos, Adams, Breece, Presta, De Vos, and Sidhu. Comprehensive functional maps of the antigen-binding site of an anti-ErbB2 antibody obtained by shotgun scanning mutagenesis. Journal of Molecular Biology, 2002. vol. 320, pp. 415-428.*

Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*

Wu, Nie, Huse, and Watkins. Humanization of a murine monoclonal antibody by simultaneous optimization of framework and CDR residues. Journal of Molecular Biology, 1999. vol. 294, pp. 151-162.*

Holm, Jafari, and Sundstrom. Functional mapping and single chain construction of the anti-cytokeratin 8 monoclonal antibody TS1. Molecular Immunology, 2007. vol. 44, pp. 1075-1084.*

Buchsbaum, Donald J. et al., Antitumor efficacy of TRA-8 anti-DR5 monoclonal antibody alone or in combination with chemotherapy and/or radiation therapy in a human breast cancer model. *Clin. Cancer Res.*, 9:3731-3741 (Sep. 1, 2003).

(Continued)

*Primary Examiner* — Anne M. Gussow
(74) *Attorney, Agent, or Firm* — Foley & Lardner LLP

(57) ABSTRACT

This invention relates generally to the preparation of TRAIL receptor-binding agents and uses of the same. In particular, the present invention relates to the preparation of anti-TRAIL receptor antibodies which recognize a common antigen determinant (i.e., epitope) shared by TRAIL-R1 and TRAIL-R2 receptors and their use for TRAIL receptor detection and modulation of TRAIL receptor-mediated function. The TRAIL receptor-binding agents are useful to induce apoptosis in human cancer cells. These targets may either express one or both TRAIL-R1 or TRAIL-R2. The invention provides for the use of the TRAIL receptor-binding agents of the invention in cancer therapy.

9 Claims, 32 Drawing Sheets

OTHER PUBLICATIONS

Degli-Esposti, Mariapia A. et al., Cloning and Characterization of TRAIL-R3, a novel member of the emerging TRAIL receptor family. *J. Exp. Med.* 186(7):1165-1170 (Oct. 6, 1997).

Ichikawa, Kimisha et al., Tumoricidal activity of a novel anti-human DR5 monoclonal antibody without hepatocyte cytotoxicity. *Nature Medicine*, 7(8):954-96- (Aug. 2001).

International Search Report and Written Opinion, Jul. 19, 2007, for PCT/CN2007/001453.

Kurbanov, Bahtier M. et al., Efficient TRAIL-R1/DR4-mediated apoptosis in melanoma cells by tumor necrosis factor-related apoptosis-inducing ligand (TRAIL). *The Journal of Investigative Dermatology*, 125:1010-1019 (2005).

Leverkus, Martin et al., TRAIL-induced apoptosis and gene induction in HaCaT Keratinocytes: differential contribution of TRAIL receptors 1 and 2. *The Journal of Investigative Dermatology*, 121:149-155 (2003).

Liu, Xue-Song et al., Preparation and characterization of a set of monoclonal antibodies to TRAIL and TRAIL receptors DR4, DR5, DcR1, and DcR2. *Hybridoma and Hybridomics*, 22(2):121-125 (2003).

McCarthy, Mary M. et al., Evaluating the Expression and prognostic value of TRAIL-R1 and TRAIL-R2 in breast cancer. *Clin. Cancer Res.*, 11(14):5188-5194 (Jun. 15, 2005).

Miller, Kathy et al., Design, construction, and in vitro analyses of multivalent antibodies. *The Journal of Immunology*, 170:4854-4861 (2003).

Motoki, Kazuhiro et al., Enhanced apoptosis and tumor regression induced by a direct agonist antibody to tumor necrosis factor-related apoptosis-inducing ligand receptor 2. *Clin. Cancer Res.*, 11(8):3126-3135 (Apr. 15, 2005).

Muhlenbeck, Frank et al., The tumor necrosis factor-related apoptosis-inducing ligand receptors TRAIL-R1 and TRAIL-R2 have distinct cross-linking requirements for initiation of apoptosis and are non-redundant in JNK activation. *The Journal of Biological Chemistry*, 275(41):32208-32213 (Oct. 13, 2000).

Vermot-Desroches, Claudine et al., Characterization of monoclonal antibodies directed against trail or trail receptors. *Cellular Immunology*, 236:86-91 (2005).

Yuanfang et al., Analysis of TRAIL receptor expression using anti-TRAIL death receptor-5 monoclonal antibodies. *Chinese Medical Journal*, 116(6):947-950 (2003).

Examiner's First Report for Australian Pat. Appln. No. 2007247688, dated Jun. 18, 2010.

Supplementary European Search Report and Search Opinion for EPO Pat. Appln. No. 07721026.8, dated May 19, 2010.

* cited by examiner

CTB003 Vκ

A

```
GACATCCAGATGACCCAATCTTCATCCTCCTTTTCTGTATCTCTAGGAGACAGAGTCACC
 D  I  Q  M  T  Q  S  S  S  F  S  V  S  L  G  D  R  V  T

ATTACTTGCAAGGCAGGTGAGGACATATATAATCGGTTAGCCTGGTATCAGCAGAAACCA
 I  T  C  K  A  G  E  D  I  Y  N  R  L  A  W  Y  Q  Q  K  P

GGAAATGCTCCTAGGCTCTTAATATCTGGTGCAACCAATTTGGAAACTGGGGTTCCTTCA
 G  N  A  P  R  L  L  I  S  G  A  T  N  L  E  T  G  V  P  S

AGATTCAGTGGCAGTGGATCTGGAAAGGATTACACTCTCAGCATTACCAGTCTTCAGACT
 R  F  S  G  S  G  S  G  K  D  Y  T  L  S  I  T  S  L  Q  T

GAAGATGTTGCTACTTATTACTGTCAACAGTATTGGAGTACTCCGCTC   SEQ ID NO.: 1
 E  D  V  A  T  Y  Y  C  Q  Q  Y  W  S  T  P  L    SEQ ID NO.: 2
```

CTB003 VH

B

```
GAGGTGCATCTCGTGGAGTCTGGGGGAGGCTTAGTGAGGCCTGGAGGGTCCCTGAAACTC
 E  V  H  L  V  E  S  G  G  G  L  V  R  P  G  G  S  L  K  L

TCCTGTGCGGCCTCTGGATTCGCTTTCAGTAGCTATGACATGTCTTGGGTTCGCCAGACT
 S  C  A  A  S  G  F  A  F  S  S  Y  D  M  S  W  V  R  Q  T

CCGGAGAAGAGGCTGGAGTGGGTCGCATACATTAGTGATGGTGGTGGTATCACCTACTAT
 P  E  K  R  L  E  W  V  A  Y  I  S  D  G  G  G  I  T  Y  Y

CCAGACACAATGAAGGGCCGACTCACCATCTCCAGAGACAATGCCAAGAATACCCTGTCC
 P  D  T  M  K  G  R  L  T  I  S  R  D  N  A  K  N  T  L  S

CTGCAAATGAGCAGTCTGAAGTCTGAGGACACAGCCATGTATTACTGTGCAAGACATATT
 L  Q  M  S  S  L  K  S  E  D  T  A  M  Y  Y  C  A  R  H  I

ACTATGGTGGTAGGACCCTTTGCT  SEQ ID NO.: 7
 T  M  V  V  G  P  F  A   SEQ ID NO.: 8
```

Figure 1

A
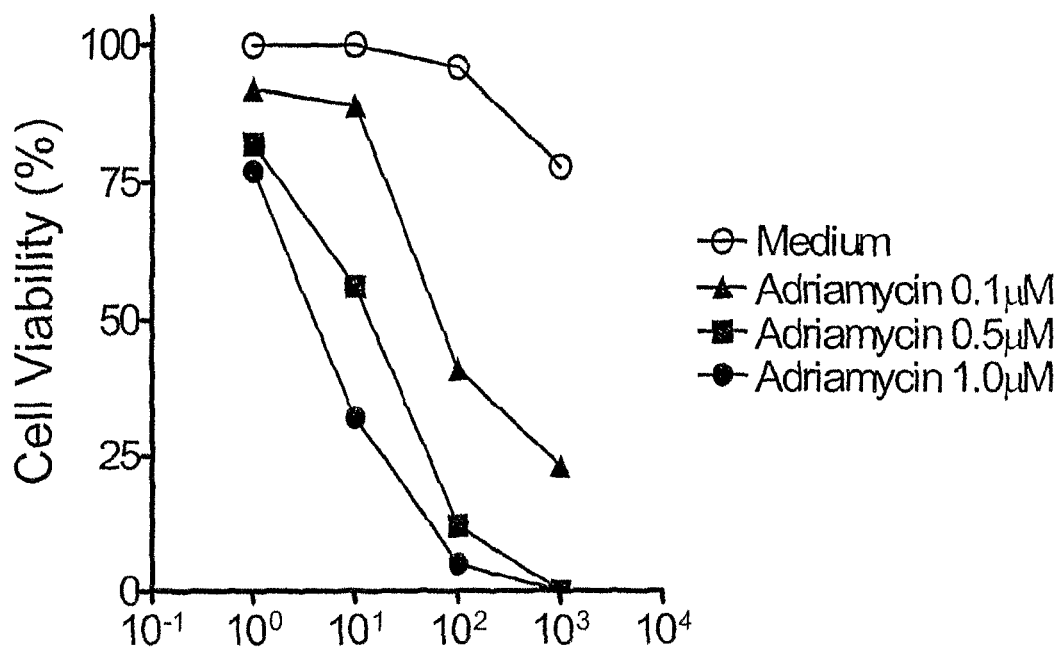
B
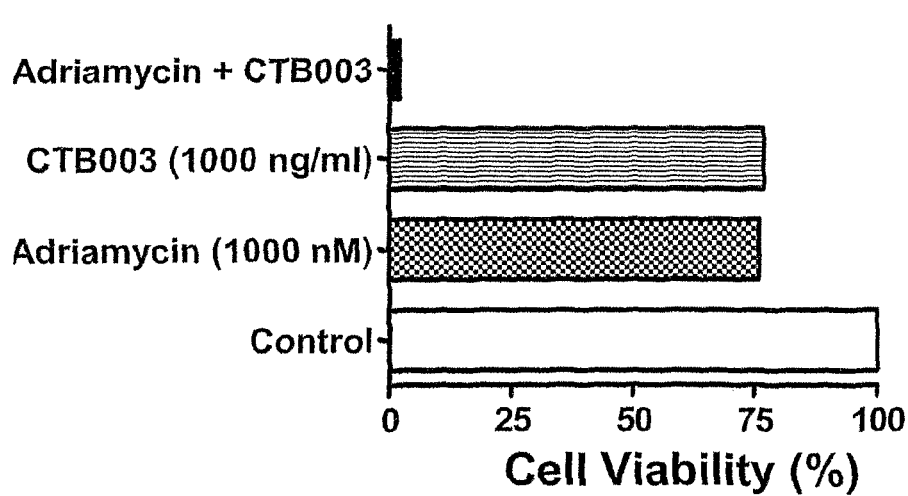
Figure 5

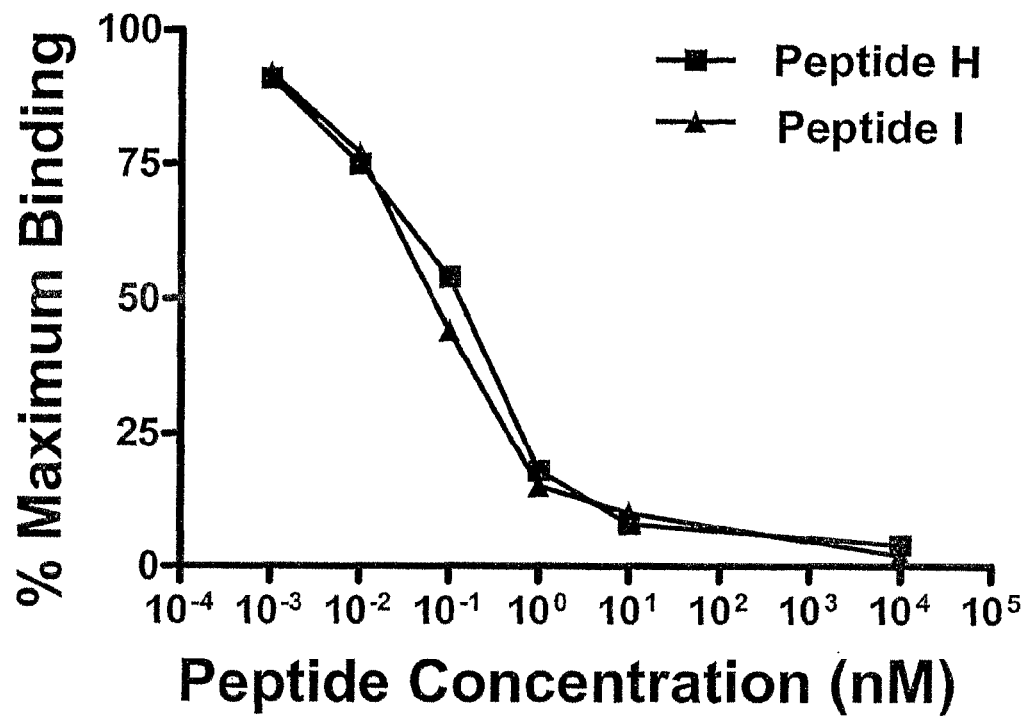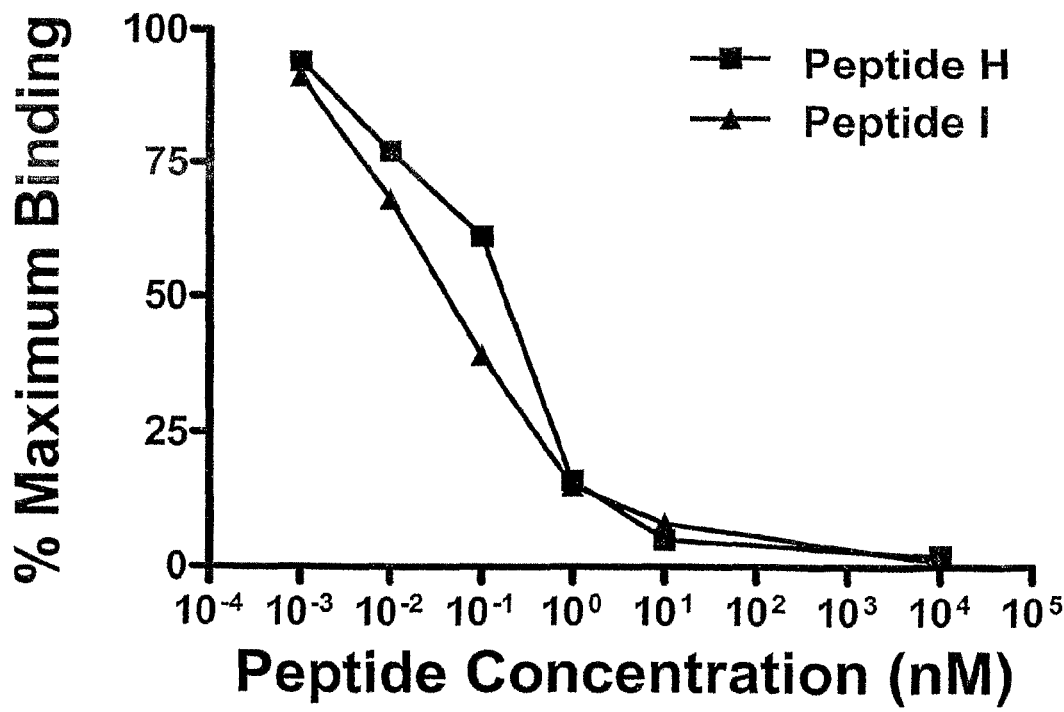
Figure 20

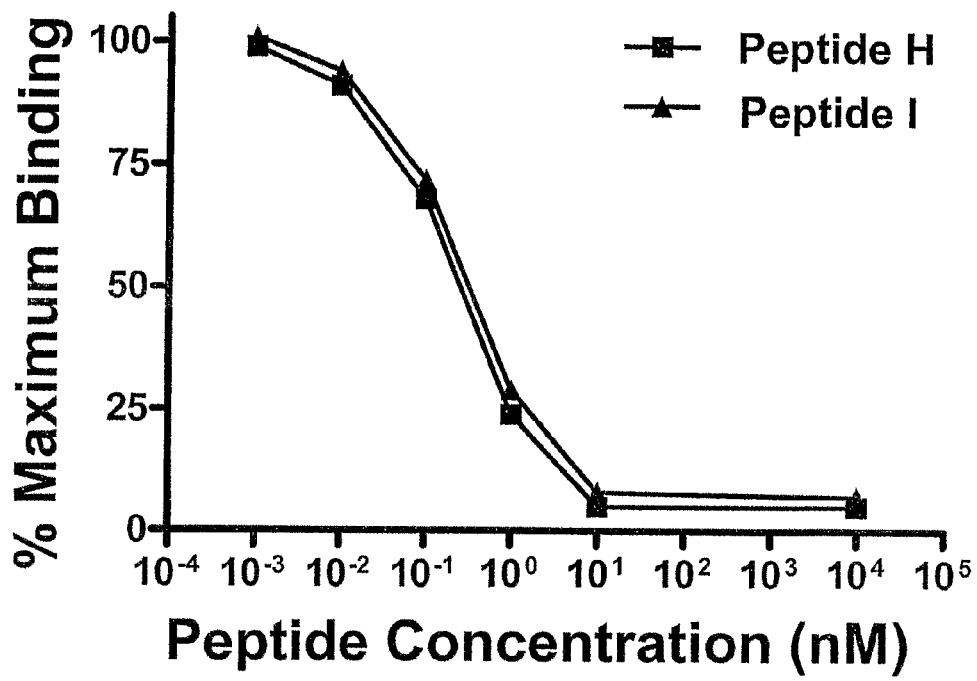
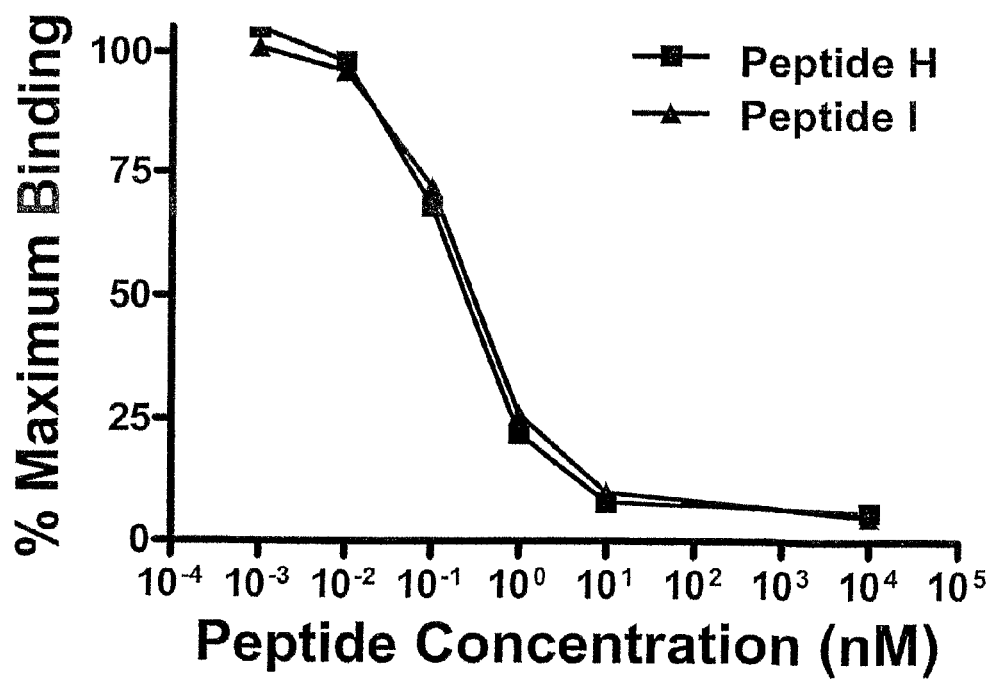
Figure 24

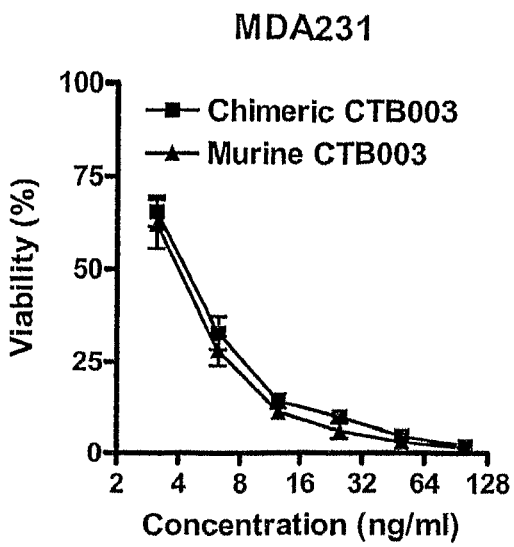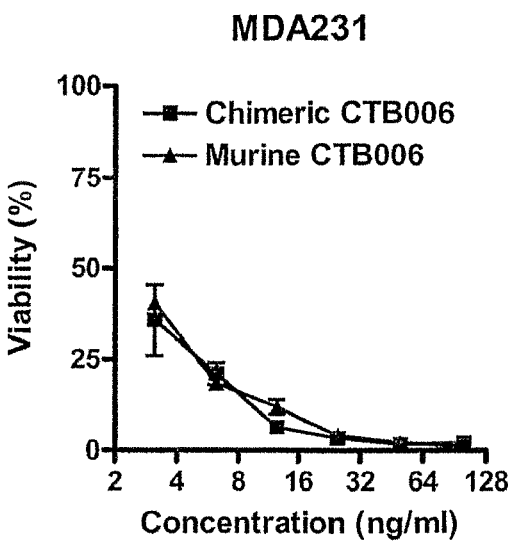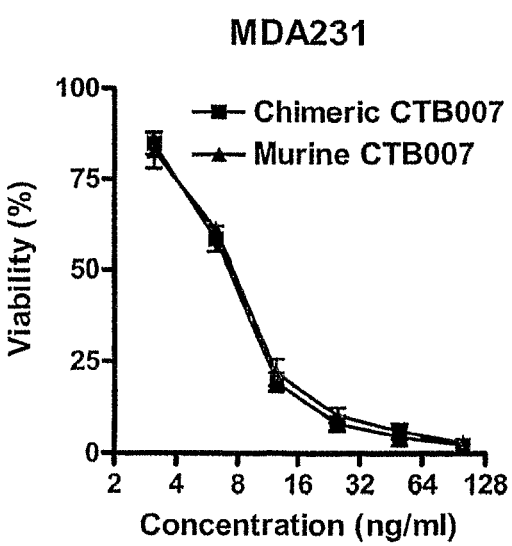
Figure 25

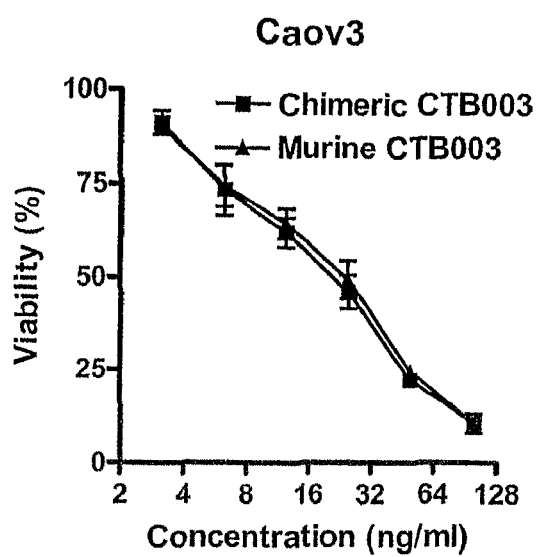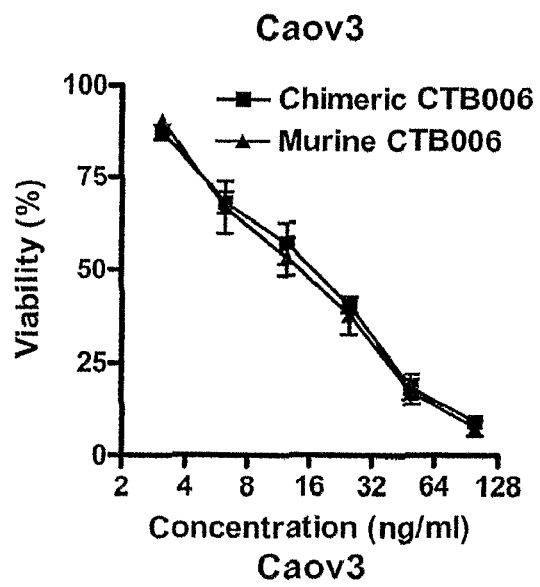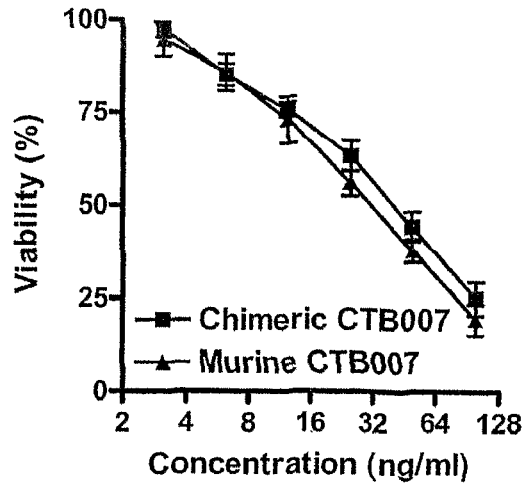
Figure 28

| | | |
|---|---|---|
| TRAIL-R1 (aa218-aa233) | VKDCTPWSDIECVHKE | SEQ ID NO.: 45 |
| TRAIL-R2 (aa167-aa182) | VGDCTPWSDIECVHKE | SEQ ID NO.: 46 |
| TRAIL-R3 (aa178-aa193) | VSNCTSWDDIQCVEEF | SEQ ID NO.: 47 |
| TRAIL-R4 (aa169-aa184) | VSNCTPRSDIKCKNES | SEQ ID NO.: 48 |

Figure 31

TRAIL RECEPTOR-BINDING AGENTS AND USES OF THE SAME

FIELD OF THE INVENTION

This invention relates generally to the preparation of TRAIL receptor-binding agents and uses of the same. In particular, the present invention relates to the preparation of anti-TRAIL receptor antibodies that recognize a common antigen determinant (i.e., epitope) shared by TRAIL-R1 and TRAIL-R2 and their use for TRAIL receptor detection and modulation of TRAIL receptor-mediated function.

BACKGROUND OF THE INVENTION

TRAIL was identified in the 90s of the last century. Soon after TRAIL was discovered, the attention was paid to its potential as an anti-cancer agent for cancer therapy. This was based on the ability of TRAIL to selectively kill tumor cells but not normal cells. Importantly, anti-tumor efficacy of TRAIL can be significantly enhanced by many current cancer therapies (for example, chemotherapy and radiation therapy). On the other hand, TRAIL can sensitize tumor cells and increase the susceptibility of tumor cells to chemotherapy and radiation therapy. Therefore, the combination of TRAIL with chemotherapy and radiation therapy has been thought to be a very effective anti-tumor therapy in the future.

TRAIL is a member of the TNF family of proteins. A feature of some proteins of this family is their ability to induce apoptosis such as TNF-α and Fas ligand. However, due to their toxic side effect, TNF-α and Fas ligand have no value for clinical application. In contrast, TRAIL exhibits a selective killing to tumor cells, its clinical value is obvious. To date, five receptors for TRAIL have been identified, two of which, DR4 (TRAIL-R1) and DR5 (TRAIL-R2), are capable of transducing the apoptosis signal while the other three DcR1 (TRAIL-R3), DcR2 (TRAIL-R4), and osteoprotegerin (OPG) do not transduce the apoptosis signal. All five receptors for TRAIL share significant homology in their extracellular ligand binding domains. The intracellular segments of both DR4 and DR5 contain a conserved functional domain, so called "death domain", which is responsible for transducing apoptosis signals.

After several years of study, the major biological function of TRAIL has been well known. TRAIL plays an important role in immune surveillance to tumor cells. Activated T lymphocytes and NK cells express high levels of TRAIL, which arms these immune competent cells to kill tumor cells. Animal studies indicate that knockout of TRAIL leads to increased incidence of tumor with age. Therefore, defective or insufficient expression of TRAIL might be a critical factor of tumorigenesis.

Because the apoptosis-inducing function of TRAIL is mediated by its receptors, research on TRAIL receptor system has been extensive. Early studies suggest that many normal cells may express the death receptors (TRAIL-R1 and TRAIL-R2) for TRAIL at the transcriptional level. With the availability of anti-death receptor antibodies, it has been believed that normal cells and tissues express very low levels of cell surface TRAIL-R1 and TRAIL-R2. In contrast, normal cells and tissues may express high levels of TRAIL-R3 and TRAIL-R4. This differential expression of different TRAIL receptors in normal cell may be a critical protective mechanism for normal cells to escape from TRAIL killing. Different from normal cells, most transformed tumor cells express high levels of TRAIL-R1 and TRAIL-R2 whereas the expression levels of TRAIL-R3 and TRAIL-R4 are very low. Thus, most tumor cells are susceptible to TRAIL-mediated killing. The differentially expressed TRAIL receptors between normal and tumor cells well explain the selectivity of TRAIL.

Many pre-clinical studies have confirmed that TRAIL is a safe and effective therapeutic agent for treatment of cancer. It has been shown that the systemic administration of the trimerized soluble TRAIL did not cause toxicity in experimental animals yet was able to induce regression of implanted tumors. It is even more encouraging that when TRAIL is combined with chemotherapy or radiation therapy, its anti-tumor efficacy is significantly enhanced. This synergistic effect has been demonstrated by many in vitro and in vivo experiments. In addition, TRAIL can increase the sensitivity of tumor cells to chemotherapy and radiation therapy. Because tumor cell resistance to chemotherapy and radiation therapy has been a major obstacle in treatment of cancer, the ability of TRAIL to prevent or reverse chemo or radiation resistance might be a significant advance in future cancer therapy.

However, as a therapeutic agent, TRAIL has several disadvantages. First, TRAIL has at least five receptors including both death receptors and decoy receptors, therefore lacking the selectivity to the receptors. Particularly it is hard to predict the apoptosis-inducing capability of TRAIL, when cancer cells express differentiated death receptors and decoy receptors. Second, the recombinant TRAIL has very short in vivo half-life, which limits the effective dose and anti-cancer efficacy of TRAIL in vivo. It is not convenient that patients usually receive repeated and large doses of TRAIL. Third, it is concerned that certain forms of recombinant TRAIL have potential hepatocyte toxicity.

These limitations of TRAIL as a therapeutic agent led to development of the alternatives to TRAIL. Monoclonal antibodies may selectively target the death receptors of TRAIL, which might be a more effective and safe strategy to cancer treatment.

During 25 years since the first monoclonal antibody was generated, monoclonal antibodies have demonstrated a great impact in cancer treatment. Most of those clinically effective monoclonal antibodies target antigens or receptors that are highly expressed on cancer cell surface, and block the growth signals required for tumor growth. These antibodies kill tumor cells through activation of compliments and antibody-dependent cytotoxicity (ADCC). In addition, monoclonal antibodies may be used as a tracing molecule, when conjugated with radioisotopes, toxins and drugs, to bring these therapeutic agents to cancer tissues and enhance anti-cancer efficacy.

The generation of TRAIL-R1 or TRAIL-R2 specific monoclonal antibody to replace TRAIL for cancer therapy has been successful. Several such antibodies have been in clinical trials. Preliminary results demonstrate that these antibodies not only have strong anticancer efficacy but also are safe compared to TRAIL.

Japanese pharmaceutical company, Sankyo, first developed an anti-TRAIL-R2 antibody, TRA-8. Ichikawa et al. used TRAIL-R2-Fc fusion protein as immunogen to immunize Balb/c mice. While TRA-8 did not induce apoptosis of normal cells, many tumor cells were highly susceptible to TRA-8-induced apoptosis. Although mRNA of TRAIL-R2 is widely distributed in normal tissues, the TRAIL-R2 protein was not detectable in normal tissues including live, lung, breast, kidney, spleen, ovary, hear and pancreas. However, cancer cells in these tissues expressed high levels of TRAIL-R2 protein. In addition, normal glial cells and peripheral blood cells expressed very low levels of TRAIL-R2, and are not susceptible to TRA-8-induced apoptosis, whereas gliloma cells and leukemia cells expressed high levels and are very susceptible to TRA-8-induced apoptosis. TRA-8 also exhibited several folds higher apoptosis-inducing capability than TRAIL in induction of apoptosis of tumor cells. Importantly, TRA-8 did not induce apoptosis of normal hepatocytes. When combined with chemotherapy or radiation therapy, the anti-cancer efficacy of TRA-8 is significantly enhanced. TRA-8 is currently in phase I clinical trial.

Human Genome Sciences carried out phase I trial of an anti-TRAIL-R1 antibody. Preliminary data indicate that patients well tolerated and the positive response was observed in several patients, suggesting that anti-TRAIL-R1 is a safe and effective therapeutic agent.

Many antibodies that are capable of inducing apoptosis of tumor cells are specific either for TRAIL-R1 or TRAIL-R2. A bispecific antibody to TRAIL-R1 and TRAIL-R2 has also been reported. (Lynch, US 2002/0155109). Because tumor cells may selectively express only one type of death receptors, therefore, these antibodies have a limited spectrum and unable to target all tumor cells. Meanwhile, because cancer cells may differentially express two types of the receptors and have a prefer signal transduction, the killing activity of these antibodies varies greatly. Accordingly, there is a need in the art for additional anti-TRAIL receptor antibodies to be used for TRAIL receptor detection and modulation of TRAIL receptor-mediated function.

SUMMARY OF THE INVENTION

The present invention relates to the preparation of TRAIL receptor-binding agents (e.g., antibodies) that recognize a common antigen determinant (i.e., epitope) shared by TRAIL-R1 and TRAIL-R2 and their use for TRAIL receptor detection and modulation of TRAIL receptor-mediated function. In one aspect, the invention provides a TRAIL receptor-binding agent (e.g., antibody) which binds TRAIL receptor 1 (TRAIL-R1) and/or TRAIL receptor 2 (TRAIL-R2), wherein the TRAIL receptor-binding agent (e.g., antibody), in its soluble form at low concentrations, has in vivo and in vitro cell death-inducing activity in cancer cells that express TRAIL-R1 and/or TRAIL-R2. In one embodiment, the TRAIL receptor-binding agent (e.g., antibody) binds a polypeptide TRAIL receptor 1 (TRAIL-R1) and/or TRAIL receptor 2 (TRAIL-R2) expressed on the surface of at least one cell. In one embodiment, the TRAIL receptor-binding agent (e.g., antibody) binds a polypeptide region of at least about 90 percent amino acid homology between TRAIL receptor 1 (TRAIL-R1) and/or TRAIL receptor 2 (TRAIL-R2). In one embodiment, the region of amino acid homology bound by the TRAIL receptor-binding agent (e.g., antibody) of the invention comprises an amino acid sequence VXDCTPWSDIECVHKE (SEQ ID NO.:44), wherein X is K or G and is capable of inducing cell death of a cell with TRAIL-R1 and/or TRAIL-1 receptors.

In another aspect, the invention provides a TRAIL receptor-binding agent (e.g., antibody) having the same epitope specificity as produced by mouse-mouse hybridoma CTB003 having CGMCC Accession Number 1665.

In another aspect, the invention provides a TRAIL receptor-binding agent (e.g., antibody) or an antigen-binding fragment thereof, comprising at least heavy chain CDR3 amino acid sequence of HITMVVGPFA (SEQ ID NO.:11) or the sequence with one or more conservative amino acid substitutions, wherein the TRAIL receptor-binding agent (e.g., antibody) or the fragment thereof binds TRAIL receptor 1 (TRAIL-R1) and/or TRAIL receptor 2 (TRAIL-R2), and has in vivo and in vitro cell death-inducing activity in cancer cells expressing TRAIL-R1 and/or TRAIL-R2.

In some embodiments, the TRAIL receptor-binding agent (e.g., antibody) of the invention (or an antigen-binding fragment thereof) is conjugated to a cancer therapeutic agent, wherein the therapeutic agent is preferably selected from the group consisting of a tumor-activated prodrug, a radionuclide, a chemotherapeutic drug and a toxin.

In another aspect, the invention provides an isolated nucleic acid encoding the TRAIL receptor-binding agent (e.g., antibody) the invention.

In another aspect, the invention provides a host cell or a vector comprising an isolated nucleic acid encoding a TRAIL receptor-binding agent (e.g., antibody) the invention In another aspect, the invention provides a composition comprising a TRAIL receptor-binding agent (e.g., antibody) of the invention and a pharmaceutically acceptable carrier.

In another aspect, the invention provides a commercial kit for treating a cancer comprising a TRAIL receptor-binding agent (e.g., antibody) of the invention in a container, the commercial kit, further comprising a chemotherapeutic agent and/or cancer therapeutic TRAIL receptor-binding agent (e.g., antibody) for treating a cancer, wherein the chemotherapeutic agent and/or cancer therapeutic TRAIL receptor-binding agent (e.g., antibody) is optionally placed in a separate container.

In another aspect, the invention provides an epitope of TRAIL-R1 and TRAIL-R2, comprising an amino acid sequence amino acid sequence VXDCTPWSDIECVHKE (SEQ ID NO.:44), wherein X is K or G and the epitope is recognized by a TRAIL receptor-binding agent (e.g., antibody) capable of binding TRAIL-R1 and/or TRAIL-R2 and capable of inducing cell death of a cell with TRAIL-R1 and/or TRAIL-R2 receptors. In one embodiment, the invention provides a TRAIL receptor-binding agent (e.g., antibody) generated by preparation of an immunogen containing an epitope of TRAIL-R1 and TRAIL-R2, comprising an amino acid sequence amino acid sequence VXDCTPWSDIECVHKE (SEQ ID NO.:44), wherein X is K or G and the epitope is recognized by a TRAIL receptor-binding agent (e.g., antibody) capable of binding TRAIL-R1 and/or TRAIL-R2 and capable of inducing cell death of a cell with TRAIL-R1 and/or TRAIL-R2 receptors In another aspect, the invention provides the use of the TRAIL receptor-binding agent (e.g., antibody) of the invention in the preparation of a medicament for selectively inducing cell death in cancer cells expressing TRAIL-R1 and/or TRAIL-R2.

In another aspect, the invention provides the use of the TRAIL receptor-binding agent (e.g., antibody) of the invention in the preparation of a medicament for enhancing the anti-cancer activity of other chemotherapeutic agents in cancer cells expressing TRAIL-R1 and/or TRAIL-R2, wherein the therapeutic agent is a chemotherapeutic agent, wherein the therapeutic agent is selected from the group consisting of bleomycin, carboplatin, chlorambucil, cisplatin, colchicine, cyclophosphamide, daunorubicin, actinomycin, diethylstilbestrol, doxoribicin, etoposide, 5-fluorouracil, floxuridine, melphalan, methotrexate, mitomycin, 6-mercaptopurine, paxlitaxel, teniposide, 6-thioguanine, vincristine and vinblastine.

In another aspect, the invention provides for the use of a pharmaceutically effective amount of a TRAIL receptor-binding agent (e.g., antibody) of the invention in the preparation of a medicament for treating a cancer, wherein the pharmaceutically effective amount of the TRAIL receptor-binding agent (e.g., antibody) selectively induces cell death of cancer cells expressing TRAIL-R1 and/or TRAIL-R2 polypeptide.

In another aspect, the invention provides for the use of a pharmaceutically effective amount of the TRAIL receptor-binding agent (e.g., antibody) of the invention as a medicament.

In another aspect, the invention provides a method of selectively inducing cell death of cells expressing TRAIL-R1 and/or TRAIL-R2 polypeptide in a subject in need thereof, the method comprising administering to the subject an effective amount of the TRAIL receptor-binding agent (e.g., antibody) of the invention, thereby selectively inducing cell death of cells expressing TRAIL-R1 and/or TRAIL-R2 polypeptide. In one embodiment of the method, the cells expressing TRAIL-R1 and/or TRAIL-R2 polypeptide are cancer cells. In one embodiment of the method, the cancer cells are selected from the group consisting of: breast cancer cells; liver cancer cells; pancreatic cancer cells; and colorectal cancer cells.

BRIEF DESCRIPTION OF THE DRAWINGS

The drawing figures depict preferred embodiments by way of example, not by way of limitations.

FIG. 1. A schematic diagram showing the nucleotide and amino acid sequences of variable regions of immunoglobulin heavy and light chain derived from hybridoma CGMCC 1665. Panel A shows the CTB003 $V_k$ nucleotide and amino acid sequences. Panel B shows the CTB003 $V_H$ nucleotide and amino acid sequences. The CDR sequences are underlined.

FIG. 5. Graphs showing the synergistic induction of cancer cell death with CTB003 and Adriamycin. A human breast cancer cell line (BT474) was incubated with various concentrations of CTB003 in the absence or presence of various concentrations of Adriamycin overnight. Cell viability was determined by ATPLite cell viability assay. Panel A shows a graph of cell viability (%) as a function of CTB003 concentration (ng/ml). Panel B shows a bar graph of cell viability (%) observed for various treatment groups.

FIG. 20. Graphs showing the experimental confirmation of the antigenic epitope of TRAIL-R1 and TRAIL-R2 recognized by CTB003. The polypeptide inhibition assay was used to determine the epitope recognized by CTB003 in TRAIL-R1 and TRAIL-R2. ELISA plate was coated with TRAIL-R1 or TRAIL-R2-Fc fusion protein, and incubated with CTB003 in the absence or presence of various concentrations of polypeptides (I and H) encoding an extracellular domains of TRAIL-R1 and TRAIL-R2, respectively. The data are expressed as the percent (%) maximum binding of binding of CTB003 to TRAIL-R1 (panel A) or TRAIL-R2 (panel B) observed as a function of peptide concentration (nM).

FIG. 24. Graphs demonstrating the confirmation of the antigenic epitope of TRAIL-R1 and TRAIL-R2 recognized by hCTB003 (i.e., humanized chimeric CTB003; a.k.a., chimeric CTB003). The polypeptide inhibition assay was used to determine the epitope recognized by hCTB003 in TRAIL-R1 and TRAIL-R2. ELISA plate was coated with TRAIL-R1 or TRAIL-R2-Fc fusion protein, and incubated with CTB003 in the absence or presence of various concentrations of with polypeptides (I and H) encoding an extracellular domains of TRAIL-R1 and TRAIL-R2, respectively. The data are expressed as the percent (%) maximum binding of binding of hCTB003 to TRAIL-R1 (panel A) or TRAIL-R2 (panel B) observed as a function of peptide concentration (nM).

FIG. 25. Graphs comparing the effect of murine and humanized chimeric TRAIL receptor-binding agents of the invention on human breast cancer cell line MDA231 growth in vitro. Panel A is a graph of cell viability (%) as a function of the concentration (ng/ml) of either CTB003 (murine) or hCTB003 (humanized chimeric; a.k.a., chimeric CTB003). Panel B is a graph of cell viability (%) as a function of the concentration (ng/ml) of either CTB006 (murine) or hCTB006 (humanized chimeric a.k.a., chimeric CTB006). Panel C is a graph of cell viability (%) as a function of the concentration (ng/ml) of either CTB007 (murine) or hCTB007 (humanized chimeric a.k.a., chimeric CTB007).

FIG. 28. Graphs comparing the effect of murine and humanized chimeric TRAIL receptor-binding agents of the invention on human ovarian cancer cell line Caov3 growth in vitro. Panel A is a graph of cell viability (%) as a function of the concentration (ng/ml) of either CTB003 (murine) or hCTB003 (humanized chimeric a.k.a., chimeric CTB003). Panel B is a graph of cell viability (%) as a function of the concentration (ng/ml) of either CTB006 (murine) or hCTB006 (humanized chimeric a.k.a., chimeric CTB006). Panel C is a graph of cell viability (%) as a function of the concentration (ng/ml) of either CTB007 (murine) or hCTB007 (humanized chimeric a.k.a., chimeric CTB007).

FIG. 31. A schematic diagram showing the amino acid sequence alignment of a select region of human TRAIL receptors.

DETAILED DESCRIPTION OF THE INVENTION

Figure 2:
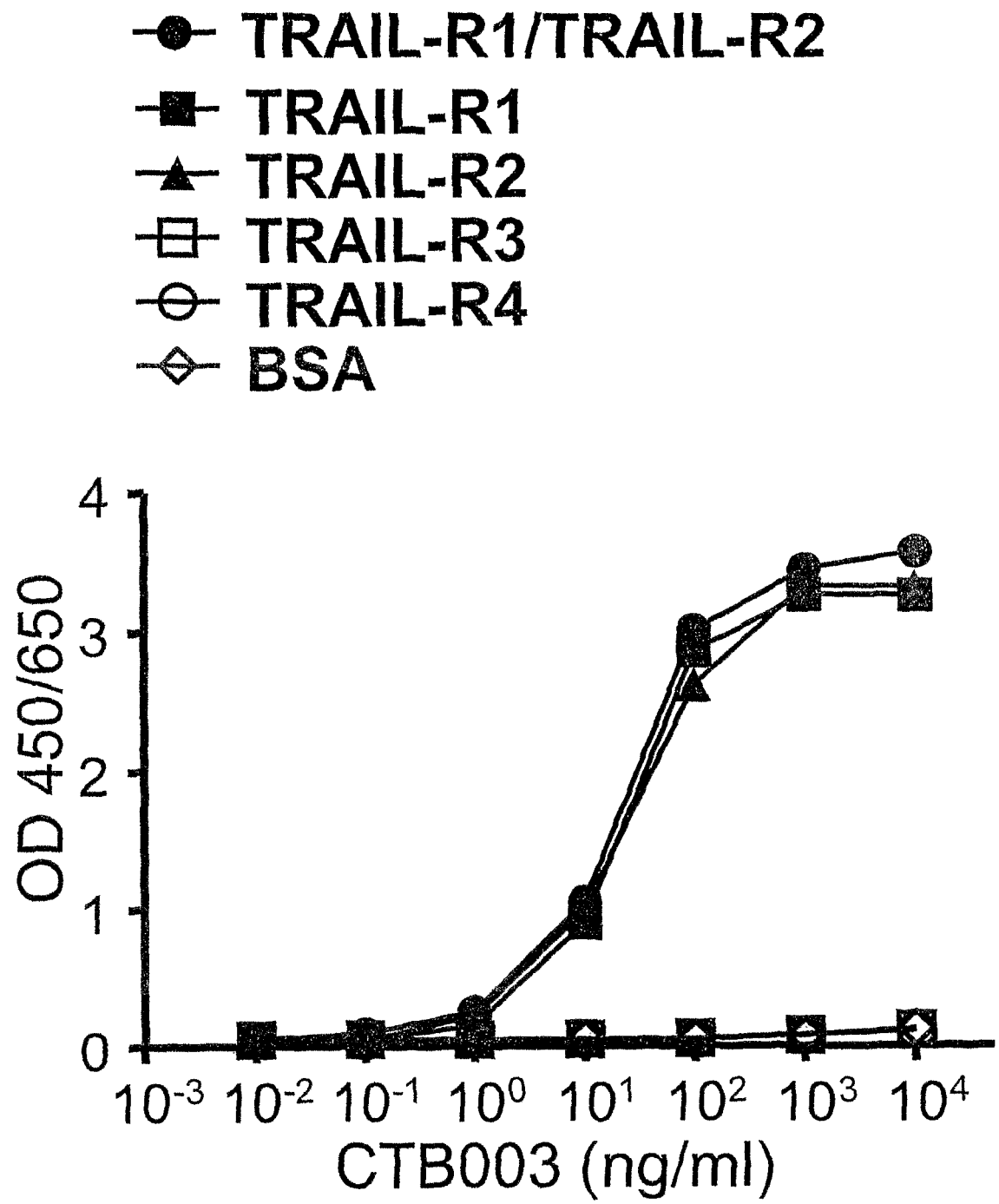
FIG. 2. A graph showing binding characteristics of CTB003. A recombinant human IgG1-Fc fusion protein containing the heterodimeric form of the extracellular domain of human TRAIL-R1 and TRAIL-R2, or a recombinant human IgG1-Fc fusion protein containing the homodimeric form of TRAIL1, TRAIL-R2, TRAIL-R3 or TRAIL-R4 was immobilized onto ELISA plate, and incubated with various concentrations of CTB003. After reaction with HRP-conjugated goat anti-mouse IgG1, a TMB substrate was added to reveal color reaction. The binding capacity was determined by the OD values of CTB003 to each protein. The data are expressed as the OD 450/650 as a function of CTB003 concentration (ng/ml).

General. It is to be appreciated that certain aspects, modes, embodiments, variations and features of the invention are described below in various levels of detail in order to provide a substantial understanding of the present invention.

The invention generally provides TRAIL receptor-binding agents (e.g., antibodies) which can simultaneously bind to two types of the death receptors to enhance its anti-tumor spectrum and activity. This invention discloses agents that bind equally to TRAIL-R1 and TRAIL-R2, and able to induce apoptosis of any tumor cells that may express single type of the receptors and both types of the receptors. Specifically, the invention provides the identification of a common "epitope" of TRAIL-R1 and TRAIL-R2 in the extracellular domain of TRAIL-R1 and/or R2 receptors to which the TRAIL receptor-binding agents of the invention bind. This epitope is about in the domain spanning amino acid residues from aa218 to aa233 of human TRAIL-R1 (aa218-aa233; VKDCTPWSDIECVHKE SEQ ID NO:45) or in the domain spanning amino acid residues from aa167 to aa182 of human TRAIL-R2 (aa167-aa182; VGDCTPWSDIECVHKE SEQ ID NO:46). Accordingly, the various aspects of the present invention relate to the preparation, expression and characterization of TRAIL receptor-binding agents.

TRAIL receptor-binding agents of the invention are useful, alone or in combination, to detect a TRAIL receptor polypeptide (a.k.a., the target polypeptide) in test sample as well as to modulate a TRAIL receptor-mediated function. TRAIL receptor-binding agents are useful to diagnose, prevent and/or treat a TRAIL receptor-related medical condition in subjects in need thereof. The TRAIL receptor-binding agents (e.g., antibody) of the present invention provide a unique biological function and broad anti-cancer activity of the anti-death receptor strategy. Although soluble TRAIL has been shown to be effective in induction of apoptosis of tumor cells in vivo, the killing activity appeared to be very low due to its very short half-life, and large (and repeated) doses are often required. The binding agents according to the present invention, are pharmaceutically more effective in animals carrying a human cancer cell lines compared to TRAIL and other monospecific anti-TRAIL-R1 or TRAIL-R2 antibody.

The various aspects of the present invention further relate to diagnostic methods and kits that use the TRAIL receptor-binding agents of the invention to identify individuals predisposed to a medical condition or to classify individuals with regard to drug responsiveness, side effects, or optimal drug dose. In other aspects, the invention provides methods for the use of TRAIL receptor-binding agents to prevent or treat TRAIL receptor-mediated disorders as well as to screen and/or validate ligands, e.g., small molecules that bind a TRAIL receptor polypeptide. Accordingly, various particular embodiments that illustrate these aspects follow.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and the claims. Generally, enzymatic reactions and purification steps are performed according to the manufacturer's specifications. The techniques and procedures are generally performed according to conventional methods in the art and various general references (see generally, Sambrook et al., *Molecular Cloning: A Laboratory Manual,* 2d Ed. (Cold Spring Harbor Laboratory Press, Cold Spring Harbor, N.Y., 1989), which are provided throughout this document.

Unless defined otherwise, all technical and scientific terms used herein generally have the same meaning as commonly understood by one of ordinary skill in the art to which this invention belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well known and commonly employed in the art. Standard techniques are used for nucleic acid and peptide synthesis. Standard techniques, or modifications thereof, are used for chemical syntheses and chemical analyses. All references cited herein are incorporated herein by reference in their entireties and for all purposes to the same extent as if each individual publication, patent, or patent application was specifically and individually incorporated by reference in its entirety for all purposes.

Select Abbreviations. Abbreviations of select biochemistry and hematology terms are summarized below in Table 1 and Table 2, respectively.

TABLE 1

Select Biochemistry Terms

| | |
|---|---|
| ALT | alanine aminotransferase |
| AST | aspartate aminotransferase |
| ALP | alkaline phosphatase |
| CK | creatine phosphokinase |
| γ-GT | γ-glutamylaminoacyltransferase |
| BUN | blood urea nitrogen |
| Crea | creatinine |
| Alb | albumin |
| TP | total protein |

TABLE 1-continued

Select Biochemistry Terms

| | |
|---|---|
| Tchol | total cholesterol |
| TG | triglyceride |
| Tbil | total bilirubin |
| Glu | glucose |
| Na | sodium |
| Ca | calcium |
| K | potassium |
| Cl | chlorine |

TABLE 2

Select Hematology Terms

| | |
|---|---|
| RBC | red blood cell count |
| Hb | hemoglobin |
| Hct | hematocrit |
| MCV | mean corpuscular volume |
| MCH | mean corpuscular hemoglobin |
| MCHC | mean corpuscular hemoglobin concentration |
| RDW | red(cell) distribution width |
| Plat | platelet |
| MPV | mean platelet volume |
| PDW | platelet distribution width |
| WBC | white blood cell count |
| WBC-D.C | white blood cell differential count |
| Ret | reticulocytes |

Definitions. The definitions of certain terms as used in this specification are provided below. Definitions of other terms may be found in the *Illustrated Dictionary of Immunology,* 2nd Edition (Cruse, J. M. and Lewis, R. E., Eds., Boca Raton, Fla.: CRC Press, 1995). The terms "DR4" and "TRAIL-R1", "DR5" and "TRAIL-R2", involved in the invention, can be used interchangeably. Unless indicated otherwise, the terms when used herein refer to human protein and gene.

As used herein, the term "biological activity" of the TRAIL receptor-binding agents (e.g., antibody) of the invention or TRAIL receptor-related polypeptides the antibody fragments thereof can bind TRAIL-R1 and/or TRAIL-R2, and has in vivo and in vitro cell death-inducing activity in cancer cells.

As used herein, the term "TRAIL receptor" refers to a member of the TNF receptor family. Human TRAIL receptors are cell surface receptors for TRAIL (AP02 ligand). To date, five receptors for TRAIL have been identified, two of which, DR4 (TRAIL-R1; CD261 or Death Receptor 4) and DR5 (TRAIL-R2; CD262 or Death Receptor 5), are capable of transducing the apoptosis signal while the other three DcR1 (TRAIL-R3; CD263 or Decoy Receptor 1), DcR2 (TRAIL-R4; CD264 or Decoy Receptor 2), and osteoprotegerin (OPG) do not transduce the apoptosis signal. Binding of trimeric TRAIL to TRAIL R1 or TRAIL R2 induces apoptosis by oligomerization of these receptors. TRAIL R1 and TRAIL R2 are composed of extracellular cysteine-rich domains, a transmembrane domain and a cytoplasmic death domain. TRAIL R3 and TRAIL R4 also have extracellular cysteine-rich domains but TRAIL R3 lacks cytoplasmic death domain and TRAIL R4 has a truncated one. All five receptors for TRAIL share significant homology in their extracellular ligand binding domains. The intracellular segments of both DR4 and DR5 contain a conserved functional domain, so called "death domain", which is responsible for transducing apoptosis signals. Death Domain is responsible for apoptosis signal transduction.

As used herein, the administration of an agent or drug to a subject or subject includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, β-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, the term "antibody" means a polypeptide comprising a framework region from an immunoglobulin gene or fragments thereof that specifically binds and recognizes an antigen, e.g., a TRAIL receptor polypeptide. Use of the term antibody is meant to include whole antibodies, including single-chain whole antibodies, and antigen-binding fragments thereof. The term "antibody" includes bispecific antibodies and multispecific antibodies so long as they exhibit the desired biological activity or function.

As used herein, the term "antibody-related polypeptide" means antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the invention are any combinations of variable region(s) and hinge region, $CH_1$, $CH_2$, and $CH_3$ domains. Antibody-related molecules useful as binding agents of the invention include, e.g., but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., *Nature* 341: 544-546, 1989), which consists of a $V_H$ domain; and (vi) an isolated complementarity determining region (CDR). As such "antibody fragments" can comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments. Single-chain antibody molecules may comprise a polymer with a number of individual molecules, for example, dimmer, trimer or other polymers.

As used herein, the term "biological sample" means sample material derived from or contacted by living cells. The term "biological sample" is intended to include tissues, cells and biological fluids isolated from a subject, as well as tissues, cells and fluids present within a subject. Biological samples of the invention include, e.g., but are not limited to, whole blood, plasma, semen, saliva, tears, urine, fecal material, sweat, buccal, skin, cerebrospinal fluid, and hair. Biological samples can also be obtained from biopsies of internal organs or from cancers. Biological samples can be obtained from subjects for diagnosis or research or can be obtained from undiseased individuals, as controls or for basic research.

As used herein, the term "CDR-grafted antibody" means an antibody in which at least one CDR of an "acceptor" antibody is replaced by a CDR "graft" from a "donor" antibody possessing a desirable antigen specificity.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See generally, Robinson et al., PCT/US86/02269; Akira et al., European Patent Application 184,187; Taniguchi, European Patent Application 171,496; Morrison et al., European Patent Application 173,494; Neuberger et al, WO 86/01533; Cabilly et al. U.S. Pat. No. 4,816,567; Cabilly et al., European Patent Application 125,023; Better et al., *Science* 240: 1041-1043, 1988; Liu et al., *Proc Natl Acad Sci USA* 84: 3439-3443, 1987; Liu et al., *J Immunol* 139: 3521-3526, 1987; Sun et al., *Proc Natl Acad Sci USA* 84: 214-218, 1987; Nishimura et al., *Cancer Res* 47: 999-1005, 1987; Wood et al., *Nature* 314: 446-449, 1885; and Shaw et al., *J. Natl Cancer Inst* 80: 1553-1559, 1988.

As used herein, the term "comparison window" means a segment of any one of the number of contiguous positions selected from the group consisting of from 20 to 600 amino acids or nucleotides, usually about 50 to about 200, more usually about 100 to about 150 in which a sequence can be compared to a reference sequence of the same number of contiguous positions after the two sequences are optimally aligned.

As used herein, the term "consensus FR" means a framework (FR) antibody region in a consensus immunoglobulin sequence. The FR regions of an antibody do not contact the antigen.

As used herein, the term "consensus sequence" refers to the sequence formed from the most frequently occurring amino acids (or nucleotides) in a family of related sequences (See e.g., Winnaker, Frown Genes to Clones (Verlagsgesellschaft, Weinheim, Germany 1987). That is, in a family of proteins, each position in the consensus sequence is occupied by the amino acid occurring most frequently at that position in the family. If two amino acids occur equally frequently, either can be included in the consensus sequence.

As used herein, the term "contacted" when applied to a cell refers to the process by which a TRAIL receptor-binding agent of the present invention, antibody, antibody composition, cytotoxic agent or moiety, gene, protein and/or antisense sequence, is delivered to a target cell or is placed in direct proximity with the target cell. This delivery can be in vitro or in vivo and can involve the use of a recombinant vector system.

As used herein, the term "cytotoxic moiety" means a moiety that inhibits cell growth or promotes cell death when proximate to or absorbed by a cell. Suitable cytotoxic moieties in this regard include radioactive agents or isotopes (radionuclides), chemotoxic agents such as differentiation inducers, inhibitors and small chemotoxic drugs, toxin proteins and derivatives thereof, as well as nucleotide sequences (or their antisense sequence). Therefore, the cytotoxic moiety can be, by way of non-limiting example, a chemotherapeutic agent, a photoactivated toxin or a radioactive agent.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen binding sites. Diabodies are described more fully in, e.g., EP 404,097; WO 93/11161; and 30 Hollinger et al., Proc. Natl. Acad. Sci. USA, 90: 6444-6448 (1993).

As used herein, the term "effector cell" means an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens. An effector cell can also phagocytose a target antigen, target cell, metastatic cancer cell, or microorganism.

As used herein, the term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. In one embodiment, an "epitope" of TRAIL-R1 and TRAIL-R2 is a common region in the extracellular domain of TRAIL-R1 and/or -R2 receptors to which the TRAIL receptor-binding agent of the invention binds. In one embodiment of the invention, this epitope is about in the domain spanning amino acid residues from aa218 to aa233 of TRAIL-R1 of SEQ ID NO:45 or in the domain spanning amino acid residues from aa167 to aa182 of TRAIL-R2 of SEQ ID NO:46.

To screen for TRAIL receptor-binding agents which bind to an epitope, a routine cross-blocking assay such as that described in Antibodies, *A Laboratory Manual*, Cold Spring Harbor Laboratory, Ed Harlow and David Lane (1988), can be performed. This assay can be used to determine if a test a TRAIL receptor binding agent binds the same site or epitope as an TRAIL-R1 and/or TRAIL-R2 antibody of the invention. Alternatively, or additionally, epitope mapping can be performed by methods known in the art. For example, the antibody sequence can be mutagenized such as by alanine scanning, to identify contact residues. In a different method, peptides corresponding to different regions of TRAIL-R1 and TRAIL-R2 can be used in competition assays with the test antibodies or with a test antibody and an antibody with a characterized or known epitope.

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated, e.g., the diseases associated with target polypeptide. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with each other, or with one or more additional therapeutic compounds (e.g., a multispecific TRAIL receptor-binding agent of the invention may be used in combination with one or more monospecific TRAIL receptor-binding agents.

As used herein, "expression" includes but is not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, a "fusion polypeptide" comprises a TRAIL receptor polypeptide operatively-linked to a polypeptide having an amino acid sequence corresponding to a polypeptide that is not substantially homologous to the TRAIL receptor polypeptide, e.g., a polypeptide that is different from the TRAIL receptor polypeptide and that is derived from the same or a different organism.

As used herein, the term "gene" means a segment of DNA that contains all the information for the regulated biosynthesis of an RNA product, including promoters, exons, introns, and other untranslated regions that control expression.

As used herein, the term "genotype" means an unphased 5' to 3' sequence of nucleotide pairs found at one or more polymorphic or mutant sites in a locus on a pair of homologous chromosomes in an individual. As used herein, genotype includes a full-genotype and/or a sub-genotype.

As used herein, the term "human sequence antibody" includes antibodies having variable and constant regions (if present) derived from human germline immunoglobulin sequences. The human sequence antibodies of the invention can include amino acid residues not encoded by human germline immunoglobulin sequences (e.g., mutations introduced by random or site-specific mutagenesis in vitro or by somatic mutation in vivo). Such antibodies can be generated in non-human transgenic animals, e.g., as described in PCT Publication Nos. WO 01/14424 and WO 00/37504. However, the term "human sequence antibody", as used herein, is not intended to include antibodies in which CDR sequences derived from the germline of another mammalian species, such as a mouse, have been grafted onto human framework sequences (e.g., humanized antibodies).

As used herein, the term "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3.

The humanized antibody optionally also will comprise at least a portion of an immunoglobulin constant region (Fc), typically that of a human immunoglobulin. For further details, see Jones et al., Nature 321:522-525 (1986); Reichmann et al., Nature 332:323-329 (1988); and Presta, Curr. Op. Strict. Biol. 2:593-596 (1992). "amino acid sequence modification(s)" of the TRAIL-R1 and/or TRAIL-R2 binding antibodies described herein are contemplated. For example, it may be desirable to improve the binding affinity and/or other biological properties of the antibody. Amino acid sequence variants of the TRAIL-R1 and/or TRAIL-R2 binding antibody are prepared by introducing appropriate nucleotide changes into the antibody nucleic acid, or by peptide synthesis. Such modifications include, for example, deletions from, and/or insertions into and/or substitutions of, residues within the amino acid sequences of the TRAIL-R1 and/or TRAIL-R2 binding antibody. Any combination of deletion, insertion, and substitution is made to obtain the antibody of interest, as long as the obtained antibody possesses the desired properties. The modification also includes the change of the pattern of glycosylation of the protein. A useful method for identification of preferred locations for mutagenesis is called "alanine scanning mutagenesis" as described by Cunningham and Wells in *Science,* 244:1081-1085 (1989). The mutated antibody is then screened for the desired activity. The invention includes antibody variants with one or more amino acid addition, deletion and/or substitution of the amino acid sequence defined by hybridoma CTB003 having CGMCC Accession Number 1665 provided that the antibody variant possesses the desired properties.

As used herein, the term "hypervariable region" refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 52A-55 (142) and 96-101 (1-13) in the $V_H$ (Chothia and Lesk *J. Mol. Biol.* 196:901-917 (1987)).

As used herein, the terms "identical" or percent "identity", when used in the context of two or more nucleic acids or polypeptide sequences, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." This term also refers to, or can be applied to, the compliment of a test sequence. The term also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An "isolated" or "purified" polypeptide or biologically-active portion thereof is substantially free of cellular material or other contaminating polypeptides from the cell or tissue source from which the TRAIL receptor-binding agent is derived, or substantially free from chemical precursors or other chemicals when chemically synthesized. For example, an isolated TRAIL receptor-binding agent which is an anti-TRAIL receptor antibody would be free of materials that would interfere with diagnostic or therapeutic uses of the agent. Such interfering materials may include enzymes, hormones and other proteinaceous and nonproteinaceous solutes.

As used herein, the phrase "induce cell death" or "capable of inducing cell death" refers to ability of the TRAIL receptor binding agents of the invention to make a viable cell become nonviable. Cell death and cell viability can be determined by various method in the art such as trypan blue exclusion assay and other cell viability assays. In the invention, the cell death is specially induced by "apoptosis", or called "programmed cell death", which determined by binding of annexin V, fragment of DNA, cell shrinkage, dilation of endoplasmic reticulum, cell fragmentation, and/or formation of membrane vesicles (called apoptotic bodies). Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase on hypodiploid cells. A target cell is one which express TRAIL-R1 and/or TRAIL-R2, preferably the cell is a tumor cell, e.g. a breast, colon, ovarian, stomach, endometrial, endothelial, liver, brian, salivary gland, lung, kidney, thyroid, pancreatic or bladder cell.

As used herein, the term "intact antibody" means an antibody that has at least two heavy (H) chain polypeptides and two light (L) chain polypeptides interconnected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$, and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: $FR_1$, $CDR_1$, $FR_2$, $CDR_2$, $FR_3$, $CDR_3$, $FR_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

As used herein, the term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, malignant melanoma, invading pathogens, cells or tissues infected with pathogens, or, in cases of autoimmunity or pathological inflammation, normal human cells or tissues.

As used herein, the terms "immunologically cross-reactive" and "immunologically-reactive" are used interchangeably to mean an antigen which is specifically reactive with an antibody which was generated using the same ("immunologically-reactive") or different ("immunologically cross-reactive") antigen. Generally, the antigen is TRAIL receptor polypeptide, a variant or subsequence thereof.

As used herein, the term "immunologically-reactive conditions" means conditions which allow an antibody, generated to a particular epitope of an antigen, to bind to that epitope to a detectably greater degree than the antibody binds to substantially all other epitopes, generally at least two times above background binding, preferably at least five times above background. Immunologically-reactive conditions are dependent upon the format of the antibody binding reaction and typically are those utilized in immunoassay protocols. See, Harlow & Lane, *Antibodies, A Laboratory Manual* (Cold Spring Harbor Publications, New York, 1988) for a description of immunoassay formats and conditions.

As used herein, the term "lymphocyte" means any of the mononuclear, nonphagocytic leukocytes, found in the blood, lymph, and lymphoid tissues, e.g., B and T lymphocytes.

As used herein, the term "medical condition" includes, but is not limited to, any condition or disease manifested as one or more physical and/or psychological symptoms for which treatment and/or prevention is desirable, and includes previously and newly identified diseases and other disorders.

As used herein, the term "modulator" includes inhibitors and activators. Inhibitors are agents that, e.g., bind to, partially or totally block stimulation, decrease, prevent, delay activation, inactivate, desensitize, or down regulate the activity of TRAIL receptor polypeptide, e.g., antagonists. Activators are agents that, e.g., bind to, stimulate, increase, open, activate, facilitate, enhance activation, sensitize or up regulate the activity of TRAIL receptor polypeptide, e.g., agonists. Modulators include agents that, e.g., alter the interaction of TRAIL receptor polypeptide with: proteins that bind activators or inhibitors, receptors, including proteins, peptides, lipids, carbohydrates, polysaccharides, or combinations of the above, e.g. lipoproteins, glycoproteins, and the like. Modulators include genetically modified versions of a naturally-occurring TRAIL receptor polypeptide, e.g., with altered activity, as well as naturally-occurring and synthetic ligands, antagonists, agonists, small chemical molecules and the like.

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al, *Nature* 352:624-628 (1991) and Marks et al., *J. Mol. Biol.* 222:581-597 (1991), for example.

As used herein, the term "neutralizing antibody" means an antibody molecule that is able to eliminate or significantly reduce at least one (1) biological function of a TRAIL receptor polypeptide or a TRAIL receptor-like polypeptide.

As used herein, the term "nucleotide pair" means the two nucleotides bound to each other between the two nucleotide strands.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration.

As used herein, the term "polyclonal antibody" means a preparation of antibodies derived from at least two (2) different antibody-producing cell lines. The use of this term includes preparations of at least two (2) antibodies that contain antibodies that specifically bind to different epitopes or regions of an antigen.

As used herein, the term "polynucleotide" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons. In a particular embodiment, the polynucleotide contains polynucleotide sequences from a TRAIL receptor gene.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature. In a particular embodiment, the polypeptide contains polypeptide sequences from a TRAIL receptor protein.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, e.g., recombinant cells express genes that are not found within the native (non-recombinant) form of the cell or express native genes that are otherwise abnormally expressed, under expressed or not expressed at all.

As used herein, the phrase "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule to increase the serum half life of the antibody, one may incorporate a salvage receptor binding epitope into the antibody (especially an antibody fragment) as described in U.S. Pat. No. 5,739,277, for example.

As used herein, the terms "single chain antibodies" or "single chain Fv (scFv)" refer to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv). See, e.g., Bird et al., *Science* 242: 423-426, 1988; and Huston et al., *Proc. Natl. Acad. Sci. USA*, 85: 5879-5883, 1988). Such single chain antibodies are included by reference to the term "antibody" fragments, and can be prepared by recombinant techniques or enzymatic or chemical cleavage of intact antibodies.

As used herein, the term "small molecule" means a composition that has a molecular weight of less than about 5 kDa and more preferably less than about 2 kDa. Small molecules can be, e.g., nucleic acids, peptides, polypeptides, glycopeptides, peptidomimetics, carbohydrates, lipids, lipopolysaccharides, combinations of these, or other organic or inorganic molecules.

As used herein, the term "specific binding" means the contact between a TRAIL receptor-binding agent and an antigen with a binding affinity of at least $10^{-6}$ M. Preferred binding agents bind with affinities of at least about $10^{-7}$ M, and preferably $10^{-8}$ M to $10^{-9}$ M, $10^{-10}$ M, $10^{-11}$ M, or $10^{-12}$ M.

As used herein, the phrase "stringent hybridization conditions" means conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can also be achieved with the addition of destabilizing agents, such as formamide. For selective or specific hybridization, a positive signal is at least two times background, preferably 10 times background hybridization. Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C.

As used herein, the term "subject" means that preferably the subject is a mammal, such as a human, but can also be an animal, e.g., domestic animals (e.g., dogs, cats and the like), farm animals (e.g., cows, sheep, pigs, horses and the like) and laboratory animals (e.g., monkey, rats, mice, rabbits, guinea pigs and the like).

As used herein, the term "substitution" is one of mutations that is generally used in the art. Those substitution variants have at least one amino acid residue in the TRAIL-R1 and/or TRAIL-R2 binding antibody molecule replaced by a different residue. The sites of greatest interest for substitutional mutagenesis include the hypervariable regions, but FR alterations are also contemplated. "Conservative substitutions" are shown in the Table below under the heading of "preferred substitutions". If such substitutions result in a change in biological activity, then more substantial changes, denominated "exemplary substitutions" in Table 3, or as further described below in reference to amino acid classes, may be introduced and the products screened.

TABLE 3

Amino Acid Substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

A particularly preferred type of substitutional variant involves substituting one or more hypervariable region residues of a parent antibody. A convenient way for generating such substitutional variants involves affinity maturation using phage display. Specifically, several hypervariable region sites (e.g. 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding TRAIL-R1 and/or —R2 receptors. Alternatively, or additionally, it may be beneficial to analyze a crystal structure of the antigen-antibody complex to identify contact points between the antibody and TRAIL-R1 and/or —R2 receptors. Such contact residues and neighbouring residues are candidates for substitution according to the techniques elaborated herein. Once such variants are generated, the panel of variants is subjected to screening as described herein and antibodies with similar or superior properties in one or more relevant assays may be selected for further development. The invention includes antibody variants with one or more amino acid substitution(s), especially conservative substitutions, to the hypervariable domains of the immunoglobulin heavy or light chain defined by hybridoma CTB003 having CGMCC Accession Number 1665 provided that the antibody variant possesses the desired properties.

As used herein, the term "target cell" means any cell in a subject (e.g., a human or animal) that can be targeted by the TRAIL receptor-binding agent of the invention.

As used herein, the term "therapeutic agent" is intended to mean a compound that, when present in an effective amount, produces a desired therapeutic effect on a subject in need thereof.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for a cancer expressing TRAIL-R1 and/or TRAIL-R2 if, after receiving a therapeutic amount of a TRAIL-R1 and/or TRAIL-R2 binding antibody of the invention according to the methods of the present invention, the subject shows observable and/or measurable reduction in or absence of one or more signs and symptoms of the particular disease. For example, for cancer, reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues.

As used herein, the term "variable" refers to the fact that certain segments of the variable domains differ extensively in sequence among antibodies. The V domain mediates antigen binding and define specificity of a particular antibody for its particular antigen. However, the variability is not evenly distributed across the amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Compositions of the Invention

TRAIL receptor-binding Agents of the Invention. In one aspect, the present invention provides TRAIL receptor-binding agent compositions, a.k.a., the binding agent. In one embodiment, the binding agent of the invention is an intact antibody directed to a TRAIL receptor polypeptide, homolog or derivative thereof. The binding agents of interest may be ones which bind specifically to TRAIL-R1 and/or TRAIL-R2, but do not "substantively" (or "substantially") bind other TRAIL receptors such as TRAIL-R3 or TRAIL-R4. That is to say, the antibody of interest may not significantly cross-react with other TRAIL receptors such as TRAIL-R3 or TRAIL-R4. In such embodiments, the extent of binding of the binding agent of the invention to these proteins will be less than about 10%, preferably, less than 5%, less than 1%, as determined by fluorescence activated cell sorting (FACS) analysis, ELISA or radioimmunoprecipitation (RIA).

Binding agents of the present invention can be described or specified in terms of the epitope(s) or portion(s) of a polypeptide of the present invention which are recognized or specifically bound by the binding agent, e.g., a region of the TRAIL receptor polypeptide that is located on the surface of the polypeptide (e.g., a hydrophilic region). In one embodiment, the invention provides TRAIL receptor-binding agents, e.g., antibodies or antibody-related polypeptides directed to a TRAIL receptor polypeptide (a.k.a., a target polypeptide) comprising an amino acid sequence of VXDCTPWSDIECVHKE (SEQ ID NO.: 44), wherein amino acid X is preferably selected from K or G. Such binding agents possess a unique functional characteristic. By recognizing a common epitope shared by TRAIL-R1 and TRAIL-R2, the binding agents are able to bind either single type of TRAIL-R1 or TRAIL-R2, or both type of TRAIL-R1 and TRAIL-R2. In one embodiment of the invention, the TRAIL-R1 or TRAIL-R2 receptor polypeptide bound by the TRAIL receptor binding agent of the invention is expressed on the surface of one or more cells. The binding agent selectively induces apoptosis of tumor cells in vivo and in vitro. The cancer cells may express TRAIL-R1 or TRAIL-R2 alone or co-express both. Based on its broad anti-cancer activity, the present invention has utility as a reagent for apoptosis signalling research, as well as a therapeutic effective against cells expressing TRAIL receptors illustratively including broad classes of cancer cells.

In select embodiments, the invention provides the TRAIL receptor-binding agents summarized in Table 4.

TABLE 4

Select TRAIL Receptor-Binding Agents

| Binding Agent | Type | Description |
|---|---|---|
| CTB003 | Murine Monoclonal Antibody | Murine monoclonal antibody directed to a common epitope shared by TRAIL-R1 and TRAIL-R2 polypeptides with a polypeptide sequence of VXDCTPWSDIECVHKE (SEQ ID NO.: 44), wherein amino acid X is preferably selected from K or G. |

TABLE 4-continued

Select TRAIL Receptor-Binding Agents

| Binding Agent | Type | Description |
|---|---|---|
| HuCTB003 (hCTB003) | Humanized Chimeric Antibody | Humanized chimeric monoclonal antibody directed to a common epitope shared by TRAIL-R1 and TRAIL-R2 polypeptides with a polypeptide sequence of VXDCTPWSDIECVHKE (SEQ ID NO.: 44), wherein amino acid X is preferably selected from K or G. |
| CTB006 | Murine Monoclonal Antibody | Murine monospecific antibody directed to TRAIL-R2 receptor. |
| HuCTB006 (hCTB006) | Humanized Chimeric Antibody | Monospecific humanized chimeric monoclonal antibody directed to TRAIL-R2 receptor. |
| CTB007 | Murine Monoclonal Antibody | Murine monospecific antibody directed to TRAIL-R1 receptor. |
| HuCTB007 (hCTB007) | Humanized Chimeric Antibody | Monospecific humanized chirneric monoclonal antibody directed to TRAIL-R1 receptor. |

Deposits of biological materials associated with the TRAIL receptor-binding agents summarized in Table 4 (above) were made with the China General Microbiological Culture Collection Center (CGMCC), China Committee for Culture Collection of Microorganisms, P.O. Box 2714, Beijing 100080, The People's Republic of China as detailed in Table 5 below.

TABLE 5

Biological Deposits

| Name of Depository | Materials | Date | Accession Number |
|---|---|---|---|
| CTB003 | Mouse-mouse hybridoma | Mar. 28, 2006 | 1665 |
| CTB006 | Mouse-mouse hybridoma | Apr. 20, 2006 | 1691 |
| CTB007 | Mouse-mouse hybridoma | Jun. 09, 2006 | 1733 |
| hCTB003LC (pcDNAIII-hCTB003-LC) | Plasmid DNA of human CTB003 light chain | Apr. 13, 2007 | 2000 |
| hCTB003HC (pcDNAIII-hCTB003-HC) | Plasmid DNA of human CTB003 heavy chain | Apr. 13, 2007 | 2001 |
| hCTB006LC (pcDNAIII-hCTB006-LC) | Plasmid DNA of human CTB006 light chain; | Apr. 13, 2007 | 2002 |
| hCTB006HC (pcDNAIII-hCTB006-HC) | Plasmid DNA of human CTB006 heavy chain | Apr. 13, 2007 | 2003 |
| hCTB007LC (pcDNAIII-hCTB007-LC) | Plasmid DNA of human CTB007 light chain | Apr. 13, 2007 | 2004 |
| hCTB007HC (pcDNAIII-hCTB007-HC) | Plasmid DNA of human CTB007 heavy chain | Apr. 13, 2007 | 2005 |

In another embodiment, the present invention affords a method of elucidating other agonistic epitopes shared by TRAIL-R1 and TRAIL-R2, which can be used for generation of an apoptosis-inducing antibody through binding to TRAIL-R1 and/or TRAIL-R2. The binding agents directed against said epitope may have a differing variable or CDR region but should have the binding and functional characteristics of the antibody of the present invention. As a means for targeting antibody production, hydropathy plots showing regions of hydrophilicity and hydrophobicity can be generated by any method well known in the air, including, e.g., the Byte Doolittle or the Flopp Woods methods, either with or without Fourier transformation (see, e.g., Hopp and Woods, *Proc. Nat. Acad. Sci. USA* 78: 3824-3828 (1981); Kyte and Doolittle, *J. Mol. Biol.* 157: 105-142 (1982)). The epitope(s) or polypeptide portion(s) can be specified as described herein, e.g., by N-terminal and C-terminal positions, by size in contiguous amino acid residues. The present invention includes binding agents that specifically bind polypeptides of the present invention, and allows for the exclusion of the same. The present invention includes binding agents that specifically bind epitopes which are conformational epitopes or nonconformational epitopes. As noted above, conformational epitopes or nonconformational epitopes are distinguished in that the binding to the former but not the latter is lost in the presence of denaturing solvents.

Binding agents of the present invention can also be described or specified in terms of their cross-reactivity. Binding agents that do not bind any other analog, ortholog, or homolog of the target polypeptide of the present invention are included. Binding agents that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are binding agents which only bind polypeptides encoded by polynucleotides which hybridize to a polynucleotide of the present invention under stringent hybridization conditions (as described herein). One aspect, the invention provides TRAIL receptor-binding agent (e.g., an antibody) which binds TRAIL receptor 1 (TRAIL-R1) polypeptide and/or TRAIL receptor 2 (TRAIL-R2) polypeptide, wherein the binding agent (antibody), in its soluble form at low concentrations, has in vivo and in vitro cell death-inducing activity in cancer cells that express TRAIL-R1 and/or TRAIL-R2 polypeptide. In one embodiment, the TRAIL receptor-binding agent binds a TRAIL receptor 1 (TRAIL-R1) polypeptide and/or TRAIL receptor 2 (TRAIL-R2) polypeptide expressed on the surface of at least one cell. That is, the TRAIL receptor-binding agent of the invention may bind TRAIL-R1 and/or TRAIL-R2 receptor polypeptide expressed on a single cell or to TRAIL-R1/-R2 polypeptide expressed on more that one cell (e.g., two cells). In one embodiment, the TRAIL receptor-binding agent binds a polypeptide region of at least about 90 percent amino acid homology (e.g., identity) between TRAIL receptor 1 (TRAIL-R1) and/or TRAIL receptor 2 (TRAIL-R2). In one embodiment, the TRAIL receptor-binding agent binds a polypeptide region of at least about 95 percent amino acid homology (e.g., identity) between TRAIL receptor 1 (TRAIL-R1) and/or TRAIL receptor 2 (TRAIL-R2). In one embodiment, the TRAIL receptor-binding agent binds a polypeptide region of at least about 98 percent amino acid homology (e.g., identity) between TRAIL receptor 1 (TRAIL-R1) and/or TRAIL receptor 2 (TRAIL-R2). In one embodiment, the TRAIL receptor-binding agent of the invention binds to a region of homology between TRAIL-R1 and TRAIL-R2 polypeptides, wherein the region comprises an amino acid sequence VXDCTPWSDIECVHKE (SEQ ID NO.:44), wherein X is K or G. The amino acid homology (e.g., identity) can be calculated using methods known in the art and described herein)

Binding agents of the present invention can also be described or specified in terms of their binding affinity. Preferred binding affinities include those with a dissociation constant or $K_d$ less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-4}$M, $10^{-14}$M, $5\times10^{-15}$M, and $10^{-15}$M. In one embodiment, the invention provides TRAIL receptor binding agents that at least bind human TRAIL-R1 and/or TRAIL-R2, with a $K_d$ value of no higher than $1\times10^{-8}$, preferably a $K_d$ value no higher than about $1\times10^{-1}$.

TRAIL receptor-binding agents within the scope of the present invention include, e.g., but are not limited to, monoclonal, polyclonal, chimeric, humanized, diabody, and human monoclonal and human polyclonal antibodies which specifically bind the target polypeptide, a homolog, derivative or a fragment thereof. As used herein, a "TRAIL receptor-like polypeptide" means a polypeptide that is different from TRAIL receptor polypeptide but which is immunologically-reactive with a TRAIL receptor-binding agent of the invention. A TRAIL receptor-like polypeptide may be derived from the same organism or a different organism as a TRAIL receptor polypeptide. A TRAIL receptor-like polypeptide may be encoded by the same gene or a different gene as a TRAIL receptor polypeptide. The antibodies useful as binding agents of the present invention include, e.g., but are not limited to, IgG (including $IgG_1$, $IgG_2$, $IgG_3$, and $IgG_4$), IgA (including $IgA_1$ and $IgA_2$), IgD, IgE, or IgM, and IgY.

In another embodiment, the binding agent of the invention is an antibody-related polypeptide directed to TRAIL receptor polypeptide, homolog or derivative thereof. Typically, the antigen-binding region of a binding agent, e.g., the anti-TRAIL receptor-binding region, will be most critical in specificity and affinity of binding of the binding agent of the invention. In some embodiments, the TRAIL receptor-binding agent is an anti-TRAIL receptor polypeptide antibody, such as an anti-TRAIL receptor polypeptide monoclonal antibody, an anti-TRAIL receptor polypeptide chimeric antibody, and an anti-TRAIL receptor polypeptide humanized antibody which have been modified by, e.g., deleting, adding, or substituting portions of the antibody. For example, an anti-TRAIL receptor polypeptide antibody intended meant to increase half-life, e.g., serum half-life, stability or affinity of the antibody.

In one embodiment, selection of antibodies that are specific to a particular domain of a TRAIL receptor polypeptide is facilitated by generation of hybridomas that bind to the fragment of a TRAIL receptor polypeptide possessing such a domain. Thus, TRAIL receptor-binding agents which are antibodies that are specific for a desired domain within a TRAIL receptor polypeptide, or derivatives, fragments, analogs or homologs thereof, are also provided herein.

The present invention further includes antibodies which are anti-idiotypic to the binding agents of the present invention. The binding agents of the present invention can be monospecific, bispecific, trispecific or of greater multispecificity. Multispecific binding agents can be specific for different epitopes of a TRAIL receptor polypeptide of the present invention or can be specific for both a TRAIL receptor polypeptide of the present invention as well as for heterologous compositions, such as a heterologous polypeptide or solid support material. See, e.g., WO 93/17715; WO 92/08802; WO 91/00360; WO 92/05793; Tutt et al., *J. Immunol.* 147: 60-69 (1991); U.S. Pat. Nos. 5,573,920, 4,474,893, 5,601,819, 4,714,681, 4,925,648; 6,106,835; Kostelny et al., *J. Immunol.* 148: 1547-1553 (1992). The binding agents of the invention can be from any animal origin including birds and mammals. Preferably, the binding agents are human, murine, rabbit, goat, guinea pig, camel, horse, or chicken. The binding agents of the invention are suitable for administration to a subject where it is desirable, e.g., to modulate a TRAIL receptor polypeptide function. Accordingly, it is further an object of the invention to provide for TRAIL receptor-binding agent compositions that are TRAIL receptor modulators, e.g., functional antagonists or functional agonists of a TRAIL receptor polypeptide. It is also an object of the invention to provide for TRAIL receptor-binding agent compositions that are partial antagonists and partial agonists of a TRAIL receptor polypeptide. Likewise included are neutralizing anti-TRAIL receptor antibodies which bind the TRAIL receptor polypeptide. In preferred embodiments, the binding agent of the invention will be purified: (1) to greater than 95% by weight of antibody as determined by the Lowry method (Lowry et al., *J. Biol. Chem.* 193. 265. 1951) and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated binding agent includes the polypeptide in situ within recombinant cells since at least one component of the antibody's natural environment will not be present. Ordinarily, however, a TRAIL receptor-binding agent, e.g., an isolated anti-TRAIL receptor antibody, will be prepared by at least one purification step. The invention further relates to structure-based methods useful in identifying, designing and producing compounds which act as modulators of a TRAIL receptor polypeptide.

The binding agents of the present invention can be used either alone or in combination with other compositions. For example, the TRAIL receptor-binding agents of the invention can be used in combination with one or more anti-TRAIL-receptor monoclonal antibodies known in the art, e.g., but not limited to those described by Zhou et al., US 2003/0198637; Zhou et al., *US* 2003/0190687; and anti-TRAIL-R2 antibody, TRA-8 (Sankyo).

The TRAIL receptor-binding agents of the present invention can further be recombinantly fused to a heterologous polypeptide at the N- or C-terminus or chemically conjugated (including covalently and non-covalently conjugations) to polypeptides or other compositions. For example, TRAIL receptor-binding agents of the present invention can be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314, 995; and EP 0 396 387.

In certain embodiments, the TRAIL receptor-binding agents of the present invention are anti-TRAIL receptor antibodies or anti-TRAIL receptor antibody-related polypeptides that are coupled or conjugated to one or more therapeutic or cytotoxic moieties to yield a TRAIL receptor-binding agent conjugate protein of the invention. The TRAIL receptor-binding agent conjugate protein of the invention can be used to modify a given biological response or create a biological response (e.g., to recruit effector cells). The therapeutic moiety is not to be construed as limited to classical chemical therapeutic agents. For example, the therapeutic moiety can be a protein or polypeptide possessing a desired biological activity. Such proteins can include, e.g., an enzymatically active toxin, or active fragment thereof, such as abrin, ricin A, Pseudomonas exotoxin, or diphtheria toxin; a protein such as tumor necrosis factor or interferon-alpha; or, biological response modifiers such as, e.g., lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors. Methods of Preparing a TRAIL receptor-Binding Agents of the Invention General Overview. Initially, a target polypeptide is chosen to which a binding agent of the invention (e.g., anti-TRAIL receptor antibody) can be raised. Techniques for generating binding agents directed to target polypeptides are well known to those skilled in the art. Examples of such techniques include, e.g., but are not limited to, those involving display libraries, xeno or humab mice, hybridomas, and the like. Target polypeptides within the scope of the present invention include any polypeptide or polypeptide derivative which is capable of exhibiting antigenicity. Examples include, but are not limited to, proteins (e.g., receptors, enzymes, hormones, growth factors), peptides, glycoproteins, lipoproteins, TRAIL receptor polypeptides, and the like. Exemplary target polypeptides also include bacterial, fungal and viral pathogens that cause human disease, such as HIV, hepatitis (A, B, & C), influenza, herpes, Giardia, malaria, Leishmiania, Staphylococcus aureus, Pseudomonas aeruginosa. Other target polypeptides are human proteins whose expression levels or compositions have been correlated with human disease or other phenotype. Other targets polypeptides of interest include tumor cell antigens and viral particle antigens.

It should be understood that not only are naturally-occurring antibodies suitable as binding agents for use in accordance with the present disclosure, but recombinantly engineered antibodies and antibody fragments, e.g., antibody-related polypeptides, which are directed to TRAIL receptor polypeptide are also suitable.

Binding agents, e.g., anti-TRAIL receptor antibodies, that can be subjected to the techniques set forth herein include monoclonal and polyclonal antibodies, and antibody fragments such as Fab, Fab', F(ab')$_2$, Fd, scFv, diabodies, antibody light chains, antibody heavy chains and/or antibody fragments. Methods useful for the high yield production of antibody Fv-containing polypeptides, e.g., Fab' and F(ab')$_2$ antibody fragments have been described. See U.S. Pat. No. 5,648, 237.

Generally, a binding agent is obtained from an originating species. More particularly, the nucleic acid or amino acid sequence of the variable portion of the light chain, heavy chain or both, of an originating species antibody having specificity for a target polypeptide antigen is obtained. Originating species is any species which was useful to generate the binding agent of the invention or library of binding agents, e.g., rat, mice, rabbit, chicken, monkey, human, and the like.

In preferred embodiments, TRAIL receptor-binding agents are anti-TRAIL receptor antibodies. Phage or phagemid display technologies are useful techniques to derive the binding agents of the present invention. Anti-TRAIL receptor antibodies useful in the present invention are "human antibodies," (e.g., antibodies isolated from a human) or "human sequence antibodies." Human antibodies can be made by a variety of methods known in the art including phage display methods. See also, U.S. Pat. Nos. 4,444,887, 4,716,111, 5,545,806, and 5,814,318; and WO 98/46645, WO 98/50433, WO 98/24893, WO 98/16654, WO 96/34096, WO 96/33735, and WO 91/10741. Methods useful for the identification of nucleic acid sequences encoding members of multimeric polypeptide complex by screening polyphage particles have been described. Rudert et al., U.S. Pat. No. 6,667, 150. Also, recombinant immunoglobulins can be produced. Cabilly, U.S. Pat. No. 4,816,567; Cabilly et al., U.S. Pat. No. 6,331,415 and Queen et al., Proc, Nat'l Acad. Sci. USA 86: 10029-10033, 1989. Techniques for generating and cloning monoclonal antibodies are well known to those skilled in the art. The TRAIL receptor-binding agent of the invention preferably have a high immunoreactivity, that is, percentages of antibodies molecules that are correctly folded so that they can specifically bind their target antigen. Expression of sequences encoding binding agents, e.g., antibodies of the invention, can be carried out in E. coli as described below. Such expression usually results in immunoreactivity of at least 80%, 90%, 95% or 99%.

Certain truncations of these proteins or genes perform the regulatory or enzymatic functions of the full sequence protein or gene. For example, the nucleic acid sequences coding therefore can be altered by substitutions, additions, deletions or multimeric expression that provide for functionally equivalent proteins or genes. Due to the degeneracy of nucleic acid coding sequences, other sequences which encode substantially the same amino acid sequences as those of the naturally occurring proteins may be used in the practice of the present invention. These include, but are not limited to, nucleic acid sequences including all or portions of the nucleic acid sequences encoding the above polypeptides, which are altered by the substitution of different codons that encode a functionally equivalent amino acid residue within the sequence, thus producing a silent change. It is appreciated that the nucleotide sequence of an immunoglobulin according to the present invention tolerates sequence homology variations of up to 25% as calculated by standard methods ("Current Methods in Sequence Comparison and Analysis," Macromolecule Sequencing and Synthesis, Selected Methods and Applications, pp. 127-149, 1998, Alan R. Liss, Inc.) so long as such a variant forms an operative antibody which recognizes TRAIL-R1 and TRAIL-R2. For example, one or more amino acid residues within a polypeptide sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present invention are proteins or fragments or derivatives thereof which are differentially modified during or after translation, e.g., by glycosylation, photolytic cleavage, linkage to an antibody molecule or other cellular ligands, etc. Additionally, an inhibitor encoding nucleic acid sequence can be mutated in vitro or in vivo to create and/or destroy translation, initiation, and/or termination sequences or to create variations in coding regions and/or form new restriction endonuclease sites or destroy pre-existing ones, to facilitate further in vitro modification. Any technique for mutagenesis known in the art can be used, including but not limited to in vitro site directed mutagenesis, J. Biol. Chem. 253:6551, use of Tab linkers (Pharmacia), and the like.

Preparation of Polyclonal Antisera and Immunogens, Methods of generating antibodies or antibody fragments of the invention typically include immunizing a subject (generally a non-human subject such as a mouse or rabbit) with the purified TRAIL receptor polypeptide or with a cell expressing the TRAIL receptor polypeptide. Any immunogenic portion of the TRAIL receptor polypeptide can be employed as the immunogen. An appropriate immunogenic preparation can contain, e.g., a recombinantly-expressed TRAIL receptor polypeptide or a chemically-synthesized TRAIL receptor polypeptide. An isolated TRAIL receptor polypeptide, or a portion or fragment thereof, can be used as an immunogen to generate a TRAIL receptor-binding agent that binds to the TRAIL receptor polypeptide, or a portion or fragment using standard techniques for polyclonal and monoclonal antibody preparation. The full-length TRAIL receptor polypeptide can be used or, alternatively, the invention provides for the use of the TRAIL receptor polypeptide fragments as immunogens. The TRAIL receptor polypeptide comprises at least four amino acid residues of the amino acid sequence shown in SEQ ID NO: 1, and encompasses an epitope of the TRAIL receptor polypeptide such that an antibody raised against the peptide forms a specific immune complex with the TRAIL receptor polypeptide. Preferably, the antigen peptide comprises at least 5, 8, 10, 15, 20, or 30 amino acid residues. Longer antigenic peptides are sometimes preferable over shorter antigenic peptides, depending on use and according to methods well known to those skilled in the art. Typically, the immunogen will be at least about 8 amino acyl residues in length, and preferably at least about 10 acyl residues in length. Multimers of a given epitope are sometimes more effective than a monomer.

If needed, the immunogenicity of the TRAIL receptor polypeptide (or fragment thereof) can be increased by fusion or conjugation to a hapten such as keyhole limpet hemocyanin (KLH) or ovalbumin (OVA). Many such haptens are known in the art. One can also combine the TRAIL receptor polypeptide with a conventional adjuvant such as Freund's complete or incomplete adjuvant to increase the subject's immune reaction to the polypeptide. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guérin and *Corynebacterium parvum*, or similar immunostimulatory compounds. These techniques are standard in the art.

For convenience, immune responses are often described in the present invention as being either "primary" or "secondary" immune responses. A primary immune response, which is also described as a "protective" immune response, refers to an immune response produced in an individual as a result of some initial exposure (e.g., the initial "immunization") to a particular antigen, e.g., a TRAIL receptor polypeptide. Such an immunization can occur, e.g., as the result of some natural exposure to the antigen (e.g., from initial infection by some pathogen that exhibits or presents the antigen) or from antigen presented by cancer cells of some tumor in the individual (e.g., malignant melanoma). Alternatively, the immunization can occur as a result of vaccinating the individual with a vaccine containing the antigen. For example, the vaccine can be a TRAIL receptor vaccine comprising one or more antigens from a TRAIL receptor polypeptide or a TRAIL receptor-like polypeptide.

A primary immune response can become weakened or attenuated over time and can even disappear or at least become so attenuated that it cannot be detected. Accordingly, the present invention also relates to a "secondary" immune response, which is also described here as a "memory immune response." The term secondary immune response refers to an immune response elicited in an individual after a primary immune response has already been produced.

Thus, a secondary or immune response can be elicited, e.g., to enhance an existing immune response that has become weakened or attenuated, or to recreate a previous immune response that has either disappeared or can no longer be detected. As an example, and not by way of limitation, a secondary immune response can be elicited by re-introducing to the individual an antigen, e.g., a TRAIL receptor polypeptide or a TRAIL receptor-like polypeptide, that elicited the primary immune response (e.g., by re-administrating a vaccine). However, a secondary immune response to an antigen can also be elicited by administrating other agents that can not contain the actual antigen. For example, the present invention provides methods for potentiating a secondary immune response by administrating a TRAIL receptor-binding agent to an individual. In such methods the actual antigen need not necessarily be administered with the TRAIL receptor-binding agent and the composition containing the TRAIL receptor-binding agent need not necessarily contain the antigen. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by $CD4^+$ cells. A first exposure to an antigen primes the immune system and additional exposure(s) results in a DTH.

Following appropriate immunization, the TRAIL receptor-binding agent, e.g., anti-TRAIL receptor polyclonal antibody can be prepared from the subject's serum. If desired, the antibody molecules directed against the TRAIL receptor polypeptide can be isolated from the mammal (e.g., from the blood) and further purified by well known techniques, such as polypeptide A chromatography to obtain the IgG fraction.

Monoclonal Antibody. In one embodiment of the present invention, the binding agent is an anti-TRAIL receptor monoclonal antibody. In one embodiment of the present invention, the anti-TRAIL receptor monoclonal antibody is a human anti-TRAIL receptor monoclonal antibody. For preparation of monoclonal antibodies directed towards a particular TRAIL receptor polypeptide, or derivatives, fragments, analogs or homologs thereof, any technique that provides for the production of antibody molecules by continuous cell line culture can be utilized. Such techniques include, but are not limited to, the hybridoma technique (see, e.g., Kohler & Milstein, 1975. Nature 256: 495-497); the trioma technique; the human B-cell hybridoma technique (see, e.g., Kozbor, et al., 1983. Immunol. Today 4: 72) and the EBV hybridoma technique to produce human monoclonal antibodies (see, e.g., Cole, et al., 1985. In: MONOCLONAL ANTIBODIES AND CANCER THERAPY, Alan R. Liss, Inc., pp. 77-96). Human monoclonal antibodies can be utilized in the practice of the invention and can be produced by using human hybridomas (see, e.g., Cote, et al., 1983. Proc Natl Acad Sci USA 80: 2026-2030) or by transforming human B-cells with Epstein Barr Virus in vitro (see, e.g., Cole, et al., 1985. In: MONOCLONAL ANTIBODIES AND CANCER THERAPY, Alan R. Liss, Inc., pp. 77-96). For example, a population of nucleic acids that encode regions of antibodies can be isolated. PCR utilizing primers derived from sequences encoding conserved regions of antibodies is used to amplify sequences encoding portions of antibodies from the population and then reconstruct DNAs encoding antibodies or fragments thereof, such as variable domains, from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the TRAIL receptor polypeptide. Alternatively, hybridomas expressing anti-TRAIL receptor monoclonal antibodies can be prepared by immunizing a subject and then isolating hybridomas from the subject's spleen using routine methods. See, e.g., Milstein et al., (Galfre and Milstein, *Methods Enzymol* (1981) 73: 3-46). Screening the hybridomas using standard methods will produce monoclonal antibodies of varying specificity (i.e., for different epitopes) and affinity. A selected monoclonal antibody with the desired properties, e.g., TRAIL receptor binding, can be used as expressed by the hybridoma, it can be bound to a molecule such as polyethylene glycol (PEG) to alter its properties, or a cDNA encoding it can be isolated, sequenced and manipulated in various ways. Synthetic dendrimeric trees can be added a reactive amino acid side chains, e.g., lysine to enhance the immunogenic properties of the TRAIL receptor polypeptide. Also, CPG-dinucleotide technique can be used to enhance the immunogenic properties of the TRAIL receptor polypeptide. Other manipulations include substituting or deleting particular amino acyl residues that contribute to instability of the antibody during storage or after administration to a subject, and affinity maturation techniques to improve affinity of the antibody of the TRAIL receptor polypeptide.

Hybridoma Technique. In one embodiment, the binding agent of the invention is an anti-TRAIL receptor monoclonal antibody produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies. A Laboratory Manual* Cold Spring Harbor Laboratory, Cold Spring Harbor, N.Y., 349 (1988); Hammerling et al., *Monoclonal Antibodies And T-Cell Hybridomas*, 563-681 (1981). Other methods for producing hybridomas and monoclonal antibodies are well known to those of skill in the art.

Phage Display Technique. As noted above, the binding agents of the present invention can be produced through the application of recombinant DNA and phage display technology. For example, binding agents of the invention, e.g., anti-TRAIL receptor antibodies, can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g., human or murine) by selecting directly with antigen, typically antigen bound or captured to a solid surface or bead. Phage used in these methods are typically filamentous phage including fd and M13 with Fab, Fv or disulfide stabilized Fv antibody domains are recombinantly fused to either the phage gene III or gene VIII protein. In addition, methods can be adapted for the construction of Fab expression libraries (see, e.g., Huse, et al., *Science* 246: 1275-1281, 1989) to allow rapid and effective identification of monoclonal Fab fragments with the desired specificity for a TRAIL receptor polypeptide, e.g., a polypeptide or derivatives, fragments, analogs or homologs thereof. Other examples of phage display methods that can be used to make the binding agents of the present invention include those disclosed in Huston et al., *Proc. Natl. Acad. Sci. U.S.A.*, 85: 5879-5883, 1988; Chaudhary et al., *Proc. Natl. Acad. Sci. U.S.A.*, 87: 1066-1070, 1990; Brinkman et al., *J. Immunol. Methods* 182: 41-50, 1995; Ames et al., *J. Immunol. Methods* 184: 177-186, 1995; Kettleborough et al., *Eur. J. Immunol.* 24: 952-958, 1994; Persic et al., *Gene* 187: 9-18, 1997; Burton et al., *Advances in Immunology* 57: 191-280, 1994; PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743. Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including, human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in WO 92/22324; Mullinax et al., *BioTechniques* 12: 864-869, 1992; and Sawai et al., *AJRI* 34: 26-34, 1995; and Better et al., *Science* 240: 1041-1043, 1988.

Generally, hybrid antibodies or hybrid antibody fragments that are cloned into a display vector can be selected against the appropriate antigen in order to identify variants that maintained good binding activity, because the antibody or antibody fragment will be present on the surface of the phage or phagemid particle. See e.g. Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Expression of Recombinant TRAIL receptor-Binding Agent. As noted above, the binding agents of the present invention can be produced through the application of recombinant DNA technology. Recombinant polynucleotide constructs encoding a TRAIL receptor-binding agent of the present invention typically include an expression control sequence operably-linked to the coding sequences of anti-TRAIL receptor antibody chains, including naturally-associated or heterologous promoter regions. As such, another aspect of the invention includes vectors containing one or more nucleic acid sequences encoding a TRAIL receptor-binding agent of the present invention. For recombinant expression of one or more the polypeptides of the invention, the nucleic acid containing all or a portion of the nucleotide sequence encoding the TRAIL receptor-binding agent is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Learner et al., U.S. Pat. Nos. 6,291,160; 6,680,192.

In general, expression vectors useful in recombinant DNA techniques are often in the form of plasmids. In the present specification, "plasmid" and "vector" can be used interchangeably as the plasmid is the most commonly used form of vector. However, the invention is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression in that subject of a compound. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences encoding the TRAIL receptor-binding agent, and the collection and purification of the TRAIL receptor-binding agent, e.g., cross-reacting anti-TRAIL receptor antibodies. See, generally, U.S. Application No. 20020199213. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. Vectors can also encode signal peptide, e.g., pectate lyase, useful to direct the secretion of extracellular antibody fragments. See U.S. Pat. No. 5,576,195.

The recombinant expression vectors of the invention comprise a nucleic acid encoding a compound with TRAIL receptor-binding properties in a form suitable for expression of the nucleic acid in a host cell, which means that the recombinant expression vectors include one or more regulatory sequences, selected on the basis of the host cells to be used for expression that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., TRAIL receptor-binding agents), include, e.g., but are not limited to, 3-phosphoglycerate kinase and other glycolytic enzymes. Inducible yeast promoters include, among others, promoters from alcohol dehydrogenase, isocytochrome C, and enzymes responsible for maltose and galactose utilization. In one embodiment, a polynucleotide encoding a TRIAL receptor-binding agent of the invention is operably-linked to an ara B promoter and expressible in a host cell. See U.S. Pat. No. 5,028,530. The expression vectors of the invention can be introduced into host cells to thereby produce polypeptides or peptides, including fusion polypeptides, encoded by nucleic acids as described herein (e.g., TRAIL receptor-binding agents, etc.).

Another aspect of the invention pertains to TRAIL receptor-binding agent-expressing host cells, which contain a nucleic acid encoding one or more TRAIL receptor-binding agents. The recombinant expression vectors of the invention can be designed for expression of a TRAIL receptor-binding agent in prokaryotic or eukaryotic cells. For example, a TRAIL receptor-binding agent can be expressed in bacterial cells such as *Escherichia coli*, insect cells (using baculovirus expression vectors), fungal cells, e.g., yeast, yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, e.g. using T7 promoter regulatory sequences and T7 polymerase. Methods useful for the preparation screening of polypeptides having predetermined property, e.g., TRAIL receptor-binding agents, via expression of stochastically generated polynucleotide sequences has been described. See U.S. Pat. Nos. 5,763, 192; 5,723,323; 5,814,476; 5,817,483; 5,824,514; 5,976,862; 6,492,107; 6,569,641.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathionie S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) *Gene* 69: 301-315) and pET 11d (Studier et al., GENE EXPRESSION TECHNOLOGY: METHODS IN ENZYMOLOGY 185, Academic Press, San Diego, Calif. (1990) 60-89). Methods for targeted assembly of distinct active peptide or protein domains to yield multifunctional polypeptides via polypeptide fusion has been described by Pack et al., U.S. Pat. Nos.

6,294,353; 6,692,935. One strategy to maximize recombinant polypeptide expression, e.g., a TRAIL receptor-binding agent, in *E. coli* is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression lost, e.g., *E. coli* (see, e.g., Wada, et al., 1992. Nucl. Acids Res. 20: 2111-2118). Such alteration of nucleic acid sequences of the invention can be carried out by standard DNA synthesis techniques.

In another embodiment, the TRAIL receptor-binding agent expression vector is a yeast expression vector. Examples of vectors for expression in yeast *Saccharomyces cerivisae* include pYepSec1 (Baldari, et al., 1987. EMBO J. 6: 229-234), pMFa (Kurjan and Herskowitz, *Cell* 30: 933-943, 1982), pJRY88 (Schultz et al., *Gene* 54: 113-123, 1987), pYES2 (Invitrogen Corporation, San Diego, Calif.), and picZ (InVitrogen Corp, San Diego, Calif.). Alternatively, a TRAIL receptor-binding agent can be expressed in insect cells using baculovirus expression vectors. Baculovirus vectors available for expression of polypeptides, e.g., TRAIL receptor-binding agents, in cultured insect cells (e.g., SF9 cells) include the pAc series (Smith, et al., *Mol. Cell. Biol.* 3: 2156-2165, 1983) and the pVL series (Lucklow and Summers, 1989. Virology 170: 31-39).

In yet another embodiment, a nucleic acid encoding a TRAIL receptor-binding agent of the invention is expressed in mammalian cells using a mammalian expression vector. Examples of mammalian expression vectors include, e.g., but are not limited to, pCDM8 (Seed, *Nature* 329: 840, 1987) and pMT2PC (Kaufman, et al., *EMBO J.* 6: 187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells useful for expression of the TRAIL receptor-binding agents of the present invention. See, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., *Genes Dev.* 1: 268-277, 1987), lymphoid-specific promoters (Calame and Eaton, *Adv. Immunol.* 43: 235-275, 1988), in particular promoters of T cell receptors (Winoto and Baltimore, EMBO J. 8: 729-733, 1989) and immunoglobulins (Banerji, et al., 1983. Cell 33: 729-740; Queen and Baltimore, *Cell* 33: 741-748, 1983.), neuron-specific promoters (e.g., the neurofilament promoter; Byrne and Ruddle, *Proc. Natl. Acad. Sci. USA* 86: 5473-5477, 1989), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the α-fetoprotein promoter (Campes and Tilghman, *Genes Dev.* 3: 537-546, 1989).

The invention further provides a recombinant expression vector comprising a DNA molecule encoding a TRAIL receptor-binding agent of the invention cloned into the expression vector in an antisense orientation. That is, the DNA molecule is operatively-linked to a regulatory sequence in a manner that allows for expression (by transcription of the DNA molecule) of an RNA molecule that is antisense to a TRAIL receptor-binding agent mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antigen se genes. See, e.g., Weintraub, et al., "Antisense RNA as a molecular tool for genetic analysis," Reviews-Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a TRAIL receptor-binding agent can be expressed in bacterial cells such as *E. coli*, insect cells, yeast or mammalian cells. Mammalian cells are a preferred host for expressing nucleotide segments encoding immunoglobulins or fragments thereof. See Winnacker, *From Genes To Clones*, (VCH Publishers, NY, 1987). A number of suitable host cell lines capable of secreting intact heterologous proteins have been developed in the art, and include Chinese hamster ovary (CHO) cell lines, various COS cell lines, HeLa cells, L cells and myeloma cell lines. Preferably, the cells are nonhuman. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Queen et al., *Immunol. Rev.* 89: 49, 1986. Preferred expression control sequences are promoters derived from endogenous genes, cytomegalovirus, SV40, adenovirus, bovine papillomavirus, and the like. Co et al., *J. Immunol.* 148: 1149, 1992. Other suitable host cells are known to those skilled in the art.

Vector DNA can be introduced into prokaryotic or eukaryotic cells via conventional transformation or transfection techniques. As used herein, the terms "transformations" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation, biolistics or viral-based transfection can be used for other cellular hosts.

Other methods used to transform mammalian cells include the use of polybrene, protoplast fusion, liposomes, electroporation, and microinjection (see generally, Sambrook et al., Molecular Cloning). Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. The vectors containing the DNA segments of interest can be transferred into the host cell by well known methods, depending on the type of cellular host.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the TRAIL receptor-binding agent or can be introduced on a separate vector. Cells stably transfected with the introduced nucleic acid can be identified by drug selection (e.g., cells that have incorporated the selectable marker gene will survive, while the other cells die).

A host cell that includes a TRAIL receptor-binding agent of the present invention, such as a prokaryotic or eukaryotic host cell in culture, can be used to produce (i.e., express) recombinant TRAIL receptor-binding agent. In one embodiment, the method comprises culturing the host cell of invention (into which a recombinant expression vector encoding the TRAIL receptor-binding agent has been introduced) in a suitable medium such that the TRAIL receptor-binding agent is produced. In another embodiment, the method further comprises the step of isolating the TRAIL receptor-binding agent from the medium or the host cell. Once expressed, collections of the TRAIL receptor-binding agents, e.g., the anti-TRAIL receptor antibodies or the anti-TRAIL receptor antibody-related polypeptides are purified from culture media and host cells. The TRAIL receptor-binding agents can be purified according to standard procedures of the art, including HPLC purification, column chromatography, gel electrophoresis and the like. In one embodiment, the TRAIL receptor-binding agent is produced in a host organism by the method of Boss et al., U.S. Pat. No. 4,816,397. Usually, anti-TRAIL receptor antibody chains are expressed with signal sequences and are thus released to the culture media. However, if the anti-TRAIL receptor antibody chains are not naturally secreted by host cells, the anti-TRAIL receptor antibody chains can be released by treatment with mild detergent. Purification of recombinant polypeptides is well known in the art and include ammonium sulfate precipitation, affinity chromatography purification technique, column chromatography, ion exchange purification technique, gel electrophoresis and the like (see generally Scopes, Protein Purification (Springer-Verlag, N.Y., 1982).

Polynucleotides encoding TRAIL receptor-binding agents, e.g., the anti-TRAIL receptor antibody coding sequences, can be incorporated in transgenes for introduction into the genome of a transgenic animal and subsequent expression in the milk of the transgenic animal. See, e.g., U.S. Pat. Nos. 5,741,957, 5,304,489, and 5,849,992. Suitable transgenes include coding sequences for light and/or heavy chains in operable linkage with a promoter and enhancer from a mammary gland specific gene, such as casein or β-lactoglobulin. For production of transgenic animals, transgenes can be microinjected into fertilized oocytes, or can be incorporated into the genome of embryonic stem cells, and the nuclei of such cells transferred into enucleated oocytes.

Single Chain Antibodies. In one embodiment, the binding agent of the invention is a single chain anti-TRAIL receptor antibody. According to the invention, techniques can be adapted for the production of single-chain antibodies specific to a TRAIL receptor polypeptide (see, e.g., U.S. Pat. No. 4,946,778). Examples of techniques which can be used to produce single-chain Fvs and antibodies of the invention include those described in U.S. Pat. Nos. 4,946,778 and 5,258,498; Huston et al., *Methods in Enzymology*, 203: 46-88, 1991; Shu, L. et al., *Proc. Natl. Acad. Sci. USA*, 90: 7995-7999, 1993; and Skerra et al., *Science* 240: 1038-1040, 1988.

Chimeric and Humanized Antibodies. In one embodiment, the binding agent of the invention is a chimeric anti-TRAIL receptor antibody. In one embodiment, the binding agent of the invention is a humanized anti-TRAIL receptor antibody. In one embodiment of the invention, the donor and acceptor antibodies are monoclonal antibodies from different species. For example, the acceptor antibody is a human antibody (to minimize its antigenicity in a human), in which case the resulting CDR-grafted antibody is termed a "humanized" antibody.

Recombinant anti-TRAIL receptor antibodies, such as chimeric and humanized monoclonal antibodies, comprising both human and non-human portions, can be made using standard recombinant DNA techniques, and are within the scope of the invention. For some uses, including in vivo use of the binding agent of the invention in humans as well as use of these agents in vitro detection assays, it is preferable to use chimeric, humanized, or human anti-TRAIL receptor antibodies. Such chimeric and humanized monoclonal antibodies can be produced by recombinant DNA techniques known in the art. Such useful methods include, e.g., but are not limited to, methods described in International Application No. PCT/US86/02269; U.S. Pat. No. 5,225,539; European Patent No. 184187, European Patent No. 171496; European Patent No. 173494; PCT International Publication No. WO 86/01533; U.S. Pat. Nos. 4,816,567; 5,225,539; European Patent No. 125023; Better, et al., 1988. *Science* 240: 1041-1043; Liu, et al., 1987. *Proc. Natl. Acad. Sci. USA* 84: 3439-3443; Liu, et al., 1987. *J. Immunol.* 139: 3521-3526; Sun, et al., 1987. *Proc. Natl. Acad. Sci. USA* 84: 214-218; Nishimura, et al., 1987. *Cancer Res.* 47: 999-1005; Wood, et al., 1985. *Nature* 314: 446-449; Shaw, et al., 1988. *J. Natl. Cancer Inst.* 80: 1553-1559); Morrison (1985) *Science* 229: 1202-1207; Oi, et al. (1986) *BioTechniques* 4: 214; Jones, et al., 1986. *Nature* 321: 552-525; Verhoeyan, et al., 1988. *Science* 239: 1534; Morrison, *Science* 229: 1202, 1985; Oi et al., *BioTechniques* 4: 214, 1986; Gillies et al., *J. Immunol. Methods*, 125: 191-202, 1989; U.S. Pat. No. 5,807,715; and Beidler, et al., 1988. *J. Immunol.* 141: 4053-4060. For example, antibodies can be humanized using a variety of techniques including CDR-grafting (EP 0 239 400; WO 91/09967; U.S. Pat. Nos. 5,530, 101; 5,585,089; 5,859,205; 6,248,516; EP460167), veneering or resurfacing (EP 0 592 106; EP 0 519 596; Padlan E. A., *Molecular Immunology*, 28: 489-498, 1991; Studnicka et al., *Protein Engineering* 7: 805-814, 1994; Roguska et al., *PNAS* 91: 969-973, 1994), and chain shuffling (U.S. Pat. No. 5,565, 332). In one embodiment, a cDNA encoding a murine anti-TRAIL receptor monoclonal antibody is digested with a restriction enzyme selected specifically to remove the sequence encoding the F/c constant region, and the equivalent portion of a cDNA encoding a human Fc constant region is substituted (see Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al U.S. Pat. No. 4,816,567; Cabilly et al., European Patent Application 125,023; Better et al. (1988) Science 240: 1041-1043; Liu et al. (1987) Proc Natl Acad Sci USA 84: 3439-3443; Liu et al. (1987) J Immunol 139: 3521-3526; Sun et al. (1987) *Proc Natl Acad Sci USA* 84: 214-218; Nishimura et al. (1987) *Cancer Res* 47: 999-1005; Wood et al. (1985) *Nature* 314: 446-449; and Shaw et al. (1988) *J. Natl Cancer Inst* 80: 1553-1559); U.S. Pat. Nos. 6,180,370; 6,300,064; 6,696,248; 6,706,484; 6,828,422.

In one embodiment, the present invention allows the construction of humanized anti-TRAIL receptor antibodies that are unlikely to induce a human anti-mouse antibody (hereinafter referred to as "HAMA") response, while still having an effective antibody effector function. As used herein, the terms "human" and "humanized", in relation to antibodies, relate to any antibody which is expected to elicit a therapeutically tolerable weak immunogenic response in a human subject. In one embodiment, the present invention provides for a humanized TRAIL-R1 and/or TRAIL-R2 dual-specific antibody, CTB003 or hCTB003 heavy and light chain immunoglobulins.

CDR Antibodies. In one embodiment, the binding agent of the invention is an anti-TRAIL receptor CDR antibody. Generally the donor and acceptor antibodies used to generate the anti-TRAIL receptor CDR antibody are monoclonal antibodies from different species; typically the acceptor antibody is a human antibody (to minimize its antigenicity in a human), in which case the resulting CDR-grafted antibody is termed a "humanized" antibody. The graft may be of a single CDR (or even a portion of a single CDR) within a single $V_H$ or $V_L$ of the acceptor antibody, or can be of multiple CDRs (or portions thereof) within one or both of the $V_H$ and $V_L$. Frequently all three CDRs in all variable domains of the acceptor antibody will be replaced with the corresponding donor CDRs, though one need replace only as many as necessary to permit adequate binding of the resulting CDR-grafted antibody to MetAp3. Methods for generating CDR-grafted and humanized antibodies are taught by Queen et al. U.S. Pat. Nos. 5,585,089, 5,693,761; 5,693,762; and Winter U.S. Pat. No. 5,225,539; and EP 0682040. Methods useful to prepare $V_H$ and $V_L$ polypeptides are taught by Winter et al., U.S. Pat. Nos. 4,816,397; 6,291,158; 6,291,159; 6,291,161; 6,545,142; EP 0368684; EP0451216; EP0120694.

After selecting suitable framework region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) can be produced by oligonucleotide synthesis and/or PCR. The nucleic acid encoding CDR regions can also be isolated from the originating species antibodies using suitable restriction enzymes and ligated into the target species framework by ligating with suitable ligation enzymes. Alternatively, the framework regions of the variable chains of the originating species antibody can be changed by site-directed mutagenesis.

Since the hybrids are constructed from choices among multiple candidates corresponding to each framework region, there exist many combinations of sequences which are amenable to construction in accordance with the principles described herein. Accordingly, libraries of hybrids can be assembled having members with different combinations of individual framework regions. Such libraries can be electronic database collections of sequences or physical collections of hybrids.

This process typically does not alter the acceptor antibody's FRs flanking the grafted CDRs. However, one skilled in the art can sometimes improve antigen binding affinity of the resulting anti-TRAIL receptor CDR grafted antibody by replacing certain residues of a given FR to make the FR more similar to the corresponding FR of the donor antibody. Preferred locations of the substitutions include amino acid residues adjacent to the CDR, or which are capable of interacting with a CDR (see, e.g., U.S. Pat. No. 5,585,089, especially columns 12-16). Or one skilled in the art can start with the donor FR and modify it to be more similar to the acceptor FR or a human consensus FR. Techniques for making these modifications are known in the art. Particularly if the resulting FR fits a human consensus FR for that position, or is at least 90% or more identical to such a consensus FR, doing so may not increase the antigenicity of the resulting modified anti-TRAIL receptor CDR antibody significantly compared to the same antibody with a fully human FR.

Fusion Proteins. In one embodiment, the binding agent of the invention is a fusion protein. The TRAIL receptor-binding agents of the present invention, when fused to a second protein, can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present invention can also be engineered to improve characteristics of the TRAIL receptor-binding agent. For instance, a region of additional amino acids, particularly charged amino acids, can be added to the N-terminus of the TRAIL receptor-binding agent to improve stability and persistence during purification from the host cell or subsequent handling and storage. Also, peptide moieties can be added to the TRAIL receptor-binding agent to facilitate purification. Such regions can be removed prior to final preparation of the TRAIL receptor-binding agent. The addition of peptide moieties to facilitate handling of polypeptides are familiar and routine techniques in the art. The TRAIL receptor-binding agent of the invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci, USA* 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., *Cell* 37: 767, 1984.

Thus, any of these above fusions can be engineered using the polynucleotides or the polypeptides of the present invention. Also, the fusion protein can show an increased half-life in vivo.

Fusion proteins having disulfide-linked dimeric structures (due to the IgG) can be more efficient in binding and neutralizing other molecules, than the monomeric secreted protein or protein fragment alone. Fountoulakis et al., *J. Biochem.* 270: 3958-3964, 1995.

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, e.g., improved pharmacokinetic properties. See EP-A 0232 262. Alternatively, deleting the Fc part after the fusion protein has been expressed, detected, and purified, would be desired. For example, the Fc portion can hinder therapy and diagnosis if the fusion protein is used as an antigen for immunizations. In drug discovery, e.g., human proteins, such as hIL-5, have been fused with Fc portions for the purpose of high-throughput screening assays to identify antagonists of hIL-5. Bennett et al., *J Molecular Recognition* 8: 52-58, 1995; Johanson et al., *J. Biol. Chem.*, 270: 9459-9471, 1995.

De-immunization of Therapeutic Proteins by T Cell Epitope Modification. Many therapeutic proteins in clinical use have been shown to elicit unwanted antibody responses, which in some cases have been linked to adverse events. In one embodiment of the present invention, recombinant anti-TRAIL receptor antibodies, TRAIL receptor polypeptides or TRAIL receptor-binding agent are rendered non-immunogenic, or less immunogenic, to a given species by identifying in their amino acid sequences one or more potential epitopes for T-cells of the given species and modifying the amino acid sequence to eliminate at least one of the T-cell epitopes. This eliminates or reduces the immunogenicity of the polypeptide or protein when exposed to the immune system of the given species. Monoclonal antibodies and other immunoglobulin-like molecules can particularly benefit from being de-immunized in this way—for example, mouse-derived immunoglobulins can be de-immunized for human therapeutic use. Methods for de-immunizing a polypeptide or protein in the art. See, e.g., Carr, et al. U.S. Pat. Application 20030153043; and De Groot, et al., *AIDS Res. and Human Retroviruses* 13: 539-541 (1997); Schafer, et al., *Vaccine* 16: 1880-1884 (1998); De Groot, et al., *Dev. Biol.* 112: 71-80 (2003); De Groot, et al., *Vaccine* 19: 4385-4395 (2001); Reijonen and Kwok *Methods* 29: 282-288; Novak, et al., *J. Immunology* 166: 6665-6670 (2001).

In one embodiment, TRAIL receptor-binding agents of the invention are prepared using genomic DNA or ESTs encoding candidate binding agents as part of fusion proteins which form inclusion bodies upon expression in host cells. Methods useful to prepare genomic DNA or ESTs encoding candidate binding agents as part of fusion proteins which form inclusion bodies upon expression in host cells have been described. See U.S. Pat. No. 6,653,068; U.S. Ser. No. 20040157291. For example, the inclusion bodies are useful to generate binding partners, e.g., TRAIL receptor-binding agents, which bind specifically to the target (poly)peptide.

TRAIL receptor-Binding Agent Conjugate Protein. As noted above, in certain preferred embodiments, the TRAIL receptor-binding agent of the present invention are anti-TRAIL receptor antibodies coupled or conjugated to one or more therapeutic or cytotoxic moieties to yield a TRAIL receptor-binding agent conjugate protein of the invention. Optionally, the TRAIL receptor-binding agents of the invention of this invention are useful as TRAIL receptor-binding agent-cytotoxin conjugate molecules, as exemplified by the administration for treatment of neoplastic disease.

In general, therapeutic moieties can be conjugated to the TRAIL receptor-binding agent of the invention, e.g., by any suitable technique, with appropriate consideration of the need for pharmokinetic stability and reduced overall toxicity to the subject. A therapeutic, cytotoxic, or labelling/imaging agent (i.e., a "moiety") can be coupled to a suitable TRAIL receptor-binding agent either directly or indirectly (e.g., via a linker group). A direct reaction between a moiety and a TRAIL receptor-binding agent is possible when each possesses a functional group capable of reacting with the other. For example, a nucleophilic group, such as an amino or sulfhydryl group, can be capable of reacting with a carbonyl-containing group, such as an anhydride or an acid halide, or with an allyl group containing a good leaving group (e.g., a halide). Alternatively, a suitable chemical linker group can be used. A linker group can function as a spacer to distance the TRAIL receptor-binding agent from a moiety in order to avoid interference with binding capabilities. A linker group can also serve to increase the chemical reactivity of a substituent on a moiety or a TRAIL receptor-binding agent, and thus increase the coupling efficiency. An increase in chemical reactivity can also facilitate the use of moieties, or functional groups on moieties, which otherwise would not be possible.

Suitable linkage chemistries include maleimidyl linkers and alkyl halide linkers (which react with a sulfhydryl on the antibody moiety) and succinimidyl linkers (which react with a primary amine on the antibody moiety). Several primary amine and sulfhydryl groups are present on immunoglobulins, and additional groups can be designed into recombinant immunoglobulin molecules. It will be evident to those skilled in the art that a variety of bifunctional or polyfunctional reagents, both homo- and hetero-functional (such as those described in the catalogue of the Pierce Chemical Co., Rockford, Ill.), can be employed as a linker group. Coupling can be affected, e.g., through amino groups, carboxyl groups, sulfhydryl groups or oxidized carbohydrate residues (see, e.g., U.S. Pat. No. 4,671,958).

As an alternative coupling method, a moiety can be coupled to the TRAIL receptor-binding agents of the invention, e.g., through an oxidized carbohydrate group at a glycosylation site, as described in U.S. Pat. Nos. 5,057,313 and 5,156,840. Yet another alternative method of coupling a TRAIL receptor-binding agent to a moiety is by the use of a non-covalent binding pair, such as streptavidin/biotin, or avidin/biotin. In these embodiments, one member of the pair is covalently coupled to the TRAIL receptor-binding agent and the other member of the binding pair is covalently coupled to the moiety.

Cleavable linkers. Where a cytotoxic or therapeutic moiety is more potent when free from the TRAIL receptor-binding agent portion of the immunoconjugates of the present invention, it can be desirable to use a linker group which is cleavable during or upon internalization into a cell, or which is gradually cleavable over time in the extracellular environment. A number of different cleavable linker groups have been described. Examples of the intracellular release of a cytotoxic moiety from these linker groups include, e.g., but are not limited to, cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

In one embodiment, the TRAIL receptor-binding agent of the invention is coupled to more than one therapeutic, cytotoxic and/or imaging moiety. By poly-derivatizing the TRAIL receptor-binding agent of the invention, several cytotoxic strategies can be simultaneously implemented, a TRAIL receptor-binding agent can be made useful as a contrasting agent for several visualization techniques, or a therapeutic antibody can be labeled for tracking by a visualization technique. In one embodiment, multiple molecules of a cytotoxic moiety are coupled to one TRAIL receptor-binding agent. In one embodiment, the TRAIL receptor-binding agent of the invention is coupled to a mixture of at least two moieties selected from the group consisting of: a cytotoxic moiety; therapeutic moiety; and labelling/imaging moiety. That is, more than one type of moiety can be coupled to one TRAIL receptor-binding agent. For instance, a therapeutic moiety, such as a polynucleotide or antisense sequence, can be conjugated to a TRAIL receptor-binding agent in conjunction with a chemotoxic or radiotoxic moiety, to increase the effectiveness of the chemo- or radiotoxic therapy, as well as lowering the required dosage necessary to obtain the desired therapeutic effect. Regardless of the particular embodiment, immunoconjugates with more than one moiety can be prepared in a variety of ways. For example, more than one moiety can be coupled directly to a TRAIL receptor-binding agent, or linkers that provide multiple sites for attachment (e.g., dendrimers) can be used. Alternatively, a carrier with the capacity to hold more than one cytotoxic moiety can be used.

As explained above, a TRAIL receptor-binding agent can bear the moiety(ies) in a variety of ways, including covalent bonding either directly or via a linker group, and non-covalent associations. In one embodiment, the TRAIL receptor-binding coupled protein can be combined with encapsulation carriers. This is especially useful in chemotoxic therapeutic embodiments, as they can allow the therapeutic compositions to gradually release a TRAIL receptor-binding agent chemotoxic moiety over time while concentrating it in the vicinity of the target cells.

TRAIL receptor-Binding Agent Conjugated with Radionuclides. In one embodiment, the TRAIL receptor-binding agent of the present invention is coupled with a cytotoxic moiety which is a radionuclide. Preferred radionuclides for use as cytotoxic moieties of the invention are radionuclides which are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use. $^{131}$I is particularly preferred, as are other O-radiation emitting nuclides, which have an effective range of several millimeters. $^{123}$I, $^{125}$I, $^{131}$I, or $^{211}$At can be conjugated to the TRAIL receptor-binding agent for use in the compositions and methods utilizing any of several known conjugation reagents, including Iodogen, N-succinimidyl 3 [$^{211}$At]astatobenzoate, N-succinimidyl 3 [$^{131}$I]iodobenzoate (SIB), and, N-succinimidyl 5-[$^{131}$I]iodob-3-pyridinecarboxylate (SIPC). Any iodine isotope can be utilized in the recited iodo-reagents. Other radionuclides can be conjugated to the TRAIL receptor-binding agent of the invention by suitable chelation agents known to those of skill in the nuclear medicine arts.

Chemotoxic moieties. In one embodiment, the TRAIL receptor-binding agent of the present invention is coupled with a chemotoxic moiety. Preferred chemotoxic agents useful in the present invention include, but are not limited to, small-molecule drugs such as methotrexate, and pyrimidine and purine analogs. Preferred chemotoxin differentiation inducers include phorbol esters and butyric acid.

Chemotoxic moieties can be directly conjugated to the TRAIL receptor-binding agent of the invention. In one embodiment, the TRAIL receptor-binding agent of the invention is coupled to a cytotoxic moiety via a chemical linker. In another embodiment, a moiety is encapsulated in a carrier, which is, in turn, is coupled to the TRAIL receptor-binding agent of the invention.

Protein Toxins. In one embodiment, the TRAIL receptor-binding agent of the present invention is coupled with a protein toxin moiety. Preferred toxin proteins for use as cytotoxic moieties of the invention, include, e.g., but are not limited to, *Actinomycetes* or *Streptomyces* antibiotics, duocarmycin, taxol, cytochalasin B, gramicidin D, ethidium bromide, emetine, mitomycin, etoposide, tenoposide, vincristinie, vinblastine, colchicin, doxortibicin, daunorubiciin, dihydroxy anthracin didne, initoxantronie, mithramycin, actinomycin D, 1-dehydrotestosterone, glucocorticoids, procaine, tetracaine, lidocaine, propranolol, and puromycin and analogs or homologs thereof. Preferred toxin proteins for use as cytotoxic moieties further include ricin, abrin, diphtheria toxin, cholera toxin, gelonin, *Pseudomonas* exotoxin, *Shigella* toxin, pokeweed antiviral protein, and other toxin proteins known in the medicinal biochemistry arts. As these toxin agents can elicit undesirable immune responses in the subject, especially if injected intravascularly, it is preferred that they be encapsulated in a carrier for coupling to the TRAIL receptor-binding agents of the invention, e.g., the anti-TRAIL receptor antibody and the antibody-related polypeptides of the invention.

Enzymatically-Active Toxins. In one embodiment, the TRAIL receptor-binding agent of the present invention is coupled with an enzymatically active toxin. The enzymatically active toxin can be of bacterial or plant origin, or an enzymatically active fragment ("A chain") of such a toxin. Enzymatically active toxins and fragments thereof useful in the present invention are diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, and enomycin. Conjugates of the TRAIL receptor-binding agent of the present invention with cytotoxic moieties are made using a variety of bifunctional protein coupling agents. Examples of such reagents are SPDP, IT, bifunctional derivatives of imidoesters such a dimethyl adipimidate HCl, active esters such as disuccinimidyl suberate, aldehydes such as glutaraldehyde, bis-azido compounds such as bis (p-azidobenzoyl) hexanediamine, bis-diazonium derivatives such as bis-(p-diazoniumbenzoyl)-ethylenediamine, diisocyanates such as tolylene 2,6-diisocyanate, and bis-active fluorine compounds such as 1,5-difluoro-2,4-dinitrobenzene. The lysing portion of a toxin can be joined to the Fab fragment of antibodies, e.g., the TRAIL receptor-binding agent.

Therapeutic Moieties. In one embodiment, the TRAIL receptor-binding agent of the present invention is coupled with a therapeutic moiety. A therapeutic moiety of the present invention includes, e.g., but is not limited to, anti-metabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), doxorubicin (adriamycin), cisplatin, bleomycin sulfate, carmustine, chlorambucil, cyclophosphamide hydroxyurea or ricin A, and anti-mitotic agents (e.g., vincristine and vinblastine).

Techniques for conjugating such therapeutic moiety to a TRAIL receptor-binding agent of the present invention are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Deliveiy", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", *Immunol. Rev.,* 62: 119-58 (1982).

Labeled TRAIL receptor-Binding Agent. In one embodiment, the TRAIL receptor-binding agent of the present invention is coupled with a label moiety, i.e., detectable group. The particular label or detectable group conjugated to the TRAIL receptor-binding agent of the invention is not a critical aspect of the invention, so long as it does not significantly interfere with the specific binding of the TRAIL receptor-binding agent of the present invention to the TRAIL receptor polypeptide or the TRAIL receptor-like polypeptide. The detectable group can be any material having a detectable physical or chemical property. Such detectable labels have been well-developed in the field of immunoassays and imaging, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^{3}$H, $^{14}$C, $^{35}$S, $^{125}$I, $^{121}$I, $^{112}$In, $^{99}$mTc), other imaging agents such as microbubbles (for ultrasound imaging), $^{18}$F, $^{14}$C, $^{15}$O, (for Positron emission tomography), $^{99m}$TC, $^{111}$In (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that described the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals (6$^{th}$ Ed., Molecular Probes, Inc., Eugene Oreg.).

The label can be coupled directly or indirectly to the desired component of an assay according to methods well known in the art. As indicated above, a wide variety of labels can be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, e.g., biotin, thyroxine, and cortisol, it can be used in conjunction with the labeled, naturally-occurring anti-ligands. Alternatively, any haptenic or antigenic compound can be used in combination with an antibody, e.g., an anti-TRAIL receptor antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds useful as labelling moieties, include, but are not limited to, e.g., fluorescein and its derivatives, rhodamine and its derivatives, dansyl, umbelliferone, and the like. Chemiluminescent compounds useful as labelling moieties, include, but are not limited to, e.g., luciferin, and 2,3-dihydrophthalazinediones, e.g., luminol. For a review of various labeling or signal-producing systems which can be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally simple colorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies, e.g., the anti-TRAIL receptor antibodies. In this case, antigen-coated particles are agglutinated by samples comprising the target antibodies. In this format, none of the components need be labeled and the presence of the target antibody is detected by simple visual inspection.

Formulations of Pharmaceutical Compositions. The TRAIL receptor-binding agent of the present invention can be incorporated into pharmaceutical compositions suitable for administration. The pharmaceutical compositions generally comprise at least one TRAIL receptor-binding agent and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (see, e.g., *Remington's Pharmaceutical Sciences*, Mack Publishing Co., Easton, Pa. 18$^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the TRAIL receptor-binding agent are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the TRAIL receptor-binding agent, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. The TRAIL receptor-binding agent named in this invention can be present in unsalified or unesterified form, or in salified and/or esterified form, and the naming of such TRAIL receptor-binding agent is intended to include both the original (unsalified and unesterified) compound and its pharmaceutically-acceptable salts and esters. Also, certain TRAIL receptor-binding agent named in this invention can be present in more than one stereoisomeric form, and the naming of such TRAIL receptor-binding agent is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present invention.

Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the TRAIL receptor-binding agent, use thereof in the compositions is contemplated. Supplementary active compounds can also be incorporated into the compositions.

A pharmaceutical composition of the invention is formulated to be compatible with its intended route of administration. The TRAIL receptor-binding agent compositions of the present invention can be administered by parenteral, topical, intravenous, oral, subcutaneous, intraarterial, intradermal, transdermal, rectal, intracranial, intraperitoneal, intranasal; intramuscular route or as inhalants. The most typical route of administration of an immunogenic agent, e.g., the TRAIL receptor polypeptide, is subcutaneous although other routes can be equally effective. The next most common route is intramuscular injection. This type of injection is most typically performed in the arm or leg muscles. In some methods of the invention, agents are injected directly into a particular tissue where deposits have accumulated, e.g. intracranial injection. Intramuscular injection on intravenous infusion are preferred for administration of the TRAIL receptor-binding agent, e.g., an anti-TRAIL receptor antibody. In some methods, particular TRAIL receptor-binding agents of the invention are injected directly into the cranium. In some methods, the TRAIL receptor-binding agents of the invention are administered as a sustained release composition or device, such as a Medipad™ device.

The TRAIL receptor-binding agent of the invention can optionally be administered in combination with other agents that are at least partly effective in treating various diseases including various TRAIL receptor-related diseases. In the case of administration into the central nervous system of a subject, the TRAIL receptor-binding agent of the invention can also be administered in conjunction with other agents that increase passage of the agents of the invention across the blood-brain barrier.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the TRAIL receptor-binding agent in the required amount in an appropriate solvent with one or a combination of ingredients enumerated above, as required, followed by filtered sterilization. Generally, dispersions are prepared by incorporating the binding agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The agents of this invention can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the binding agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the TRAIL receptor-binding agent are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the TRAIL receptor-binding agent is formulated into ointments, salves, gels, or creams as generally known in the art.

The TRAIL receptor-binding agent can also be prepared as pharmaceutical compositions in the form of Suppositories (e.g., with conventional suppository bases such as cocoa butter and other glycerides) or retention enemas for rectal delivery.

In one embodiment, the TRAIL receptor-binding agent is prepared with carriers that will protect the TRAIL receptor-binding agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of binding agent calculated to produce the desired therapeutic effect in association with the required pharmaceutical carrier. The specification for the dosage unit forms of the invention are dictated by and directly dependent on the unique characteristics of the binding agent and the particular therapeutic effect to be achieved, and the limitations inherent in the art of compounding such TRAIL receptor-binding agent for the treatment of a subject.

The nucleic acid molecules of the invention can be inserted into vectors and used as gene therapy vectors. Gene therapy vectors can be delivered to a subject by, e.g., intravenous injection, local administration (see, e.g., U.S. Pat. No. 5,328,470) or by stereotactic injection (see, e.g., Chen, et al., 1994. *Proc. Natl. Acad. Sci. USA* 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

Identifying and Characterizing the TRAIL Receptor-Binding Agents of the Invention Methods for identifying and/or screening the binding agents of the invention. Methods useful to identify and screen the binding agents, e.g., anti-TRAIL receptor antibodies and anti-TRAIL receptor antibody-related polypeptides, that possess the desired specificity to the TRAIL receptor polypeptide include any immunologically-mediated techniques known within the art. Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen A; et al., *Immunity*, 2: 373-80, 1995); (3) antigen presenting cells can be incubated with whole protein antigen and the presentation of that antigen on MHC detected by either T lymphocyte activation assays or biophysical methods (Harding et al., *Proc. Natl. Acad. Sci.*, 86: 4230-4, 1989); (4) mast cells can be incubated with reagents that cross-link their Fc-epsilon receptors and histamine release measured by enzyme immunoassay (Siraganian et al., *TIPS*, 4: 432-437, 1983); and (5) enzyme-linked immunosorbent assay (ELISA).

Similarly, products of an immune response in either a model organism (e.g., mouse) or a human subject can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood*, 72: 1310-5, 1988); (3) the proliferation of peripheral blood mononuclear cells in response to mitogens or mixed lymphocyte reaction can be measured using $^3$H-thymidine; (4) the phagocytic capacity of granulocytes, macrophages, and other phagocytes in PBMCs can be measured by placing PMBCs in wells together with labeled particles (Peters et al., *Blood*, 72: 1310-5, 1988); and (5) the differentiation of immune system cells can be measured by labeling PBMCs with antibodies to CD molecules such as CD4 and CD8 and measuring the fraction of the PBMCs expressing these markers.

In one embodiment, TRAIL receptor-binding agents of the invention are selected using display of candidate binding agents on the surface of replicable genetic packages. See, e.g., U.S. Pat. Nos. 5,514,548; 5,837,500; 5,871,907; 5,885,793; 5,969,108; 6,225,447; 6,291,650; 6,492,160; EP 585 287; EP 605522; EP 616640; EP 1024191; EP 589 877; EP 774 511; EP 844 306. Methods useful for producing/selecting a filamentous bacteriophage particle containing a phagemid genome encoding for a binding molecule with a desired specificity has been described. See, e.g., EP 774 511; U.S. Pat. Nos. 5,871,907; 5,969,108; 6,225,447; 6,291,650; 6,492, 160.

In one embodiment, TRAIL receptor-binding agents of the invention are selected using display of candidate binding agents on the surface of a yeast host cell. Methods useful for the isolation of scFv polypeptides by yeast surface display have been described by Kieke et al., *Protein Eng.* 1997 November; 10(11): 1303-10.

In one embodiment, TRAIL receptor-binding agents of the invention are selected using ribosome display. Methods useful for identifying ligands in peptide libraries using ribosome display have been described by Mattheakis et al., *Proc. Natl. Acad. Sci. USA* 91: 9022-26, 1994; and Hanes et al., *Proc. Natl. Acad. Sci. USA* 94: 4937-42, 1997.

In one embodiment, TRAIL receptor-binding agents of the invention are selected using tRNA display of candidate binding agents. Methods useful for in vitro selection of ligands using tRNA display have been described by Merryman et al., *Chem. Biol.*, 9: 741-46, 2002.

In one embodiment, TRAIL receptor-binding agents of the invention are selected using RNA display. Methods useful for selecting peptides and proteins using RNA display libraries have been described by Roberts et al *Proc. Natl. Acad. Sci. USA*, 94: 12297-302, 1997; and Nemoto et al., *FEBS Lett.*, 414: 405-8, 1997. Methods useful for selecting peptides and proteins using unnatural RNA display libraries have been described by Frankel et al., *Curr. Opin. Struct. Biol.*, 13: 506-12, 2003.

In one embodiment, TRAIL receptor-binding agents of the invention are expressed in the periplasm of gram negative bacteria and mixed with labeled TRAIL receptor polypeptide. See WO 02/34886. In clones expressing recombinant polypeptides with affinity for the TRAIL receptor polypeptide, the concentration of the labeled TRAIL receptor polypeptide bound to the binding agents is increased and allows the cells to be isolated from the rest of the library as described in Harvey et al., *Proc. Natl Acad. Sci.* 22: 9193-98 2004 and U.S. Pat. Publication No. 2004/0058403.

After selection of the desired TRAIL receptor-binding agent, it is contemplated that it can be produced in large volume by any technique known to those skilled in the art, e.g., prokaryotic or eukaryotic cell expression and the like. The TRAIL receptor-binding agents which are, e.g., but not limited to, anti-TRAIL receptor hybrid antibodies or fragments can be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which can be manipulated as described herein, thereby producing a vector for the expression of a hybrid antibody heavy chain.

Measurement of TRAIL receptor Binding. In one embodiment, a TRAIL receptor binding assay refers to an assay format wherein a TRAIL receptor polypeptide and a TRAIL receptor-binding agent are mixed under conditions suitable for binding between the TRAIL receptor polypeptide and the TRAIL receptor-binding agent and assessing the amount of binding between the TRAIL receptor polypeptide and the TRAIL receptor-binding agent. The amount of binding is compared with a suitable control, which can be the amount of binding in the absence of the TRAIL receptor polypeptide, the amount of the binding in the presence of non-specific immunoglobulin composition, or both. The amount of binding can be assessed by any suitable method. Binding assay methods include, e.g., ELISA, radioreceptor binding assays, scintillation proximity assays, cell surface receptor binding assays, fluorescence energy transfer assays, liquid chromatography, membrane filtration assays, and the like. Biophysical assays for the direct measurement of TRAIL receptor polypeptide binding to TRAIL receptor-binding agents are, e.g., nuclear magnetic resonance, fluorescence, fluorescence polarization, surface plasmon resonance (BIACOR chips) and the like. Specific binding is determined by standard assays known in the art, e.g., radioligand binding assays, ELISA, FRET, immunoprecipitation, SPR, NMR (2D-NMR), mass spectroscopy and the like. If the specific binding of a candidate TRAIL receptor-binding agent is at least 1 percent greater than the binding observed in the absence of the candidate TRAIL receptor-binding agent, the candidate TRAIL receptor-binding agent is useful as a TRAIL receptor-binding agent of the invention.

Co-crystals of the TRAIL receptor polypeptides and the TRAIL receptor-binding agents are also provided by the present invention as a method of determining molecular interactions. Conditions suitable for binding between the TRAIL receptor-binding agent and a TRAIL receptor polypeptide will depend on the compound and its ligand and can be readily determined by one of ordinary skill in the art.

Measurement of TRAIL receptor-Binding Agent Biological Activity. The TRAIL receptor-binding agents of the present invention, e.g., anti-TRAIL receptor antibodies and anti-TRAIL receptor antibody-related polypeptides, can be specified as agonists or antagonists for biological activities comprising specific activities disclosed herein. For example, TRAIL receptor agonists and antagonists, which are TRAIL receptor-binding agents can be made using methods known in the art. See e.g., WO 96/40281; U.S. Pat. No. 5,811,097; Deng et al., *Blood* 92: 1981-1988, 1998; Chen et al., *Cancer Res.*, 58: 3668-3678, 1998; Harrop et al., *J. Immunol.* 161: 1786-1794, 1998; Zhu et al., *Cancer Res.*, 58: 3209-3214, 1998; Yoon et al., *J. Immunol.*, 160: 3170-3179, 1998; Prat et al., *J. Cell. Sci.*, 111: 237-247, 1998; Pitard et al., *J. Immunol Methods*, 205: 177-190, 1997; Liautard et al., *Cytokinde*, 9: 233-241, 1997; Carlson et al., *J. Biol. Chem.*, 272: 11295-11301, 1997; Taryman et al., *Neuron*, 14: 755-762, 1995; Muller et al., *Structure*, 6: 1153-1167, 1998; Bartunek et al., *Cytokinde*, 8: 14-20, 1996. The biological activity, namely the agonist or antagonist properties of TRAIL receptor-binding agents can be characterized using any conventional in vivo and in vitro assays that have been developed to measure the biological activity of the TRAIL receptor polypeptide.

Uses of the Trail Receptor-Binding Agents of the Invention

General. The binding agents of the invention are useful in methods known in the art relating to the localization and/or quantitation of a TRAIL receptor polypeptide (e.g., for use in measuring levels of the TRAIL receptor polypeptide within appropriate physiological samples, for use in diagnostic methods, for use in imaging the polypeptide, and the like). In one embodiment, TRAIL receptor-binding agents that contain the antibody derived binding domain, are useful as pharmacologically-active compositions (hereinafter "Therapeutics"). Binding agents of the invention are useful to isolate a TRAIL receptor polypeptide by standard techniques, such as affinity chromatography or immunoprecipitation. A TRAIL receptor-binding agent of the invention can facilitate the purification of natural immunoreactive TRAIL receptor polypeptides or immunoreactive TRAIL receptor-like polypeptides from biological samples, e.g., cells as well as recombinantly-produced immunoreactive TRAIL receptor polypeptides or TRAIL receptor-like polypeptides expressed in a host system. Moreover, TRAIL receptor-binding agent can be used to detect an immunoreactive TRAIL receptor polypeptide or an immunoreactive TRAIL receptor-like polypeptide (e.g., in a cellular lysate or cell supernatant) in order to evaluate the abundance and pattern of expression of the immunoreactive polypeptide. The TRAIL receptor-binding agents of the invention can be used diagnostically to monitor immunoreactive TRAIL receptor and/or immunoreactive TRAIL receptor-like immunoreactive polypeptide levels in tissue as part of a clinical testing procedure, e.g., to determine the efficacy of a given treatment regimen. As noted above, the detection can be facilitated by coupling (i.e., physically linking) the TRAIL receptor-binding agent of the invention to a detectable substance.

Detection of TRAIL receptor Polypeptide Expression. An exemplary method for detecting the presence or absence of a TRAIL receptor polypeptide or a TRAIL receptor-like polypeptide in a biological sample involves obtaining a biological sample from a test subject and contacting the biological sample with a TRAIL receptor-binding agent of the invention capable of detecting a TRAIL receptor polypeptide or a TRAIL receptor-like polypeptide such that the presence of a TRAIL receptor polypeptide or a TRAIL receptor-like polypeptide is detected in the biological sample. An example of a TRAIL receptor-binding agent is an antibody raised against SEQ ID NO: 1, capable of binding to a TRAIL receptor polypeptide or a TRAIL receptor-like polypeptide, preferably an antibody with a detectable label. The term "labeled", with regard to the binding agent is intended to encompass direct labeling of the binding agent by coupling (i.e., physically linking) a detectable substance to the binding agent, as well as indirect labeling of the binding agent by reactivity with another compound that is directly labeled. Examples of indirect labeling include detection of a primary antibody using a fluorescently-labeled secondary antibody and end-labeling of a DNA probe with biotin such that it can be detected with fluorescently-labeled streptavidin.

The detection method of the invention can be used to detect a TRAIL receptor polypeptide or a TRAIL receptor-like polypeptide in a biological sample in vitro as well as in vivo. In vitro techniques for detection of a TRAIL receptor polypeptide or a TRAIL receptor-like polypeptide include enzyme linked immunosorbent assays (ELISAs), Western blots, immunoprecipitations, and immunofluorescence. Furthermore, in vivo techniques for detection of a TRAIL receptor polypeptide or a TRAIL receptor-like polypeptide include introducing into a subject a labeled TRAIL receptor-binding agent, e.g., an anti-TRAIL receptor antibody. For example, the antibody can be labeled with a radioactive marker whose presence and location in a subject can be detected by standard imaging techniques. In one embodiment, the biological sample contains polypeptide molecules from the test subject.

Immunoassay and Imaging. A TRAIL receptor-binding agent of the present invention can be used to assay TRAIL receptor polypeptide levels or TRAIL receptor-like polypeptide levels in a biological sample using antibody-based techniques. For example, protein expression in tissues can be studied with classical immunohistological methods. Jalkanen, M. et al., *J. Cell. Biol*, 101: 976-985, 1985; Jalkanen, M. et al., *J. Cell. Biol.* 105: 3087-3096, 1987. Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radio-isotopes or other radioactive agent, such as iodine ($^{125}$I, $^{121}$I), carbon ($^{14}$C), sulfur ($^{35}$S), tritium ($^{3}$H), indium ($^{112}$In), and technetium ($^{99}$mTc), and fluorescent labels, such as fluorescein and rhodamine, and biotin.

In addition to assaying secreted TRAIL receptor polypeptide levels or TRAIL receptor-like polypeptide levels in a biological sample, secreted TRAIL receptor polypeptide levels or TRAIL receptor-like polypeptide levels can also be detected in vivo by imaging. A TRAIL receptor-binding agent, e.g., an anti-TRAIL receptor antibody labels or markers for in vivo imaging of the TRAIL receptor polypeptide levels or the TRAIL receptor-like polypeptide include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the TRAIL receptor-binding agent by labeling of nutrients for the relevant scFv clone.

A TRAIL receptor-binding agent which has been labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled TRAIL receptor-binding agent will then preferentially accumulate at the location of cells which contain the specific target polypeptide. For example, in vivo tumor imaging is described in S. W. Burchiel et al., *Tumor, Imaging. The Radiochemical Detection of Cancer* 13 (1982).

Thus, the invention provides a diagnostic method of a medical condition, which involves: (a) assaying the expression of a polypeptide by measuring binding of a TRAIL receptor-binding agent of the present invention in cells or body fluid of an individual; (b) comparing the level of gene expression with a standard gene expression level, whereby an increase or decrease in the assayed polypeptide gene expression level compared to the standard expression level is indicative of a medical condition.

Diagnostic uses. The TRAIL receptor-binding compositions of the invention are useful in diagnostic methods. As such, the present invention provides methods using the binding agents of the invention useful in the diagnosis of TRAIL receptor-related medical conditions in a subject. Binding agents of the invention may be selected such that they have any level of epitope binding specificity and very high binding affinity to the TRAIL receptor polypeptide. In general, the higher the binding affinity of an binding agent the more stringent wash conditions can be performed in an immunoassay to remove nonspecifically bound material without removing target polypeptide. Accordingly, TRAIL receptor-binding agents of the invention useful in diagnostic assays usually have binding affinities of at least $10^8$, $10^9$, $10^{10}$, $10^{11}$ or $10^{12}$ $M^{-1}$. Further, it is desirable that TRAIL receptor-binding agents used as diagnostic reagents have a sufficient kinetic on-rate to reach equilibrium under standard conditions in at least 12 hours, preferably at least five (5) hours and more preferably at least one (1) hour.

Some methods of the invention employ polyclonal preparations of anti-TRAIL receptor antibodies and anti-TRAIL receptor antibody compositions of the invention as diagnostic reagents, and other methods employ monoclonal isolates. The use of polyclonal mixtures has a number of advantages compared to compositions made of one monoclonal anti-TRAIL receptor antibody. By binding to multiple sites on a TRAIL receptor polypeptide, polyclonal anti-TRAIL receptor antibodies or other polypeptides, one can generate a stronger signal (for diagnostics) than a monoclonal that binds to a single site on the TRAIL receptor polypeptide or the TRAIL receptor-like polypeptide. Further, a polygonal preparation can bind to numerous variants of a prototypical target sequence (e.g., allelic variants, species variants, strain variants, drug-induced escape variants) whereas a monoclonal antibody can bind only to the prototypical sequence or a narrower range of variants thereto. However, monoclonal anti-TRAIL receptor antibodies are advantageous for detecting a single antigen in the presence or potential presence of closely related antigens.

In methods employing polyclonal human anti-TRAIL receptor antibodies prepared in accordance with the methods described above, the preparation typically contains an assortment of TRAIL receptor-binding agents, e.g., antibodies, with different epitope specificities to the target polypeptide. In some methods employing monoclonal antibodies, it is desirable to have two antibodies of different epitope binding specificities. A difference in epitope binding specificities can be determined by a competition binding assay.

Although TRAIL receptor-binding agents which are human antibodies can be used as diagnostic reagents for any kind of sample, they are most useful as diagnostic reagents for human biological samples. TRAIL receptor-binding agents can be used to detect a given TRAIL receptor polypeptide in a variety of standard assay formats. Such formats include immunoprecipitation, Western blotting, ELISA, radioimmunoassay, and immunometric assays. See Harlow & Lane, *Antibodies, A Laboratory Manual* (Cold Spring Harbor Publications, New York, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue or body fluid of a subject.

Immunometric or sandwich assays are a preferred format for the diagnostic methods of the present invention. See U.S. Pat. Nos. 4,376,110, 4,486,530, 5,914,241, and 5,965,375. Such assays use one TRAIL receptor-binding agent, e.g., an anti-TRAIL receptor antibody or a population of anti-TRAIL receptor antibodies immobilized to a solid phase, and another anti-TRAIL receptor antibody or a population of anti-TRAIL receptor antibodies. Typically, the solution anti-TRAIL receptor antibody or population of anti-TRAIL receptor antibodies is labeled. If an antibody population is used, the population typically contains antibodies binding to different epitope specificities within the target polypeptide. Accordingly, the same population can be used for both solid phase and solution antibody. If anti-TRAIL receptor monoclonal antibodies are used, first and second TRAIL receptor monoclonal antibodies having different binding specificities are used for the solid and solution phase. Solid phase and solution antibodies can be contacted with target antigen in either order or simultaneously. If the solid phase antibody is contacted first, the assay is referred to as being a forward assay. Conversely, if the solution antibody is contacted first, the assay is referred to as being a reverse assay. If the target is contacted with both antibodies simultaneously, the assay is referred to as a simultaneous assay. After contacting the TRAIL receptor polypeptide with the anti-TRAIL receptor antibody, a sample is incubated for a period that usually varies from about 10 min to about 24 hr and is usually about 1 hr. A wash step is then performed to remove components of the sample not specifically bound to the anti-TRAIL receptor antibody being used as a diagnostic reagent. When solid phase and solution antibodies are bound in separate steps, a wash can be performed after either or both binding steps. After washing, binding is quantified, typically by detecting label linked to the solid phase through binding of labeled solution antibody. Usually for a given pair of antibodies or populations of antibodies and given reaction conditions, a calibration curve is prepared from samples containing known concentrations of target antigen. Concentrations of the TRAIL receptor polypeptide in samples being tested are then read by interpolation from the calibration curve. Analyte can be measured either from the amount of labeled solution antibody bound at equilibrium or by kinetic measurements of bound labeled solution antibody at a series of time points before equilibrium is reached. The slope of such a curve is a measure of the concentration of the TRAIL receptor polypeptide in a sample Suitable supports for use in the above methods include, e.g., nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™ (Amersham Pharmacia Biotech, Piscataway N.J., and the like. Immobilization can be by absorption or by covalent attachment. Optionally, anti-TRAIL receptor antibodies can be joined to a linker molecule, such as biotin for attachment to a surface bound linker, such as avidin.

Predictive Medicine. The invention also pertains to the field of predictive medicine in which diagnostic assays, prognostic assays, pharmacogenomics, and monitoring clinical trials are used for prognostic (predictive) purposes to treat prophylactically a subject. Accordingly, one aspect of the invention relates to diagnostic assays for determining TRAIL receptor polypeptide expression in a biological sample (e.g., blood, serum, cells, tissue) in order to determine whether subject is afflicted with a disease or disorder, or is at risk of developing a disorder, associated with aberrant TRAIL receptor polypeptide expression.

The invention also provides for prognostic (or predictive) assays for determining whether an individual is at risk of developing a disorder associated with TRAIL receptor polypeptide expression or activity. Such assays can be used for prognostic or predictive purpose to thereby prophylactically treat an individual prior to the onset of a disorder characterized by or associated with a TRAIL receptor polypeptide. Furthermore, the methods of the present invention can also be used to assess whether an individual expresses a TRAIL receptor polypeptide or a polymorphic form of the TRAIL receptor polypeptide in instances where a TRAIL receptor-binding agent of the present invention has greater affinity for the TRAIL receptor polypeptide for its polymorphic form (or vice versa).

The levels of certain polypeptides in a particular tissue (or in the blood) of a subject may be indicative of the toxicity, efficacy, rate of clearance or rate of metabolism of a given drug when administered to the subject. The methods described herein can also be used to determine the levels of such polypeptide(s) in subjects to aid in predicting the response of such subjects to these drugs. Another aspect of the invention provides methods for determining TRAIL receptor polypeptide expression in an individual to thereby select appropriate therapeutic or prophylactic compounds for that individual (referred to herein as "pharmacogenomics"). Pharmacogenomics allows for the selection of compounds (e.g., drugs) for therapeutic or prophylactic treatment of an individual based on the genotype of the individual (e.g., the genotype of the individual examined to determine the ability of the individual to respond to a particular compound).

The binding of a TRAIL receptor-binding agent of the invention to a TRAIL receptor polypeptide or a TRAIL receptor-like polypeptide, e.g., can be utilized to identify a subject having or at risk of developing a disorder associated with the TRAIL receptor polypeptide or TRAIL receptor-like polypeptide expression or activity (which are described above). Alternatively, the prognostic assays can be utilized to identify a subject having or at risk for developing the disease or disorder. Thus, the invention provides a method for identifying a disease or disorder associated with an aberrant TRAIL receptor polypeptide or TRAIL receptor-like polypeptide expression or activity in which a test sample is obtained from a subject and a TRAIL receptor-binding agent is detected, wherein the presence of an alteration of TRAIL receptor-binding agent is diagnostic for a subject having or at risk of developing a disease or disorder associated with an aberrant TRAIL receptor polypeptide or TRAIL receptor-like polypeptide expression or activity. As used herein, a "test sample" refers to a biological sample obtained from a subject of interest.

Furthermore, the prognostic assays described herein can be used to determine whether a subject can be administered a compound (e.g., an agonist, antagonist, peptidomimetic, polypeptide, peptide, nucleic acid, small molecule, or other drug candidate) to treat a disease or disorder associated with an aberrant TRAIL receptor polypeptide or TRAIL receptor-like polypeptide expression or activity. For example, such methods can be used to determine whether a subject can be effectively treated with a compound for a TRAIL receptor polypeptide or TRAIL receptor-like polypeptide-associated disorder. Thus, the invention provides methods for determining whether a subject can be effectively treated with a compound for a disorder associated with an aberrant TRAIL receptor polypeptide or TRAIL receptor-like polypeptide expression or activity in which a test sample is obtained and the TRAIL receptor polypeptide or the TRAIL receptor-like polypeptide is detected using the TRAIL receptor-binding agent (e.g., wherein the presence of the TRAIL receptor polypeptide or the TRAIL receptor-like polypeptide is diagnostic for a subject that can be administered the compound to treat a disorder associated with an aberrant TRAIL receptor polypeptide or TRAIL receptor-like polypeptide expression or activity).

The level of the TRAIL receptor polypeptide or the TRAIL receptor-like polypeptide in a blood or tissue sample obtained from a subject is determined and compared with the level found in a blood sample or a sample from the same tissue type obtained from an individual who is free of the disease. An overabundance (or underabundance) of the TRAIL receptor polypeptide or TRAIL receptor-like polypeptide in the sample obtained from the subject suspected of having the TRAIL receptor polypeptide or TRAIL receptor-like polypeptide-associated disease compared with the sample obtained from the healthy subject is indicative of the TRAIL receptor polypeptide or TRAIL receptor-like polypeptide-associated disease in the subject being tested. Further testing may be required to make a positive diagnosis.

There are a number of diseases in which the degree of overexpression (or underexpression) of certain TRAIL receptor polypeptide or TRAIL receptor-like polypeptide molecules known to be indicative of whether a subject with the disease is likely to respond to a particular type of therapy or treatment. Thus, the method of detecting a TRAIL receptor polypeptide or TRAIL receptor-like polypeptide in a sample can be used as a method of prognosis, e.g., to evaluate the likelihood that the subject will respond to the therapy or treatment. The level of the relevant prognostic polypeptide in a suitable tissue or blood sample from the subject is determined and compared with a suitable control, e.g., the level in subjects with the same disease but who have responded favorably to the treatment. The degree to which the prognostic polypeptide is overexpressed (or underexpressed) in the sample compared with the control may be predictive of likelihood that the subject will not respond favorably to the treatment or therapy. The greater the overexpression (or underexpression) relative to the control, the less likely the subject will respond to the treatment.

There are a number of diseases in which the degree of overexpression (or underexpression) of certain target polypeptides, referred to herein as "predictive polypeptides," is known to be indicative of whether a subject will develop a disease. Thus, the method of detecting a TRAIL receptor polypeptide or TRAIL receptor-like polypeptide in a sample can be used as a method of predicting whether a subject will develop a disease. The level of the relevant predictive polypeptide in a suitable tissue or blood sample from a subject at risk of developing the disease is determined and compared with a suitable control, e.g., the level in subjects who are not at risk of developing the disease. The degree to which the predictive polypeptide is overexpressed (or underexpressed) in the sample compared with the control may be predictive of likelihood that the subject will develop the disease. The greater the overexpression (or underexpression) relative to the control, the more likely the subject will development the disease.

The methods described herein can be performed, e.g., by utilizing pre-packaged diagnostic kits comprising at least one probe reagent., e.g., TRAIL receptor-binding agent described herein, which can be conveniently used, e.g., in clinical settings to diagnose subjects exhibiting symptoms or family history of a disease or illness involving a TRAIL receptor polypeptide or TRAIL receptor-like polypeptide. Furthermore, any cell type or tissue in which TRAIL receptor polypeptide or TRAIL receptor-like polypeptide is expressed can be utilized in the prognostic assays described herein.

Prophylactic and Therapeutic Use of TRAIL Receptor-Binding Agents.

General. The TRAIL receptor-binding agents of the present invention are useful to prevent or treat disease. Specifically, the invention provides for both prophylactic and therapeutic methods of treating a subject at risk of (or susceptible to) a disorder or having a disorder associated with an aberrant TRAIL receptor-binding agent expression or activity. Accordingly, the present invention provides methods for the prevention and/or treatment of a TRAIL receptor-related medical condition in a subject comprising administering an effective amount of a TRAIL receptor-binding agent to a subject in need thereof. For example, a subject can be administered a TRAIL receptor-binding agent compositions of the present invention in an effort to replace absent or decreased levels of the TRAIL receptor polypeptide (e.g., insulin), to supplement absent or decreased levels of a different polypeptide (e.g., an anti-TRAIL receptor antibody), to inhibit the activity of a polypeptide (e.g., an oncogene), to activate the activity of a TRAIL receptor polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

The TRAIL receptor-binding agents of the present invention are useful in potential prophylactic and therapeutic applications implicated in a variety of disorders in a subject including, but not limited to: those involving development, differentiation, and activation of bone cells; in diseases or pathologies of cells in blood circulation such as red blood cells and platelets; various immunological disorders and/or pathologies; pulmonary diseases and disorders; autoimmune and inflammatory diseases; cardiovascular diseases; metabolic diseases; reproductive diseases, renal diseases, diabetes, brain trauma, cancer growth and metastasis; viral infections, cancer therapy; periodontal disease; tissue regeneration; acute lymphoblastic leukemia; gliomas; neurologic diseases; neurodegenerative disorders; Alzheimer's disease; Parkinson's disorder; and hematopoietic disorders.

In a preferred embodiment of the invention, a pharmaceutically effective amount of an anti-TRAIL-R1 and TRAIL-R2 antibody induces cell death by contact with a target cell. A pharmaceutically effective amount of an antibody recognizing TRAIL-R1 and TRAIL-R2 or a humanized antibody recognizing TRAIL-R1 and TRAIL-R2 is an amount administered to an individual sufficient to cause a desired effect. Desired effects of administration of a pharmaceutically effective amount of TRAIL-R1 and TRAIL-R2 recognizing antibodies include death of a target cell, growth inhibition of a target cell, stimulation of TRAIL-R1 and TRAIL-R2, and binding to TRAIL-R1 and/or TRAIL-R2 in a target cell. A target cell is a cell that expresses TRAIL-R1 and/or TRAIL-R2 and includes abnormally growing cells such as human carcinoma cells and leukemia cells. Also included is a cell with a pathological condition, in which those where cell proliferation is abnormal or dysregulated such as malignant or benign cancer. Accordingly, in some embodiments of the invention, the anti-TRAIL receptor binding agents of the invention are useful in methods for the prevention or treatment of the growth and/or metastasis of cancers, e.g., but not limited to, breast cancer, liver cancer, prostate cancer, ovarian cancer, lung cancer, brain cancer, pancreatic cancer, and colorectal cancer, in subjects in need thereof. In one embodiment, the TRAIL receptor-binding agents of the invention have in vitro apoptosis-inducing activity wherein the binding agent can induce at least 30% cell death at the concentrations equal or lower than 10 μg/ml, preferably at least 50%, 70%, 90%, more preferably 100% cell death. In one embodiment, the TRAIL receptor-binding agents of the invention have in vivo apoptosis-inducing activity wherein the binding agent can reduce at least 30% tumor size in human cancer xenograft models when treated with the doses equal or less than 10 mg/kg body weight, preferably, at least 50%, 70%, 90%, more preferably 100%.

When used in vivo for therapy, the TRAIL receptor-binding agents, e.g., the anti-TRAIL receptor antibodies of the present invention are administered to the subject in effective amounts (i.e., amounts that have desired therapeutic effect). They will normally be administered parenterally. The dose and dosage regimen will depend upon the degree of the TRAIL receptor-related disease or disorder, the characteristics of the particular TRAIL receptor-binding agent used, e.g., its therapeutic index, the subject, and the subject's history. Advantageously, the TRAIL receptor-binding agent is administered continuously over a period of 1-2 weeks, intravenously to treat cells in the vasculature and subcutaneously and intraperitoneally to treat regional lymph nodes.

Optionally, the administration is made during the course of adjunct therapy such as combined cycles of radiation, chemotherapeutic treatment, or administration of tumor necrosis factor, interferon or other cytoprotective or immunomodulatory agent. As such the binding agents of the present invention and a compound useful in adjunct therapy may be administrated simultaneously and sequentially to a subject in need of administration thereof. In one embodiment, the TRAIL receptor-binding agents of the present invention may be used for enhancing therapeutic efficacy of a therapeutic antibody, particularly, anti-TRAIL-R1 or anti-TRAIL-R2 mono-specific antibody.

The antibody of the present invention is also operative in conjunction with a sensitizer. A sensitizer as used herein is defined to include any stimulus that induces apoptosis including organic molecules such as chemotherapeutic agents and radiation agents, which may significantly enhance the efficacy of the antibody of the present invention. On the other hand, the antibody of the present invention may be used for enhancing the therapeutic efficacy of chemotherapy and radiation therapy. Also, it can be used for preventing or reversing the development of tumor cell resistance to chemotherapy and radiation therapy. The antibody of the present invention is also operative as a sensitizer to facilitate apoptosis of cancer cells induced by a mono-specific antibody for TRAIL-R1 or TRAIL-R2.

In the context of a malignancy therapy, the antibody of the invention, especially, CTB003 and hCTB003, is able to induce apoptosis of most TRAIL-sensitive tumor cells. CTB003 exhibits a strong tumoricidal activity in vivo. The majority of tumor cells detailed herein express cell surface TRAIL-R1 and/or TRAIL-R2 and their susceptibility to CTB003 or hCTB003 induced cell death paralleled their susceptibility to TRAIL. CTB003 or hCTB003 bypasses the decoy receptors to induce apoptosis. A mouse-mouse hybridoma, CTB003, that produces the antibody of the present invention has been deposited and an Accession Number CGMCC1665 has been assigned. It is appreciated that the techniques and results detailed with regard to the agonistic human TRAIL-R1 and/or TRAIL-R2 dual specific monoclonal antibody CTB003 and hCTB003 are wholly extendable and applicable to the similar kinds of dual specific antibodies. This advantage generally extends to humanized dual specific antibodies of the present invention.

For parenteral administration, the TRAIL receptor-binding agent will be formulated in a unit dosage injectable form (solution, suspension, emulsion) in association with a pharmaceutically-acceptable parenteral vehicle. Such vehicles are inherently nontoxic, and non-therapeutic.

Use of anti-TRAIL receptor IgM antibodies can be preferred for certain applications. However, IgG molecules by being smaller can be more able than IgM molecules to localize to certain types of infected cells. There is evidence that complement activation in vivo leads to a variety of biological effects, including the induction of an inflammatory response and the activation of macrophages (Unanue and Benecerraf, Textbook of Immunology, 2nd Edition, Williams & Wilkins, p. 218 (1984)). The increased vasodilation accompanying inflammation can increase the ability of various agents to localize in infected cells. Therefore, TRAIL receptor-antibody combinations of the type specified by this invention can be used therapeutically in many ways. Additionally, antigen, e.g., purified TRAIL receptor polypeptide, fragments or analogs thereof, (Hakomori, *Ann. Rev. Immunol.* 2: 103, 1984) or anti-idiotypic antibodies (Nepom et al., *Proc. Natl. Acad. Sci. USA* 81: 2864, 1985; Koprowski et al., *Proc. Natl. Acad. Sci. USA* 81: 216, 1984) relating to such antigens could be used to induce an active immune response in human subjects. Such a response includes the formation of antibodies capable of activating human complement for a desirable biological effect, e.g., target cell destruction.

Disease and Disorders. Diseases and disorders that are characterized by increased (relative to a subject not suffering from the disease or disorder) levels or biological activity of a TRAIL receptor polypeptide can be treated with a TRAIL receptor-binding agent-based therapeutic compounds that antagonize (i.e., reduce or inhibit) activity, which can be administered in a therapeutic or prophylactic manner. Therapeutic compounds that can be utilized include, but are not limited to: (i) an aforementioned TRAIL receptor-binding agent; and (ii) nucleic acids encoding a TRAIL receptor-binding agent.

Diseases and disorders that are characterized by decreased (relative to a subject not suffering from the disease or disorder) levels or biological activity of a TRAIL receptor polypeptide can be treated with a TRAIL receptor-binding agent-based therapeutic compounds that increase (i.e., are agonists to) the TRAIL receptor activity. Therapeutics that upregulate activity can be administered in a therapeutic or prophylactic manner. Therapeutics that can be utilized include, but are not limited to, a TRAIL receptor-binding agent that increases bioavailability.

Increased or decreased levels can be readily detected by quantifying the TRAIL receptor-binding agent-induced peptides and/or RNA, by obtaining a subject's tissue sample (e.g., from biopsy tissue) and assaying it in vitro for RNA or peptide levels, structure and/or activity of the expressed TRAIL receptor polypeptide (or mRNAs of an aforementioned polypeptide). Methods that are well known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods. In one aspect, the invention provides a method for preventing, in a subject, a disease or condition associated with an aberrant TRAIL receptor expression or activity, by administering to the subject a TRAIL receptor-binding agent that modulates TRAIL receptor polypeptide expression or at least one TRAIL receptor polypeptide activity.

Subjects at risk for a disease that is caused or contributed to by aberrant TRAIL receptor polypeptide expression or activity can be identified by, e.g., any or a combination of diagnostic or prognostic assays as described herein. In prophylactic applications, pharmaceutical compositions or medicaments of TRAIL receptor-binding agents are administered to a subject susceptible to, or otherwise at risk of a disease or condition (i.e., an immune disease) in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. Administration of a prophylactic TRAIL receptor-binding agent can occur prior to the manifestation of symptoms characteristic of the aberrancy, such that a disease or disorder is prevented or, alternatively, delayed in its progression. Depending upon the type of aberrancy, e.g., a TRAIL receptor-binding agent which acts as a TRAIL receptor agonist or a TRAIL receptor antagonist can be used for treating the subject. The appropriate compound can be determined based on screening assays described herein.

Therapeutic Methods. Another aspect of the invention includes methods of modulating TRAIL receptor polypeptide expression or activity in a subject for therapeutic purposes. The modulatory method of the invention involves contacting a cell with a TRAIL receptor-binding agent of the present invention, that modulates one or more of the activities of the TRAIL receptor polypeptide activity associated with the cell. In therapeutic applications, compositions or mendicants are administered to a subject suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically or prophylactically-effective dose.

A compound that modulates a TRAIL receptor polypeptide activity is described herein, and may include, e.g., a nucleic acid encoding a TRAIL receptor-binding agent or a TRAIL receptor-binding agent-related polypeptide. In one embodiment, the TRAIL receptor-binding agent stimulates one or more TRAIL receptor polypeptide activity. Examples of such stimulatory compounds include a TRAIL receptor-binding agent and a nucleic acid molecule encoding a TRAIL receptor-binding agent that has been introduced into the cell. In another embodiment, the TRAIL receptor-binding agent inhibits one or more TRAIL receptor polypeptide activity. These modulatory methods can be performed in vitro (e.g., by culturing the cell with the TRAIL receptor-binding agent) or, alternatively, in vivo (e.g., by administering the TRAIL receptor-binding agent to a subject). As such, the invention provides methods of treating an individual afflicted with a TRAIL receptor-associated disease or disorder characterized by aberrant expression or activity of a TRAIL receptor polypeptide or nucleic acid molecules encoding a TRAIL receptor polypeptide. In one embodiment, the method involves administering a TRAIL receptor-binding agent (e.g., a compound identified by a screening assay described herein), or combination TRAIL receptor-binding agents that modulates (e.g., up-regulates or down-regulates) TRAIL receptor polypeptide expression or activity. In another embodiment, the method involves administering a TRAIL receptor-binding agent or a nucleic acid molecule encoding a TRAIL receptor-binding agent as therapy to compensate for reduced or aberrant TRAIL receptor polypeptide expression or activity. Stimulation of TRAIL receptor polypeptide activity is desirable in situations in which TRAIL receptor polypeptide is abnormally down-regulated.

Determination of the Biological Effect of the TRAIL receptor-Binding Agent-Based Therapeutic. In various embodiments of the invention, suitable in vitro or in vivo assays are performed to determine the effect of a specific TRAIL receptor-binding agent-based therapeutic and whether its administration is indicated for treatment of the affected tissue in a subject.

In various embodiments, in vitro assays can be performed with representative cells of the type(s) involved in the subject's disorder, to determine if a given TRAIL receptor-binding agent-based therapeutic exerts the desired effect upon the cell type(s). Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

Treatment regime and Effective Dosages. Some compositions include a combination of multiple (e.g., two or more) TRAIL receptor-binding agents of the invention. In some compositions, each of the TRAIL receptor-binding agents thereof of the composition is a monoclonal antibody or a human sequence antibody that binds to a distinct, pre-selected epitope of a one or more TRAIL receptor polypeptide.

Effective doses of the TRAIL receptor-binding agents of the present invention, e.g., anti-TRAIL receptor antibodies or anti-TRAIL receptor antibody cytotoxin conjugates, for the treatment of TRAIL receptor-related conditions and diseases described herein vary depending upon many different factors, including means of administration, target site, physiological state of the subject, whether the subject is human or an animal, other medications administered, and whether treatment is prophylactic or therapeutic. Usually, the subject is a human but nonhuman mammals including transgenic mammals can also be treated. Treatment dosages need to be titrated to optimize safety and efficacy.

Typically, an effective amount of the compositions of the present invention, sufficient for achieving a therapeutic or prophylactic effect, range from about 0.000001 mg per kilogram body weight per day to about 10,000 (100) mg per kilogram body weight per day. Preferably, the dosage ranges are from about 0.0001 mg per kilogram body weight per day to about 100 mg per kilogram body weight per day. For administration with a TRAIL receptor-binding agent, e.g., an anti-TRAIL receptor antibody, the dosage ranges from about 0.0001 to 100 mg/kg, and more usually 0.01 to 5 mg/kg every week, every two weeks or every three weeks, of the host body weight. For example dosages can be 1 mg/kg body weight or 10 mg/kg body weight every week, every two weeks or every three weeks or within the range of 1-10 mg/kg every week, every two weeks or every three weeks. In one embodiment, a single dosage of antibody range from 0.1-10,000 micrograms per kg body weight. In one embodiment, antibody concentrations in a carrier range from 0.2 to 2000 micrograms per delivered milliliter. An exemplary treatment regime entails administration once per every two weeks or once a month or once every 3 to 6 months. In some methods, two or more TRAIL receptor binding agents with different binding specificities are administered simultaneously, in which case the dosage of each antibody administered falls within the ranges indicated. A TRAIL receptor-binding agent, e.g., an anti-TRAIL receptor antibody is usually administered on multiple occasions. Intervals between single dosages can be weekly, monthly or yearly. Intervals can also be irregular as indicated by measuring blood levels of antibody in the subject. In some methods, dosage is adjusted to achieve a plasma TRAIL receptor-binding agent, e.g., an anti-TRAIL receptor antibody concentration, of 1-1000 μg/ml and in some methods 25-300 μg/ml. Alternatively, a TRAIL receptor-binding agent, e.g., an anti-TRAIL receptor antibody, can be administered as a sustained release formulation, in which case less frequent administration is required. Dosage and frequency vary depending on the half-life of the TRAIL receptor-binding agent in the subject. In general, human anti-TRAIL receptor antibodies show the longest half life, followed by humanized anti-TRAIL receptor antibodies, chimeric anti-TRAIL receptor antibodies, and nonhuman anti-TRAIL receptor antibodies. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patent can be administered a prophylactic regime. Doses for nucleic acids encoding TRAIL receptor immunogens range from about 10 ng to 1 g, 100 ng to 100 mg, 1 μg to 10 mg, or 30-300 μg DNA per subject. Doses for infectious viral vectors vary from 10-100, or more, virions per dose.

Toxicity. Preferably, an effective amount (e.g., dose) of the TRAIL receptor-binding agents described herein will provide therapeutic benefit without causing substantial toxicity to the subject. Toxicity of the TRAIL receptor-binding agent described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the TRAIL receptor-binding agent described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

Kits. Also within the scope of the invention are kits comprising the TRAIL receptor-binding agent compositions (e.g., antibody cytotoxin conjugates, monoclonal antibodies, human sequence antibodies, human antibodies, multispecific and bispecific molecules) of the invention and instructions for use. The kits are useful for detecting the presence of a TRAIL receptor polypeptide or a TRAIL receptor-like polypeptide in a biological sample. For example, the kit can comprise: a labeled TRAIL receptor-binding agent capable of binding a TRAIL receptor polypeptide or a TRAIL receptor-like polypeptide in a biological sample; means for determining the amount of the TRAIL receptor polypeptide or TRAIL receptor-like polypeptide in the sample; and means for comparing the amount of the TRAIL receptor polypeptide or the TRAIL receptor-like polypeptide in the sample with a standard. The kit components, (e.g., reagents) can be packaged in a suitable container. The kit can further comprise instructions for using the kit to detect the TRAIL receptor polypeptide or the TRAIL receptor-like polypeptide.

In one embodiment, a composition kit of the present invention comprises the combination of the antibody of the present invention with a disease inhibiting compound, wherein the compound is anti-tumor drug such radioisotope, chemotherapeutic agent, therapeutic antibody or cytokine.

The following EXAMPLES are presented in order to more fully illustrate the preferred embodiments of the invention.

These EXAMPLEs should in no way be construed as limiting the scope of the invention, as defined by the appended claims.

EXAMPLES

Example 1

General Approach to the Preparation and Characterization of a Murine Trail Receptor-Binding Agent of the Invention In particular, the TRAIL-R1 and/or TRAIL-R2 dual-specific monoclonal antibody CTB003 may be obtained by culturing a hybridoma which, in turn, may be obtained by immunizing a mouse with human TRAIL-R1 and/or TRAIL-R2 and subsequently fusing the spleen cells or lymph node cells from the mouse with mouse myeloma cells.

Preparation of a monoclonal antibody involves the following steps:
1. purification of a protein for use as an antigen;
2. preparation of antibody producing cells: after last immunizing an animal, serum sample was collected and analyzed for the titers of specific antibody production in order to determine whether antibody producing cells have been generated.
3. preparation of myeloma cells;
4. fusing the antibody producing cells and myeloma cells;
5. selecting a hybridoma producing a desired antibody;
6. preparing a single cell clone (cloning);
7. culturing the hybridoma cells for large scale preparation of the monoclonal antibody;
8. purifying the monoclonal antibody
9. analyzing the biological activities and the specificity of a monoclonal antibody.

The procedure for the preparation of the invented antibody is detailed below with reference to the above described steps. This method for preparing an antibody of the present invention is intended only to be illustrative of the methods of preparation and is not limited thereto. Other known procedures may be followed.

A. Preparation of Antigen

The present invention utilizes a hetero-dimerized recombinant protein comprising the extracellular domains of TRAIL-R1 and TRAIL-R2 as an immunogen to induce an antibody recognizing both receptors.

The cDNAs encoding the extracellular domain of TRAIL-R1 and TRAIL-R2 were fused with a cDNA encoding the Fc portion of human IgG1. The fused cDNAs were further cloned into an expression vector, pcDNAIII (Invitrogen). QBI-293A cells were co-transfected with the expression vectors pcDNAIII-TRAIL-R1-Fc and pcDNAIII-TRAIL-R2-Fc. 48 hours after transfection, the secreted fusion protein in culture supernatants were purified by Protein A chromatography.

Alternatively, a peptide comprising the amino acid sequence of SEQ ID No. 15 and/or SEQ ID No. 16, may be chemically synthesized by a known method such as the Sanger method, and used as the antigen.

B: Preparation of Monoclonal Antibody a: Immunization of Mice.

The immunogen prepared in step (a) is mixed with an adjuvant, such as Freund's complete or incomplete adjuvant. Other suitable experimental animals may include rats, guinea pigs, rabbits, dogs, chickens, horses, pigs, cows and sheep. Suitable administration routes to immunize an experimental animal include the subcutaneous, intraperitoneal, intravenous, intradermal, and intramuscular injections, with subcutaneous and intraperitoneal injections being preferred. Immunizations are optionally performed by a single dose or, by several repeated doses at appropriate intervals. The antibody production of immunized animals is determined by serum levels of an antigen-specific antibody. When high titers of antibody is achieved, animals can be used as a source for preparation of antibody-producing cells. In general, the antibody-producing cells may be collected at 3-5 days after the last injection with an immunogen.

Methods for analyzing serum antibody titers include various well known techniques such as radioimmunoassay (hereinafter, referred to as "RIA"), solid-phase enzyme immunoassay (hereinafter, referred to as "ELISA"), fluorescent antibody assay and passive hemagglutination assay, with RIA and ELISA preferred for reasons of detection sensitivity, rapidity, accuracy and potential for automation. RIA and ELISA are preferred.

Determination of antibody titers by ELISA: first, purified or partially purified TRAIL-R1-Fc/TRAIL-R2-Fc is adsorbed onto the surface of a solid phase, such as a 96-well ELISA plate. After blocking any remaining surface, the well surfaces are contacted with serially diluted samples of mouse sera. An enzyme-labeled, anti-mouse antibody, as the secondary antibody, is added to be bound to the mouse antibody. The antibody titer is estimated by determining absorbance change due to color development caused by the alteration of the substrate or the like.

b: Preparation of Myeloma Cells

Cells from established mouse cell lines serve as the source of myeloma cells, including P3X63Ag8U.1 (P3-U1), P3/NSI/1-Ag4-1(NS-1), Sp2/0-Ag14 (SP-2), P3X63Ag8.653 and P3X63Ag8 (X63), which can be acquired from ATCC. The cell line selected is serially transferred into an appropriate medium, such as 8-azaguanine medium. 8-azaguanine medium includes Iscove's Modified Dulbecco's Medium (hereinafter referred to as "IMDM") or Dulbecco's, Modified Eagle Medium (hereinafter referred to as "DMEM"). RPMI-1640 medium supplemented with glutamine, 2-mercaptoethanol, gentamicin, fetal calf serum (hereinafter referred to as "FCS"), and 8-azaguanine.

c: Cell Fusion

Lymphocytes and plasma cells obtained from any suitable part of the animal are precursor cells to produce the antibody. Lymphocyte or plasma cell sources include spleen, lymph nodes, peripheral blood, or any appropriate combination thereof, with spleen cells being the most common source. After the last booster injection, single lymphocyte suspension is prepared from lymphoid tissue in which antibody producing cells are present. The fusion technique includes washing spleen and myeloma cells with serum-free medium (such as RPMI 1640) or phosphate buffered saline (hereinafter referred to as "PBS") so that the number ratio of spleen cells to myeloma cells is approximately between 5:1 and 10:1, and then centrifuged. After the supernatant has been discarded and the pelleted cells sufficiently loosened, 1 ml of serum-free medium containing 50% (w/v) polyethylene glycol (m.w. 1,000 to 4,000) is added dropwise with mixing. Subsequently, 10 ml of serum-free medium is slowly added and then centrifuged. The supernatant is discarded again, and the pelleted cells are suspended in an appropriate amount of HAT medium containing a solution of hypoxanthine, aminopterin and thymidine (hereinafter referred to as "HAT").

d: Selection of Hybridomas

After fusion, any unfused myeloma cells and any myeloma-myeloma fusions are unable to survive in HAT medium. On the other hand, fusions of antibody producing cells with each other, as well as hybridomas of antibody producing cells with myeloma cells can survive, the former only having a limited life. Accordingly, continued incubation in HAT medium results in selection of only the desired hybridomas. The resulting hybridomas grow into colonies that are then transferred into HAT medium lacking aminopterin (HT medium). Thereafter, aliquots of the culture supernatant are removed to determine antibody titer by, for example, ELISA.

e: Cloning of Hybridoma

Hybridomas which have been shown to produce specific antibodies, using a method similar to that described in step b) to determine antibody titer, are then transferred to another plate for cloning. Suitable cloning methods include: the limiting dilution method, in which hybridomas are diluted to contain one cell per well of a plate and then cultured; the soft agar method in which colonies are recovered after culturing in soft agar medium; a method of using a micromanipulator to separate a single cell for culture; and "sort-a-clone", in which single cells are separated by a cell sorter. The cloning procedure according to, for example, the limiting dilution method is repeated 2 to 4 times for each well demonstrating an antibody titer, and clones having stable antibody titers are selected as antibody producing hybridomas.

The mouse-mouse hybridoma CTB003 which is a basis for antibodies of the present invention was deposited with CGMCC on Mar. 28, 2006, and has the accession number CGMCC1665.

f: Preparation and Purification of Monoclonal Antibody

Preparation of monoclonal antibody by cell culture: after obtaining stable antibody-Producing hybridoma, culture of selected hybridoma may be expanded. The supernatant from the large-scale culture is then harvested and purified by a suitable method, such as affinity chromatography and gel filtration. The hybridoma may also be grown intraperitoneally in a syngeneic mouse, such as a BALB/c mouse or a nu/nu mouse, to obtain ascites containing an anti-TRAIL-R1 and TRAIL-R2 monoclonal antibody in large quantities.

g: Characterization of Monoclonal Antibody

The isotype and the subclass of the monoclonal antibody may be determined by ELISA. Quantification of antibody concentration may be performed by the Folin-Lowry method, or by calculation based on the absorbance at 280 nm/1.4 (OD280)=Immunoglobulin 1 mg/ml).

C: Analysis of the Specificity of a Monoclonal Antibody

In order to obtain a monoclonal antibody that binds TRAIL-R1 and TRAIL-R2 but not other TRAIL-receptors such as TRAIL-R3 and TRAIL-R4, ELISA plate is coated with the following recombinant proteins: 1. TRAIL-R1 and TRAIL-R2 hetero-dimer antigen, 2. TRAIL-R1-Fc fusion antigen, 3) TRAIL-R2-Fc fusion antigen, 4. TRAIL-R3-Fc fusion antigen 5. TRAIL-R4-Fc fusion antigen, and BSA as negative control. After incubation with various concentrations of purified antibody, HRP-conjugated goat anti-mouse IgG is added. After TMB substrate reaction, the optical density is recorded in a ELISA plate reader. The optical density values are used to estimate the binding of an antibody to the corresponding antigens. CTB003 exhibits a dose-dependent binding to TRAIL-R1/TRAIL-R2 heterodimer antigen as well as TRAIL-R1-Fc or TRAIL-R2-Fc fusion antigen, but not to TRAIL-R3-Fc, TRAIL-R4-Fc fusion antigen and BSA, indicating that CTB003 is an antibody recognizing TRAIL-R1 and/or TRAIL-R2.

D. Analysis of the Function of a Monoclonal Antibody a: Induction of Apoptosis of Human Malignant Tumor Cells In Vitro A panel of human cancer lines are incubated with various concentrations of the antibody overnight, cell viability after antibody treatment is used for determination of the killing activity.

b: Tumoricidal Activity of CTB003 In Vivo.

Tumoricidal activity of CTB003 is evaluated in human tumor cell xenograft models. Nude mice are subcutaneously inoculated with human cancer cells. After visible tumor growth, the tumor-bearing mice were i.p. injected with CTB003. The degree of reduction of tumor size after treatment is used for evaluation of in vivo tumoricidal activity.

E. Analysis of Antibody Sequence

Total RNA is isolated from hybridoma cells and used as a template. cDNA is synthesized by reverse transcriptase. The cDNAs encoding the variable region of immunoglobulin heavy chain are obtained by PCR using a panel of 15 $V_H$ 5' primers and one CH 3' primer. The cDNAs encoding the variable region of immunoglobulin light chain are obtained by PCR using a panel of 8 VK 5' primers and one CK 3' primer. The PCR products are further cloned into the TA cloning vector (Invitrogen). Five independent clones are picked and sequenced. The CDR1, CDR2 and CRD3 sequences are determined by their high variability and their location in the heavy and chains.

F. Identification of Antibody Recognizing Epitope

Preparation of a series of antigens: a panel of antigens comprise whole or partial antigenic epitope recognized by an antibody. These antigens may be obtained through chemical synthesis of polypeptides or through recombinant DNA technology. After a region containing an epitope is determined, accurate mapping is accomplished by further shortening a polypeptide containing an epitope. In addition, a competitive inhibition assay with a polypeptide containing an epitope may be utilized to confirm the epitope.

Example 2

Preparation of a Heterodimeric Form of TRAIL-R1 and TRAIL-R2 Antigen

1. Cloning of TRAIL-R1 and TRAIL-R2 cDNA

DNA encoding the human TRAIL-R1 and TRAIL-R2 protein was cloned by the following RT-PCR method using:

a) Template

The total RNA of HeLa cells was extracted by using TRIzol Reagent (GIBCO BRL). The template for the PCR reaction used cDNA that was obtained by using the First-Strand cDNA synthesis kit (Amersham Pharmacia Biotech) according to the instruction manual provided with the kit.

b) PCR Primers

The following oligonucleotide primers were synthesized for the PCR:

```
                                  (DR5p1: SEQ ID NO.: 49)
5'-gacgatgcccgatctactttaaggg-3';

(DR5p2: SEQ ID NO.: 50)
5'-ccactgggtgatgttggatggg-3';

(DR4p1: SEQ ID NO.: 51)
5'-gacgatgcccgatctactttaaggg-3';

(DR4p2: SEQ ID NO.: 52)
5'-gacgatgcccgatctactttaaggg-3';
``` c) PCR Reaction

Composition of the PCR reaction solution:
template cDNA, 5 µl of total 33 µl reaction
primer DR5p1, 10 pmol;
primer DR5p2, 10 pmol;
10×. concentrated PCR buffer (provided with the kit), 10 µl;
dNTPs (each 2.5 mM), 4 µl; and
Taq polymerase (Promega), 5 units.
Sterile distilled water was added to the solution to a total volume of 100 µl.

The PCR reaction was conducted as follows. The solution was first heated at 94° C. for 2 minutes, after which a cycle of heating to 94° C. for 30 sec, 52° C. for 1 minute and 72° C. for 3 minutes, was repeated 40 times. After completion of this procedure, the reaction solution was heated at 72° C. for 10 minutes. The amplified DNA fragments, thus obtained, were separated on a 1% agarose gel containing 0.25 ug/ml ethidium bromide. The bands were determined to contain the desired DNA fragments and recovered using the Gene Clean kit (BIO101).

d) TA Cloning of PCR Products

The DNA fragment was cloned using the TA Cloning Kit (Invitrogen, Calif.). This was performed as follows: The DNA fragment recovered from the PCR reaction solution, together with 50 ng of pCR2.1 vector which was provided with the TA Cloning kit, was mixed with 1 µl of 10× ligase reaction buffer (6 mM Tris-HCl (pH 7.5), 6 mM magnesium chloride, 5 mM sodium chloride, 7 mM .beta.-mercaptoethanol, 0.1 mM ATP, 2 mM DTT, 1 mM spermidine, and 0.1 mg/ml bovine serum albumin), to which 4 units of T4 DNA ligase (1 µl) had been added. The total volume of the mixture was adjusted to 10 µl with sterile deionized water, and the resulting ligase solution was incubated at 14° C. for 15 hours. After this time, 2 µl of the ligase reaction solution was added to 50 µl of competent $E.$ $coli$ strain TOP10F, which was provided with the TA cloning kit and brought to competence in accordance with the instruction manual, and the resulting mixture was kept on ice for 30 minutes, then at 42° C. for 30 seconds, and again on ice for 5 minutes. Next, 500 µl of medium containing 2% v/v tryptone, 0.5% (w/v) yeast extract, 0.05% w/v sodium chloride, 2.5 mM potassium chloride, 1 mM magnesium chloride, and 20 mM glucose (hereinafter referred to as "SOC" medium) was added to the culture, and the mixture was incubated for 1 hour at 37° C. with shaking. After this time, the culture was spread on an L-broth agar plate (1% v/v tryptone, 0.5% w/v yeast extract, 0.5% w/v sodium chloride, 0.1% w/v glucose, and 0.6% w/v bacto-agar (Difco)), containing 100 µg/ml. Ampicillin resistant colonies appearing on the plate were selected and scraped off with a platinum transfer loop, and cultured in L-broth medium containing 100 µg/ml ampicillin at 37° C., overnight, with shaking at 200 r.p.m. After incubation, the cells were harvested by centrifugation, from which plasmid DNA was prepared by the alkali method. The cDNA encoding the extracellular domain of TRAIL-R1 or TRAIL-R2 was further cloned into pcDNA3 expression vector (Invitrogen, CA) containing a cDNA encoding the Fc portion of human IgG1. Thereby, a fused cDNA encoding the TRAIL-R1-Fc or TRAIL-R2-Fc fusion protein was obtained.

2. Expression and Purification of TRAIL-R1-Fc and TRAIL-R2-Fc Fusion Protein

QBI-293A cells were co-transfected with pcDNAIII-TRAIL-R1-Fc and pcDNAIII-TRAIL-R2-Fc. The culture media were harvested after transfection for 48 hours.

Total 500 ml of collected supernatants of above transfected cells was applied to a ProteinA-Sepharose CL-4B affinity chromatography (Pharmacia). The flow rate was 2 ml per minute. After culture supernatant was passed through, the column was washed with 50 ml PBS. The protein was eluted with elution buffer (0.1 M glycine (pH 2.4), 0.15 M NaCl). The optical density of each eluted fraction (1 ml) was measured at OD280 nm. The fractions with OD280>0.1 were collected. After addition of 100 µl of neutralization buffer (1M Tris-HCL pH8.5), the eluates were placed separately in dialysis tubing, and the eluates dialyzed against 1 liter of PBS (pH 7.5) at 4° C. The dialysis buffer were changed twice. The purified protein was concentrated to 1 mg/ml and stored at −80° C. The purity of the protein was greater than 95% as determined by SDS-PAGE. At the non-reducing condition, the molecular weight of purified protein was 90 kD whereas at the reducing condition, the molecular weight was 45 kD.

3. Characterization of Recombinant TRAIL-R1-Fc and TRAIL-R2 Fusion Protein

ELISA plate was coated with 2 µg/ml of goat anti-human IgG in PBS at 4° C. overnight. After washing three times with PBS, the plate was blocked with 3% BSA PBS at room temperature for one hour. 10 µg/ml purified fusion protein was added and incubated at 37° C. for one hour. After washing three times with PBS, 2 µg/ml monoclonal anti-TRAIL-R1 and anti-TRAIL-R2 antibodies were added at 37° C. for another hour. The unbound antibodies were removed by washing three time with PBS and then HRP-conjugated goat anti-mouse IgG was added at 37 DC for 30 minutes. After washing three times with PBS, TMB substrate buffer was added for 10 minutes and then the reaction was stopped by adding 2N $H_2SO_4$. The values of optical density were recorded in a ELISA plate reader with a dual wavelength at 450 nm/650 nm.

The results are summarized in Table 6. Anti-TRAIL-R1 and anti-TRAIL-R2 monoclonal antibodies react with the purified fusion protein but not with human IgG.

TABLE 6

|  | Anti-TRAIL-R1 (CTB007) | Anti-TRAIL-R2 (CTB006) |
|---|---|---|
| TRAIL-R1/TRAIL-R2 dimer | 3.286 | 3.453 |
| Human IgG1 | 0.026 | 0.028 |

Characterization of heterodimeric TRAIL-R1 and TRAIL-R2 fusion: ELISA plate was coated with 1 µg/ml anti-TRAIL-R1 (CTB007) or anti-TRAIL-R2 (CTB006) at 4° C. overnight. After washing three times with PBS, the plate was blocked with 3% BSA PBS. 100 ng/ml of the purified dimeric TRAIL-R1/TRAIL-R2 fusion protein was then added at 37° C. for one hour. After washing three times with PBS, 100 ng/ml of HRP-conjugated anti-TRAIL-R1 and anti-TRAIL-R2 antibody was added for another hour. After washing three times with PBS, TMB substrate buffer was added for 10 minutes and then the reaction was stopped by adding 2N $H_2SO_4$. The values of optical density were recorded in a ELISA plate reader with a dual wavelength at 450 nm/650 nm. The results in Table 7 demonstrate that while coating antibody is anti-TRAIL-R1, HRP-conjugated anti-TRAIL-R2 reacts with the fusion protein. Similarly, while coating antibody is anti-TRAIL-R2, HRP-conjugated anti-TRAIL-R1 reacts with the fusion protein as well. In contrast, the reactions with an antibody pair, TRAIL-R1/TRAIL-R1, or TRAIL-R2/TRAIL-R2, exhibit a weak reaction. These results indicate that the majority of the purified protein is in a heterodimeric form of TRAIL-R1/TRAIL-R2.

TABLE 7

Characterization of heterodimeric fusion of protein of TRAIL-R1/TRAIL-R2

|  | Anti-TRAIL-R1 (CTB007) | Anti-TRAIL-R2 (CTB006) |
|---|---|---|
| Anti-TRAIL-R1 CTB007-HRP | 0.358 | 3.286 |
| Anti-TRAIL-R2CTB006-HRP | 3.432 | 0.289 |

Example 3

Generation of Monoclonal Antibodies Against Human TRAIL-R1 and TRAIL-R2

1. Immunization

Female, Balb/c mice (Jackson Laboratory, Bar Harbor, Me.) of 6-8 weeks of age, were immunized with the affinity-purified human TRAIL-R1 and TRAIL-R2-Fc fusion protein. For the initial foot-pad immunization, the fusion protein (50 µg) was emulsified in Freund's complete adjuvant (Difco, Detroit, Mich.). The mice were then boosted with four injections of 50 µg of fusion protein administered without adjuvant every other day. Three days after the last injection, lymphocytes from the local lymph nodes were collected.

2. Cell Fusion

Single cell suspension was prepared from lymph nodes, and mixed with NS1 myeloma cells at a ratio of 2:1. The resulting mix was washed three times with PRMI-1640. One ml, 37° C. prewarmed, of 50% (w/v) polyethylene glycol 1500 (Boehringer Manheim) was then slowly added to the tube, all the while stirring the pellet using the tip of a pipette. Subsequently, 50 ml of serum-free RPMI medium, prewarmed to 37° C., was slowly added. The resulting mix was then centrifuged, the supernatant discarded and 50 ml of HAT medium containing 12% (v/v) FCS were added while stirring gently with the tip of a pipette. The suspension was dispensed into 96-well cell culture microplates at 100 µl/well and incubated at 37° C. in an atmosphere of 5% (v/v) $CO_2$ for 7-10 days.

3. Screening of Monoclonal Antibody

ELISA plates were coated with 1 µg/ml heterodimeric TRAIL-R1 and TRAIL-R2-Fc fusion protein at 4° C. overnight. After washing three times with PBS, the plate was blocked with 3% BSA PBS at room temperature for one hour. 100 µl hybridoma culture supernatant was then added at 37° C. for one hour. After washing three times with PBS, HRP-conjugated anti-mouse IgG antibody was added for 30 minutes. After washing three times with PBS, TMB substrate buffer was added for 10 minutes and then the reaction was stopped by adding 2N $H_2SO_4$. The values of optical density were recorded in a ELISA plate reader with a dual wavelength at 450 nm/650 nm.

All positive clones were subjected to a secondary confirmatory screening to rule out TRAIL-R1 or TRAIL-R2 monospecific clones as well as false positive clones reacting with human IgG1. ELISA plates were coated with 1 µg/ml heterodimeric TRAIL-R1 and TRAIL-R2-Fc fusion protein, TRAIL-R1-Fc, TRAIL-R2-Fc, or human IgG1, respectively at 4° C. overnight. After washing three times with PBS, the plate was blocked with 3% BSA PBS at room temperature for one hour. 100 µl hybridoma culture supernatant was then added at 37° C. for one hour. After washing three times with PBS, IRP-conjugated anti-mouse IgG antibody was then added for 30 minutes. After washing three times with PBS, TMB substrate buffer was added for 10 minutes and then the reaction was stopped by adding 2N $H_2SO_4$. The values of optical density were recorded in a ELISA plate reader with a dual wavelength at 450 nm/650 nm.

Among all 250 positive clones, approximately 40% reacted with TRAIL-R1-Fc, 25% reacted with TRAIL-R2-Fc, the rests reacted with human IgG1. Only one clone designed as CTB003 reacted with heterodimeric TRAIL-R1 and TRAIL-R2-Fc fusion protein, TRAIL-R1-Fc, TRAIL-R2-Fc, but not with human IgG1. Therefore, CTB003 was selected as a dual specific clone to TRAIL-R1 and/or TRAIL-R2.

4. Cloning by Limiting Dilution

The original CTB003 hybridoma cells were diluted to 0.3 cell per ml with RPMI-1640 containing 12% FCS and cultured in two 96-well plates in the presence of $10^5$ thymocytes of Balb/c mice as feeder cells. 7-10 days later, 100 µl culture supernatants were collected and antibody production was determined by ELISA as described above. The positive clones were subcloned three times by limiting dilution.

The cloned CTB003 retains the reactivity with TRAIL-R and TRAIL-R2 but not with human IgG1, therefore confirming its dual specific reactivity. CTB003 hybridoma clone has been deposited to GCMCC with an Accessing Number of GCMCC 1665.

Isotype of CTB003 was determined as murine IgG1 kappa by mouse immunoglobulin isotype test kit.

5. Purification of CTB003 Monoclonal Antibody

Purification of CTB003 from culture supernatants: were applied to a Protein G-Sepharose CL-4B affinity chromatography (Pharmacia). The flow rate was 2 ml per minute. After culture supernatant was passed through and the column was washed with 50 ml PBS. The protein was eluted with elution buffer (0.1 M glycine (pH 2.4), 0.15 M NaCl). The optical density of each eluted fraction (1 ml) was measured at OD280 nm. The fractions with OD280>0.1 were collected. After addition of 100 µl of neutralization buffer (1M Tris-HCL pH8.5), the eluates were placed separately in dialysis tubing, and the eluates dialyzed against 1 liter of PBS (pH 7.5) at 4° C. The dialysis buffer was changed twice. The purified protein was concentrated to 1 mg/ml, sterilized and stored at −4° C. until use.

Example 4

Binding Specificity of CTB003 to TRAIL Receptors

As all of the receptors for TRAIL and other proteins of the TNFR family share significant homology, the specificity of exemplary antibody CTB003 for TRAIL-R1 and TRAIL-2 was determined by ELISA with a panel of soluble forms of TRAIL receptors as antigen as described above. ELISA plate was coated with the following recombinant proteins at 1 µg/ml in PBS at 4° C. overnight: 1. TRAIL-R1 and TRAIL-R2 hetero-dimer antigen, 2. TRAIL-R1-Fc fusion antigen, 3. TRAIL-R2-Fc fusion antigen, 4. TRAIL-R3-Fc fusion antigen, 5. TRAIL-R4-Fc fusion antigen, or BSA as negative control. After washing three times with PBS, the plate was blocked with 3% BSA PBS at room temperature for one hour. The plate was incubated with various concentrations of purified CTB003 at 37° C. for one hour. After washing three times with PBS, HRP-conjugated anti-mouse IgG antibody was then added for 30 minutes. After washing three times with PBS, TMB substrate buffer was added for 10 minutes and then the reaction was stopped by adding 2N $H_2SO_4$. The values of optical density were recorded in a ELISA plate reader with a dual wavelength at 450 nm/650 nm. CTB003 exhibited a dose-dependent binding to TRAIL-R1/TRAIL-R2 heterodimer antigen as well as TRAIL-R1-Fc or TRAIL-R2-Fc fusion antigen. In the ranges of tested antibody concentrations, CTB003 does not react with TRAIL-R3-Fc, TRAIL-R4-Fc fusion antigen and BSA (FIG. 2).

Example 5

In Vitro Apoptosis-Inducing Activity of CTB003

Figure 3:
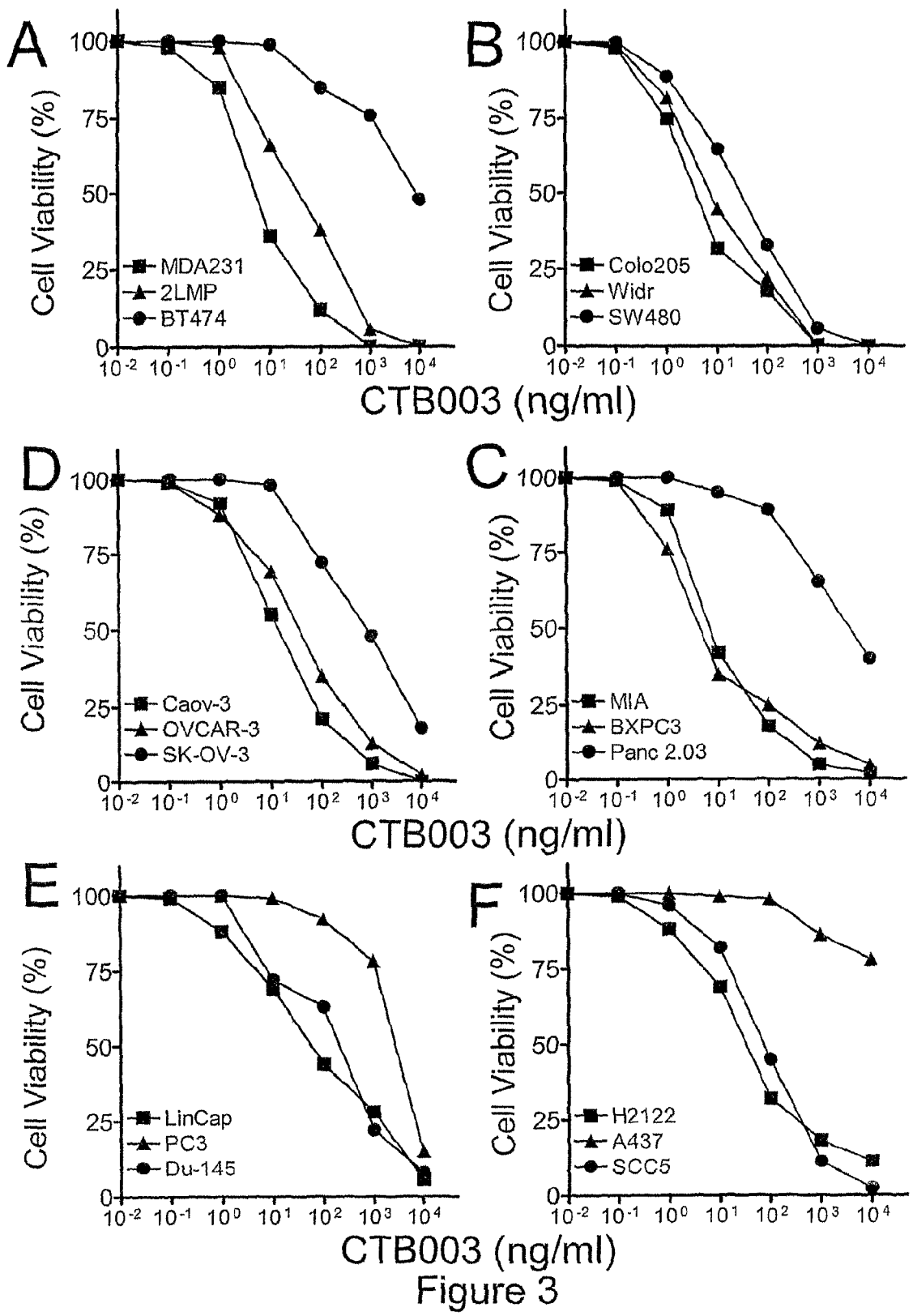
FIG. 3. Graphs showing the dose-response relationship of CTB003 in induction of apoptosis of human cancer cells. A panel of human cancer cell lines: Panel A. breast cancer; Panel B. colon cancer; Panel C. pancreatic cancer; Panel D. ovarian cancer; Panel E. prostate cancer; and Panel F. lung cancer were incubated with various concentrations of CTB003 overnight. Cell viability was determined by ATPLite assay using a medium control as 100% cell viability.

1. Human Cancer Cell Lines:

A panel of human cancer cell lines were used for evaluation of in vitro apoptosis-inducing activity of CTB003, including:

three human breast cancer cell lines (FIG. 3, panel A); three human colon cancer cell lines (FIG. 3, panel B); three human pancreatic cancer cell lines (FIG. 3, panel C); three human ovarian cancer cell lines (FIG. 3, panel D); three human prostate cancer cell lines (FIG. 3, panel E); three human lung cancer cell lines (FIG. 3, panel F). All cell lines were tested to be positive for cell surface expression of TRAIL-R1 and TRAIL-R2 by flow cytometry. (All cells were purchased from ATCC).

2. ATPLite Assay to Determine Cell Viability 1,000 target cells per well were cultured in 96-well plates in the presence of seven concentrations of 10-fold diluted CTB003 with the highest concentration at 1000 ng/ml and the lowest concentration at 0.01 ng/ml. After culture at 37° C. overnight, cell viability was determined using the ATPLite kit according to the manufacturer's instructions (Packard Instruments, Meriden, Conn.): add 50 µl of cell lysis buffer and then 50 µl of substrate buffer. The reaction was counted in a luminescent reader. Cell viability was calculated as (cpm of treated cells/emp of control cells)×100%.

3. Dose-Dependent Killing of Tumor Cells by CTB003

These results demonstrated that CTB003 exhibits a variable killing activity to most tested human tumor cells. Among three tested human breast cancer cell lines, the viability of two cell lines was reduced below 10% after treatment (FIG. 3, panel A). The viability of all three colon cell lines was below 10% (FIG. 3, panel B). While all human pancreatic cancer cell lines were susceptible to CTB003, two out of three human pancreatic cancer cell lines were more sensitive to CTB003. There was less than 5% viable cells after treatment with 1000 ng/ml CTB003 (FIG. 3, panel C). While all human ovarian cancer cells were susceptible to CTB003, two out of three human ovarian cancer cells were more susceptible (FIG. 3, panel D). All three human prostate cancer lines were sensitive to CTB003 (FIG. 3, panel E). Two out of three human lung cancer lines were susceptible to CTB003 treatment whereas one cell line appeared to be resistant to CTB003. The results indicate that CTB003 has the killing activity in most types of human cancer cells tested.

4. Time-Dependent Killing of Tumor Cells by CTB003.

Figure 4:
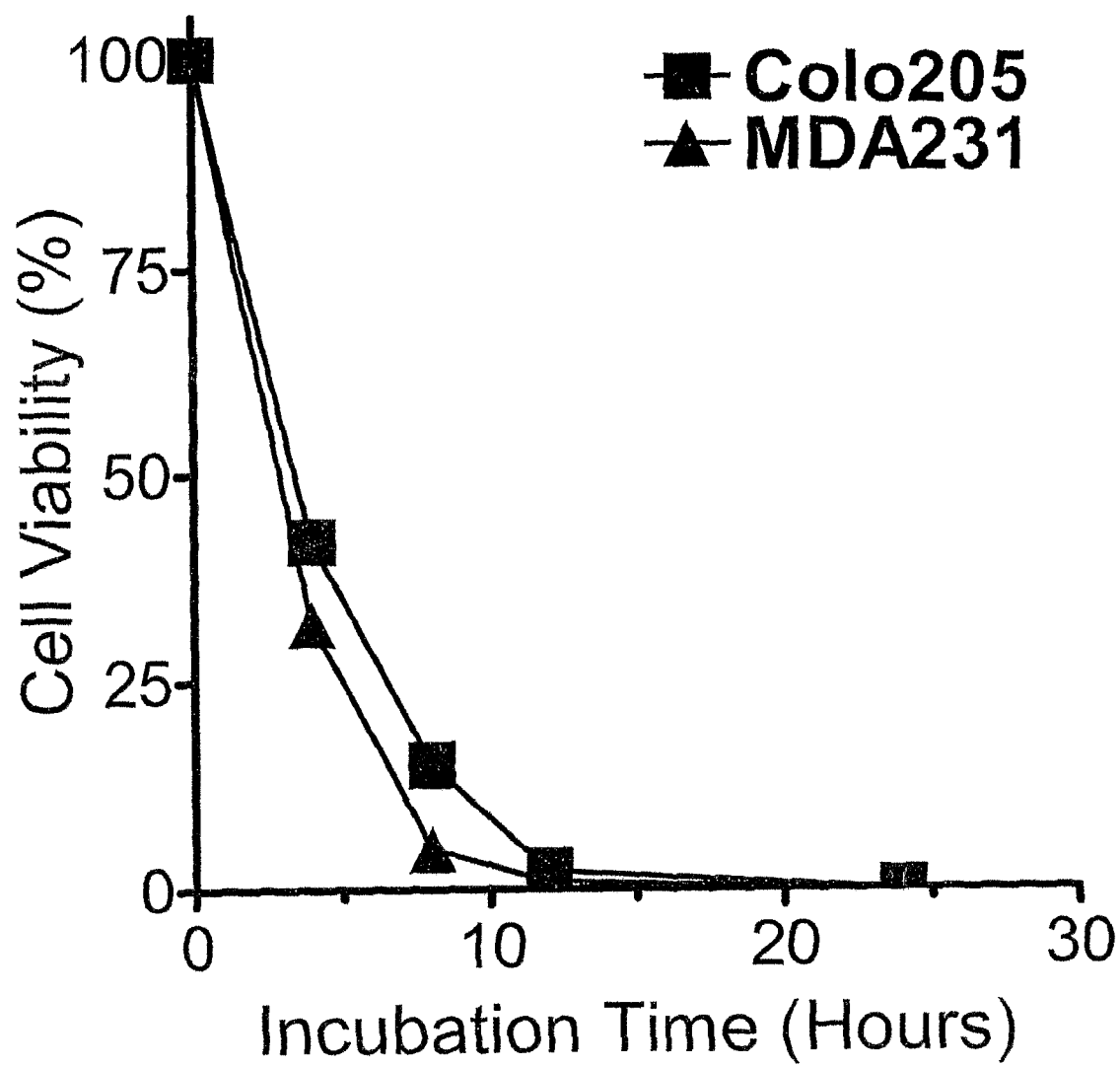
FIG. 4. A graph showing the time-dependent response of CTB003 in induction of apoptosis of cancer cells. Human breast cancer cells (MDA231) and colon cancer cells (Colo205) were incubated with 1000 ng/ml CTB003 for indicated time points and cell viability was determined by ATPLite assay. The data are expressed as cell viability (%) as a function of incubation time (hours).

Human colon cancer cells (Colo205) or human breast cancer cells (MDA231) were culture in 96-well plates at 1000 cells per well in the presence of 1000 ng/ml CTB003 for the indicated time points. Cell viability was determined by ATPLite assay at the end of each time point. After the cells were treated with 1000 ng/ml CTB003, cell viability of treated Colo205 and MDA 231 was determined at 4, 8, 12 and 24 h time point. The results demonstrate that the killing activity of CTB003 is time-dependent. Viable cells of both cell lines were reduced below 50% at 4 h after treatment, and 5% at 24 h after treatment (FIG. 4).

Example 6

Synergistic Killing Activity of CTB003 with Chemotherapeutic Drugs

1. Human Cancer Cell Lines.

In order to determine the synergistic killing activity of CTB003 with chemotherapeutic agents, a panel of human cancer cell lines were selected that were less sensitive to CTB003-mediated killing compared with other cancer cell lines. The cell lines selected for study included: human breast cancer cells (BT474), human colon cancer cells (SW620), human lung cancer cells (A437), human colon cancer cells (SW1116), and human pancreatic cancer cells (Panc 1). All cells were purchased from ATCC.

2. Chemotherapeutic Drugs

Chemotherapeutic drugs tested include: Adriamycin, Taxol, Cisplatin and CTP-11 and Gemcitabine.

3. ATPLite Assay to Determine Cell Viability 1,000 target cells per well were cultured in 96-well plates in the presence of four concentrations of 10-fold diluted CTB003 with the highest concentration at 1000 ng/ml and the lowest concentration at 10 ng/ml with three different concentrations of a chemotherapeutic drug. After culture at 37° C. overnight, cell viability was determined using the ATPLite kit according to the manufacturer's instructions (Packard Instruments, Meriden, Conn.): add 50 µl of cell lysis buffer and then 50 µl of substrate buffer. The reaction was counted in a luminescent reader. Cell viability was calculated as (cpm of treated cells/cmp of control cells)×100%.

4. Synergistic Killing of Human Breast Cancer Cells (BT474) by CTB003 and Adriamycin.

In the absence of Adriamycin, CTB003 exhibited a weak killing activity to BT474 cells. Cell viability was only reduced by 20% with 1000 ng/ml CTB003 alone. However, Adriamycin synergistically enhanced CTB003 killing in a dose-dependent fashion. In the presence 0.1 µM Adriamycin, cell viability was reduced to less than 25%, whereas with higher concentrations of Adriamycin (0.5 and 1.0 µM), cell viability was less than 5% at the same concentration of CTB003 (FIG. 5, panel A). The synergistic effect of CTB003 with Adriamycin is presented in FIG. 5, panel B. Using the ATPLite count obtained from medium control wells as 100% cell viability, the percent of cell viability in treated wells was calculated as following: the count of treated wells is divided by the count of control wells, and then times 100%. The results are presented as an average of triplicated wells.

5. Synergistic Killing of Human Colon Cancer Cells (SW620) by CTB003 and Taxol.

Figure 6:
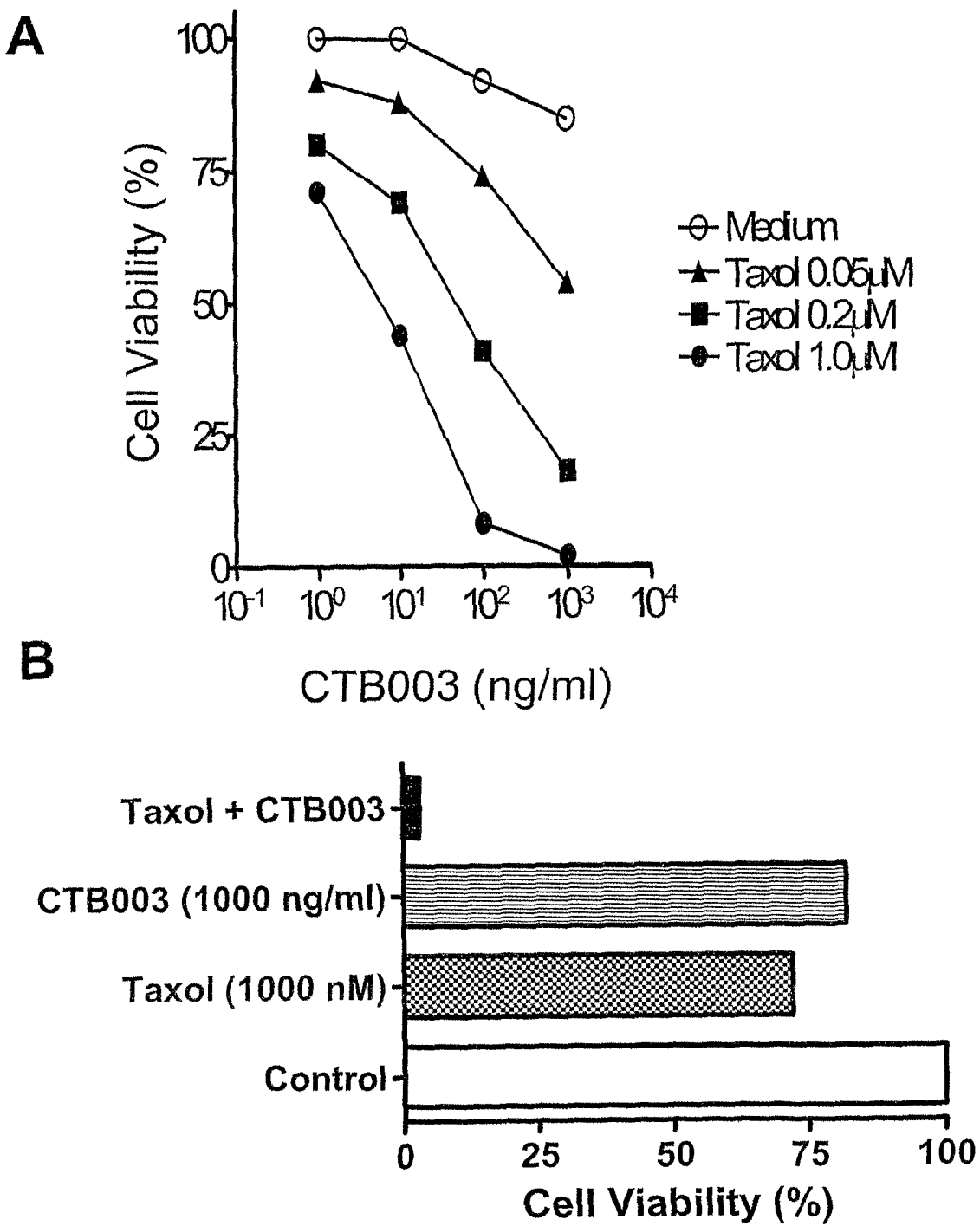
FIG. 6. Graphs showing the synergistic induction of cancer cell death with CTB003 and Taxol. A human colon cancer cell line (SW620) was incubated with various concentrations of CTB003 in the absence or presence of various concentrations of Taxol overnight. Cell viability was determined by ATPLite cell viability assay. Panel A shows a graph of cell viability (%) as a function of CTB003 concentration (ng/ml). Panel B shows a bar graph of cell viability (%) observed for various treatment groups.

In the absence of Taxol, CTB003 exhibited a weak killing activity to SW620 cells. Cell viability was only reduced by 20% with 1000 ng/ml CTB003 alone. However, Taxol synergistically enhanced CTB003 killing in a dose-dependent fashion. In the presence 0.2 µM Taxol, cell viability was reduced to less than 25%, whereas with a higher concentration of Taxol (1.0 µM), cell viability was less than 5% at the same concentration of CTB003 (FIG. 6, panel A). The synergistic effect of CTB003 with Taxol is presented in FIG. 6, panel B. Using the ATPLite count obtained from medium control wells as 100% cell viability, the percent of cell viability in treated wells was calculated as following: the count of treated wells is divided by the count of control wells, and then times 100%. The results are presented as an average of triplicated wells.

6. Synergistic Killing of Human Lung Cancer Cells (A437) by CTB003 and Cisplatin.

Figure 7:
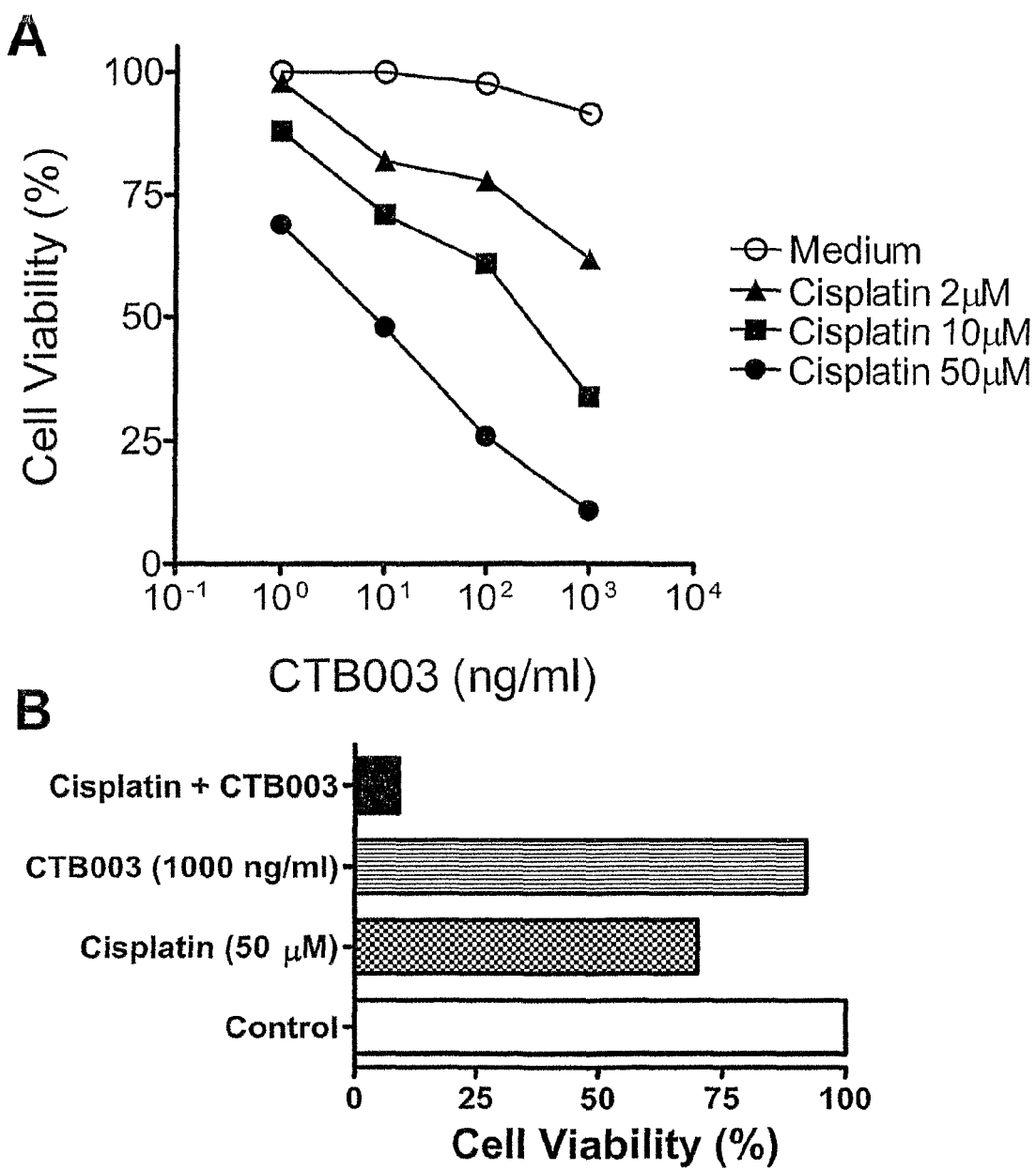
FIG. 7. Graphs showing the synergistic induction of cancer cell death with CTB003 and cisplatin. A human lung cancer cell line (A437) was incubated with various concentrations of CTB003 in the absence or presence of various concentrations of cisplatin overnight. Cell viability was determined by ATPLite cell viability assay. Panel A shows a graph of cell viability (%) as a function of CTB003 concentration (ng/ml). Panel B shows a bar graph of cell viability (%) observed for various treatment groups.

In the absence of Cisplatin, CTB003 does not have a killing activity to A437 cells. In contrast, Cisplatin synergistically enhanced CTB003 killing in a dose-dependent fashion. In the presence 50 µM Cisplatin, cell viability was reduced to less than 20% (FIG. 7, panel A). The synergistic effect of CTB003 with Cisplatin is presented in FIG. 7, panel B. Using the ATPLite count obtained from medium control wells as 100% cell viability, the percent of cell viability in treated wells was calculated as following: the count of treated wells is divided by the count of control wells, and then times 100%. The results are presented as an average of triplicated wells.

7. Synergistic Killing of Human Colon Cancer Cells (SW1116) by CTB003 and CTP-11.

Figure 8:
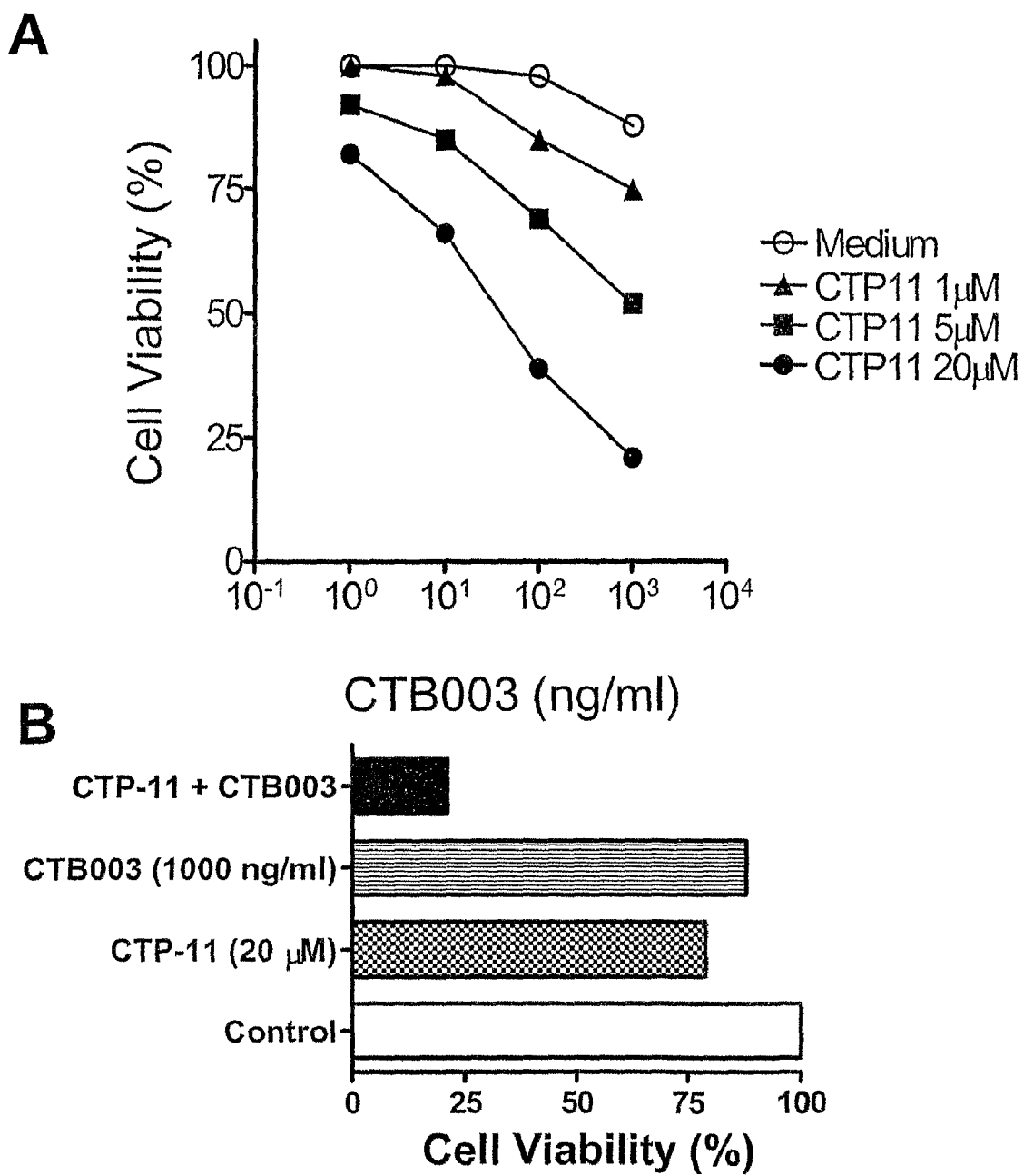
FIG. 8. Graphs showing the synergistic induction of cancer cell death with CTB003 and CTP-11. A human colon cancer cell line (SW1116) was incubated with various concentrations of CTB003 in the absence or presence of various concentrations of CTP-11 overnight. Cell viability was determined by ATPLite cell viability assay. Panel A shows a graph of cell viability (%) as a function of CTB003 concentration (ng/ml). Panel B shows a bar graph of cell viability (%) observed for various treatment groups.

In the absence of CTP-11, CTB003 exhibits a weak killing activity to SW116 cells. Cell viability was only reduced by 10% with 1000 ng/ml CTB003 alone. However, CTP-11 synergistically enhanced CTB003 killing in a dose-dependent fashion. In the presence 5 μM CTP-11, cell viability was reduced to 50%, whereas with a higher concentration of CTP-11 (20 μM), cell viability was less than 25% at the same concentration of CTB003 (FIG. 8, panel A). The synergistic effect of CTB003 with CPT-11 is presented in FIG. 8, panel B. Using the ATPLite count obtained from medium control wells as 100% cell viability, the percent of cell viability in treated wells was calculated as following: the count of treated wells is divided by the count of control wells, and then times 100%. The results are presented as an average of triplicated wells.

8. Synergistic Killing of Human Pancreatic Cancer Cells (Panc-1) by CTB003 and Gemcitabine.

Figure 9:
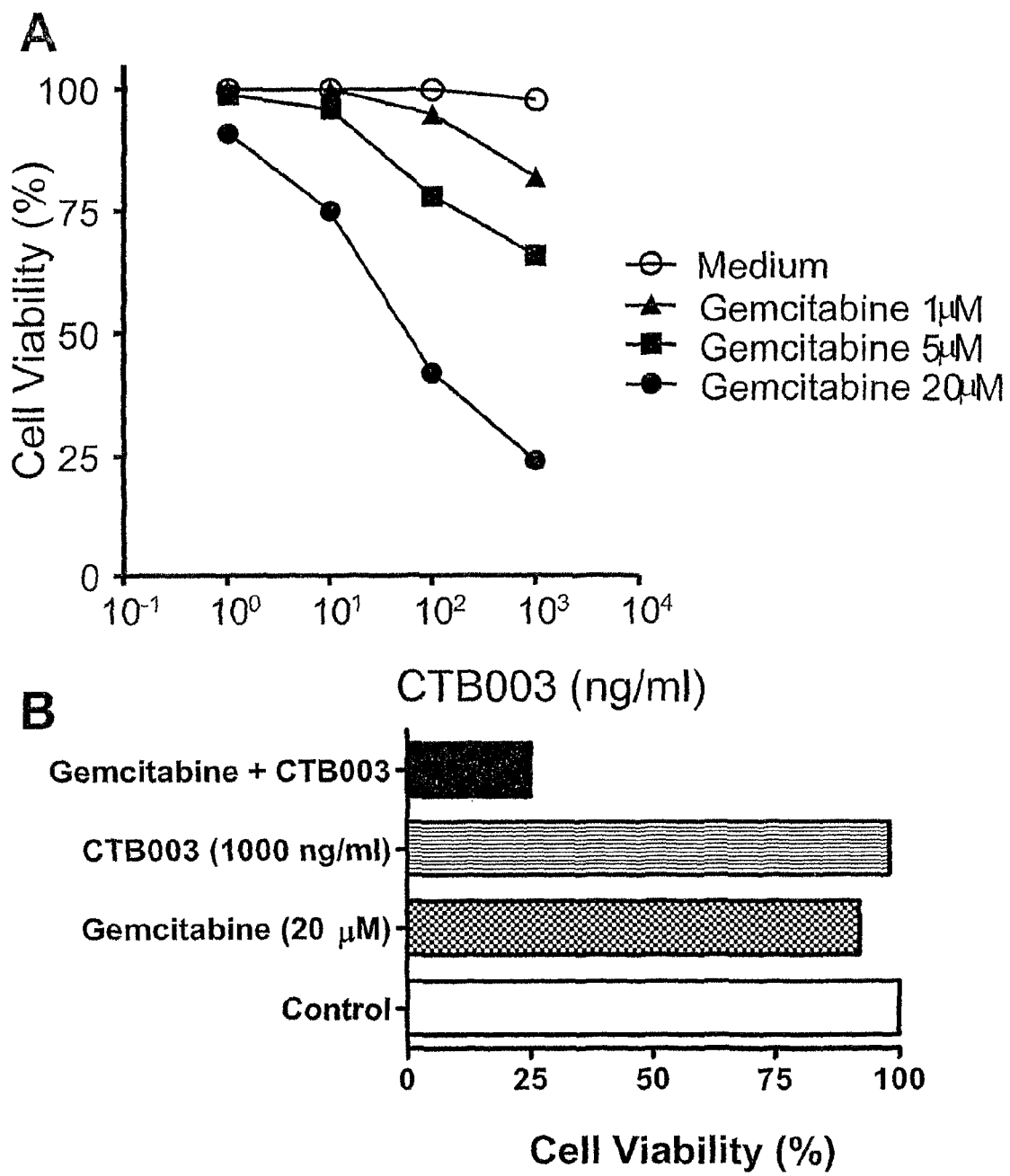
FIG. 9. Graphs showing the synergistic induction of cancer cell death with CTB003 and Gemcitabine. A human pancreatic cancer cell line (PANC1) was incubated with various concentrations of CTB003 in the absence or presence of various concentrations of Gemcitabine overnight. Cell viability was determined by ATPLite cell viability assay. Panel A shows a graph of cell viability (%) as a function of CTB003 concentration (ng/ml). Panel B shows a bar graph of cell viability (%) observed for various treatment groups.

In the absence of Gemcitabine, CTB003 was unable to kill Panc-1 cells. However, Gemcitabine synergistically enhanced CTB003 killing in a dose-dependent fashion. In the presence 1 μM Gemcitabine, cell viability was reduced by 25%, whereas with a higher concentration of Gemcitabine (10 μM), cell viability was less than 25% at the same concentration of CTB003 (FIG. 9, panel A). The synergistic effect of CTB003 with Gemcitabine is presented in FIG. 9, panel B. Using the ATPLite count obtained from medium control wells as 100% cell viability, the percent of cell viability in treated wells was calculated as following: the count of treated wells is divided by the count of control wells, and then times 100%. The results are presented as an average of triplicated wells.

Example 7

Synergistic Killing Activity of CTB003 with Anti-TRAIL-R1 or Anti-TRAIL-R2 Mono-Specific Monoclonal Antibody 1. Human Cancer Cell Lines.

In order to determine the synergistic killing activity of CTB003 with anti-TRAIL-R1 or anti-TRAIL-R2 mono-specific antibody, a human colon cancer cell line (SW1116) was selected. CTB003 or anti-TRAIL-R1 or anti-TRAIL-R2 alone did not induce cell killing in SW1116 cells.

2. Mono-Specific Anti-TRAIL-R1 or Anti-TRAIL-R2 Antibody

CTB007 is an monoclonal antibody against TRAIL-R1 which induces apoptosis of tumor cells that express TRAIL-R1. CTB006 is a monoclonal antibody directed against TRAIL-R2 which induces apoptosis of tumor cells that express TRAIL-R2.

3. ATPLite Assay to Dateline Cell Viability 1,000 target cells per well were cultured in 96-well plates in the presence of four concentrations of 10-fold diluted CTB003 with the highest concentration at 1000 ng/ml and the lowest concentration at 10 ng/ml with three different concentrations of anti-TRAIL-R1 or anti-TRAIL-R2 antibody. After culture at 37° C. for 16 h, cell viability was determined using the ATPLite kit according to the manufacturer's instructions (Packard Instruments, Meriden, Conn.): add 50 μl of cell lysis buffer and then 50 μl of substrate buffer. The reaction was counted in a luminescent reader. Cell viability was calculated as (cpm of treated cells/cmp of control cells)×100%.

4. Synergistic Killing of Human Colon Cancer Cells (SW1116) by CTB003 and CTB007.

Figure 10:
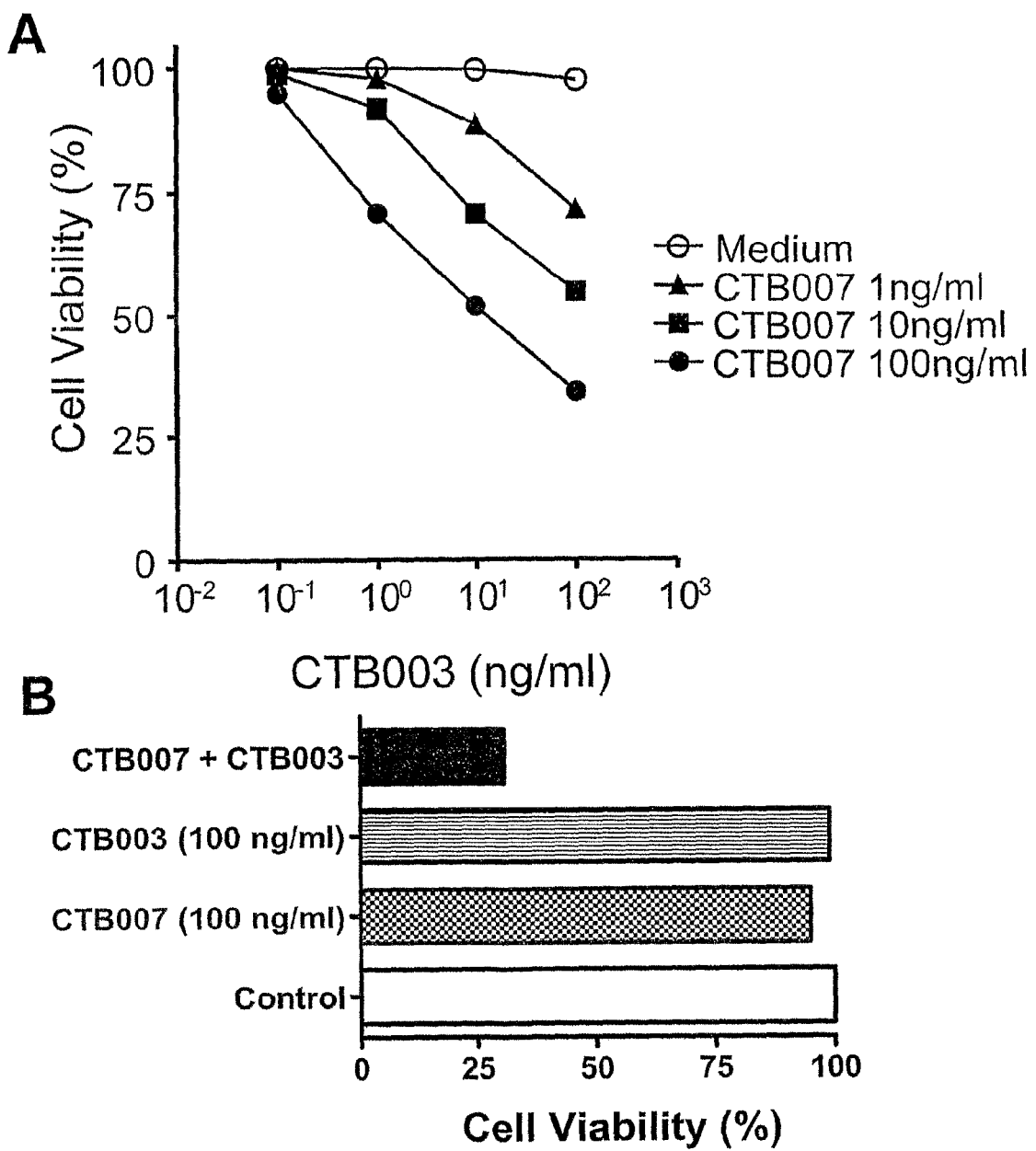
FIG. 10. Graphs showing the synergistic induction of cancer cell death with CTB003 and anti-TRAIL-R1 (CTB007). A human colon cancer cell line (SW1116) was incubated with various concentrations of CTB003 in the absence or presence of various concentrations of an anti-TRAIL-R1 antibody (CTB007) overnight. Cell viability was determined by ATPLite cell viability assay. Panel A shows a graph of cell viability (%) as a function of CTB003 concentration (ng/ml). Panel B shows a bar graph of cell viability (%) observed for various treatment groups.

In the absence of CTB007, CTB003 exhibits a weak killing activity to SW1116 cells. Cell viability was only reduced by 10% with 1000 ng/ml CTB003 alone. However, CTB007 synergistically enhanced CTB003 killing in a dose-dependent fashion. In the presence 10 ng/ml CTB007, cell viability was reduced to 50%, whereas with a higher concentration of CTB007 (100 ng/ml) cell viability was less than 25% at the same concentration of CTB003 (FIG. 10, panel A). The synergistic effect of CTB003 with CTB007 is presented in FIG. 10, panel B. Using the ATPLite count obtained from medium control wells as 100% cell viability, the percent of cell viability in treated wells was calculated as following: the count of treated wells is divided by the count of control wells, and then times 100%. The results are presented as an average of triplicated wells.

5. Synergistic Killing of Human Colon Cancer Cells (SW11116) by CTB003 and CTB006.

Figure 11:
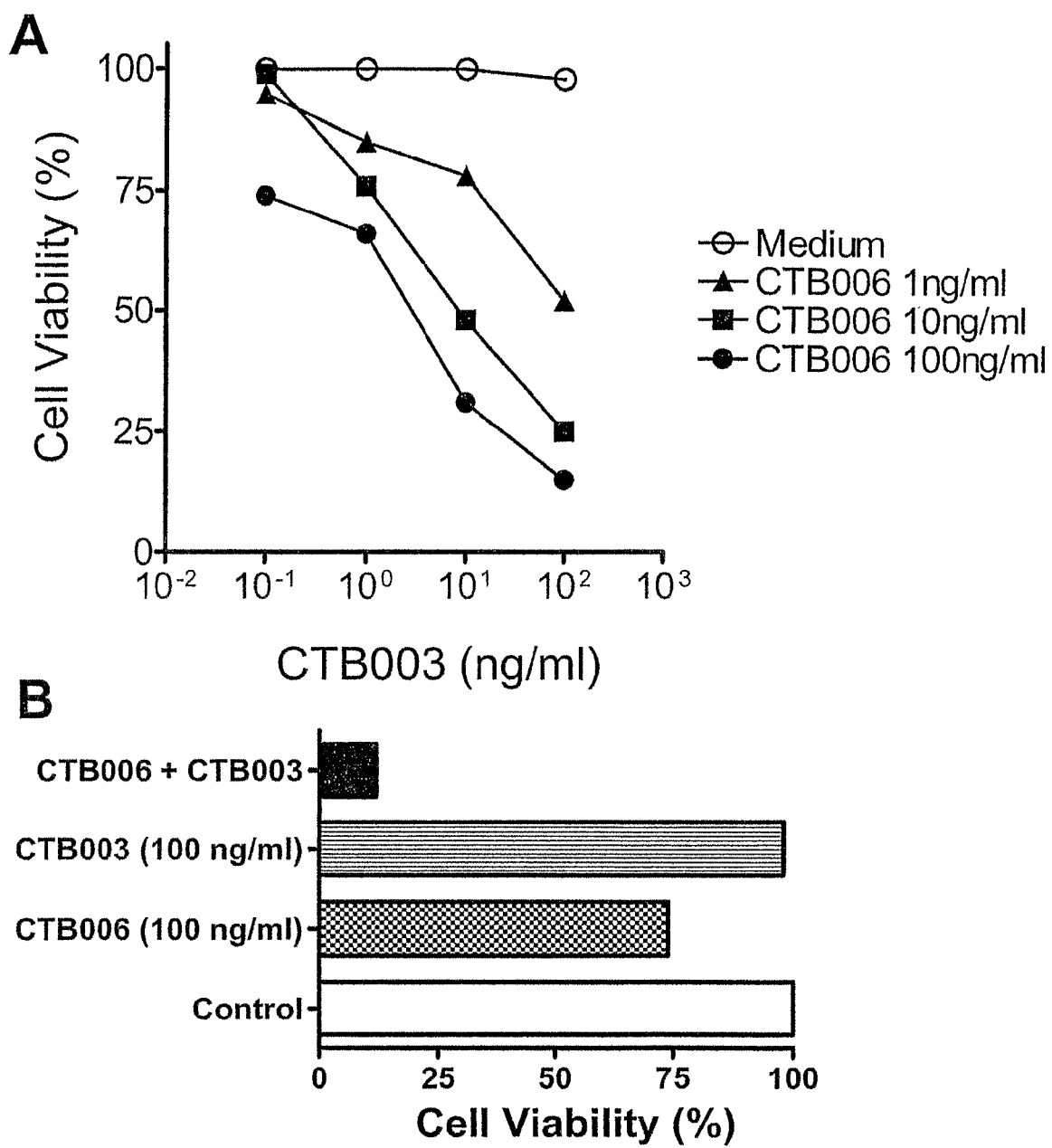
FIG. 11. Graphs showing the synergistic induction of cancer cell death with CTB003 and anti-TRAIL-R2 (CTB006). A human colon cancer cell line (SW1116) was incubated with various concentrations of CTB003 in the absence or presence of various concentrations of an anti-TRAIL-R2 antibody (CTB006) overnight. Cell viability was determined by ATPLite cell viability assay. Panel A shows a graph of cell viability (%) as a function of CTB003 concentration (ng/ml). Panel B shows a bar graph of cell viability (%) observed for various treatment groups.

In the absence of CTB007, CTB003 exhibits a weak killing activity to SW1116 cells. Cell viability was only reduced by 10% with 1000 ng/ml CTB003 alone. However, CTB006 synergistically enhanced CTB003 killing in a dose-dependent fashion. In the presence 10 ng/ml CTB006 cell viability was reduced to 50%, whereas with a higher concentration of CTB006 (100 ng/ml), cell viability was less than 25% at the same concentration of CTB003 (FIG. 11, panel A). The synergistic effect of CTB003 with CTB006 is presented in FIG. 11, panel B. Using the ATPLite count obtained from medium control wells as 100% cell viability, the percent of cell viability in treated wells was calculated as following: the count of treated wells is divided by the count of control wells, and then times 100%. The results are presented as an average of triplicated wells.

Example 8

Tumoricidal Activity of CTB003 In vivo

1. Human Cancer Cell Lines.

Human cancer cell lines that were used for generation of murine xenograft models of human cancer are: a) MDA231 human breast cancer cell line; b) 7402 human liver cancer cell line; c) Colo205 human colon cancer cell lines; and d) MIA-capa human pancreatic cancer cell line. All cells were purchased from ATCC, and cultured in DMEM supplemented with 10% FCS.

2. Xenograft Model.

Six (6) to 8 week-old Balb/c nude mice were inoculated subcutaneously with $1 \times 10^7$ human cancer cells. At day 7-14 after tumor inoculation depending on inoculated tumor cell lines, over 90% mice developed viable tumor mass. The tumor-bearing mice were randomly divided into two groups: one was untreated control group, and another was CTB003 treated group. Human cancer tumor growth was evaluated by sizes of tumor. After inoculation, tumor sizes were measured weekly.

3. Treatment of Xenograft Mice with CTB003.

The tumor-bearing mice were i.p. injected with 200 μg CTB003 twice a week with an interval of three days. The treatment was repeated six times within three weeks.

4. In vivo Anti-Tumor Activity of CTB003 in Human Breast Cancer Xenograft Model

Figure 12:
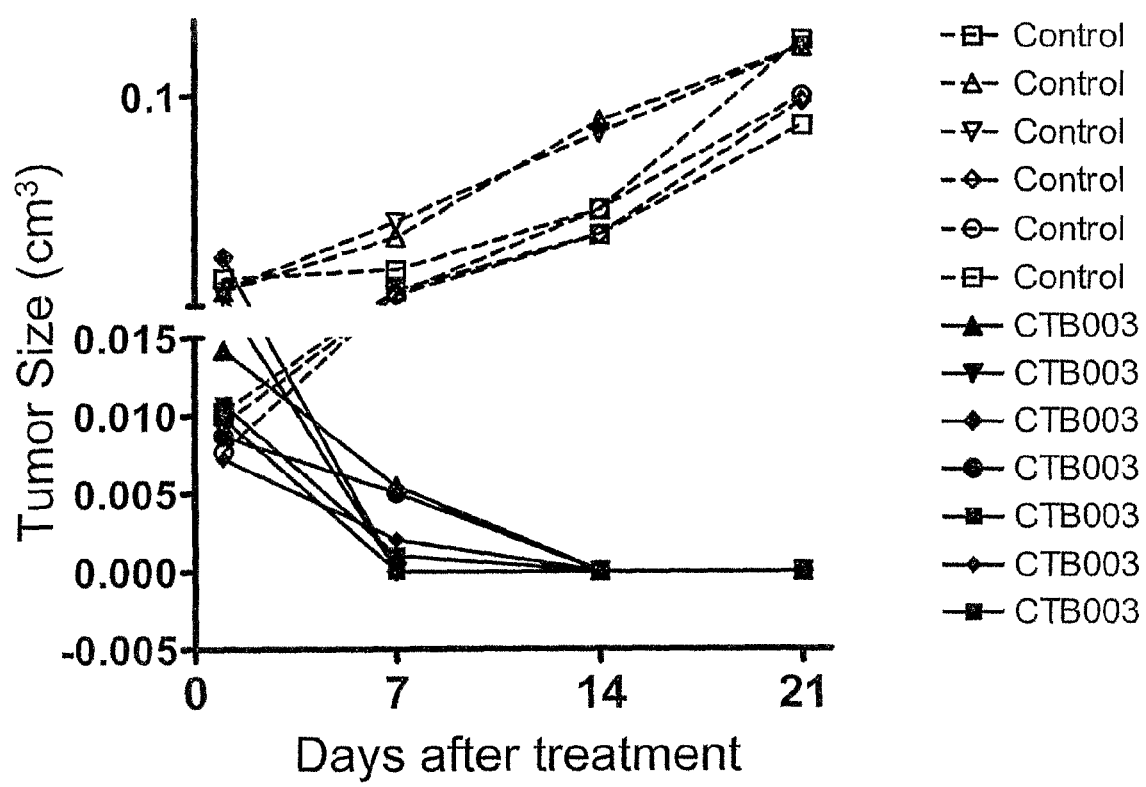
FIG. 12. A graph demonstrating the anti-tumor activity of CTB003 in vivo. Balb/c nude mice were subcutaneously inoculated with human breast cancer cells (MDA231). 10 days after inoculation, mice received i.p. injection of 200 μg CTB003, twice a week with in an interval of three days. The treatment was repeated three weeks. Tumor size was weekly measured. The data are expressed as the tumor size ($cm^3$) as a function of time (days) after treatment.
Figure 13:
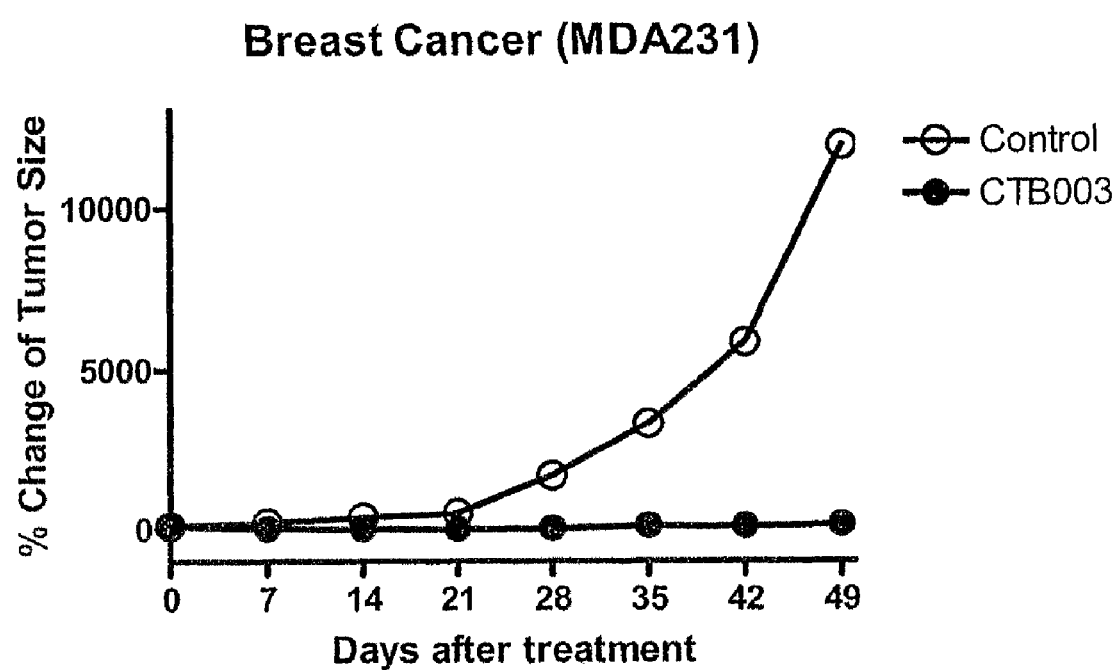
FIG. 13. Graph showing the time-dependence of the effect of murine TRAIL receptor-binding agent CTB003 on the growth of human breast cancer cell line MDA231 in an murine xenograft in vivo experimental model. Data are expressed as the % percent change in tumor size as a function of time (days) after treatment.

In untreated group the tumor doubling time was about 7 days. After treatment with CTB003 tumor size was quickly reduced. After two doses of treatment, the complete tumor regression occurred in three out of seven mice in treated group. Greater than 70% and 50% reduction Of tumor size was observed in other three mice and one mouse, respectively. After four doses of treatment, the complete tumor regression occurred in all seven mice. In contrast, tumor sizes in all mice of untreated control group continued to grow. These results indicate that CTB003 has a strong anti-tumor efficacy (FIG. 12). In another experiment, anti-tumor efficacy of CTB003 in MDA231 xenograft model was evaluated up to 49 days after inoculation with cancer cells, while 100% (8/8) mice in untreated group showed a continuing increase of tumor sizes, the majority (7/8) of CTB003 treated mice showed a complete regression of tumor (FIG. 13). As such, the TRAIL receptor binding agent of the invention shows therapeutic benefit (e.g., inhibition of tumor growth) when administered to a subject in an in vivo model of human cancer (e.g., human breast cancer). The TRAIL receptor-binding agent of the invention, as well as homologues and functional equivalents thereof (e.g., hCTB003) are, therefore, useful in methods to prevent or treat human cancer (e.g., human breast cancer) when administered in an effective amount to a subject in need thereof.

5. In Vivo Anti-Tumor Activity of CTB003 in Human Liver Cancer Xenograft Model.

Figure 14:
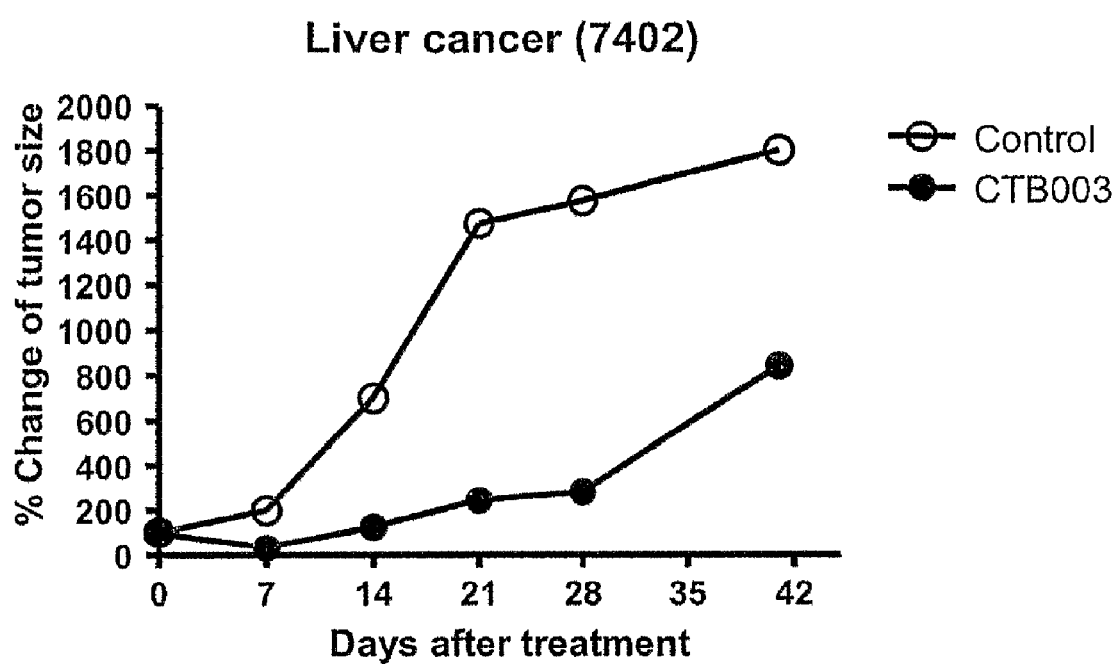
FIG. 14. Graph showing the time-dependence of the effect of murine TRAIL receptor-binding agent CTB003 on the growth of human liver cancer cell line 7402 in an murine xenograft in vivo experimental model. Data are expressed as the % percent change in tumor size as a function of time (days) after treatment.

In 7402 human liver cancer xenograft model, CTB003 exhibited a significant inhibitory activity. The tumor doubling time was approximately 10 days in untreated group compared to 35 days in CTB003 treated group (FIG. 14). As such, the TRAIL receptor-binding agent of the invention shows therapeutic benefit (e.g., inhibition of tumor growth) when administered to a subject in an in vivo model of human cancer (e.g., human liver cancer). The TRAIL receptor-binding agent of the invention, as well as homologues and functional equivalents thereof (e.g., hCTB003) are, therefore, useful in methods to prevent or treat human cancer (e.g., human liver cancer) when administered in an effective amount to a subject in need thereof.

6. In Vivo Anti-Tumor Activity of CTB003 in Human Colon Cancer Xenograft Model

Figure 15:
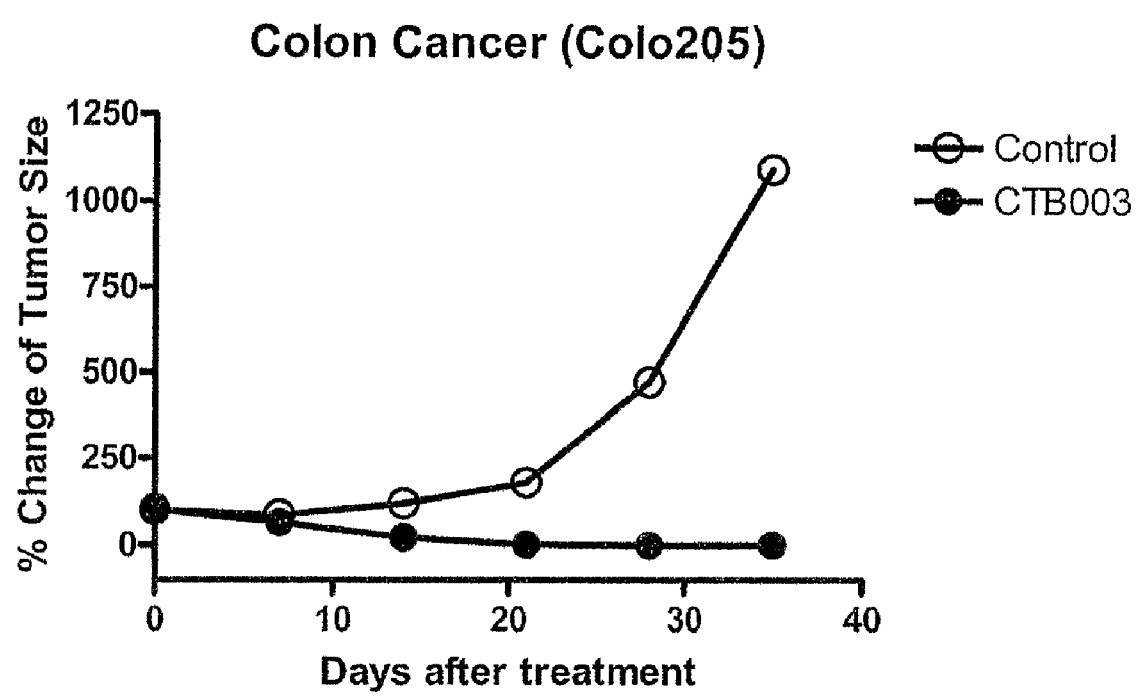
FIG. 15. Graph showing the time-dependence of the effect of murine TRAIL receptor-binding agent CTB003 on the growth of human colon cancer cell line Colo205 in an murine xenograft in vivo experimental model. Data are expressed as the % percent change in tumor size as a function of time (days) after treatment.

In Colo205 human colon cancer xenograft model, CTB003 achieved a 100% of complete tumor regression compared to 100% of tumor progression in untreated group (FIG. 15). As such, the TRAIL receptor-binding agent of the invention shows therapeutic benefit (e.g., inhibition of tumor growth) when administered to a subject in an in vivo model of human cancer (e.g., human colon cancer (e.g., colorectal cancer)). The TRAIL receptor-binding agent of the invention, as well as homologues and functional equivalents thereof (e.g., hCTB003) are, therefore, useful in methods to prevent or treat human cancer (e.g., human colon cancer) when administered in an effective amount to a subject in need thereof.

Figure 16:
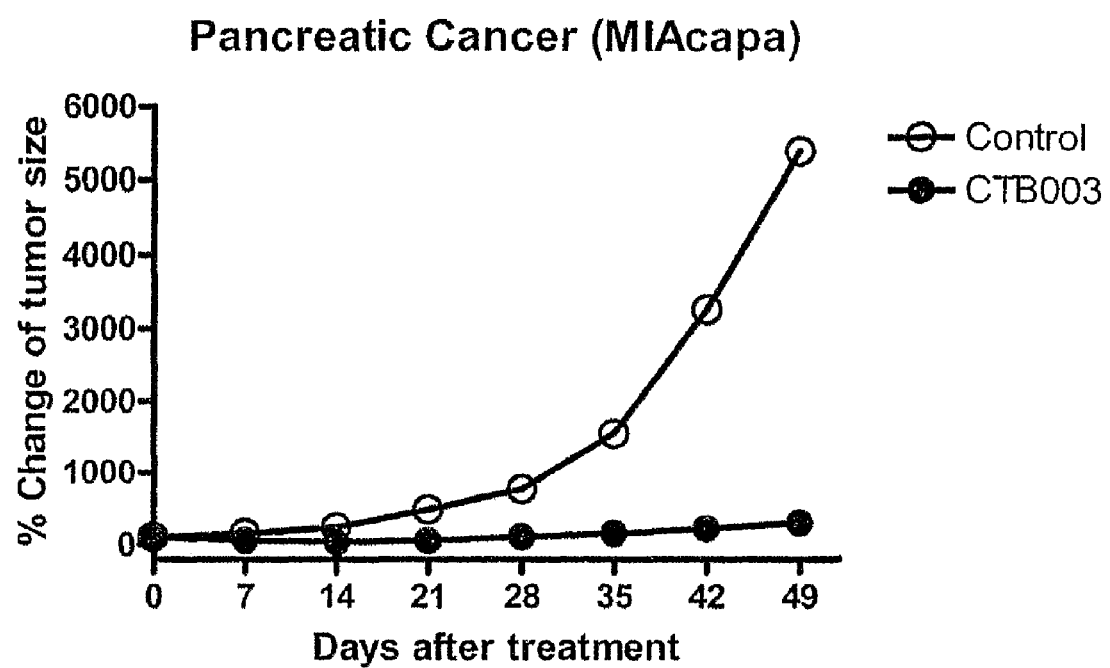
FIG. 16. Graph showing the time-dependence of the effect of murine TRAIL receptor-binding agent CTB003 on the growth of human pancreatic cancer cell line MIAcapa in an murine xenograft in vivo experimental model. Data are expressed as the % percent change in tumor size as a function of time (days) after treatment.

7. In Vivo Anti-Tumor Activity of CTB003 in Human Pancreatic Cancer Xenograft Model In MIAcapa human pancreatic cancer xenograft model, CTB003 exhibited a significant inhibitory activity. The tumor doubling time was observed as approximately 14 days in untreated group compared to 70 days in CTB003 treated group (FIG. 16). As such, the TRAIL receptor-binding agent of the invention shows therapeutic benefit (e.g., inhibition of tumor growth) when administered to a subject in an in vivo model of human cancer (e.g., pancreatic cancer)). The TRAIL receptor-binding agent of the invention, as well as homologues and functional equivalents thereof (e.g., hCTB003) are, therefore, useful in methods to prevent or treat human cancer (e.g., human pancreatic cancer) when administered in an effective amount to a subject in need thereof.

Taken together, the TRAIL receptor-binding agent of the invention show therapeutic benefit (e.g., reduction of tumor cell growth compared with tumor growth observed in untreated control subjects) when administered to subjects in in vivo models of multiple human cancers (e.g., human breast cancer; human liver cancer, human colon cancer; human pancreatic cancer). These cancers share the biological characteristic of TRAIL-R1 and/or TRAIL-R2 polypeptide expression. As discussed above, activation of functional TRAIL-R1 and/or TRAIL-R2 polypeptide on cells (including cancer cells) can lead to cell death (e.g., apoptotic cell death). The TRAIL receptor-binding agent of the invention, as well as homologues and functional equivalents thereof (e.g., hCTB003) are, therefore, useful in methods to prevent or treat human cancer cells which express TRAIL-R1 and/or TRAIL-R2 polypeptide which include, e.g., but are not limited to, breast cancer; liver cancer; colon cancer; pancreatic cancer when administered in an effective amount to a subject in need thereof.

Example 9

Synergistic In Vivo Anti-Tumor Efficacy of CTB003 and Adriamycin

1. Human Cancer Cell Line.

A human breast cancer cell line (MDA231) is used for preparation of xenograft model in nude mice.

2. Xenograft Model.

Six (6) to 8 week-old Balb/c nude mice were inoculated subcutaneously with $1 \times 10^7$ human MDA231 breast cancer cells. At day 7-10 after tumor inoculation, over 90% of mice developed viable tumor mass. The tumor-bearing mice were randomly divided into four groups: the first was an untreated control group, the second group was treated with Adriamycin alone, the third group was treated with CTB003 alone and the fourth group was treated with a combination of Adriamycin and CTB003 combination. Human breast cancer tumor growth was evaluated by measuring the size of tumor. After inoculation the tumor sizes were measured in mice weekly.

3. Treatment of Xenograft Mice with CTB003 and Adriamycin.

100 μg per dose of Adriamycin was i.p. injected twice a week for three times with an interval of three days. 200 μg per dose of CTB003 was i.p. injected twice a week with an interval of three days for total six doses. Adriamycin was given one day prior to CTB003 injection.

4. In Vivo Synergistic Anti-Tumor Efficacy of CTB003 and Adriamycin.

Figure 17:
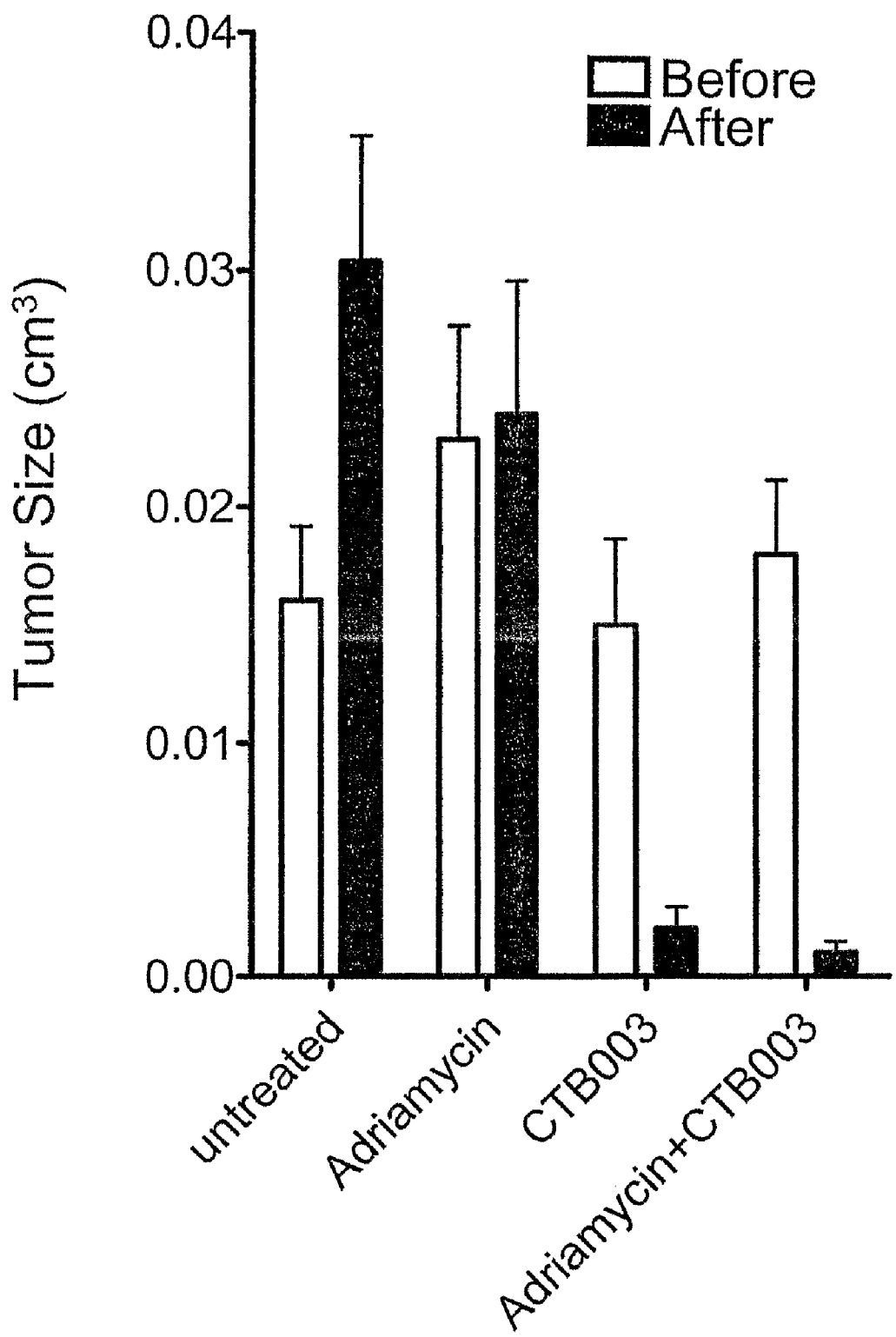
FIG. 17. Histogram showing the tumoricidal activity of CTB003 in combination with Adriamycin. Balb/c nude mice were subcutaneously inoculated with human breast cancer cells (MDA231). Ten (10) days after inoculation, mice received i.p. injection of 100 µg adriamycin first, and one day later 200 µg CTB003. Mice were treated twice a week within an interval of three days. The treatment was repeated for a period of two weeks. Tumor size was measured at two days after the last treatment. The data are expressed as tumor size ($cm^3$) as a function of treatment group (before and after). The treatment groups shown are untreated (control); adriamycin; CTB003; and adriamycin+CTB003.

In untreated group the tumor doubling time was about 7 days. After treatment with Adriamycin alone tumor inhibition was observed but tumor size reduction was not remarkable compare to that before treatment. In CTB003-treated group the tumor size was quickly reduced. After two doses of treatment, the complete tumor regression occurs in three out of seven mice in treated group. Greater than 70% and 50% reduction of tumor size is observed in other three mice and one mouse, respectively. After four doses of treatment nearly complete tumor regression occurred in all seven mice. When mice were treated with CTB003 and Adriamycin, after two cycles of treatment, the complete tumor regression occurs in five out of seven mice, and tumor sizes in the other mice were significantly smaller than the tumor size observed in mice treated with CTB003 alone. Because Adriamycin alone at a given showed little effect, the significantly increased complete tumor regression in CTB003 and Adriamycin combination treatment suggests that CTB003 and Adriamycin has a synergistic anti-tumor efficacy in vivo (FIG. 17).

As such, the TRAIL receptor-binding agent of the invention shows a synergistic therapeutic benefit (e.g., inhibition of tumor growth) when administered to a subject in an in vivo model of human cancer (e.g., human breast cancer) when in combination with another chemotherapeutic (e.g., adriamycin). The TRAIL receptor-binding agent of the invention, as well as homologues and functional equivalents thereof (e.g., hCTB003) are, therefore, useful in methods to prevent or treat human cancer (e.g., human breast cancer) when administered in an effective amount in combination with one or more chemotherapeutic agent(s) (e.g., adriamycin) to a subject in need thereof.

Example 10

In Vivo Anti-Tumor Efficacy of CTB003 and CTB006

1. Human Cancer Cell Line.

A human breast cancer cell line (MDA231) was used for preparation of xenograft model in nude mice.

2. Xenograft Model.

Six (6) to 8 week-old Balb/c nude mice were inoculated subcutaneously with 1×10⁷ human MDA231 breast cancer cells. At day 7-10 after tumor inoculation, over 90% of mice develop viable tumor mass. The tumor-bearing mice were randomly divided into four groups: the first group was an untreated control group, the second group was treated with CTB006 alone, the third group was treated with CTB003 alone and the fourth group was treated with a combination of CTB006 and CTB003. Human breast cancer tumor growth was evaluated by measuring the size of tumor. After inoculation the tumor sizes were measured in mice weekly.

3. Treatment of Xenograft Mice with CTB003 and CTB006.

The tumor-bearing mice in CTB006 treated group were i.p. injected with 100 μg CTB006 twice a week for three times with an interval of three days. The tumor-bearing mice in the CTB003 treated group were i.p. injected with 200 μg CTB003 twice a week with an interval of three days. The treatment was repeated six times within three weeks. Two antibodies were given simultaneously.

4. In Vivo Anti-Tumor Efficacy of CTB003 and Adriamycin.

Figure 18:
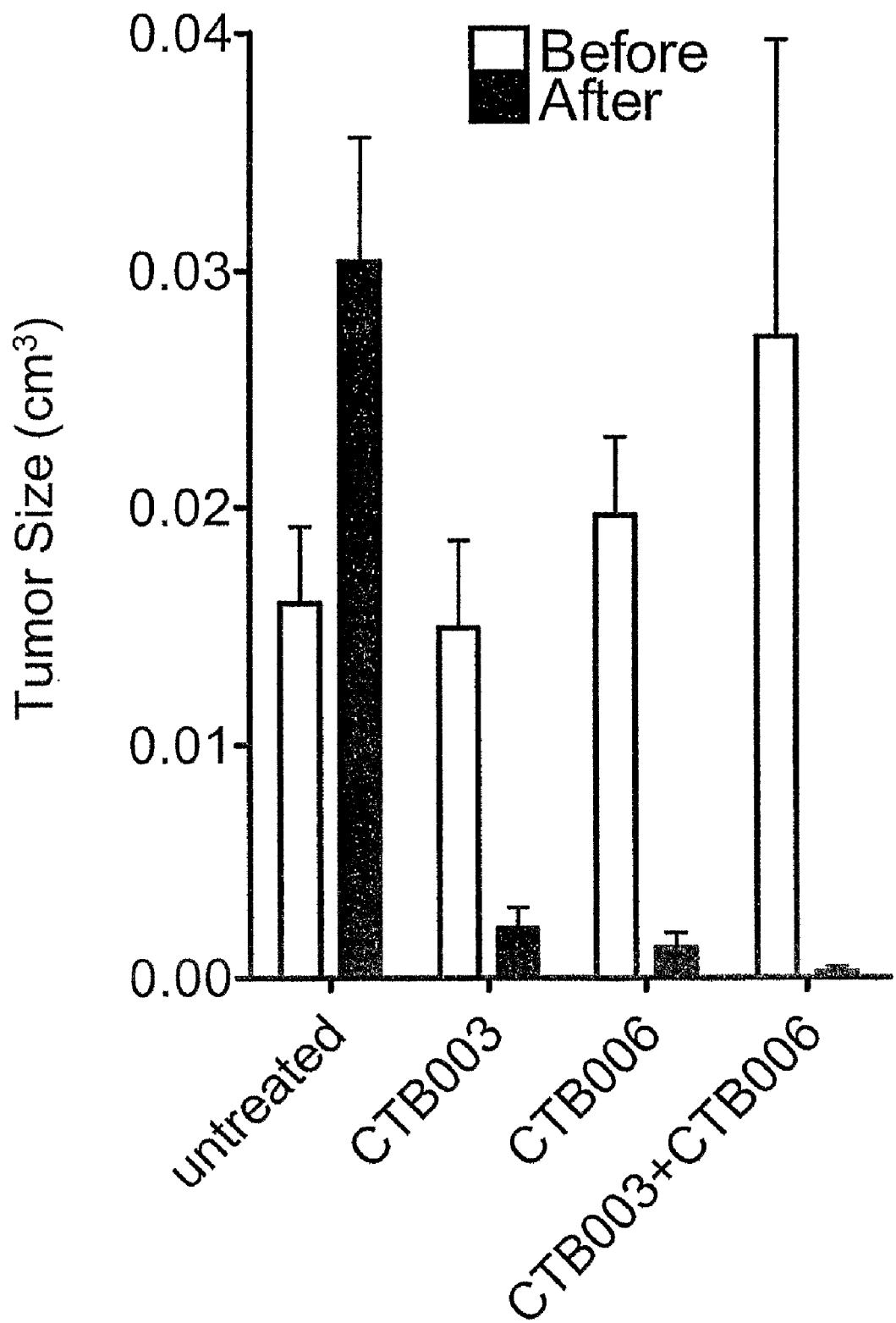
FIG. 18. Histogram showing the tumoricidal activity of CTB003 in combination with an anti-TRAIL-R2 (CTB006) in human MDA231 breast cancer xenograft model. Balb/c nude mice were subcutaneously inoculated with human breast cancer cells (MDA231). 10 days after inoculation, mice received i.p. injection of 200 µg CTB003 and CTB006. Mice were treated twice a week with in an interval of three days. The treatment was repeated for a period of two weeks. Tumor size was measured at two days after the last treatment. The data are expressed as tumor size ($cm^3$) as a function of treatment group (before and after). The treatment groups shown are untreated (control); CTB003; CTB006; and CTB003+CTB006.

In the untreated group the tumor doubling time was about 7 days. After treatment with CTB006 alone tumor inhibition was observed but tumor size reduction was not remarkable compare to that before treatment. In CTB003-treated group tumor size was quickly reduced. After two doses of treatment complete tumor regression was observed in three out of seven mice in the treated group. Greater than 70% and 50% reduction of tumor size was observed in the other three mice and one mouse, respectively. After four doses of treatment complete tumor regression occurred in all seven mice. When mice were treated with a combination of CTB003 and CTB006, after two cycles of treatment, complete tumor regression occurred in four out of seven mice, and tumor sizes in the remaining mice in the treatment group were significantly smaller than that in observed in the CTB003 alone treated group. These results indicate that CTB003 and CTB006 has a synergistic anti-tumor efficacy in vivo (FIG. 18).

As such, the TRAIL receptor-binding agent of the invention shows a therapeutic benefit (e.g., inhibition of tumor growth) when administered to a subject in an in vivo model of human cancer (e.g., human breast cancer) in combination with another TRAIL receptor-binding agent (e.g., CTB006). The TRAIL receptor-binding agent of the invention, as well as homologues and functional equivalents thereof (e.g., hCTB003) are, therefore, useful in methods to prevent or treat human cancer (e.g., human breast cancer) when administered in an effective amount in combination with another TRAIL receptor-binding agent (e.g., CTB006; hCTB006) to a subject in need thereof.

Example 11

Analysis of Sequences of the Variable Region of the Heavy and Light Chain of CTB003

1. Cloning of cDNAs Encoding the Variable Region of Heavy and Light Chain of CTB003.

Total RNA is isolated from CTB003 hybridoma. cDNA is synthesized by reverse transcription, which is used as a PCR template for cloning the cDNAs encoding the variable region of heavy and light chain of CTB003.

2. Synthesis of PCR Oligonucleotide Primers:

```
a) 15 heavy chain variable region primers
(containing a Sfi I restriction site) as follows:
VH1 (49mer):
                                       (SEQ ID NO.: 53)
5'-GGA ACC CTT TGG CCC AGC CGG CCA TGG CC(C or G)

AGG T (C or T) C AGC T(C or G or T)C AGC AGT C-3'

VH2 (49mer):
                                       (SEQ ID NO.: 54)
5'-GGA ACC CTT TGG CCC AGC CGG CCA TGG CCC AGG TTC ACC TGC AGC A(A or G)T C-3'

VH3 (49mer):
                                       (SEQ ID NO.: 55)
5'-GGA ACC CTT TGG CCC AGC CGG CCA TGG CCC AGG T(A or G)C AGC TGA AGG AGT C-3'

VH4 (49mer):
                                       (SEQ ID NO.: 56)
5'-GGA ACC CTT TGG CCC AGC CGG CCA TGG CCC AGG TCC AAC T(A or C or G)C AGC A(A or G)C C-3'

VH5 (49mer):
                                       (SEQ ID NO.: 57)
5'-GGA ACC CTT TGG CCC AGC CGG CCA TGG CCC AGA TCC AGT TGG T(A or C or G)C AGT C-3'

VH6 (49mer):
                                       (SEQ ID NO.: 58)
5'-GGA ACC CTT TGG CCC AGC CGG CCA TGG CCC AGG TGC AGC TGA AG(C or G) A(C or G)T C-3'

VH7 (49mer):
                                       (SEQ ID NO.: 59)
5'-GGA ACC CTT TGG CCC AGC CGG CCA TGG CCG AGG TGC AG(C or G) (G or T)GG TGG AGT C-3'

VH8 (49mer):
                                       (SEQ ID NO.: 60)
5'-GGA ACC CTT TGG CCC AGC CGG CCA TGG CCG AAG TGA

ARS TTG AGG AGT C-3'

VH9 (49mer):
                                       (SEQ ID NO.: 61)
5'-GGA ACC CTT TGG CCC AGC CGG CCA TGG CCG A(G or T)G T(C or G)(A or C or G) AGC TTC AGG AGT C-3'
```

```
VH10 (49mer):
                                          (SEQ ID NO.: 62)
5'-GGA ACC TTT TGG CCC AGC CGG CCA TGG CCG AGG TGA A(C or G)(C or G) TGG TGG AAT C-3'

VH11 (49mer):
                                          (SEQ ID NO.: 63)
5'-GGA ACC TTT TGG CCC AGC CGG CCA TGG CCG AGG TGA AGC TG(A or G) TGG A(A or G)T C-3'

VH12 (49mer):
                                          (SEQ ID NO.: 64)
5'-GGA ACC TTT TGG CCC AGC CGG CCA TGG CCG A(A or G)G TGA AGC TG(A or G) TGG AGT C-3'

VH13 (49mer):
                                          (SEQ ID NO.: 65)
5'-GGA ACC TTT TGG CCC AGC CGG CCA TGG CCG AAG TGC

AGC TGT TGG AGA C-3'

VH14 (49mer):
                                          (SEQ ID NO.: 66)
5'-GGA ACC TTT TGG CCC AGC CGG CCA TGG CCG A(A or G)G TGA AGC TTC TC(C or G) AGT C-3'

VH15 (48mer):
                                          (SEQ ID NO.: 67)
5'-GGA ACC TTT TGG CCC AGC CGG CCA TGG CCC A(A or

G)G TTA CTC TGA AAG AGT-3' b) IgG constant region primer:
IgG CH (20mer):
                                          (SEQ ID NO.: 68)
5'-TAR CCY TTG ACM AGG CAT CC-3' c) 8 light chain variable region primers:
VK1 (32mer):
                                          (SEQ ID NO.: 69)
5'-TAT TCG TCG ACG GAT ATT GTG ATG AC(C or G or T)

CAG (A or G or T)C-3'

VK2 (32mer):
                                          (SEQ ID NO.: 70)
5'-TAT TCG TCG ACG GAT (A or G)TT (G or T)TG ATG ACC CA(A or G) AC-3'

VK3 (32mer):
                                          (SEQ ID NO.: 71)
5'-TAT TCG TCG ACG GAA AAT GTG CTC ACC CAG TC-3'

VK4 (32mer):
                                          (SEQ ID NO.: 72)
5'-TAT TCG TCG ACG GA(C or T) ATT GTG ATG ACA CAG

TC-3'

VK5 (32mer):
                                          (SEQ ID NO.: 73)
5'-TAT TCG TCG ACG GAC ATC CAG ATG ACA CAG AC-3'

VK6 (32mer):
                                          (SEQ ID NO.: 74)
5'-TAT TCG TCG ACG GA(C or T) ATT GTG CTS AC(C or T) CA(A or G) TC-3'

VK7 (32mer):
                                          (SEQ ID NO.: 75)
5'-TAT TCG TCG ACG GAC ATC CAG ATG AC(C or T) CA(A or G) TC-3'

Vk8 (32mer):
                                          (SEQ ID NO.: 76)
5'-TAT TCG TCG ACG CAA ATT GTT CTC ACC CAG TC-3' d) Kappa light chain constant region primer:
IgG CK (18mer):
                                          (SEQ ID NO.: 77)
5'-CGT TCA CTG CCA TCA ATC -3'
```

3. PCR Reaction:

In order to obtain a cDNA encoding the heavy chain variable region of CTB003, total 15 PCR reactions were set, whereas 8 reactions were set for a cDNA encoding the light chain variable region. Composition of the PCR reaction solution: template cDNA 5 µl, 10 pmol 5' primer: VH1-VH15 or VK1-VK8, 10 pmol 3' primer CH or CK, 10 µl 10×. concentrated PCR buffer, 4 µl dNTPs (each 2.5 mM), 5 units Taq polymerase (Promega). Sterile distilled water was added to the solution to a total volume of 100 µl. The PCR reaction was conducted as follows. The solution was first heated at 94° C. for 2 minutes, after which a cycle of heating to 94° C. for 30 sec, 52° C. for 1 minute and 72° C. for 3 minutes, was repeated 40 times. After completion of this procedure the reaction solution was heated at 72° C. for 10 minutes. The amplified DNA fragments, thus obtained, were separated on a 1% agarose gel containing 0.25 ug/ml ethidium bromide. The bands determined to contain the desired DNA fragments were recovered using the Gene Clean kit (BIO101).

4. TA Cloning of PCR Products

The DNA fragment was cloned using the TA Cloning Kit (Invitrogen, CA). This was performed as follows: the DNA fragment recovered from the PCR reaction solution, together with 50 ng of pCR2.1 vector which is provided with the TA Cloning kit, was mixed with 1 µl of 10× ligase reaction buffer (6 mM Tris-HCl (pH 7.5), 6 mM magnesium chloride, 5 mM sodium chloride, 7 mM .beta.-mercaptoethanol, 0.1 mM ATP, 2 mM DTT, 1 mM spermidine, and 0.1 mg/ml bovine serum albumin), to which 4 units of T4 DNA ligase (1 µl) had been added. The total volume of the mixture was adjusted to 10 µl with sterile deionized water, and the resulting ligase solution was incubated at 14° C. for 15 hours. After this time, 2 µl of the ligase reaction solution was added to 50 µl of competent E. coli strain TOP10F, which was provided with the TA cloning kit and brought to competence in accordance with the instruction manual, and the resulting mixture was kept on ice for 30 minutes, then at 42° C. for 30 seconds, and again on ice for 5 minutes. Next, 500 µl of medium containing 2% v/v tryptone, 0.5% w/v yeast extract, 0.05% w/v sodium chloride, 2.5 mM potassium chloride, 1 mM magnesium chloride, and 20 mM glucose (hereinafter referred to as "SOC" medium) was added to the culture and the mixture was incubated for 1 hour at 37° C. with shaking. After this time the culture was spread on an L-broth agar plate (1% v/v tryptone, 0.5% w/v yeast extract, 0.5% w/v sodium chloride, 0.1% w/v glucose, and 0.6% w/v bacto-agar (Difco)) Ampicillin resistant colonies appearing on the plate were selected and scraped off with a platinum transfer loop, and cultured in L-broth medium containing 100 µg/ml ampicillin at 37° C., overnight, with shaking at 200 r.p.m. After incubation the cells were harvested by centrifugation from which plasmid DNA was prepared by the alkali method.

5. Sequence Analysis:

Five individual TA clones were randomly picked. DNA was purified and sequences bi-directionally using M13 primers.

6. Results:

PCR reaction yielded specific DNA products using VH1 and VK1 primers. The sequences of the variable region of light and heavy chain are illustrated in FIG. 1.

Example 12

Analysis of Epitope Recognized by CTB003

1. Synthesis of Polypeptides Encoding the Extracellular Domain of TRAIL-R2:

```
Peptide A.  TRAIL-R2 (aa52-aa81)
                                   (SEQ ID NO.: 6)
ESALITQQDLAPQQRAAPQQKRSSPSEGLC Peptide B.  TRAIL-R2 (aa72-aa101)
                                   (SEQ ID NO.: 7)
KRSSPSEGLCPPGHHISEDGRDCISCKYGQ Peptide C.  TRAIL-R2 (aa92-aa121)
                                   (SEQ ID NO.: 79)
RDCISCKYGQDYSTHWNDLLFCLRCTRCDS Peptide D.  TRAIL-R2 (aa112-aa141)
                                   (SEQ ID NO.: 80)
FCLRCTRCDSGEVELSPCTTTRNTVCQCEE Peptide E.  TRATL-R2 (aa132-aa161)
                                   (SEQ ID NO.: 81)
TRNTVCQCEEGTFREEDSPEMCRKCRTGCP Peptide F.  TRAIL-R2 (aa154-aa183)
                                   (SEQ ID NO.: 82)
RKCRTGCPRGMVKVGDCTPWSDIECVHKES Peptide. G  TRAIL-R2 (aa164-aa193)
                                   (SEQ ID NO.: 83)
MVKVGDCTPWSDIECVHKESGTKHSGEAPA
```

2. Competitive Inhibition ELISA.

ELISA plate was coated with 1 μg/ml TRAIL-R2-Fc fusion protein in PBS at 4° C. overnight. After washing three times with PBS, the plate was blocked with 3% BSA PBS at room temperature for one hour. 1 μg/ml CTB003 was added with various concentrations of TRAIL-R2 polypeptide, A, B, C, D, E, F, G, respectively, at 37° C. for 1 h. The unbound antibodies were removed by washing three time with PBS, and then HRP-conjugated goat anti-mouse IgG1 was added at 37° C. for 30 minutes. After washing three times with PBS, TMB substrate buffer was added for 10 minutes and then the reaction was stopped by adding 2N $H_2SO_4$. The values of optical density were recorded in a ELISA plate reader with a dual wavelength at 450 nm/650 nm.

The OD value in the absence of a peptide as a maximum binding of CTB003 to TRAIL-R2. The competitive inhibition of various concentrations of a peptide to the binding of CTB003 to TRAIL-R2 was calculated as a percentage of maximum binding.

Figure 19:
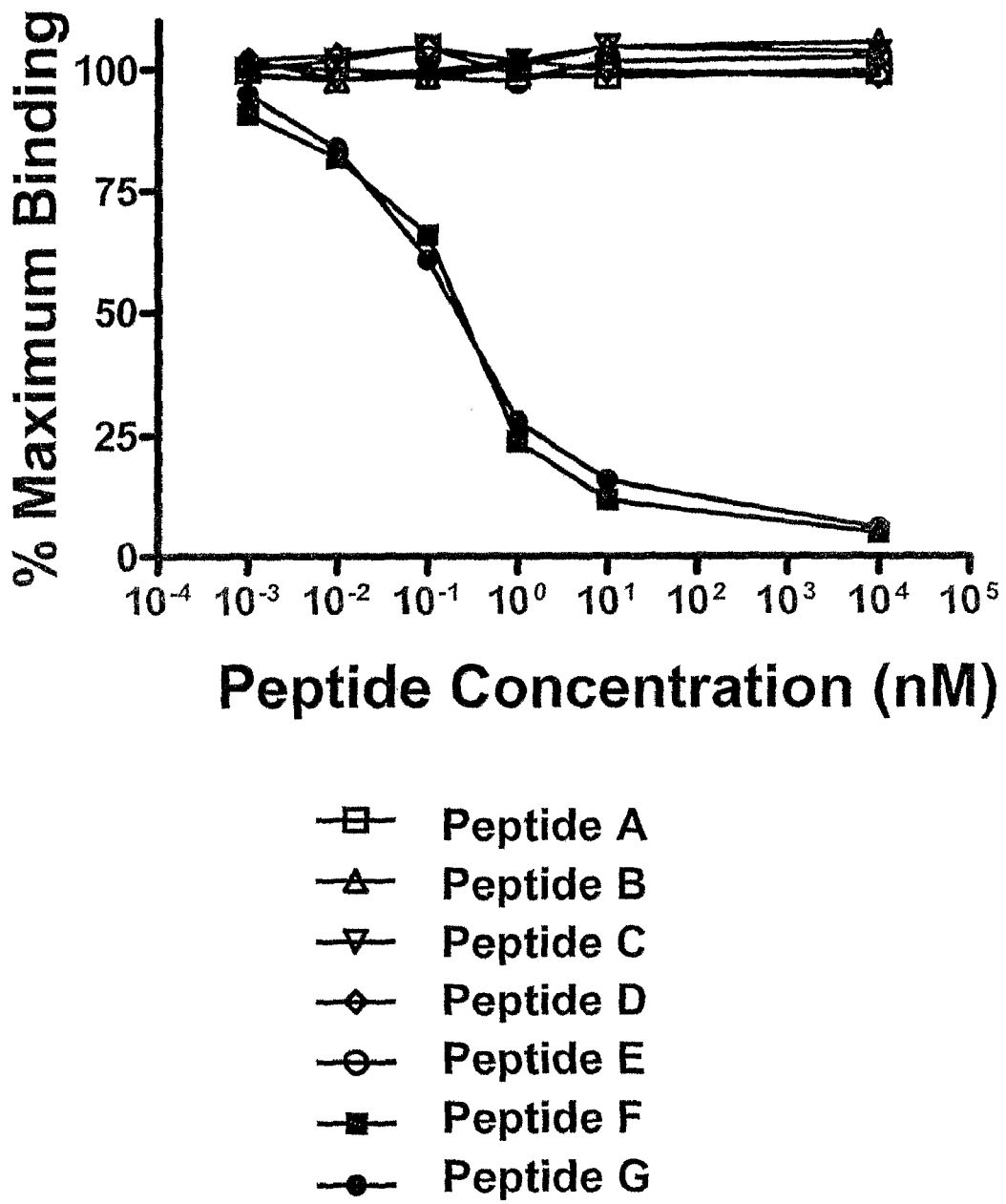
FIG. 19. Graph showing the analysis of antigenic epitope of TRAIL-R2 recognized by CTB003. The polypeptide inhibition assay was used to determine the epitope recognized by CTB003 in TRAIL-R2. ELISA plate was coated with TRAIL-R2-Fc fusion protein, and incubated with a series of polypeptide (A-G) encoding the different portions of the extracellular domain of TRAIL-R2. The data are expressed as the percent (%) maximum binding of binding of CTB003 to TRAIL-R2 observed as a function of peptide concentration (nM).

3. Results:

As shown in FIG. 19, unlike the other peptides tested (i.e., peptides A-E), peptide F and peptide G inhibited the binding of CTB003 to TRAIL-R2 in a dose-dependent manner. Therefore, an epitope recognized by CTB003 locates in a sequence between aa 163 to aa 211 of TRAIL-R2.

4. Synthesis of Polypeptides Encoding the Extracellular Domain of TRAIL-R2 and TRAIL-R1.

To further confirm the epitope of CTB003, the amino acid sequence homology of the extracellular domain of TRAIL-R1 and TRAIL-R2 were compared. A highly homologous region was identified between aa 167 to aa 182 of TRAIL-R2 and aa 218 to aa 233 of TRAIL-R1 but not in a corresponding region of TRAIL-R3 and TRAIL-R4 (FIG. 31). Therefore, it was hypothesized that the epitope recognized by CTB003 in both TRAIL-R1 and TRAIL-R22: might locate in this region. To test this hypothesis a peptide H and a peptide I were synthesized as follows:

```
                                          (SEQ ID NO.: 46)
Peptide H.  TRAIL-R2 (aa167-aa182) VGDCTPWSDIECVHKE (SEQ ID NO.: 45)
Peptide I.  TRAIL-R1 (aa218-aa233) VKDCTPWSDIECVHKE
```

5. Competitive Inhibition ELISA.

ELISA plate was coated with 1 μg/ml TRAIL-R1 or TRAIL-R2-Fc fusion protein in PBS at 4° C. overnight. After washing three times with PBS, the plate was blocked with 3% BSA PBS at room temperature for one hour. 1 μg/ml CTB003 was added with various concentrations of polypeptide H and polypeptide I, respectively, at 37° C. for 1 h. The unbound antibodies were removed by washing three time with PBS, and then HRP-conjugated goat anti-mouse IgG1 was added at 37° C. for 30 minutes. After washing three times with PBS, TMB substrate buffer was added for 10 minutes and then the reaction was stopped by adding 2N $H_2SO_4$. The values of optical density were recorded in a ELISA plate reader with a dual wavelength at 450 nm/650 nm. The OD value in the absence of a peptide as a maximum binding of CTB003 to TRAIL-R1 or TRAIL-R2. The competitive inhibition of various concentrations of a peptide to the binding of CTB003 to TRAIL-R2 was calculated as a percentage of maximum binding.

6. Results:

As shown in FIG. 20, panel A, both peptide H or I inhibited the binding of CTB003 to TRAIL-R1 in a dose-dependent manner. Likewise, as shown in FIG. 20, panel B, both peptide H or I inhibited the binding of CTB003 to TRAIL-R2 in a dose-dependent manner. Therefore, an epitope recognized by CTB003 locates in a sequence between aa 167 to aa 182 of TRAIL-R2 and aa 218 to aa 233 of TRAIL-R1 (i.e., region of sequence homology between TRAIL-R1 and TRAIL-R2). To the Applicant's knowledge this is the first identification of this region as an epitope common to TRAIL-R1 and TRAIL-R2 polypeptides, which can be targeted for generation of an agonistic antibody to induce apoptosis of cancer cells expressing either TRAIL-R1 or TRAIL-R2 or both.

Example 13

Preparation and Characterization of Mouse Human Chimeric CTB003, CTB006 and CTB007 TRAIL Receptor-Binding Agents of the Invention I. Preparation of Mouse-Human Chimeric CTB003, CTB006 and CTB007 TRAIL Receptor-Binding Agents Murine variable-region genes. The heavy and light-chain variable regions used for construction of a mouse-human chimeric antibody were derived from a mouse-mouse hybridoma CTB003 (CGMCC NO. 1665), CTB006 (CGMCC NO. 1691) or CTB007 (CGMCC NO. 1733). These heavy- and light-chain clones were used as templates for PCR mutagenesis to incorporate restriction sites for cloning into the TA cloning vector.

Cloning of human IgG1 constant-region cDNAs. The cDNA clones encoding human IgG1 heavy- and light chain constant region were cloned by RT-PCR using total RNA isolated from mononuclear cells of human peripheral blood.

After the sequences were confirmed, the cDNAs were cloned into an expression vector (pcDNAIII).

Construction of the chimeric CTB003, CTB006 and CTB007 expression vectors. The cloned heavy- and light-chain variable-region cDNAs derived from the hybridomas as described above were used as templates for PCR with primers that incorporate restriction sites for ligation into the pcDNAIII expression vector in which the cDNA for human IgG1 heavy- or light chain constant region had been incorporated in the correct reading frame. The PCR products were first ligated into pCRII, cloned in E. coli, and sequenced again to ensure that no mutations occurred during introduction of the new restriction sites. The light- and heavy-chain variable-region products were cloned into the DraIII and BsiWI (kappa light-chain) and MluI and NheI (gamma 1 heavy-chain) sites of the Ig expression vector, respectively. The resulting completed expression vectors were named pcDNAIII-hCTB003LC, pcDNAII-hCTB003LC, pcDNAIII-hCTB006LC, pcDNAIII-hCTB0061-LC, pcDNAIII-hCTB007LC, pcDNAIII-hCTB0074C. These cDNA clones and expression vectors were deposited to China General Microbiological Culture Collection Center (GCMCC) on Apr. 13, 2007 as detailed above.

Transfection of CHO cells for expression of the chimeric antibodies and selection of antibody-producing clones. The paired plasmids: pcDNAIII-hCTB003LC and pcDNAIII-hCTB003HC; pcDNAIII-hCTB006LC and pcDNAIII-hCTB006HC; or pcDNAIII-hCTB007LC and pcDNAIII-hCTB007HC, were separately introduced into Chinese hamster ovary (CHO) cells by DNA-liposome-mediated transfection. Briefly, 2 µg of plasmid DNA was mixed with 8 µl of Lipofectamine (Gibco, Gaithersberg, Md.) in a final volume of 1 ml of serum-free medium. The transfection mixture was allowed to incubate for 5 h at 37° C. The cells were washed, fresh medium was added, and the cells were incubated for 48 h. The cells were harvested, resuspended in medium containing G418 (400 µg/ml; Gibco), and plated at different dilutions in 12-well plates. Chimeric-antibody production by cells grown under antibiotic selection was measured by enzyme-linked immunosorbent assay (ELISA). ELISA plates are coated with either 2 µg of TRAIL-R1-Fc or TRAIL-R2-Fc fusion protein and binding of mAbs (i.e., monoclonal antibodies) in culture supernatants were detected with a HRP-conjugated goat anti-human kappa-light-chain-specific antibody (SoutherBiotech, Birmingham, Ala.).

Purification of chimeric antibodies. Chimeric IgG antibodies were purified from tissue culture supernatants by protein A affinity chromatography (Pharmacia). 500 ml culture supernatant from transfected CHO cells was passed through a protein A-sepharose column at a flow rate of 2 ml per minute. After culture supernatant was passed through, the column was washed with 50 ml PBS. The protein was eluted with elution buffer (0.1 M glycine (pH 2.4), 0.15 M NaCl). The optical density of each eluted fraction (1 ml) was measured at OD280 nm. The fractions with OD280>0.1 were collected. After addition of 100 µl of neutralization buffer (1M Tris-HCL pH8.5), the eluates were placed separately in dialysis tubing, and the eluates dialyzed against 1 liter of PBS (pH 7.5) at 4° C. The dialysis buffer was changed twice. The purified protein was concentrated to 1 mg/ml, sterilized and stored at −4° C. until use. The purity of human chimeric antibodies was determined to greater than 95% by 10% SDS-PAGE.

II. Binding Characteristics of Chimeric CTB003, CTB006 and CTB007 to TRAIL Receptors The binding activity of the chimeric CTB003, CTB006 and CTB007 to TRAIL receptor were compared to their parental murine antibodies by ELISA. ELISA plate was coated with the following recombinant proteins at 1 µg/ml in PBS at 4° C. overnight: 1. TRAIL-R1 and TRAIL-R2 hetero-dinner antigen, 2. TRAIL-R1-Fc fusion antigen, 3. TRAIL-R2-Fc fusion antigen, 4. TRAIL-R3-Fc fusion antigen, 5. TRAIL-R4-Fc fusion antigen, or BSA as negative control. After washing three times with PBS, the plate was blocked with 3% BSA PBS at room temperature for one hour. The plate was incubated with various concentrations of purified the chimeric or the parental murine antibodies at 37° C. for one hour. The unbound antibodies were removed by washing three time with PBS, and then HRP-conjugated goat anti-mouse IgG1 for murine antibodies or HRP-conjugated goat anti-human kappa for human chimeric antibodies was added at 37° C. for 30 minutes. After washing three times with PBS, TMB substrate buffer was added for 10 minutes and then the reaction was stopped by adding 2N $H_2SO_4$. The values of optical density were recorded in a ELISA plate reader with a dual wavelength at 450 nm/650 nm.

Figure 21:
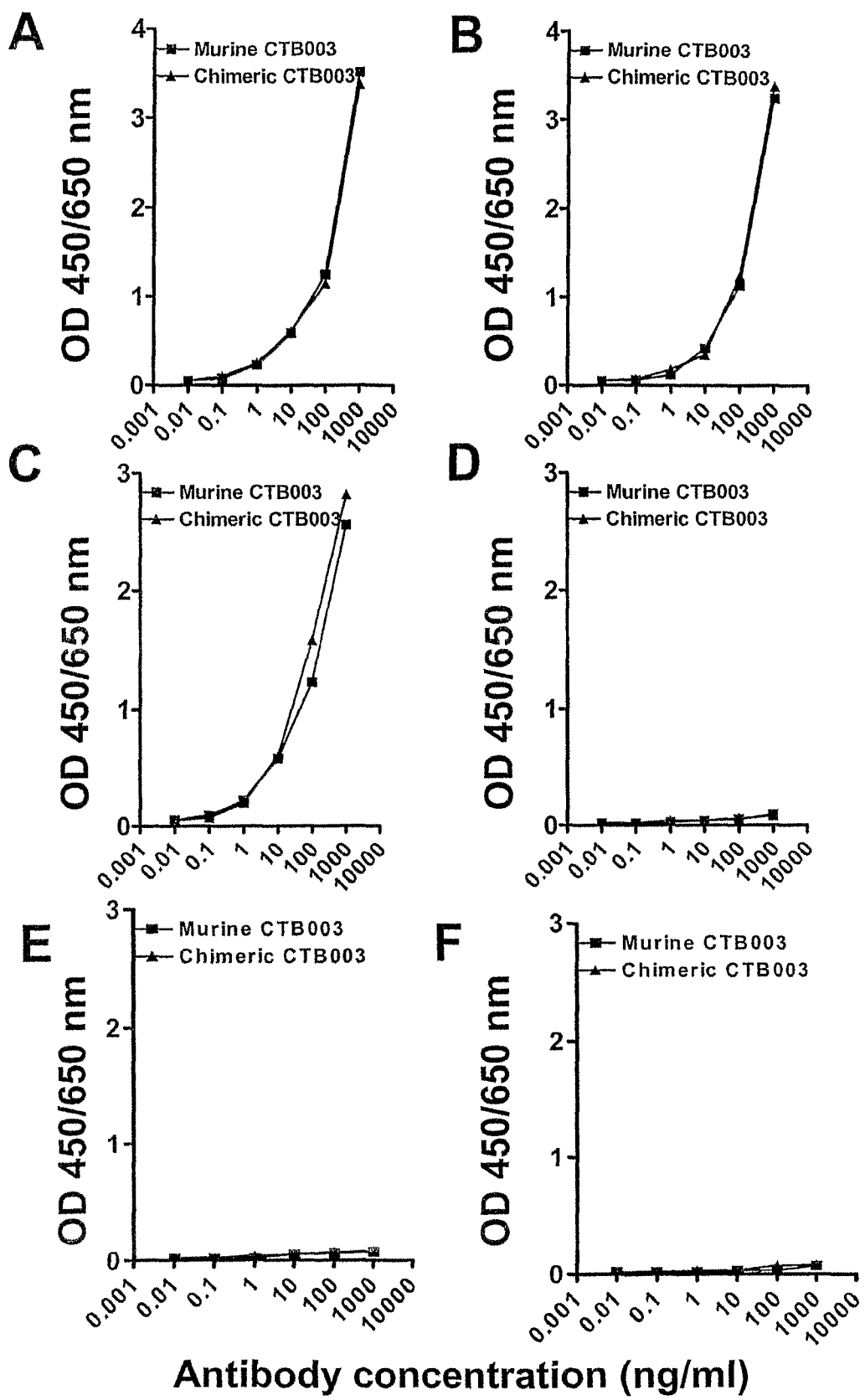
FIG. 21. Graphs showing comparisons of the binding characteristics of CTB003 (murine) and hCTB003 (humanized chimeric) TRAIL receptor-binding agents. A recombinant human IgG1-Fc fusion protein containing the extracellular domain of TRAIL-R1/TRAIL-R2 heterodimer antigen (panel A), TRAIL-R1-Fc (panel B), TRAIL-R2-Fc (panel C), TRAIL-R3-Fc (panel D), TRAIL-R4-Fc (panel E), or BSA (control; panel F) were immobilized onto an ELISA plate, and incubated with various concentrations (ng/ml) of CTB003 (murine) or hCTB003 (humanized chimeric; a.k.a., chimeric CTB003). After reaction with HRP-conjugated goat anti-mouse IgG1 for CTB003 (murine), or HRP-conjugate goat anti-human kappa, a TMB substrate was added to reveal color reaction. The binding capacity was determined by the OD values of CTB003 or hCTB003 to each protein. The data in each panel (A-F) are expressed as the OD 450/650 as a function of antibody concentration (ng/ml) (i.e., CTB003 concentration (ng/ml) or chimeric CTB003 concentration (ng/ml)).

The chimeric CTB003 exhibited a dose-dependent binding to TRAIL-R1/TRAIL-R2 heterodimer antigen (FIG. 21, panel A) as well as TRAIL-R1-Fc (FIG. 21, panel B) or TRAIL-R2-Fc (FIG. 21, panel C) fusion antigen, and the binding kinetics virtually indistinguishable from the binding characteristics observed for the parental murine CTB003. In the ranges of tested antibody concentrations, the chimeric CTB003 does not react with TRAIL-R3-Fc (FIG. 21, panel D), TRAIL-R4-Fc (FIG. 21, panel E) fusion antigen or BSA (FIG. 21, panel F).

Figure 22:
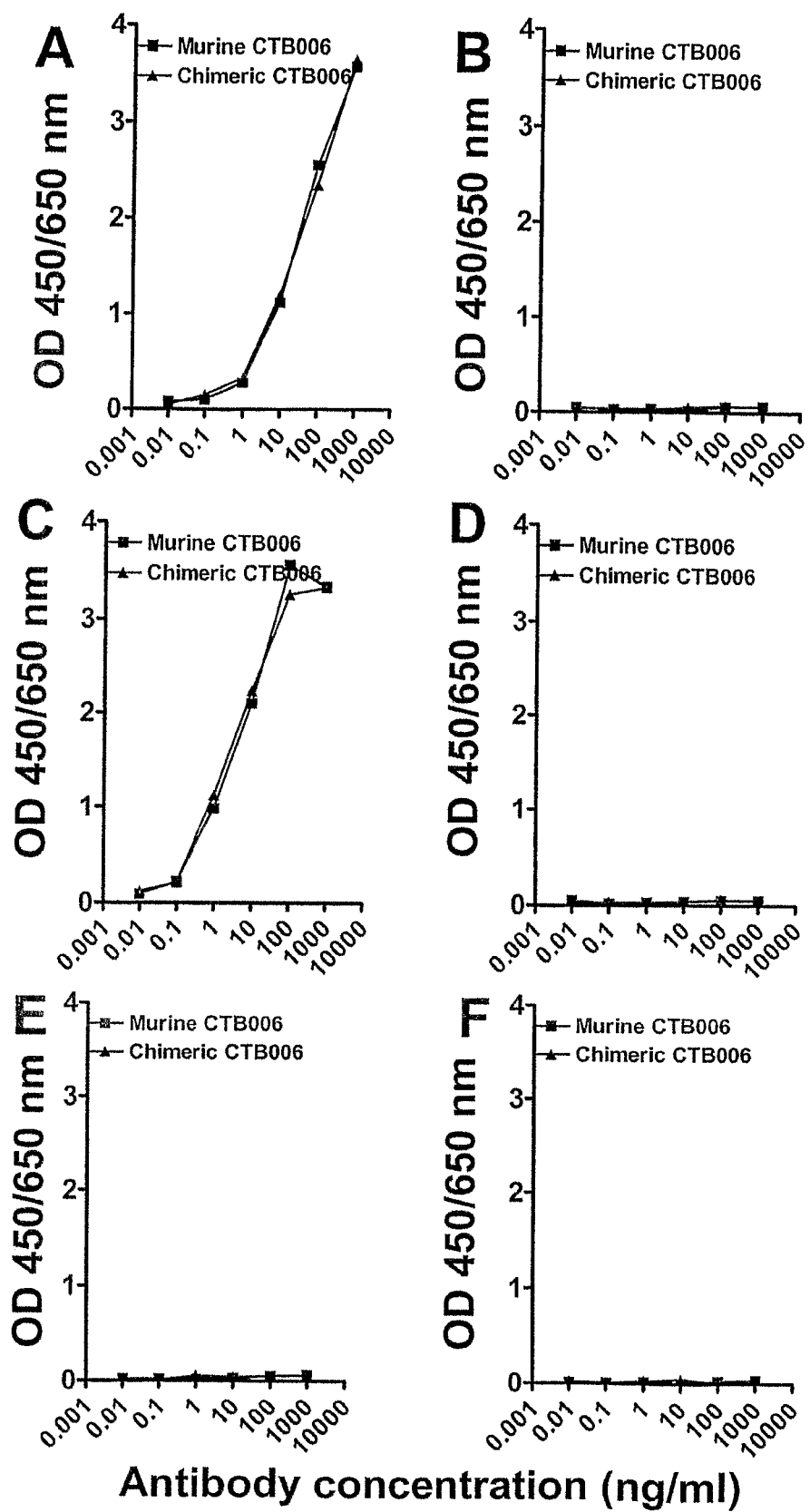
FIG. 22. Graphs showing comparisons of the binding characteristics of CTB006 (murine) and hCTB006 (humanized chimeric; a.k.a., chimeric CTB006) TRAIL receptor-binding agents. A recombinant human IgG1-Fc fusion protein containing the extracellular domain of TRAIL-R1/TRAIL-R2 heterodimer antigen (panel A), TRAIL-R1-Fc (panel B), TRAIL-R2-Fc (panel C), TRAIL-R3-Fc (panel D), TRAIL-R4-Fc (panel E), or BSA (control; panel F) were immobilized onto an ELISA plate, and incubated with various concentrations (ng/ml) of CTB006 (murine) or hCTB006 (humanized chimeric). After reaction with HRP-conjugated goat anti-mouse IgG, for CTB006 (murine), or HRP-conjugate goat anti-human kappa, a substrate was added to reveal color reaction. The binding capacity was determined by the OD values of CTB006 or hCTB006 to each protein. The data in each panel (A-F) are expressed as the OD 450/650 as a function of antibody concentration (ng/ml) (i.e., CTB006 concentration (ng/ml) or chimeric CTB006 concentration (ng/ml)).
Figure 23:
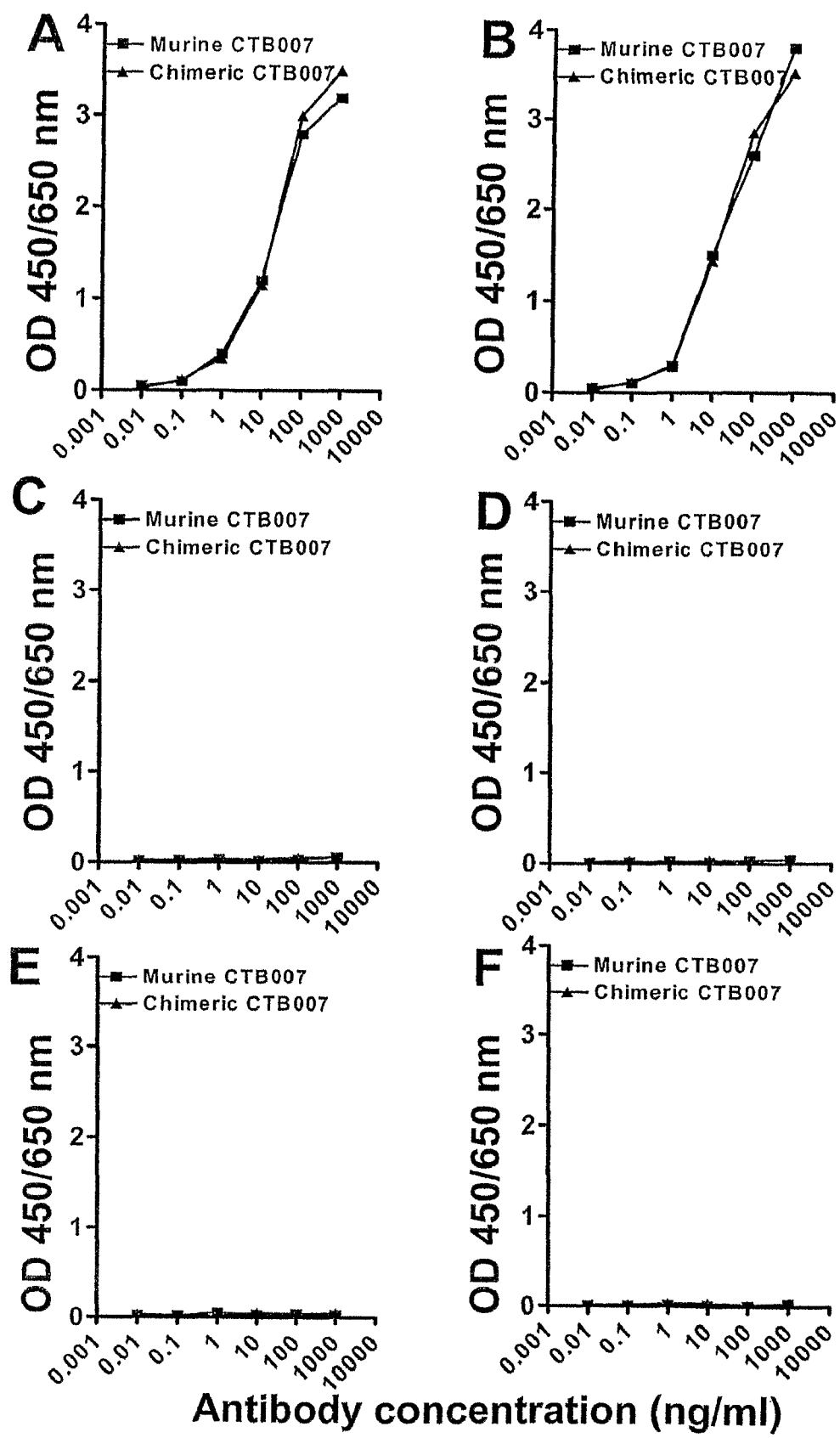
FIG. 23. Graphs showing comparisons of the binding characteristics of CTB007 (murine) and hCTB007 (humanized chimeric; a.k.a., chimeric CTB007) TRAIL receptor-binding agents. A recombinant human IgG1-Fc fusion protein containing the extracellular domain of TRAIL-R1/TRAIL-R2 heterodimer antigen (panel A), TRAIL-R1-Fc (panel B), TRAIL-R2-Fc (panel C), TRAIL-R3-Fc (panel D), TRAIL-R4-Fc (panel E), or BSA (control; panel F) were immobilized onto an ELISA plate, and incubated with various concentrations (ng/ml) of CTB007 (murine) or hCTB007 (humanized chimeric). After reaction with HRP-conjugated goat anti-mouse IgG, for CTB003 (murine), or HRP-conjugate goat anti-human kappa, a substrate was added to reveal color reaction. The binding capacity was determined by the OD values of CTB007 or hCTB007 to each protein. The binding capacity was determined by the OD values of CTB007 or hCTB007 to each protein. The data in each panel (A-F) are expressed as the OD 450/650 as a function of antibody concentration (ng/ml) (i.e., CTB007 concentration (ng/ml) or chimeric CTB007 concentration (ng/ml)).

Characterization of chimeric CTB006 and chimeric CTB007 are summarized in FIGS. 22 and 23, respectively. Binding characteristics of the humanized chimeric forms of these binding agents were also essentially indistinguishable from their murine parental counterparts. That is, the chimeric CTB006 exhibited a dose-dependent binding to TRAIL-R1/TRAIL-R2 heterodimer antigen (FIG. 22, panel A) as well as TRAIL-R2-Fc (FIG. 22, panel C) fusion antigen, and the binding kinetics are very similar to those of the parental murine CTB006. In the ranges of tested antibody concentrations, the chimeric CTB006 does not react with TRAIL-R1-Fc (FIG. 22, panel B), TRAIL-R3-Fc (FIG. 22, panel D), TRAIL-R4-Fc (FIG. 22, panel E) fusion antigen or BSA (FIG. 22, panel F).

The chimeric CTB007 exhibited a dose-dependent binding to TRAIL-R1/TRAIL-R2 heterodimer antigen (FIG. 23, panel A) as well as TRAIL-R1-Fc (FIG. 23, panel B) fusion antigen, and the binding kinetics are very similar to those of the parental murine CTB007. In the ranges of tested antibody concentrations, CTB007 does not react with TRAIL-R2-Fc (FIG. 23, panel C), TRAIL-R3-Fc (FIG. 23, panel D), TRAIL-R4-Fc (FIG. 23, panel E) fusion antigen or BSA (FIG. 23, panel F).

Similar to the study described in Example 12, competitive inhibition ELISA was performed in reciprocal experiments with TRAIL-R1 and TRAIL-R2 fusion polypeptides to further map the epitope specificity of the human chimer CTB003. As shown in FIG. 24, panel A, both peptide H or I inhibited the binding of humanized chimeric CTB003 to TRAIL-R1 in a dose-dependent manner. Likewise, as shown in FIG. 20, panel B, both peptide H or I inhibited the binding of humanized chimeric CTB003 to TRAIL-R2 in a dose-dependent manner. Therefore, an epitope recognized by humanized chimeric CTB003 locates in a sequence between aa 167 to aa 182 of TRAIL-R2 and aa 218 to aa 233 of TRAIL-R1 (i.e., region of sequence homology between TRAIL-R1 and TRAIL-R2). Significantly, the binding characteristics of both humanized chimeric CTB003 binding agent essentially indistinguishable from the murine CTB003.

To determine if these binding agents shared the same biological properties, in vitro apoptosis-inducing activity of the chimeric CTB003 was compared with murine CTB003 in a number of cancer cell lines as described below.

III. In Vitro Apoptosis-Inducing Activity of the Chimeric CTB003, CTB006 and CTB007

A panel of human cancer cell lines were used for evaluation of in vitro apoptosis-inducing activity of the chimeric CTB003, CTB006 and CTB007, including: a human breast cancer cell line, MDA231; a human colon cancer cell line, Colo205; a human pancreatic cancer cell line, MIAcapa; a human ovarian cancer cell line, CaOvc 3; a human prostate cancer cell line, Du145; and a human lung cancer cell line, H2122.

ATPLite assay was used to determine cell viability and $IC_{50}$ of each antibody. 1,000 target cells per well were cultured in 96-well plates in the presence of seven concentrations of 10-fold diluted chimeric antibody or their correspondent parental murine antibody with the highest concentration at 1000 ng/ml and the lowest concentration at 0.01 ng/11 After culture at 37° C. overnight cell viability was determined using the ATPLite kit according to the manufacturer's instructions (Packard Instruments, Meriden, Conn.): add 50 µl of cell lysis buffer and then 50 µl of substrate buffer. The reaction was counted in a luminescent reader. Cell viability was calculated as (cpm of treated cells/cmp of control cells)×100%. A dose-dependent killing curve is generated. The $IC_{50}$ was calculated by linear regression. The results are presented as MEAN±SD of triplicated cultures.

dose-response relationships to their corresponding parental murine antibodies. These results indicate that all engineered chimeric antibodies retain the apoptosis-inducing activity of their murine parental antibodies.

The apoptosis-inducing activity of human chimeric and murine antibodies is presented as the $IC_{50}$ in Table 8, which demonstrate that the recombinant chimeric CTB003, CTB006 and CTB007 exhibit a very similar $IC_{50}$ to their murine parental antibodies in all tested human cancer cells. Based on the common binding characteristics and in vitro biological responses observed between humanized chimeric CTB003 and murine CTB003 it is asserted that one ordinary skill would recognize that the humanized chimeric CTB003 would also yield inhibition of tumor growth in vivo like the murine CTB003. As such, the binding agents of the invention (e.g., hCTB003) are useful in methods to inhibit tumor growth when administered in an effective amount to a subject (including a human subject) in need thereof.

Example 14

Pre-Clinical Toxicity Study of CTB003 in Non-Human Primate

The systemic toxicity of CTB003 was evaluated in non-human primate at the National Beijing Center for Drug Safety Evaluation and Research, Beijing of China. 4-5 month-old, male rhesus monkey with a body weight of 4.5 kg, was

TABLE 8

Comparison of the killing activity of the chimeric antibody with the parent murine antibody

| | IC50 (ng/ml) | | | | | |
|---|---|---|---|---|---|---|
| | CTB003 | | CTB006 | | CTB007 | |
| Tumor lines | chimeric | murine | chimeric | murine | chimeric | murine |
| MDA231 (Human Breast Cancer) | 4.2 ± 1.2 | 3.8 ± 0.8 | 1.5 ± 0.5 | 2.2 ± 0.8 | 7.5 ± 1.1 | 8.2 ± 1.3 |
| Colo205 (Human Colorectal Cancer) | 6.6 ± 1.3 | 7.1 ± 1.8 | 6.2 ± 1.3 | 5.8 ± 0.9 | 5.9 ± 1.2 | 6.2 ± 0.9 |
| MIAcap (Human Pancreatic Cancer) | 12.5 ± 2.1 | 13.2 ± 2.3 | 10.1 ± 1.4 | 9.5 ± 2.1 | 8.8 ± 1.5 | 9.5 ± 1.1 |
| Carov 3 (Human Ovarian Cancer) | 22.5 ± 1.5 | 24.6 ± 2.3 | 18.5 ± 1.6 | 17.4 ± 2.0 | 31.6 ± 3.5 | 29.5 ± 3.0 |
| Du145 (Human Prostate Cancer) | 39.8 ± 4.2 | 25.3 ± 2.4 | 52.3 ± 6.5 | 55.6 ± 8.8 | 28.6 ± 3.2 | 31.2 ± 2.6 |
| H-2122 (Human Lung Cancer) | 29.1 ± 2.5 | 28.5 ± 2.6 | 42.1 ± 5.1 | 44.1 ± 6.5 | 22.5 ± 2.1 | 25.4 ± 2.3 |

Figure 26:
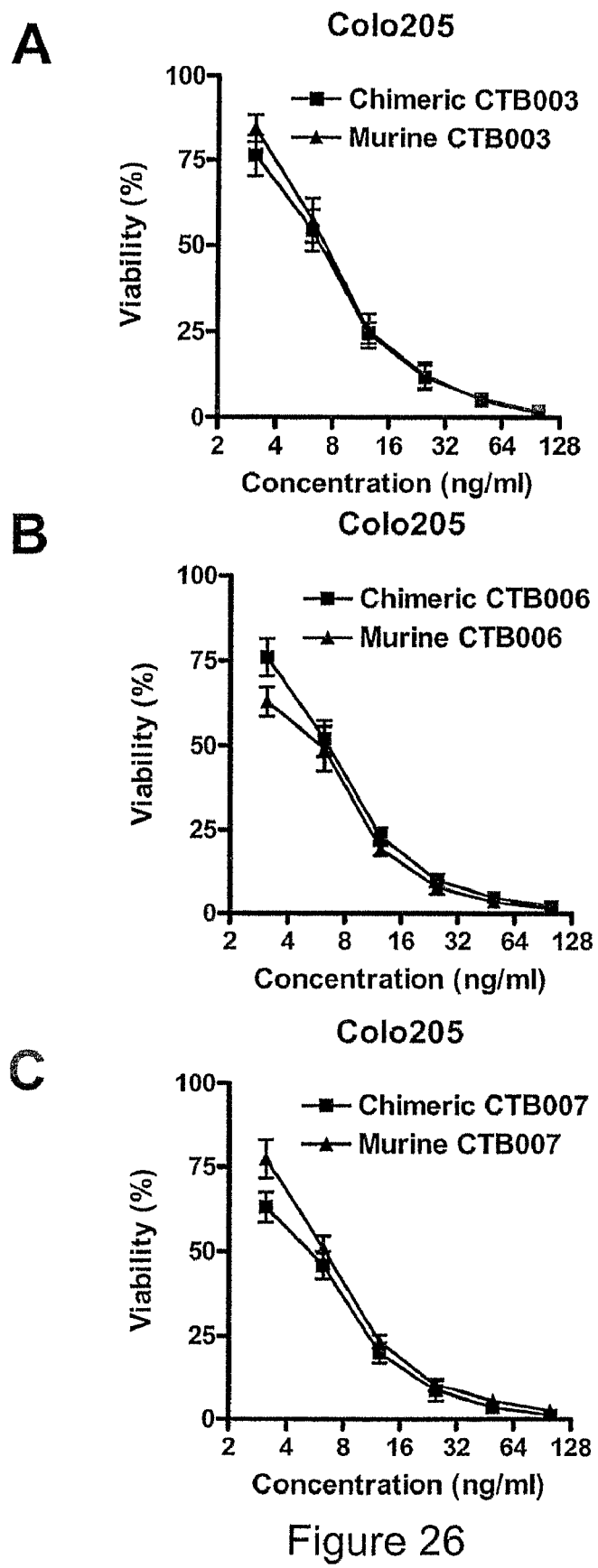
FIG. 26. Graphs comparing the effect of murine and humanized chimeric TRAIL receptor-binding agents of the invention on human colorectal cancer cell line Colo205 growth in vitro. Panel A is a graph of cell viability (%) as a function of the concentration (ng/ml) of either CTB003 (murine) or hCTB003 (humanized chimeric a.k.a., chimeric CTB003). Panel B is a graph of cell viability (%) as a function of the concentration (ng/ml) of either CTB006 (murine) or hCTB006 (humanized chimeric a.k.a., chimeric CTB006). Panel C is a graph of cell viability (%) as a function of the concentration (ng/ml) of either CTB007 (murine) or hCTB007 (humanized chimeric a.k.a., chimeric CTB007).
Figure 27:
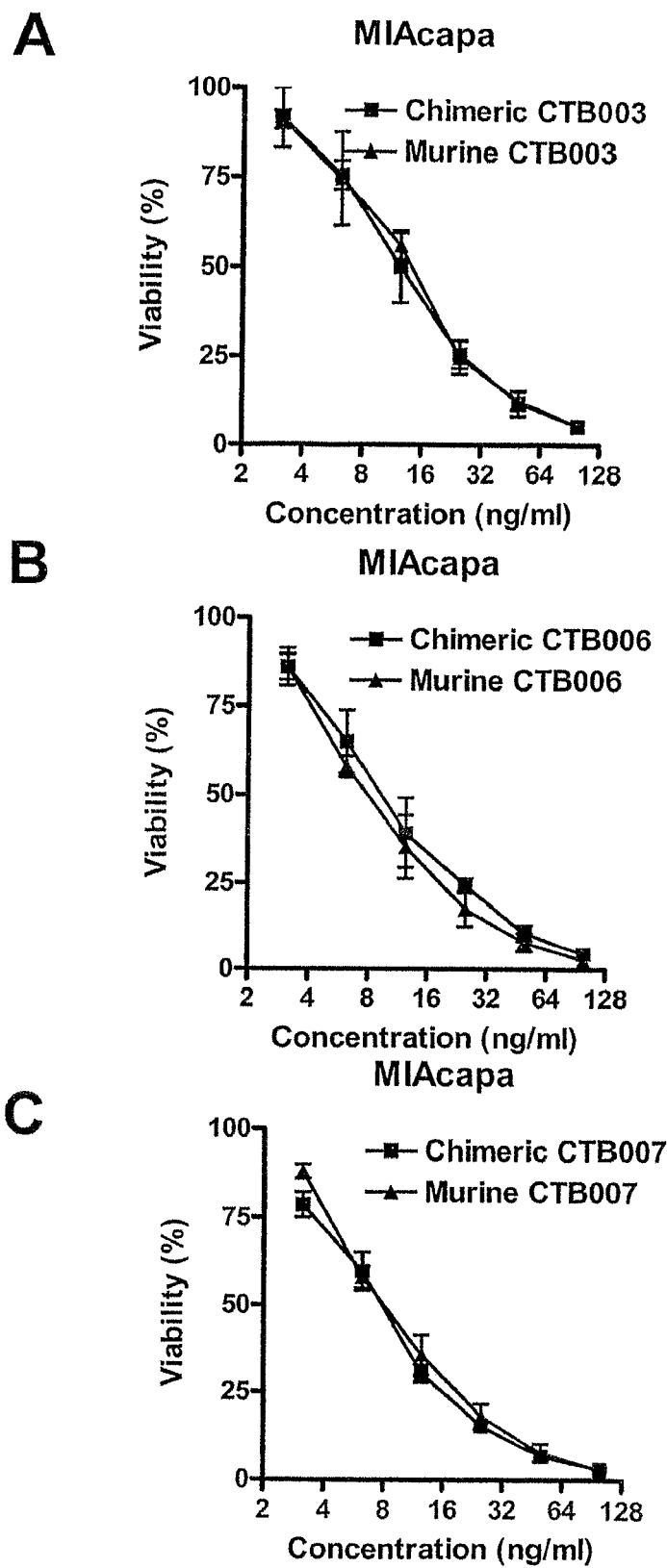
FIG. 27. Graphs comparing the effect of murine and humanized chimeric TRAIL receptor-binding agents of the invention on human pancreatic cancer cell line MIAcapa growth in vitro. Panel A is a graph of cell viability (%) as a function of the concentration (ng/ml) of either CTB003 (murine) or hCTB003 (humanized chimeric a.k.a., chimeric CTB003). Panel B is a graph of cell viability (%) as a function of the concentration (ng/ml) of either CTB006 (murine) or hCTB006 (humanized chimeric a.k.a., chimeric CTB006). Panel C is a graph of cell viability (%) as a function of the concentration (ng/ml) of either CTB007 (murine) or hCTB007 (humanized chimeric a.k.a., chimeric CTB007).
Figure 29:
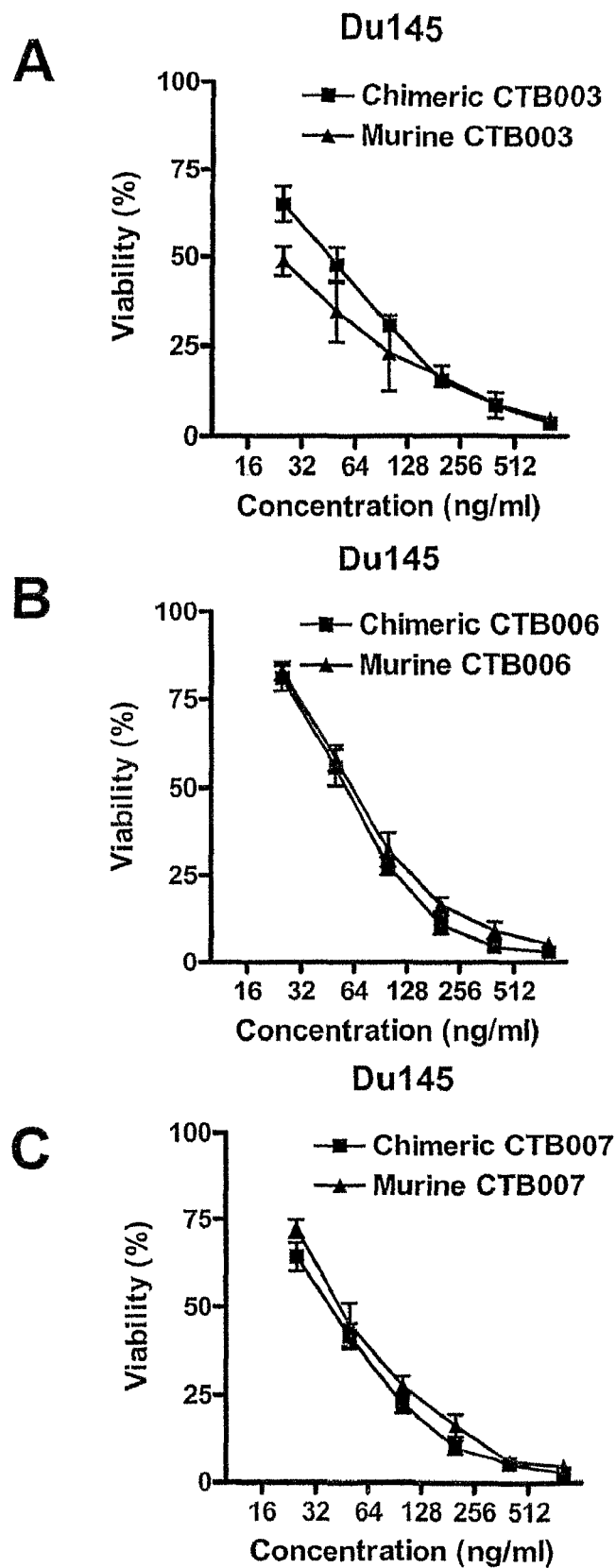
FIG. 29. Graphs comparing the effect of murine and humanized chimeric TRAIL receptor-binding agents of the invention on human prostate cancer cell line Du145 growth in vitro. Panel A is a graph of cell viability (%) as a function of the concentration (ng/ml) of either CTB003 (murine) or hCTB003 (humanized chimeric a.k.a, chimeric CTB003). Panel B is a graph of cell viability (%) as a function of the concentration (ng/ml) of either CTB006 (murine) or hCTB006 (humanized chimeric a.k.a., chimeric CTB006)$_2$ Panel C is a graph of cell viability (%) as a function of the concentration (ng/ml) of either CTB007 (murine) or hCTB007 (humanized chimeric a.k.a, chimeric CTB007).
Figure 30:
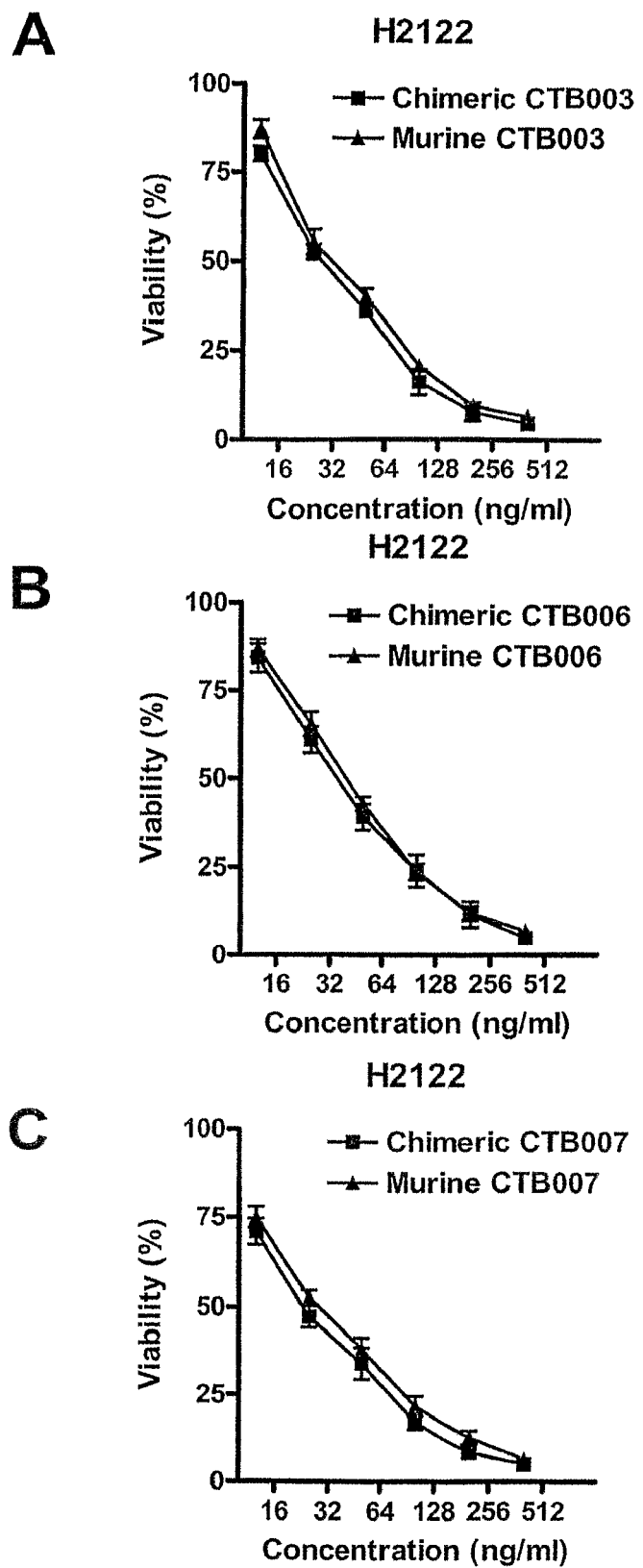
FIG. 30. Graphs comparing the effect of murine and humanized chimeric TRAIL receptor-binding agents of the invention on human lung cancer cell line H2122 growth in vitro. Panel A is a graph of cell viability (%) as a function of the concentration (ng/ml) of either CTB003 (murine) or hCTB003 (humanized chimeric a.k.a., chimeric CTB003). Panel B is a graph of cell viability (%) as a function of the concentration (ng/ml) of either CTB006 (murine) or hCTB006 (humanized chimeric a.k.a, chimeric CTB006). Panel C is a graph of cell viability (%) as a function of the concentration (ng/ml) of either CTB007 (murine) or hCTB007 (humanized chimeric a.k.a, chimeric CTB007).
Figure 32:
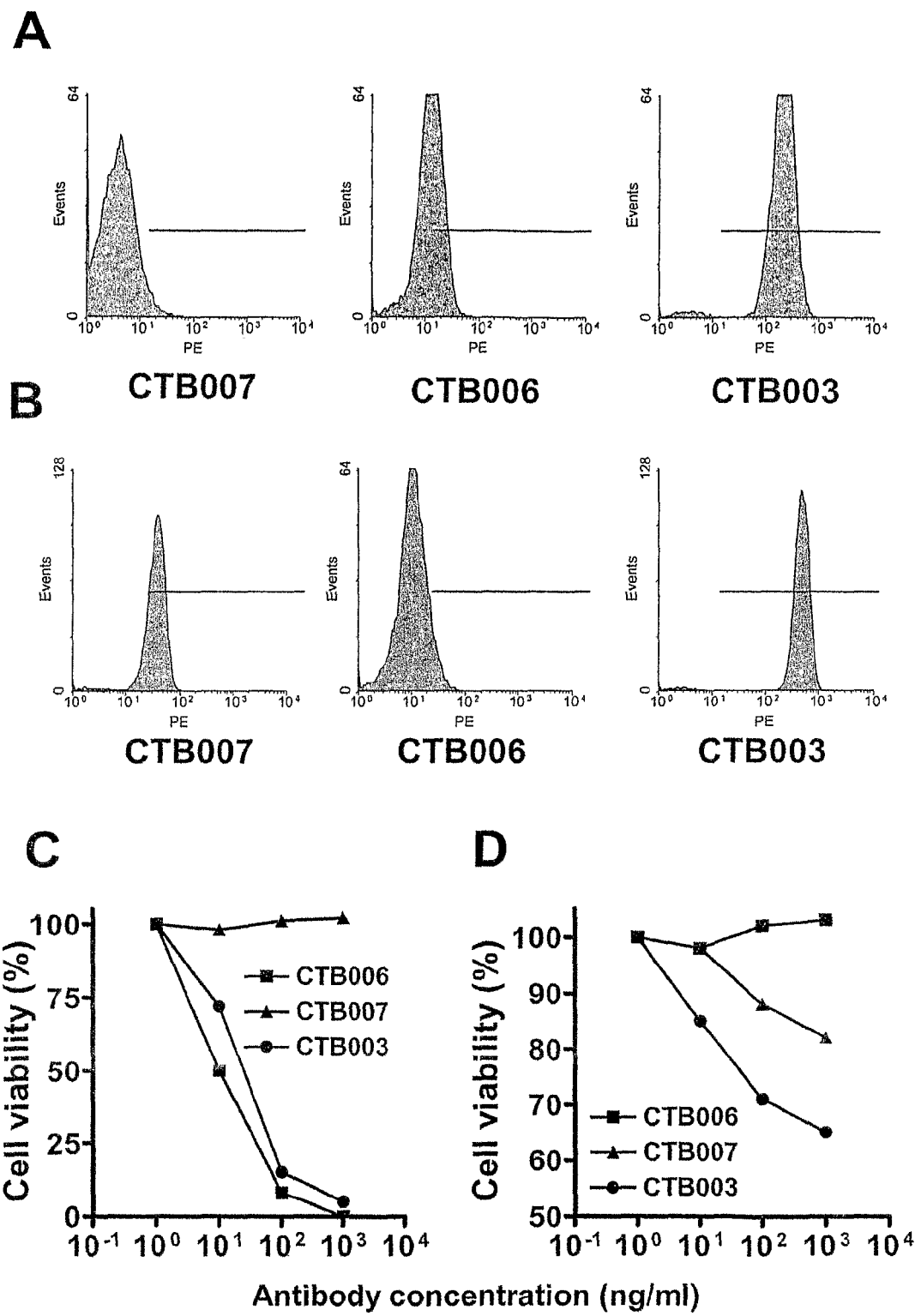
FIG. 32. Graphs showing the binding and apoptosis-inducing activity of CTB003 in tumor cells that differentially express TRAIL-R1 and TRAIL-R2. Panel A shows graphs which express the data from flow cytometry analysis of cell surface binding of CTB003, CTB006 and CTB007 to Jurkat cells. Panel B shows graphs which express the data from flow cytometry analysis of cell surface binding of CTB003, CTB006 and CTB007 to Ramos cells. Panel C is a graph showing the apoptosis-inducing activity of CTB003, CTB006 and CTB007 in Jurkat cells. Panel D is a graph showing the apoptosis-inducing activity of CTB003, CTB006 and CTB007 in Ramos cells. The data in panel C and panel D are expressed as the cell viability (%) as a function of antibody concentration (ng/ml).

All six tested human cancer cell lines, including MDA231 human breast cancer cells (FIG. 25), Colo205 human colon cancer cells (FIG. 26), MIAcapa human pancreatic cancer cells (FIG. 27), Caov3 human ovary cancer cells (FIG. 28), Du145 human prostate cancer cells (FIG. 29), and H2122 human lung cancer cells were equally susceptible to apoptosis induced by both murine CTB003 and human chimeric CTB003 (Panel A), or murine CTB006 and chimeric CTB006 (panel B) or murine CTB007 and chimeric CTB007 (panel C). The recombinant chimeric antibodies exhibited similar intravenously infused with CTB003 at a dose of 40 mg/kg. CTB003 was dissolved in PBS at 3 mg/ml, and total infusion volume is 20 ml per kg body weight. The infusion rate was 5 drops per minute and the infusion was completed within 90 minutes. The general physiological condition of treated animal was examined every day from 7 days before treatment until 15 days after treatment. Body weight, body temperature, EKG, hematology parameters, blood biochemistry parameters were examined at 7 days before treatment and at day 0, 3, 7, and 14 after treatment.

After treatment the general physical condition of animal appeared to be normal. Body weight was slightly increased and body temperature remained within normal range (Table 9).

TABLE 9

Effect of intravenous administration of CTB003 on body weight and body temperature

| Time (day) | Body weight (kg) | Body temperature (° C.) |
|---|---|---|
| −7 | 4.9 | 38.2 |
| 1 | 5.1 | 38.7 |
| 4 | 5.1 | 38.6 |
| 8 | 5.4 | 38.8 |
| 15 | 5.4 | 38.0 |

There was no significant alteration of all tested hematology parameters after treatment (Table 10), and biochemistry measurements remain normal after treatment (Table 11). The results demonstrate that systemic administration of CTB003 at a 40 mg/kg is well-tolerated in the rhesus monkey.

TABLE 10

Effect of intravenous administration of CTB003 on hematology parameters.

| Days | RBC($10^{12}$/L) | Hb(g/l) | Hct(%) | MCV(fl) | MCH(pg) | MCHC(g/l) | RDW(%) |
|---|---|---|---|---|---|---|---|
| −7 | 5.47 | 133 | 0.423 | 77.3 | 24.3 | 315 | 13.4 |
| 1 | 5.56 | 147 | 0.430 | 76.7 | 26.2 | 342 | 12.2 |
| 4 | 5.44 | 140 | 0.423 | 77.7 | 25.7 | 331 | 12.7 |
| 8 | 5.43 | 139 | 0.417 | 76.8 | 25.6 | 333 | 12.7 |
| 15 | 5.29 | 133 | 0.405 | 76.6 | 25.1 | 328 | 12.7 |

| Days | Plat($10^9$/L) | MPV(fl) | PDW(%) | Ret %(%) | Ret#($10^9$/L) | WBC($10^9$/L) | NE |
|---|---|---|---|---|---|---|---|
| −7 | 493 | 7.4 | 15.9 | 1.24 | 0.0714 | 7.5 | 19 |
| 1 | 354 | 8.0 | 15.7 | 0.67 | 0.0397 | 8.3 | 29 |
| 4 | 374 | 8.0 | 15.6 | 0.69 | 0.0392 | 8.0 | 26 |
| 8 | 359 | 8.2 | 16.2 | 1.21 | 0.0682 | 7.8 | 17 |
| 15 | 398 | 8.1 | 15.6 | 0.85 | 0.0465 | 7.0 | 28 |

| Days | LY | MO | EO | BA | — | — | — |
|---|---|---|---|---|---|---|---|
| −7 | 71 | 8 | 1 | 1 | — | — | — |
| 1 | 63 | 3 | 5 | 0 | — | — | — |
| 4 | 67 | 3 | 4 | 0 | — | — | — |
| 8 | 69 | 3 | 11 | 0 | — | — | — |
| 15 | 64 | 2 | 6 | 0 | — | — | — |

TABLE 11

Effect of intravenous administration of CTB003 on biochemistry parameters.

| Days | ALT (U/L) | AST (U/L) | ALP (U/L) | TP (g/l) | Alb (g/l) | Tchol (mmol/l) | BUN (mmol/l) |
|---|---|---|---|---|---|---|---|
| −7 | 15 | 5 | 168 | 71.8 | 34.8 | 4.27 | 5.18 |
| 1 | 30 | 15 | 196 | 67.1 | 36.3 | 2.97 | 5.89 |
| 4 | 24 | 6 | 188 | 67.9 | 36.5 | 3.56 | 6.61 |
| 8 | 25 | 15 | 162 | 55.6 | 37.6 | 3.80 | 7.22 |
| 15 | 22 | 4 | 226 | 61.9 | 34.7 | 3.05 | 6.21 |

| Days | Ca (mmol/l) | Tbil (μmol/l) | Glu (mmol/l) | Crea (μmol/l) | CK (U/L) | Na (mmol/l) | K (mmol/l) |
|---|---|---|---|---|---|---|---|
| −7 | 2.36 | 4.4 | 3.59 | 38.7 | 88 | 138 | 4.8 |
| 1 | 2.10 | 5.4 | 3.49 | 40.4 | 123 | 141 | 4.5 |
| 4 | 2.31 | 3.4 | 4.13 | 38.0 | 79 | 144 | 5.3 |
| 8 | 2.01 | 22.7 | 5.52 | 99.1 | 157 | 140 | 4.0 |
| 15 | 2.18 | 4.4 | 3.88 | 36.5 | 86 | 141 | 4.4 |

| Days | Cl (mmol/l) | TG (mmol/l) | G-GT (U/L) | — | — | — | — |
|---|---|---|---|---|---|---|---|
| −7 | 109 | 0.47 | 55 | — | — | — | — |
| 1 | 112 | 0.21 | 70 | — | — | — | — |
| 4 | 109 | 0.28 | 70 | — | — | — | — |
| 8 | 108 | 0.16 | 69 | — | — | — | — |
| 15 | 109 | 0.17 | 66 | — | — | — | — |

The results demonstrate that systemic administration of CTB003 at a 40 mg/kg is well-tolerated in the rhesus monkey.

Example 15

Pre-Clinical Toxicity Study of CTB006 and CTB007 in Non-Human Primate

The systemic toxicity of CTB006 and 007 were evaluated in nonhuman primate at the National Beijing Center for Drug Safety Evaluation and Research, Beijing of China. 4-5 month-old, female rhesus monkeys with a body weight of 4.0-4.3 kg, was intravenously infused with CTB006 or CTB007 at a dose of 40 mg/kg. CTB006 or CTB007 were dissolved in PBS at 3 mg/ml and total infusion volume was 20 ml per kg body weight. The infusion rate was 40 drops per minute and the infusion was completed within 90 minutes. The general physiological condition of treated animal was examined every day from 7 days before treatment until 15 days after treatment. Body weight, body temperature, EKG, Haematology parameters, blood biochemistry parameters were examined at 7 days before treatment and at day 0, 3, 7, and 14 after treatment.

After treatment with either CTB006 or CTB007 the general physical condition of animal appeared to be normal. Body weight was not changed and body temperature remained within normal range (Table 12).

TABLE 12

Effect of systemic administration of CTB006 or CTB007 on body weight and body temperature.

| Group | Time (Days) | Body weight (kg) | Body temperature (° C.) |
|---|---|---|---|
| CTB006 | −7 | 4.3 | 39.0 |
| | 0 | 4.1 | 38.6 |
| | 1 | 4.1 | 38.8 |
| | 3 | 4.1 | 38.9 |
| | 7 | 4.2 | 38.4 |
| | 14 | 4.3 | 38.8 |
| CTB007 | −7 | 4.0 | 39.2 |
| | 0 | 3.7 | 38.7 |
| | 1 | 3.7 | 38.5 |
| | 3 | 3.6 | 38.5 |
| | 7 | 3.8 | 38.9 |
| | 14 | 4.1 | 38.0 |

There was no significant alteration of any tested hematology parameters after treatment with CTB006 (Table 13) or CTB007 (Table 14), and all biochemistry measurements (Table 15 and Table 16) remain normal except a slight and transient increase in plasma ALT and AST after treatment, which returned back to normal at day 7 after treatment.

TABLE 13

Effect of systemic administration of CTB006 on hematology parameters

| Days | RBC($10^{12}$/L) | Hb(g/l) | Hct(%) | MCV(fl) | MCH(pg) | MCHC(g/l) | RDW(%) |
|---|---|---|---|---|---|---|---|
| −7 | 5.80 | 146 | 0.437 | 75.4 | 25.2 | 334 | 12.8 |
| 0 | 5.55 | 137 | 0.408 | 73.6 | 24.7 | 335 | 12.5 |
| 1 | 5.25 | 131 | 0.398 | 75.8 | 25.0 | 329 | 12.6 |
| 3 | — | — | — | — | — | — | — |
| 7 | 5.11 | 126 | 0.383 | 75.0 | 24.7 | 329 | 13.4 |
| 14 | 4.95 | 124 | 0.372 | 75.1 | 25.1 | 334 | 13.2 |

| Days | Plat($10^9$/L) | MPV(fl) | PDW(%) | Ret %(%) | Ret#($10^9$/L) | WBC($10^9$/L) | NE |
|---|---|---|---|---|---|---|---|
| −7 | 318 | 9.4 | 15.9 | 1.07 | 0.0666 | 9.6 | 12 |
| 0 | 311 | 8.9 | 16.2 | 1.19 | 0.0677 | 7.9 | 28 |
| 1 | 296 | 9.4 | 16.1 | 1.26 | 0.0693 | 10.0 | 14 |
| 3 | — | — | — | — | — | — | 13 |
| 7 | 297 | 9.3 | 16.3 | 2.94 | 0.1538 | 8.5 | 24 |
| 14 | 293 | 9.1 | 16.3 | 2.49 | 0.1287 | 10.4 | 18 |

| Days | LY | MO | EO | BA | — | — | — |
|---|---|---|---|---|---|---|---|
| −7 | 86 | 1 | 1 | 0 | — | — | — |
| 0 | 65 | 6 | 1 | 0 | — | — | — |
| 1 | 85 | 1 | 0 | 0 | — | — | — |
| 3 | 84 | 3 | 0 | 0 | — | — | — |
| 7 | 74 | 2 | 0 | 0 | — | — | — |
| 14 | 74 | 6 | 2 | 0 | — | — | — |

TABLE 14

Effect of systemic administration of CTB007 on hematology parameters

| Days | RBC($10^{12}$/L) | Hb(g/l) | Hct(%) | MCV(fl) | MCH(pg) | MCHC(g/l) | RDW(%) |
|---|---|---|---|---|---|---|---|
| -7 | 6.28 | 140 | 0.429 | 68.3 | 22.3 | 326 | 12.8 |
| 0 | 5.44 | 118 | 0.367 | 67.5 | 21.7 | 321 | 13.1 |
| 1 | 5.46 | 118 | 0.369 | 67.6 | 21.6 | 320 | 12.8 |
| 3 | — | — | — | — | — | — | — |
| 7 | 5.53 | 117 | 0.379 | 68.6 | 21.2 | 308 | 13.1 |
| 14 | 5.37 | 118 | 0.371 | 69.1 | 22.0 | 318 | 13.9 |

| Days | Plat($10^9$/L) | MPV(fl) | PDW(%) | Ret %(%) | Ret#($10^9$/L) | WBC($10^9$/L) | NE |
|---|---|---|---|---|---|---|---|
| -7 | 303 | 8.7 | 18.6 | 0.85 | 0.0552 | 6.7 | 15 |
| 0 | 217 | 8.5 | 17.2 | 0.68 | 0.0381 | 7.7 | 19 |
| 1 | 304 | 8.8 | 17.4 | 0.90 | 0.0502 | 10.9 | 40 |
| 3 | — | — | — | — | — | — | 18 |
| 7 | 186 | 9.2 | 17.6 | 1.59 | 0.0875 | 5.5 | 17 |
| 14 | 229 | 8.4 | 18.5 | 1.53 | 0.0838 | 5.6 | 35 |

| Days | LY | MO | EO | BA | — | — | — |
|---|---|---|---|---|---|---|---|
| -7 | 84 | 1 | 0 | 0 | — | — | — |
| 0 | 74 | 7 | 0 | 0 | — | — | — |
| 1 | 54 | 5 | 1 | 0 | — | — | — |
| 3 | 79 | 3 | 0 | 0 | — | — | — |
| 7 | 75 | 7 | 1 | 0 | — | — | — |
| 14 | 62 | 3 | 0 | 0 | — | — | — |

TABLE 15

Effect of intravenous administration of CTB006 on biochemistry parameters.

| Days | ALT (U/L) | AST (U/L) | ALP (U/L) | TP (g/l) | Alb (g/l) | Tchol (mmol/l) | BUN (mmol/l) |
|---|---|---|---|---|---|---|---|
| -7 | 72 | 29 | 223 | 80.5 | 45.2 | 4.68 | 7.69 |
| 0 | 45 | 14 | 185 | 76.6 | 44.6 | 4.26 | 7.94 |
| 1 | 98 | 162 | 172 | 72.2 | 41.4 | 3.77 | 7.41 |
| 3 | 83 | 38 | 159 | 73.6 | 42.0 | 3.92 | 8.13 |
| 7 | 67 | 23 | 182 | 74.7 | 43.0 | 4.27 | 7.64 |
| 14 | 48 | 20 | 112 | 69.9 | 43.5 | 3.47 | 6.54 |

| Days | Tbil (µmol/l) | Glu (mmol/l) | Crea (µmol/l) | CK (U/L) | Na (mmol/l) | K (mmol/l) | Cl (mmol/l) |
|---|---|---|---|---|---|---|---|
| -7 | 4.6 | 5.22 | 49.0 | 184 | 140 | 5.6 | 99 |
| 0 | 4.0 | 4.88 | 49.2 | 183 | 145 | 5.1 | 100 |
| 1 | 4.7 | 4.35 | 48.7 | 446 | 145 | 5.4 | 107 |
| 3 | 6.7 | 6.13 | 51.4 | 452 | 150 | 8.4 | 107 |
| 7 | 6.8 | 5.33 | 50.6 | 158 | 147 | 4.1 | 105 |
| 14 | 4.7 | 5.80 | 42.1 | 137 | 146 | 4.3 | 110 |

| Days | TG (mmol/l) | G-GT (U/L) | — | — | — | — | — |
|---|---|---|---|---|---|---|---|
| -7 | 0.47 | 32 | — | — | — | — | — |
| 0 | 0.21 | 30 | — | — | — | — | — |
| 1 | 0.48 | 27 | — | — | — | — | — |
| 3 | 0.56 | 35 | — | — | — | — | — |
| 7 | 0.39 | 35 | — | — | — | — | — |
| 14 | 0.20 | 41 | — | — | — | — | — |

TABLE 16

Effect of intravenous administration of CTB007 on biochemistry parameters.

| Days | ALT (U/L) | AST (U/L) | ALP (U/L) | TP (g/l) | Alb (g/l) | Tchol (mmol/l) | BUN (mmol/l) |
|---|---|---|---|---|---|---|---|
| -7 | 50 | 35 | 169 | 81.3 | 47.7 | 3.8. | 9.17 |
| 0 | 39 | 25 | 126 | 74.6 | 45.4 | 3.32 | 8.29 |
| 1 | 80 | 102 | 105 | 68.8 | 42.4 | 2.63 | 9.56 |
| 3 | 124 | 117 | 105 | 65.1 | 39.8 | 2.42 | 7.03 |

TABLE 16-continued

Effect of intravenous administration of CTB007 on biochemistry parameters.

| 7 | 80 | 30 | 117 | 71.5 | 42.5 | 2.96 | 10.08 |
|---|----|----|-----|------|------|------|-------|
| 14 | 46 | 15 | 167 | 67.9 | 39.7 | 3.92 | 6.86 |

| Days | Tbil (μmol/l) | Glu (mmol/l) | Crea (μmol/l) | CK (U/L) | Na (mmol/l) | K (mmol/l) | Cl (mmol/l) |
|------|---------------|--------------|---------------|----------|-------------|------------|-------------|
| −7 | 6.9 | 5.24 | 54.7 | 83  | 137 | 4.7 | 101 |
| 0  | 6.8 | 5.07 | 47.9 | 102 | 146 | 3.6 | 106 |
| 1  | 4.1 | 5.10 | 44.1 | 340 | 149 | 5.5 | 113 |
| 3  | 5.3 | 7.25 | 49.0 | 190 | 136 | 7.2 | 102 |
| 7  | 7.1 | 4.31 | 43.2 | 103 | 145 | 4.6 | 105 |
| 14 | 4.6 | 6.40 | 53.7 | 161 | 158 | 4.3 | 122 |

| Days | TG (mmol/l) | G-GT (U/L) | — | — | — | — | — |
|------|-------------|------------|---|---|---|---|---|
| −7 | 0.28 | 34 | — | — | — | — | — |
| 0  | 0.20 | 31 | — | — | — | — | — |
| 1  | 0.41 | 29 | — | — | — | — | — |
| 3  | 0.34 | 37 | — | — | — | — | — |
| 7  | 0.17 | 39 | — | — | — | — | — |
| 14 | 0.28 | 33 | — | — | — | — | — |

These results demonstrate that systemic administration of CTB006 or CTB007 to rhesus monkey is well-tolerated at a 40 mg/kg.

Example 16

Determination of the N-Terminal Amino Acid Sequences of the Heavy and Light Chains of CTB003, CTB006, and CTB007

In order to obtain cDNAs of the heavy and light chains of CTB003, CTB006 and CTB007, the N-terminal amino acid sequences of the heavy and light chains of CTB003, CTB006 and CTB007 were determined by known techniques. 5 μg of the affinity-purified CTB003, CTB006 and CTB007 were separated in 10% SDS-polyacrylamide gel electrophoresis ("SDS-PAGE") under the reducing condition. After electrophoresis, the proteins in the gel were transferred to a polyvinylidene difluoride membrane ("PVDF"). After transfer, the PVDF membrane was washed with washing buffer 25 mM NaCl, 10 mM sodium borate buffer (pH 8.0), then stained in a staining solution (50% v/v methanol, 20% v/v acetic acid and 0.05% (w/v) Coomassie Brilliant Blue) for 5 minutes to locate the protein bands. The PVDF membrane was then destained with 90% (v/v) aqueous methanol and the bands corresponding to the heavy chain, the band with the lower mobility and light chain, the band with the higher mobility previously located on the PDVF membrane were excised and washed with deionized water. The N-terminal amino acid sequence of the heavy and light chains were determined by the Edman automated method using a protein sequencer (PROCISE 491, ABI, USA).

The N-terminal amino acid sequence of the band corresponding to the heavy chain of CTB003 was determined to be:

```
                                          (SEQ ID NO.: 84)
Glu-Val-His-Leu-Val-Glu-Ser-Gly-Gly-Gly-Leu-Val-

Arg-Pro-Gly-Gly-Ser
``` and that of the band corresponding to the light chain of CTB003 is determined to be:

```
                                          (SEQ ID NO.: 85)
Ala-Thr-Met-Arg-Leu-Pro-Ala-Gln-Leu-Leu-Gly-Leu-

Leu-Met-Leu-Trp-Val-Ser
```

The N-terminal amino acid sequence of the band corresponding to the heavy chain of CTB006 was determined to be:

```
                                          (SEQ ID NO.: 86)
Gln-Val-Gln-Leu-Gln-Gln-Pro-Gly-Pro-Glu-Leu-Val-

Lys-Pro-Gly-Ala-Ser
``` and that of the band corresponding to the light chain of CTB006 was determined to be:

```
                                          (SEQ ID NO.: 87)
Asp-Ile-Val-Met-Thr-Gln-Ser-His-Lys-Phe-Met-Ser-

Thr-Ser-Val-Gly
```

The N-terminal amino acid sequence of the band corresponding to the heavy chain of CTB007 was determined to be:

```
                                          (SEQ ID NO.: 88)
Glu-Val-Gln-Leu-Gln-Gln-Ser-Gly-Ala-Glu-Leu-Val-

Lys-Pro-Gly-Ala-Ser.
``` and that of the band corresponding to the light chain of CTB007 is determined to be:

```
                                          (SEQ ID NO.: 89)
Asp-Ile-Gln-Met-Thr-Gln-Ser-Pro-Ala-Ser-Leu-Ser-

Val-Ser-Val.
```

Example 17

CTB003-Related Sequences

CTB003-related sequences are provided below.

The murine CTB003 light chain variable region nucleic acid sequence is shown in Table 17 below.

TABLE 17

Murine CTB003 light chain variable region nucleic acid sequence

SEQ ID NO.: 1

GACATCCAGATGACCCAATCTTCATCCTCCTTTTCTGTATCTCTAGGAGACAGAGTCACC

ATTACTTGCAAGGCAGGTGAGGACATATATAATCGGTTAGCCTGGTATCAGCAGAAACCA

GGAAATGCTCCTAGGCTCTTAATATCTGGTGCACCAATTTGGAAACTGGGGTTCCTTCAA

GATTCAGTGGCAGTGGATCTGGAAAGGATTACACTCTCAGCATTACCAGTCTTCAGACTG

AAGATGTTGCTACTTATTACTGTCAACAGTATTGGAGTACTCCGCTC

The murine CTB003 light chain variable region amino acid sequence is shown in Table 18 below.

TABLE 18

Murine CTB003 light chain variable region amino acid sequence

SEQ ID NO.: 2

D I Q M T Q S S S S F S V S L G D R V T I T C <u>K A G E D I Y N R L A</u> W Y Q Q K P G N A P R L L I S <u>G A T N L E T</u> G V P S R F S C S G S G K D Y T L S I T S L Q T S D V A T Y Y C <u>Q Q Y W S T P L</u>

The murine CTB003 light chain variable region nucleic acid and amino acid sequence are shown in Table 19 below.

The murine CTB003 light CDR1 nucleic acid and amino acid sequence are shown in Table 20 below.

TABLE 20

Murine CTB003 light CDR1 amino acid sequence

K A G E D I Y N R L A    SEQ ID NO.: 3

The murine CTB003 light CDR2 nucleic acid and amino acid sequence are shown in Table 21 below.

TABLE 21

Murine CTB003 light CDR2 amino acid sequence

G A T N L E T    SEQ ID NO.: 4

TABLE 19

Murine CTB003 light chain variable region nucleic acid and amino acid sequence

```
GACATCCAGATGACCCAATCTTCATCCTCCTTTTCTGTATCTCTAGGAGACAGAGTCACC  SEQ ID NO.: 1
 D   I   Q   M   T   Q   S   S   S   S   P   S   V   S   L   G   D   R   V   T   SEQ ID NO.: 2

ATTACTTGCAAGGCAGGTGAGGACATATATAATCGGTTAGCCTGGTATCAGCAGAAACCA
 I   T   C   K   A   G   E   D   T   Y   N   R   L   A   W   Y   Q   Q   K   P

GGAAATGCTCCTAGGCTCTTAATATCTGGTGCAACCAATTTGGAAACTGGGGTTCCTTCA
 G   N   A   P   R   L   L   I   S   G   A   T   N   L   E   T   G   V   P   S

AGATTCAGTGGCAGTGGATCTGGAAAGGATTACACTCTCAGCATTACCAGTCTTCAGACT
 R   F   S   G   S   G   K   D   Y   T   L   S   I   T   S   L   Q   T

GAAGATGTTGCTACTTATTACTGTCAACAGTATTGGAGTACTCCGCTC
 E   D   V   A   T   Y   Y   C   Q   Q   Y   W   S   T   P   L
```

The murine CTB003 light CDR3 nucleic acid and amino acid sequence are shown in Table 22 below.

TABLE 22

| Murine CTB003 light CDR3 amino acid sequence | |
|---|---|
| Q Q Y W S T P L | SEQ ID NO.: 5 |

The murine CTB003 heavy chain variable region nucleic acid sequence is shown in Table 23 below.

TABLE 23

Murine CTB003 heavy chain variable region nucicic acid sequence

GAGGTGCATCTCGTGGAGTCTGGGGGAGGCTTAGTGAGGCCTGGAGGGTCCCTGAAACTC  SEQ ID NO.: 7

TCCTGTGCGGCCTCTGGATTCGCTTTCAGTAGCTATGACATGTCTTGGGTTCGCCAGACT

CCGGAGAAGAGGCTGGAGTGGGTCGCATACATTAGTGATGGTGGTGGTATCACCTACTAT

CCAGACACAATGAAGGGCCGACTCACCATCTCCAGAGACAATGCCAAGAATACCCTGTCC

CTGCAAATGAGCAGTCTGAAGTCTGAGGACACAGCCATGTATTACTGTGCAAGACATATT

ACTATGGTGGTAGGACCCTTTGCT

The murine CTB003 heavy chain variable region amino acid sequence is shown in Table 24 below.

TABLE 24

Murine CTB003 heavy chain variable region amino acid sequence

SEQ ID NO.: 8

E V H L V E S G G D L V P P G G S L K L

S C A A S G F A F S <u>S Y D M S</u> W V R Q T

P H K R L H W V A <u>Y I S D G D G I T Y Y</u>

<u>P D T M K G</u> R L T T S R D N A K N T L S

L Q M S S L K S E D T A M Y Y C A R <u>H I</u>

<u>T M V V G P F A</u>

The murine CTB003 heavy chain variable region nucleic acid and amino acid sequence is shown in Table 25 below.

TABLE 25

Murine CTB003 heavy chain variable region nucleic acid and amino acid sequence

GAGGTGCATCTCGTGGAGTCTGGGGGAGGCTTAGTGAGGCCTGGAGGGTCCCTGAAACTC  SEQ ID NO.: 7
E   V   H   L   V   E   S   G   G   G   L   V   R   P   G   G   S   L   K   L  SEQ ID NO.: 8

TCCTGTGCGGCCTCTGGATTCGCTTTCAGTAGCTATGACATGTCTTGGGTTCGCCAGACT
S   C   A   A   S   D   F   A   F   S   S   Y   D   H   S   W   V   R   Q   T

CCGGAGAAGAGGCTDGADTDGGTCDCATACATTADTGATGGTGDTDGTATCACCTACTAT
P   E   K   R   L   H   W   V   A   Y   I   S   D   G   D   D   I   T   Y   Y

CCAGACACAATGAAGGGCCGACTCACCATCTCCAGAGACAATGCCAAGAATACCCTGTCC
P   D   T   M   K   D   R   L   T   I   S   R   D   N   A   K   N   T   L   S

CTGCAAATGAGCAGTCTGAAGTCTGAGGACACAGCCATGTATTACTGTGCAAGACATATT
L   Q   M   S   S   L   K   S   E   D   T   A   M   Y   Y   C   A   R   H   I

ACTATGGTGGTAGGACCCTTTGCT
T   M   V   V   G   P   F   A

The murine CTB003 heavy CDR1 amino acid sequence is shown in Table 26 below.

TABLE 26

| Murine CTB003 heavy CDRL amino acid sequence | |
|---|---|
| S Y D M S | SEQ ID NO.: 9 |

The murine CTB003 heavy CDR2 amino acid sequence is shown in Table 27 below.

TABLE 27

| Murine CTB003 heavy CDR2 amino acid sequence | |
|---|---|
| Y I S D G G G I T Y Y P D T M K G | SEQ ID NO.: 10 |

The murine CTB003 heavy CDR3 amino acid sequence is shown in Table 28 below.

TABLE 28

| Murine CTB003 heavy CDR3 amino acid sequence | |
|---|---|
| H I T M V V G P F A | SEQ ID NO.: 11 |

The human chimeric CTB003 light chain nucleic acid sequence is shown in Table 29 below.

TABLE 29

Human chimeric CTB003 light chain nucleic acid sequence

SEQ ID NO.: 12

ATGAGGCTCCCTGCTCAGCTCCTGGGGCTGCTAATGCTCTGGGTCTCTGG

ATCCAGTGGTGACATCCAGATGACTCAGTCTTCATCCTCCTTTTCTGTAT

CTCTAGGAGACAGAGTCACCATTACTTGCAAGGCAAGTGAGGACATATAT

AATCGGTTAGCCTGGTATCAGCAGAAGTCACCAGGAAATGCTCCTAGGCT

CTTAATATCTGGTGCAACCAGTTTGGAAACTGGGGTTCCTTCAAGATTCA

GTGGCAGTCGATCTGGAAAGGATTACACTCTCAGCATTACCAGTCTTCAG

ACTGAAGATGTTGCTACTTATTACTGTCAACAGTATTGGAGTACTCCGCT

CACGTTCGGTGCTGGGACCAAGCTGGAGCTGAAACGGGCTGTGGCTGCAC

CATCTGTCGATATCTTCCCGCCATCTGATGAGCAGTTGAAATCTGGAACT

GCCTCTGTTGTGTGCCTGCTGAATAACTTCTACCCCAGACAGGCCAAAGT

ACAGTGGAAGGTGGATAACGCCCTCCAATCGGGTAACTCCCAGGAGAGTG

TCACAGAGCAGGACAGCAAGGACAGCACCTACAGCCTCAGCAGCACCCTG

ACGCTGAGCAAGCAGACTACGAGAAACACAAAGTCTACGCCTGCGAAGTT

ACCCATCAGGGCCTGAGCTCGCCCGTCACAAAGAGCTTCAACAGGGGAGA

GTGTTAG

The human chimeric CTB003 light chain amino acid sequence is shown in Table 30 below.

TABLE 30

Human chimeric CTB003 light chain amino acid sequence

SEQ ID NO.: 13

M R L P A Q L L G L L M L W V S G S S G

D I Q M T Q S S S S F S V S L G D R V T

I T C K A S E D I Y N R L A W Y Q Q K P

G N A P R L L I S G A T S L E T G V P S

R F S G S G S G K D Y T L S I T S L Q T

E D V A T Y Y C Q Q Y W S T P L T F G A

G T K L E L K R A V A A P S V D I F P P

S D E Q L K S G T A S V V C L L N N F Y

P R E A K V Q W K V D N A L Q S G N S Q

E S V T E Q D S K D S T Y S L S S T L T

L S K A D Y E K H K V Y A C E V T H Q G

L S S P V T K S F N R G E C *

The human chimeric CTB003 light chain nucleic acid and amino acid sequence are shown in Table 31 below.

TABLE 31

Human chimeric CTB003 light chain nucleic acid and amino acid sequence

| | |
|---|---|
| ATGAGGCTCCCTGCTCAGCTCCTGGGGCTGCTAATGCTCTGGGTCTCTGGATCCAGTGGT<br>M  R  L  P  A  Q  L  L  G  L  L  M  L  W  V  S  G  S  S  G | SEQ ID NO.: 12<br>SEQ ID NO.: 13 |

GACATCCAGATGACTCAGTCTTCATCCTCCTTTTCTGTATCTCTAGGAGACAGAGTCACC
D  I  Q  M  T  Q  S  S  S  S  F  S  V  S  L  G  D  R  V  T

ATTACTTGCAAGGCAAGTGAGGACATATATAATCGGTTAGCCTGGTATCAGCAGAAACCA
I  T  C  K  A  S  E  D  I  Y  N  R  L  A  W  Y  Q  Q  K  P

GGAAATGCTCCTAGGCTCTTAATATCTGGTGCAACCAGTTTGGAAACTGGGGTTCCTTCA
G  N  A  P  R  L  L  I  S  G  A  T  S  L  E  T  G  V  P  S

AGATTCAGTGGCAGTGGATCTGGAAAGGATTACACTCTCAGCATTACCAGTCTTCAGACT
R  F  S  G  S  G  S  G  K  D  Y  T  L  S  I  T  S  L  Q  T

GAAGATGTTGCTACTTATTACTGTCAACAGTATTGGAGTACTCCGCTCACGTTCGGTGCT
E  D  V  A  T  Y  Y  C  Q  Q  Y  W  S  T  P  L  T  F  G  A

GGGACCAAGCTGGAGCTGAAACGGGCTGTGGCTGCACCATCTGTCGATATCTTCCCGCCA
G  T  K  L  E  L  K  R  A  V  A  A  P  S  V  D  I  F  P  P

TCTGATGAGCAGTTGAAATCTGGAACTGCCTCTGTTGTGTGCCTGCTGAATAACTTCTAC
S  D  E  Q  L  K  S  G  T  A  S  V  V  C  L  L  N  N  F  Y

CCCAGAGAGGCCAAAGTACAGTGGAAGGTGGATAACGCCCTCCAATCGGGTAACTCCCAG
P  R  E  A  K  V  Q  W  K  V  D  N  A  L  Q  S  G  N  S  Q

GAGAGTGTCACAGAGCAGGACAGCAAGGACAGCACCTACAGCCTCAGCAGCACCCTGACG
E  S  V  T  E  Q  D  S  K  D  S  T  Y  S  L  S  S  T  L  T

TABLE 31-continued

Human chimeric CTB003 light chain nucleic acid and amino acid sequence

```
CTGAGCAAAGCAGACTACGAGAAACACAAAGTCTACGCCTGCGAAGTTACCCATCAGGGC
 L   S   K   A   D   Y   E   K   H   K   V   Y   A   C   E   V   T   H   Q   G

CTGAGCTCGCCCGTCACAAAGAGCTTCAACAGGGGAGAGTGTTAG
 L   S   S   P   V   T   K   S   F   N   R   G   E   C   *
```

The human chimeric CTB003 heavy chain nucleic acid sequence is shown in Table 32 below.

TABLE 32

Human chimeric CTB003 heavy chain nucleic acid sequence

SEQ ED NO.: 14

```
ATGGGGANNTTGGGGCTGAGCTGGGTTTTCCTTGTTGTTATATTAGAAGG
TGTCCAGTGTGAGGTGCATCTCGTGGAGTCTGGGGGAGGCTTAGTGAGGC
CTGGAGGGTCCCTGAAACTCTCCTGTGCGGCCTCTGGATTCGCTTTCAGT
AGCTATGACATGTCTTGGGTTCGCCAGACTCCGGAGAAGAGGCTGGAGTG
GGTCGCATACATTAGTGATGGTGGTGGTATCACCTACTATCCAGACACAA
TGAAGGGCCGATTCACCATCTCCAGAGACAATGCCAAGAATACCCTGTCC
CTGCAAATGAGCAGTCTGAAGTCTGAGGACACAGCCATGTATTACTGTGC
AAGACATATTACTATGGTGGTAGGACCCTTTGCTTACTGGGGCCAAGGGA
CTCTGGTCACTGTCTCTGCAGCTAGCACCAAGGGCCCATCGGTCTTCCCC
CTGGCGCCCTGCTCCAGGAGCACCTCTGGGGGCACAGCGGCCCTGGGCTG
CCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCA
GGACTCTACTCCCTCAGCAGCGTGGTGACCGTGCCCTCCAACAGCTTGGG
CACCCAGACCTACATCTGCAACGTGAATCACAAGCCCAGCAACACCAAGG
TGGACAAGAGAGTTGAGCCCAAATCTTGTGACAAAACTCACACATGCCCA
CCGTGCCCAGCACCTGAACTCCTGGGGGGACCGTCAGTCTTCCTCTTCCC
CCCAAAACCCAAGGACACCCTCATGATCTCCCGGACCCCTGAGGTCACAT
GCGTGGTGGTGGACGTGAGCCACGAAGACCCTGAGGTCAAGTTCAACTGG
TACGTGGACGGCGTGGAGGTGCATAATGCCAAGACAAAGCCGCGGGAGGA
GCAGTACAACAGCACGTACCGTGTGGTCAGCGTCCTCACCGTCCTGCACC
AGGACTGGCTGAACGGCAAGGAGTACAAGTGCAAGGTCTCCAACAAAGGC
CTGCCAGCCCCCATCGAGAAAACCATCTCCAAAGCCAAAGGGCAGCCCCG
AGAACCACAGGTGTACACCCTGCCCCCATCCCGGGAGGAGATGACCAAGA
ACCAGGTCAGCCTGACCTGCCTGGTCAAAGGCTTCTATCCCAGCGACATC
GCCGTGGAGTGGGAGAGCAATGGGCAGCCGGAGAACAACTACAAGACCAC
GCCTCCCGTGCTGGACTCCGACGGCTCCTTCTTCCTCTATAGCAAGCTCA
CCATGGACAAGAGCAGGTGGCAGCAGGGGAACGTCTTCTCATGCTCCGTG
ATGCATGAGGCTCTGCACAACCACTACACGCAGAAGAGCCTCTCCCTGTC
TCCGGGTAAATGA
```

TABLE 33

Human chimeric CTB003 heavy chain amino acid sequence

SEQ ID NO.: 15

```
M G X L G L S W V P L V V I L E G V Q C
E V H L V E S G G G L V R P G G S L K L
S C A A S G F A F S S Y D M S W V R Q T
P E K R L E W V A Y I S D G G G I T Y Y
P D T M K G R F T I S R D N A K N T L S
L Q M S S L K S E D T A M Y Y C A R H I
T M V V G P F A Y W G Q G T L V T V S A
A S T K G P S V F P L A P C S R S T S G
G T A A L G C L V K D Y F P E P V T V S
W N S G A L T S G V H T F P A V L Q S S
G L Y S L S S V V T V P S S S L G T Q T
Y I C N V N H K P S N T K V D K R V E P
K S C D K T H T C P P C P A P E L L G G
P S V F L F P P K P K D T L M I S R T P
E V T C V V V D V S H E D P E V K F N W
Y V D G V E V H N A K T K P R E E Q Y N
S T Y R V V S V L T V L H Q D W L N G K
E Y K C K V S N K G L P A P I E K T I S
K A K G Q P R E P Q V Y T L P P S R E E
M T K N Q V S L T C L V K G F Y P S D I
A V E W E S N G Q P E N N Y K T T P P V
L D S D G S F F L Y S K L T M D K S R W
Q Q G N V F S C S V M H E A L H N H Y T
Q K S L S L S P G K *
```

The human chimeric CTB003 heavy chain nucleic acid and amino acid sequence are shown in Table 34 below.

TABLE 34

Human chimeric CTB003 heavy chain nucleic acid and amino acid sequence

| | |
|---|---|
| ATGGGGANNTTGGGGCTGAGCTGGGTTTTCCTTGTTGTTATATTAGAAGGTGTCCAGTGT | SEQ ID NO.: 14 |
|  M  G  X  L  G  L  S  W  V  F  L  V  V  I  L  E  G  V  Q  C | SEQ ID NO.: 15 |

```
GAGGTGCATCTCGTGGAGTCTGGGGGAGGCTTAGTGAGGCCTGGAGGGTCCCTGAAACTC
 E   V   H   L   V   E   S   G   G   G   L   V   R   P   G   G   S   L   K   L

TCCTGTGCGGCCTCTGGATTCGCTTTCAGTAGCTATGACATGTCTTGGGTTCGCCAGACT
 S   C   A   A   S   G   F   A   F   S   S   Y   D   M   S   W   V   R   Q   T

CCGGAGAAGAGGCTGGAGTGGGTCGCATACATTAGTGATGGTGGTGGTATCACCTACTAT
 P   E   K   R   L   E   W   V   A   Y   I   S   D   G   G   G   I   T   Y   Y

CCAGACACAATGAAGGGCCGATTCACCATCTCCAGAGACAATGCCAAGAATACCCTGTCC
 P   D   T   M   K   G   R   F   T   I   S   R   D   N   A   K   N   T   L   S

CTGCAAATGAGCAGTCTGAAGTCTGAGGACACAGCCATGTATTACTGTGCAAGACATATT
 L   Q   M   S   S   L   K   S   E   D   T   A   M   Y   Y   C   A   R   H   I

ACTATGGTGGTAGGACCCTTTGCTTACTGGGGCCAAGGGACTCTGGTCACTGTCTCTGCA
 T   M   V   V   G   P   F   A   Y   W   G   Q   G   T   L   V   T   V   S   A

GCTAGCACCAAGGGCCCATCGGTCTTCCCCCTGGCGCCCTGCTCCAGGAGCACCTCTGGG
 A   S   T   K   G   P   S   V   F   P   L   A   P   C   S   R   S   T   S   G

GGCACAGCGGCCCTGGGCTGCCTGGTCAAGGACTACTTCCCCGAACCGGTGACGGTGTCG
 G   T   A   A   L   G   C   L   V   K   D   Y   F   P   E   P   V   T   V   S

TGGAACTCAGGCGCCCTGACCAGCGGCGTGCACACCTTCCCGGCTGTCCTACAGTCCTCA
 W   N   S   G   A   L   T   S   G   V   H   T   F   P   A   V   L   Q   S   S

GGACTCTACTCCCTCAGCAGCGTGGTGACCGTGCCCTCCAGCAGCTTGGGCACCCAGACC
 G   L   Y   S   L   S   S   V   V   T   V   P   S   S   S   L   G   T   Q   T

TACATCTGCAACGTGAATCACAAGCCCAGCAACACCAAGGTGGACAAGAGAGTTGAGCCC
 Y   I   C   N   V   N   H   K   P   S   N   T   K   V   D   K   R   V   H   P

AAATCTTGTGACAAAACTCACACATGCCCACCGTGCCCAGCACCTGAACTCCTGGGGGGA
 K   S   C   D   K   T   H   T   C   P   P   C   P   A   P   E   L   L   C   G

CCGTCAGTCTTCCTCTTCCCCCCAAAACCCAAGGACACCCTCATGATCTCCCGGACCCCT
 P   S   V   F   L   F   P   P   K   P   K   D   T   L   M   I   S   R   T   P

GAGGTCACATGCGTGGTGGTGGACGTGAGCCACGAAGACCCTGAGGTCAAGTTCAACTGG
 E   V   T   C   V   V   V   D   V   S   H   E   D   P   E   V   K   F   N   W

TACGTGGACGGCGTGGAGGTGCATAATGCCAACACAAAGCCGCGGGAGGAGCAGTACAAC
 Y   V   D   G   V   E   V   H   N   A   K   T   K   P   R   E   E   Q   Y   N

AGCACGTACCGTGTGGTCAGCGTCCTCACCGTCCTGCACCAGGACTGGCTGAACGGCAAG
 S   T   Y   R   V   V   S   V   L   T   V   L   H   Q   D   W   L   N   G   K

GAGTACAAGTGCAAGGTCTCCAACAAAGGCCTCCCAGCCCCCATCGAGAAAACCATCTCC
 E   Y   K   C   K   V   S   N   K   G   L   P   A   P   I   E   K   T   I   S

AAAGCCAAAGGGCAGCCCCGAGAACCACAGGTGTACACCCTGCCCCCATCCCGGGAGGAG
 K   A   K   G   Q   P   R   E   P   Q   V   Y   T   L   P   P   S   R   E   E

ATGACCAAGAACCAGGTCAGCCTGACCTGCCTGGTCAAAGGCTTCTATCCCAGCGACATC
 M   T   K   N   Q   V   S   L   T   C   L   V   K   G   F   Y   P   S   D   I

GCCGTGGAGTGGGAGAGCAATGGGCAGCCGGAGAACAACTACAAGACCACGCCTCCCGTG
 A   V   E   W   E   S   N   G   Q   P   E   N   N   Y   K   T   T   P   P   V

CTGGACTCCGACGGCTCCTTCTTCCTCTATAGCAAGCTCACCATGGACAAGAGCAGGTGG
 L   D   S   D   G   S   F   F   L   Y   S   K   L   T   M   D   K   S   R   W

CAGCAGGGGAACGTCTTCTCATGCTCCGTGATGCATGAGGCTCTGCACAACCACTACACG
 Q   Q   G   N   V   F   S   C   S   V   M   H   E   A   L   N   H   Y   T

CAGAAGAGCCTCTCCCTGTCTCCGGGTAAATGA
 Q   K   S   L   S   L   S   P   G   K   *
```

Example 18

CTB006-Related Sequences

CTB006-related sequences are provided below.

The murine CTB006 light chain variable region nucleic acid sequence is shown in Table 35 below.

TABLE 35

Murine CTB006 light chain variable region nucleic acid sequence

| | |
|---|---|
| 1 GACATCGTCATGACCCAATCTCACAAATTCATGTCCACTTCAGTAGGAGACAGGGTCAGC | SEQ ID NO.: 16 |
| 61 ATCACCTGCAAGGCCAGTCAGGATGTGAGTACTGCTGTAGCCTGGTATCAACAAAAACCA | |
| 121 GGGCAATCTCCTAGACTACTGATTTACTGGGCATCCACCCGGCACACTGGAGTCCCTGAT | |
| 181 CGCTTCACAGGCAGTGGATCTGGGACAGATTATACTCTCACCATCAGCAGTGTGCAGGCT | |
| 241 GAAGACCAGGCACTTTATTACTGTCAGCAACATTATCGCACTCCGTGG | |

The murine CTB006 light chain variable region amino acid sequence is shown in Table 36 below.

TABLE 36

Murine CTB006 light chain variable region amino acid sequence

SEQ ID NO.: 17

```
 1 D I V M T Q S H K F M S T S V G D R V S
21 I T C K A S Q D V S T A V A W Y Q Q K P
41 G Q S P R L L I Y W A S T R H T G V P D
61 R F T G S G S G T D Y T L T I S S V Q A
81 E D Q A L Y Y C Q Q H Y R T P W
```

The murine CTB006 light chain variable region nucleic acid and amino acid sequence are shown in Table 37 below.

The murine CTB006 light CDR1 amino acid sequence are shown in Table 38 below.

TABLE 38

Murine CTB006 light CDR1 amino acid sequence

| K A S Q D V S T A V A | SEQ ID NO.: 18 |
|---|---|

The murine CTB006 light CDR2 amino acid sequence are shown in Table 39 below.

TABLE 39

Murine CTB006 light CDR2 amino acid sequence

| W A S T R H T | SEQ ID NO.: 19 |
|---|---|

TABLE 37

Murine CTB006 light chain variable region nucleic acid and amino acid sequence

| | |
|---|---|
| 1 GACATCGTCATGACCCAATCTCACAAATTCATGTCCACTTCAGTAGGAGACAGGGTCAGC | SEQ ID NO.: 16 |
| 1 D  I  V  M  T  Q  S  H  K  F  M  S  T  S  V  G  D  R  V  S | SEQ ID NO.: 17 |
| 61 ATCACCTGCAAGGCCAGTCAGGATGTGAGTACTGCTGTAGCCTGGTATCAACAAAAACCA | |
| 21 I  T  C  K  A  S  Q  D  V  S  T  A  V  A  W  Y  Q  Q  K  P | |
| 121 GGGCAATCTCCTAGACTACTGATTTACTGGGCATCCACCCGGCACACTGGAGTCCCTGAT | |
| 41 G  Q  S  P  R  L  L  I  Y  W  A  S  T  R  H  T  G  V  P  D | |
| 181 CGCTTCACAGGCAGTGGATCTGGGACAGATTATACTCTCACCATCAGCAGTGTGCAGGCT | |
| 61 R  F  T  G  S  G  S  G  T  D  Y  T  L  T  I  S  S  V  Q  A | |
| 241 GAAGACCAGGCACTTTATTACTGTCAGCAACATTATCGCACTCCGTGG | |
| 81 E  D  Q  A  L  Y  Y  C  Q  Q  H  Y  R  T  P  W | |

The murine CTB006 light CDR3 amino acid sequence are shown in Table 40 below.

TABLE 40

| Murine CTB006 light CDR3 amino acid sequence | |
| --- | --- |
| Q Q H Y R T P W | SEQ ID NO.: 20 |

The murine CTB006 heavy chain variable region nucleic acid sequence is shown in Table 41 below.

TABLE 41

Murine CTB006 heavy chain variable region nucleic acid sequence

```
  1 CAGGTCCAACTGCAGCAGCCTGGACCTGAGCTGGTGAAGCCTGGGGCTTCAGTGAGGATG        SEQ ID NO.: 21
 61 TCCTGCAAGGCTTCTGGCTACACCTTCACAAGCTACTTTATACATTGGGTGAAGCAGAGG
121 CCTGGACAGGGACTTGAGTGGATTGATGGATTTATCCTGGAAATGTTAATACTAAGTAC
181 AGTGAGAAGTTCAAGGGTAAGGCCACACTGACTGCAGACAAATCCTCCAGCACAGCCTAC
241 ATGCAGTTCAGCAGCCTGACCTCTGAGGACTCTGCGGTCTATTTCTGTGCAAGAGGGGAG
301 GCTGGGTACTTTGAC
```

The murine CTB006 heavy chain variable region amino acid sequence is shown in Table 42 below.

TABLE 42

Murine CTB006 heavy chain variable region amino acid sequence

```
                                            SEQ ID NO.: 22
  1 Q V Q L Q Q P G P E L V K P G A S V R M
 21 S C K A S G Y T F T S Y F I H W V K Q R
 41 P G Q G L E W I G W I Y P G N V N T K Y
 61 S E K F K G K A T L T A D K S S S T A Y
 81 M Q F S S L T S E D S A V Y F C A R G E
101 A G Y F D
```

The murine CTB006 heavy chain variable region nucleic acid and amino acid sequence is shown in Table 43 below.

TABLE 43

Murine CTB006 heavy chain variable region nucleic acid and amino acid sequence

```
  1 CAGGTCCAACTGCAGCAGCCTGGACCTGAGCTGGTGAAGCCTGGGGCTTCACTGAGGATG        SEQ ID NO.: 21
  1 Q   V   Q   L   Q   Q   P   G   P   E   L   V   K   P   G   A   S   V   R   M        SEQ ID NO.: 22

61 TCCTGCAAGGCTTCTGGCTACACCTTCACAAGCTACTTTATACATTGGGTGAAGCAGAGG
 21 S   C   K   A   S   G   Y   T   F   T   S   Y   F   I   H   W   V   K   Q   R

121 CCTGGACAGGGACTTGAGTGGATTGGATGGATTTATCCTGGAAATGTTAATACTAAGTAC
 41 P   G   Q   G   L   E   W   I   G   W   I   Y   P   G   N   V   N   T   K   Y

181 AGTGAGAAGTTCAAGGGTAAGGCCACACTGACTGCAGACAAATCCTCCAGCACAGCCTAC
 61 S   E   K   F   K   G   K   A   T   L   T   A   D   K   S   S   S   T   A   Y

241 ATGCAGTTCAGCAGCCTGACCTCTGAGGACTCTGCGGTCTATTTCTGTGCAAGAGGGGAG
 81 M   Q   F   S   S   L   T   S   E   D   S   A   V   Y   F   C   A   R   G   E

301 GCTGGGTACTTTGAC
101 A   G   Y   F   D
```

The murine CTB006 heavy CDR1 amino acid sequence is shown in Table 44 below.

TABLE 44

| Murine CTB006 heavy CDR1 amino acid sequence | |
| --- | --- |
| S Y F I H | SEQ ID NO.: 23 |

The murine CTB006 heavy CDR2 amino acid sequence is shown in Table 45 below.

TABLE 45

| Murine CTB006 heavy CDR2 amino acid sequence | |
| --- | --- |
| W I Y P G N V N T K Y S E K F K G | SEQ ID NO.: 24 |

The murine CTB006 heavy CDR3 amino acid sequence is shown in Table 46 below.

TABLE 46

| Murine CTB006 heavy CDR3 amino acid sequence | |
| --- | --- |
| G E A G Y F D | SEQ ID NO.: 25 |

The human chimeric CTB006 light chain nucleic acid sequence is shown in Table 47 below.

TABLE 47

Human chimeric CTB006 light chain nucleic acid sequence

```
  1 ATGAGGCTCCCTGCTCAGCTCCTGGGGCTGCTAATGCTCTGGGTCTCTGGATCCAGTGGT    SEQ ID NO.: 26
 61 GACATCGTCATGACCCAATCTCACAAATTCATGTCCACTTCAGTAGGAGACAGGGTCAGC
121 ATCACCTGCAAGGCCAGTCAGGATGTGAGTACTGCTGTAGCCTGGTATCAACAAAAACCA
181 GGGCAATCTCCTAGACTACTGATTTACTGGGCATCCACCCGGCACACTGGAGTCCCTGAT
241 CGCTTCACAGGCAGTGGATCTGGGACAGATTATACTCTCACCATCAGCAGTGTGCAGGCT
301 GAAGACCAGGCACTTTATTACTGTCAGCAACATTATCGCACTCCGTGGACGTTCGGTGGA
361 GGCACCAAGCTGGAAATCAAACGGGCTGTGGCTGCACCATCTGTCGATATCTTCCCGCCA
421 TCTGATGAGCAGTTGAAATCTGGAACTGCCTCTGTTGTGTGCCTGCTGAATAACTTCTAC
481 CCCAGAGAGGCCAAAGTACAGTGGAAGGTGGATAACGCCCTCCAATCGGGTAACTCCCAG
541 GAGAGTGTCACAGAGCAGGACAGCAAGGACAGCACCTACAGCCTCAGCAGCACCCTGACG
601 CTGAGCAAAGCAGACTACGAGAAACACAAAGTCTACGCCTGCGAAGTTACCCATCAGGGC
661 CTGAGCTCGCCCGTCACAAAGAGCTTCAACAGGGGAGAGTGTTAG
```

The human chimeric CTB006 light chain amino acid sequence is shown in Table 48 below.

TABLE 48

Human chimeric CTB006 light chain amino acid sequence

```
                                                 SEQ ID NO.: 27
  1 M R L P A Q L L G L L M L W V S G S S G
 21 D I V M T Q S H K F M S T S V G D R V S
 41 I T C K A S Q D V S T A V A W Y Q Q K P
 61 G Q S P R L L I Y W A S T R H T G V P D
 61 R F T G S G S G T D Y T L T I S S V Q A
101 E D Q A L Y Y C Q Q H Y R T P W T F G G
121 G T K L E I K R A V A A P S V D I F P P
```

TABLE 48-continued

Human chimeric CTB006 light chain amino acid sequence

```
141 S D E Q L K S G T A S V V C L L N N F Y
161 P R E A K V Q W K V D N A L Q S G N S Q
181 E S V T E Q D S K D S T Y S L S S T L T
201 L S K A D Y E K H K V Y A C E V T H Q G
221 L S S P V T K S F N R G S C *
```

The human chimeric CTB006 light chain nucleic acid and amino acid sequence are shown in Table 49 below.

TABLE 49

Human chimeric CTB006 light chain nucleic acid and amino acid sequence

```
  1 ATGAGGCTCCCTGCTCAGCTCCTGGGGCTGCTAATGCTCTGGGTCTCTGGATCCAGTGGT   SEQ ID NO.: 26
  1 M   R   L   P   A   Q   L   L   G   L   L   M   L   W   V   S   G   S   S   G      SEQ ID NO.: 27

61 GACATCGTCATGACCCAATCTCACAAATTCATGTCCACTTCAGTAGGAGACAGGGTCAGC
 21 D   I   V   M   T   Q   S   H   K   F   M   S   T   S   V   G   D   R   V   S

121 ATCACCTGCAAGGCCAGTCAGGATGTGAGTACTGCTGTAGCCTGGTATCAACAAAAACCA
 41 I   T   C   K   A   S   Q   D   V   S   T   A   V   A   W   Y   Q   Q   K   P

181 GGGCAATCTCCTAGACTACTGATTTACTGGGCATCCACCCGGCACACTGGAGTCCCTGAT
 61 G   Q   S   P   R   L   L   I   Y   W   A   S   T   R   H   T   G   V   P   D

241 CGCTTCACAGGCAGTGGATCTGGGACAGATTATACTCTCACCATCAGCAGTGTGCAGGCT
 81 R   F   T   G   S   G   S   G   T   D   Y   T   L   T   I   S   S   V   Q   A

301 GAAGACCAGGCACTTTATTACTGTCAGCAACATTATCGCACTCCGTGGACGTTCGGTGGA
101 E   D   Q   A   L   Y   Y   C   Q   Q   H   Y   R   T   P   W   T   F   G   G
```

TABLE 49-continued

Human chimeric CTB006 light chain nucleic acid and amino acid sequence

```
361 GGCACCAAGCTGGAAATCAAACGGGCTGTGGCTGCACCATCTGTCGATATCTTCCCGCCA
121  G  T  K  L  E  I  K  R  A  V  A  A  P  S  V  D  I  F  P  P

421 TCTGATGAGCAGTTGAAATCTGGAACTGCCTCTGTTGTGTGCCTGCTGAATAACTTCTAC
141  S  D  E  Q  L  K  S  G  T  A  S  V  V  C  L  L  N  N  F  Y

481 CCCAGAGAGGCCAAAGTACAGTGGAAGGTGGATAACGCCCTCCAATCGGGTAACTCCCAG
161  P  R  E  A  K  V  Q  W  K  V  D  N  A  L  Q  S  G  N  S  Q

541 GAGAGTGTCACAGAGCAGGACAGCAAGGACAGCACCTACAGCCTCAGCAGCACCCTGACG
181  E  S  V  T  E  Q  D  S  K  D  S  T  Y  S  L  S  S  T  L  T

601 CTGAGCAAAGCAGACTACGAGAAACACAAAGTCTACGCCTGCGAAGTTACCCATCAGGGC
201  L  S  K  A  D  Y  E  K  H  K  V  Y  A  C  E  V  T  H  Q  G

661 CTGAGCTCGCCCGTCACAAAGAGCTTCAACAGGGGAGAGTGTTAG
221  L  S  S  P  V  T  K  S  F  N  R  G  E  C  *
```

The human chimeric CTB006 heavy chain nucleic acid sequence is shown in Table 50 below.

TABLE 50

Human chimeric CTB006 heavy chain nucleic acid sequence

```
   1 ATGGAGTTGGGGCTGAGCTGGGTTTTCCTTGTTGTTATATTAGAAGGTGTCCAGTGTGAG    SEQ ID NO.: 28
  61 GTTCAGCTGCAGCAGTCTGGACCTGAGCTGGTGAAGCCTGGGGCTTCAGTGAGGATGTCC
 121 TGCAAGGCTTCTGGCTACACCTTCACAAGCTACTTTATACATTGGGTGAAGCAGAGGCCT
 181 GGACAGGGACTTGAGTGGATTGGATGGATTTATCCTGGAAATGTTAATACTAAGTACAGT
 241 GAGAAGTTCAAGGGTAAGGCCACACTGACTGCAGACAAATCCTCCAGCACAGCCTACATG
 301 CAGTTCAGCAGCCTGACCTCTGAGGACTCTGCGGTCTATTTCTGTGCAAGAGGGGAGGCT
 361 GGGTACTTTGACTACTGGGGCCAAGGCACCACTCTCACAGTCTCCTCAGCTAGCACCAAG
 421 GGCCCATCGGTCTTCCCCCTGGCGCCCTGCTCCAGGAGCACCTCTGGGGGCACAGCGGCC
 481 CTGGGCTGCCTGGTCAAGGACTACTTCCCCGAACCGGTGACGGTGTCGTGGAACTCAGGC
 541 GCCCTGACCAGCGGCGTGCACACCTTCCCGGCTGTCCTACAGTCCTCAGGACTCTACTCC
 601 CTCAGCAGCGTGGTGACCGTGCCCTCCAGCAGCTTGGGCACCCAGACCTACATCTGCAAC
 661 GTGAATCACAAGCCCAGCAACACCAAGGTGGACAAGAGAGTTGAGCCCAAATCTTGTGAC
 721 AAAACTCACACATGCCCACCGTGCCCAGCACCTGAACTCCTGGGGGGACCGTCAGTCTTC
 781 CTCTTCCCCCCAAAACCCAAGGACACCCTCATGATCTCCCGGACCCCTGAGGTCACATGC
 841 GTGGTGGTGGACGTGAGCCACGAAGACCCTGAGGTCAAGTTCAACTGGTACGTGGACGGC
 901 GTGGAGGTGCATAATGCCAAGACAAAGCCGCGGGAGGAGCAGTACAACAGCACGTACCGT
 961 GTGGTCAGCGTCCTCACCGTCCTGCACCAGGACTGGCTGAACGGCAAGGAGTACAAGTGC
1021 AAGGTCTCCAACAAAGGCCTCCCAGCCCCCATCGAGAAAACCATCTCCAAAGCCAAAGGG
1081 CAGCCCCGAGAACCACAGGTGTACACCCTGCCCCCATCCCGGGAGGAGATGACCAAGAAC
1141 CAGGTCAGCCTGACCTGCCTGGTCAAAGGCTTCTATCCCAGCGACATCGCCGTGGAGTGG
1201 GAGAGCAATGGGCAGCCGGAGAACAACTACAAGACCACGCCTCCCGTGCTGGACTCCGAC
1261 GGCTCCTTCTTCCTCTATAGCAAGCTCACCATGGACAAGAGCAGGTGGCAGCAGGGGAAC
1321 GTCTTCTCATGCTCCGTGATGCATGAGGCTCTGCACAACCACTACACGCAGAAGAGCCTC
1381 TCCCTGTCTCCGGGTAAATGA
```

The human chimeric CTB006 heavy chain amino acid sequence is shown in Table 51 below.

TABLE 51

Human chimeric CTB006 heavy chain amino acid sequence

SEQ ID NO.: 29

```
  1 M E L G L S W V F L V V I L E G V Q C E
 21 V Q L Q Q S G P E L V K P G A S V R M S
 41 C K A S G Y T F T S Y F I H W V K Q R P
 61 G Q G L E W I G W I Y P G N V N T K Y S
 81 E K F K C K A T L T A D K S S S T A Y M
101 Q F S S L T S E D S A V Y F C A R G E A
121 G Y F D Y W G Q G T T L T V S S A S T K
141 G P S V F P L A P C S R S T S G G T A A
161 L G C L V K D Y F P E P V T V S W N S G
181 A L T S G V H T F P A V L Q S S G L Y S
201 L S S V V T V P S S S L G T Q T Y I C N
221 V N H K P S N T K V D K R V E P K S C D
```

TABLE 51-continued

Human chimeric CTB006 heavy chain amino acid sequence

```
241 K T H T C P P C P A P E L L G G P S V F
261 L F P P K P K D T L M I S R T P E V T C
281 V V V D V S H E D P E V K F N W Y V D G
301 V E V H N A K T K P R E K Q Y N S T Y R
321 V V S V L T V L H Q D W L N G K E Y K C
341 K V S N K G L P A P I E K T I S K A K G
361 Q P R E P Q V Y T L P P S R E E M T K N
381 Q V S L T C L V K G F Y P S D I A V E W
401 E S N G Q P E N N Y K T T P P V L D S D
421 G S F F L Y S K L T M D K S R W Q Q G N
441 V F S C S V M H E A L H N H Y T Q K S L
461 S L S P G K *
```

The human chimeric CTB006 heavy chain nucleic acid and amino acid sequence are shown in Table 52 below.

TABLE 52

Human chimeric CTB006 heavy chain nucleic acid and amino acid sequence

```
  1 ATGGAGTTGGGGCTGAGCTGGGTTTTCCTTGTTGTTATATTAGAAGGTGTCCAGTGTGAG   SEQ ID NO.: 28
  1 M  E  L  G  L  S  W  V  F  L  V  V  I  L  E  G  V  Q  C  E    SEQ ID NO.: 29

61 GTTCACGTGCAGCAGTCTGGACCTGAGCTGGTAAGCCTGGGGCTTCAGTGAGGATGTCC
 21 V  Q  L  Q  Q  S  G  P  E  L  V  K  P  G  A  S  V  R  M  S

121 TGCAAGGCTTCTGGCTACACCTTCACAAGCTACTTTATACATTGGGTGAACGAGAGGCCT
 41 C  K  A  S  G  Y  T  F  T  S  Y  F  I  H  W  V  K  Q  R  P

181 GGACAGGGACTTGAGTGGATTGGATCCATTTATCCTGGAAATGTTAATACTAAGTACAGT
 61 G  Q  G  L  E  W  I  G  W  I  Y  P  G  N  V  N  T  K  Y  S

241 GAGAAGTTCAAGGGTAAGGCCACACTGACTGCAGACAAATCCTCCAGCACAGCCTACATG
 81 E  K  F  K  G  K  A  T  L  T  A  D  K  S  S  S  T  A  Y  M

301 CAGTTCAGCAGCCTGACCTCTGAGGACTCTGCGGTCTATTTCTGTGCAAGAGGGGAGGCT
101 Q  F  S  S  L  T  S  E  D  S  A  V  Y  F  C  A  R  G  E  A

361 GGGTACTTTGACTACTGGGGCCAAGGCACCACTCTCACAGTCTCCTCAGCTAGCACCAAG
121 G  Y  F  D  Y  W  G  Q  G  T  T  L  T  V  S  S  A  S  T  K

421 GGCCCATCGGTCTTCCCCCTGGCGCCCTGCTCCAGGAGCACCTCTGGGGGCACAGCGGCC
141 G  P  S  V  F  P  L  A  P  C  S  R  S  T  S  G  G  T  A  A

481 CTGGGCTGCCTGGTCAAGGACTACTTCCCCGAACCGGTGACGGTGTCGTGGAACTCAGGC
161 L  G  C  L  V  K  D  Y  F  P  E  P  V  T  V  S  W  N  S  G

541 GCCCTGACCAGCGGCGTGCACACCTTCCCGGCTGTCCTACAGTCCTCAGGACTCTACTCC
181 A  L  T  S  G  V  H  T  F  P  A  V  L  Q  S  S  G  L  Y  S

601 CTCAGCAGCGTGGTGACCGTGCCCTCCAGCAGCTTGGGCACCCAGACCTACATCTGCAAC
201 L  S  S  V  V  T  V  P  S  S  S  L  G  T  Q  T  Y  I  C  N

661 GTGAATCACAAGCCCAGCAACACCAAGGTGGACAAGAGAGTTGAGCCCAAATCTTGTGAC
221 V  N  H  K  P  S  N  T  K  V  D  K  R  V  E  P  K  S  C  D

721 AAAACTCACACATGCCCACCGTGCCCAGCACCTGAACTCCTGGGGGGACCGTCAGTCTTC
241 K  T  H  T  C  P  P  C  P  A  P  E  L  L  G  G  P  S  V  F
```

TABLE 52-continued

Human chimeric CTB006 heavy chain nucleic acid and amino acid sequence

```
 781 CTCTTCCCCCCAAAACCCAAGGACACCCTCATGATCTCCCGGACCCCTGAGGTCACATGC
 261  L  F  P  P  K  P  K  D  T  L  M  I  S  R  T  P  E  V  T  C

841 GTGGTGGTGGACGTGAGCCACGAAGACCCTGAGGTCAAGTTCAACTGGTACGTGGACGGC
 281  V  V  V  D  V  S  H  E  D  P  E  V  K  F  N  W  Y  V  D  G

901 GTGGAGGTGCATAATGCCAAGACAAAGCCGCGGGAGCAGCAGTACAACACGACCTACCGT
 301  V  E  V  H  N  A  K  T  K  P  R  E  E  Q  Y  N  S  T  Y  R

961 GTGGTCAGCGTCCTCACCGTCCTGCACCAGGACTGGCTGAACGGCAAGGAGTACAAGTGC
 321  V  V  S  V  L  T  V  L  H  Q  D  W  L  N  G  K  E  Y  K  C

1021 AAGGTCTCCAACAAAGGCCTCCCAGCCCCCATCGAGAAAACCATCTCCAAAGCCAAAGGG
 341  K  V  S  N  K  G  L  P  A  P  I  E  K  T  I  S  K  A  K  G

1081 CAGCCCCGAGAACCACAGGTGTACACCCTGCCCCCATCCCGGGAGGAGATGACCAAGAAC
 361  Q  P  R  E  P  Q  V  Y  T  L  P  P  S  R  E  E  M  T  K  N

1141 CAGGTCAGCCTGACCTGCCTGGTCAAAGGCTTCTATCCCAGCGACATCGCCGTGGAGTGG
 381  Q  V  S  L  T  C  L  V  K  G  F  Y  P  S  D  I  A  V  E  W

1201 GAGAGCAATGGGCAGCCGGAGAACAACTACAAGACCACGCCTCCCGTGCTGGACTCCGAC
 401  E  S  N  G  Q  P  E  N  N  Y  K  T  T  P  P  V  L  D  S  D

1261 GGCTCCTTCTTCCTCTATAGCAAGCTCACCATGGACAAGAGCAGGTGGCAGCAGGGGAAC
 421  G  S  F  F  L  Y  S  K  L  T  M  D  K  S  R  W  Q  Q  G  N

1321 GTCTTCTCATGCTCCGTGATGCATGAGGCTCTGGACAACCACTACACGCAGAAGACCCTC
 441  V  F  S  C  S  V  M  H  E  A  L  H  N  H  Y  T  Q  K  S  L

1381 TCCCTGTCTCCGGGTAAATGA
 461  S  L  S  P  G  K  *
```

Example 19

CTB007-Related Sequences

CTB007-related sequences are provided below.
The murine CTB007 light chain variable region nucleic acid sequence is shown in Table 53 below.

TABLE 53

Murine CTB007 light chain variable region nucleic acid sequence

```
  1 GACATCCAGATGACCCAATCTCCAGCCTCCCTATCTGTATCTGTGGGAGAAACTGTCACC      SEQ ID NO.: 30
 61 ATCACATGTCGAGCAAGTGAGAATATTTACAGTAATTTAGAATGGTATCAGCAGAAACAG
121 GGAAAATCTCCTCAGCTCCTGGTCTATGCTGCAACAAACTTAGCAGATGGTGTGCCATCA
181 AGGTTCAGTGGCAGTGGATCAGGCACACAGTATTCCCTCAAGATCAACAGCCTGCAGTCT
241 GAAGATTTTGGGAGTTATTACTGTCAACATTTTTGGGGTACTTGG
```

The murine CTB007 light chain variable region amino acid sequence is shown in Table 54 below.

TABLE 54

Murine CTB007 light chain variable region amino acid sequence

```
                                                SEQ ID NO.: 31
  1 D I Q M T Q S P A S L S V S V G E T V T
 21 I T C R A S E N I Y S N L E W Y Q Q K Q
 41 G K S P Q L L V Y A A T N L A D G V P S
 61 R F S G S G S G T Q Y S L K I N S L Q S
 81 E D F G S Y Y C Q H F W G T W
```

The murine CTB007 light chain variable region nucleic acid and amino acid sequence are shown in Table 55 below.

TABLE 55

Murine CTB007 light chain variable region nucleic acid and amino acid sequence

```
  1 GACATCCAGATGACCCAATCTCCAGCCTCCCTATCTGTATCTGTGGGAGAAACTGTCACC    SEQ ID NO.: 30
  1   D  I  Q  M  T  Q  S  P  A  S  L  S  V  S  V  G  E  T  V  T   SEQ ID NO.: 31

61 ATCACATGTCGAGCAAGTGAGAATATTTACAGTAATTTAGAATGGTATCAGCAGAAACAG
 21   I  T  C  R  A  S  E  N  I  Y  S  N  L  E  W  Y  Q  Q  K  Q

121 GGAAAATCTCCTCAGCTCCTGGTCTATGCTGCAACAAACTTAGCAGATGGTGTGCCATCA
 41   G  K  S  P  Q  L  L  V  Y  A  A  T  N  L  A  D  G  V  P  S

181 AGGTTCAGTGGCAGTGGATCAGGCACACAGTATTCCCTCAAGATCAACAGCCTGCAGTCT
 61   R  F  S  G  S  G  S  G  T  Q  Y  S  L  K  I  N  S  L  Q  S

241 GAAGATTTTGGGAGTTATTACTGTCAACATTTTTGGGGTACTTGG
 81   E  D  F  G  S  Y  Y  C  Q  H  F  W  G  T  W
```

The murine CTB007 light CDR1 amino acid sequence are shown in Table 56 below.

TABLE 56

Murine CTB007 light CDR1 amino acid sequence

R A S B N I Y S N L E    SEQ ID NO.: 32

The murine CTB007 light CDR2 amino acid sequence are shown in Table 57 below.

TABLE 57

Murine CTB007 light CDR2 amino acid sequence

A A T N L A D    SEQ ID NO.: 33

The murine CTB007 light CDR3 amino acid sequence are shown in Table 58 below.

TABLE 58

Murine CTB007 light CDR3 amino acid sequence

Q H F W G T W    SEQ ID NO.: 34

The murine CTB007 heavy chain variable region nucleic acid sequence is shown in Table 59 below.

TABLE 59

Murine CTB007 heavy chain variable region nucleic acid sequence

SEQ ID NO.: 35
```
  1 GAGGTTCAGCTGCAGCAGTCTGGGGCAGAGCTTGTGAAGCCAGGGGCCTCAGTCAAGTTG
 61 TCCTGCACAGCTTCGGGCTTCAACATTAAAGACACCTATATGCACTGGGTGAAGCAGAGG
121 CCTGAACAGGGCCTGGAGTGGATTGGAAGGATTGATCCTGCGAATGGTAATACTAAATAT
181 GACCCGAAGTTCCAGGGCAAGGCCACTATAACAGCAGACACATCCTCCAACACAGCCTAC
241 CTGCAGCTCAGCAGCCTGACATCTGAGGACACTGCCGTCTATTACTGTGCCTATTACTAC
301 GTTAGTAACGCCTGGTTTACT
```

The murine CTB007 heavy chain variable region amino acid sequence is shown in Table 60 below.

TABLE 60

Murine CTB007 heavy chain variable region amino acid sequence

SEQ ID NO.: 36

```
  1   E V Q L Q Q S G A E L V K P G A S V K L
 21   S C T A S G F N I K D T Y M H W V K Q R
 41   P E Q G L S W I G R I D P A N G N T K Y
 61   D P K F Q G K A T I T A D T S S N T A Y
 81   L Q L S S L T S E D T A V Y Y C A Y Y Y
101   V S N A W F T
```

The murine CTB007 heavy chain variable region nucleic acid and amino acid sequence is shown in Table 61 below.

TABLE 61

Murine CTB007 heavy chain variable region nucleic acid and amino acid sequence

```
  1 GAGGTTCAGCTGCAGCAGTCTGGGGCAGAGCTTGTGAAGCCAGGGGCCTCAGTCAAGTTG   SEQ ID NO.: 35
  1  E  V  Q  L  Q  Q  S  G  A  E  L  V  K  P  G  A  S  V  K  L   SEQ ID NO.: 36

61 TCCTGCACAGCTTCGGGCTTCAACATTAAAGACACCTATATGCACTGGGTGAAGCAGAGG
 21  S  C  T  A  S  G  F  N  I  K  D  T  Y  M  H  W  V  K  Q  R

121 CCTGAACAGGGCCTGGAGTGGATTGGAAGGATTGATCCTGCGAATGGTAATACTAAATAT
 41  P  E  Q  G  L  E  W  I  G  R  I  D  P  A  N  G  N  T  K  Y

181 GACCCGAAGTTCCAGGGCAAGGCCACTATAACAGCAGACACATCCTCCAACACAGCCTAC
 61  D  P  K  F  Q  G  K  A  T  I  T  A  D  T  S  S  N  T  A  Y

241 CTGCAGCTCAGCAGCCTGACATCTGAGGACACTGCCGTCTATTACTGTGCCTATTACTAC
 81  L  Q  L  S  S  L  T  S  E  D  T  A  V  Y  Y  C  A  Y  Y  Y

301 GTTAGTAACGCCTGGTTTACT
101  V  S  N  A  W  F  T
```

The murine CTB007 heavy CDR1 amino acid sequence is shown in Table 62 below.

TABLE 62

Murine CTB007 heavy CDR1 amino acid sequence

D T Y M H    SEQ ID NO.: 37

The murine CTB007 heavy CDR2 amino acid sequence is shown in Table 63 below.

TABLE 63

Murine CTB007 heavy CDR2 amino acid sequence

R I D P A N G N T K Y D P K F Q G    SEQ ID NO.: 38

The murine CTB007 heavy CDR3 amino acid sequence is shown in Table 64 below.

TABLE 64

Murine CTB007 heavy CDR3 amino acid sequence

Y Y V S N A W F T    SEQ ID NO.: 39

The human chimeric CTB007 light chain nucleic acid sequence is shown in Table 65 below.

TABLE 65

Human chimeric CTB007 light chain nucleic acid sequence

SEQ ID NO.: 40

```
  1 ATGAGGCTCCCTGCTCAGCTCCTGGGGCTGCTAATGCTCTGGGTCTCTGGATCCAGTGGT
 61 GACATCCAGATGACCCAATCTCCAGCCTCCCTATCTGTATCTGTGGGAGAAACTGTCACC
121 ATCACATGTCGAGCAAGTGAGAATATTTACAGTAATTTAGAATGGTATCAGCAGAAACAG
181 GGAAAATCTCCTCAGCTCCTGGTCTATGCTGCAACAAACTTAGCAGATGGTGTGCCATCA
241 AGGTTCAGTGGCAGTGGATCAGGCACACAGTATTCCCTCAAGATCAACAGCCTGCAGTCT
301 GAAGATTTTGGGAGTTATTACTGTCAACATTTTTGGGGTACTTGGACGTTCGGTGGAGGC
361 ACCAAGCTGGAAATCAAACGGGCTGTGGCTGCACCATCTGTCGATATCTTCCCGCCATCT
421 GATGAGCAGTTGAAATCTGGAACTGCCTCTGTTGTGTGCCTGCTGAATAACTTCTACCCC
481 AGAGAGGCCAAAGTACAGTGGAAGGTGGATAACGCCCTCCAATCGGGTAACTCCCAGGAG
541 AGTGTCACAGAGCAGGACAGCAAGGACAGCACCTACAGCCTCAGCAGCACCCTGACGCTG
601 AGCAAAGCAGACTACGAGAAACACAAAGTCTACGCCTGCGAAGTTACCCATCAGGGCCTG
661 AGCTCGCCCGTCACAAAGAGCTTCAACAGGGGAGAGTGTTAGA
```

The human chimeric CTB007 light chain amino acid sequence is shown in Table 66 below.

TABLE 66

| Human chimeric CTB007 light chain amino acid sequence | |
|---|---|
| | SEQ ID NO.: 41 |
| 1 | M R L P A Q L L G L L M L W V S G S S G |
| 21 | D I Q M T Q S P A S L S V S V G E T V T |
| 41 | I T C R A S E N I Y S N L E W Y Q Q K Q |
| 61 | G K S P Q L L V Y A A T N L A D G V P S |
| 81 | R F S G S G S G T Q Y S L K I N S L Q S |
| 101 | E D F G S Y Y C Q H F W G T W T F G G G |

TABLE 66-continued

| Human chimeric CTB007 light chain amino acid sequence | |
|---|---|
| 121 | T K L E I K R A V A A P S V D I F P P S |
| 141 | D E Q L K S G T A S V V C L L N N F Y P |
| 161 | R E A K V Q W K V D N A L Q S G N S Q E |
| 181 | S V T E Q D S K D S T Y S L S S T L T L |
| 201 | S K A D Y E K H K V Y A C E V T H Q G L |
| 221 | S S P V T K S F N R G E C * |

The human chimeric CTB007 light chain nucleic acid and amino acid sequence are shown in Table 67 below.

TABLE 67

| Human chimeric CTB007 light chain nucleic acid and amino acid sequence | | |
|---|---|---|
| 1 | ATGAGGCTCCCTGCTCAGCTCCTGGGGCTGCTAATGCTCTGGGTCTCTGGATCCAGTGGT | SEQ ID NO.: 40 |
| 1 | M R L P A Q L L G L L M L W V S G S S G | SEQ ID NO.: 41 |
| 61 | GACATCCAGATGACCCAATCTCCAGCCTCCCTATCTGTATCTGTGGGAGAAACTGTCACC | |
| 21 | D I Q M T Q S P A S L S V S V G E T V T | |
| 121 | ATCACATGTCGAGCAAGTGAGAATATTTACAGTAATTTAGAATGGTATCAGCAGAAACAG | |
| 41 | I T C R A S E N I Y S N L E W Y Q Q K Q | |
| 181 | GGAAAATCTCCTCAGCTCCTGGTCTATGCTGCAACAAACTTAGCAGATGGTGTGCCATCA | |
| 61 | G K S P Q L L V Y A A T N L A D G V P S | |
| 241 | AGGTTCAGTGGCAGTGGATCAGGCACACAGTATTCCCTCAAGATCAACAGCCTGCAGTCT | |
| 81 | R F S G S G S G T Q Y S L K I N S L Q S | |
| 301 | GAAGATTTTGGGAGTTATTACTGTCAACATTTTTGGGGTACTTGGACGTTCGGTGGAGGC | |
| 101 | E D F G S Y Y C Q H F W G T W T F G G G | |
| 361 | ACCAAGCTGGAAATCAAACGGGCTGTGGCTGCACCATCTGTCGATATCTTCCCGCCATCT | |
| 121 | T K L E I K R A V A A P S V D I F P P S | |
| 421 | GATGAGCAGTTGAAATCTGGAACTGCCTCTGTTGTGTGCCTGCTGAATAACTTCTACCCC | |
| 141 | D E Q L K S G T A S V V C L L N N F Y P | |
| 481 | AGAGAGGCCAAAGTACAGTGGAAGGTGGATAACGCCCTCCAATCGGGTAACTCCCAGGAG | |
| 161 | R E A K V Q W K V D N A L Q S G N S Q E | |
| 541 | AGTGTCACAGAGCAGGACAGCAAGGACAGCACCTACAGCCTCAGCAGCACCCTGACGCTG | |
| 181 | S V T E Q D S K D S T Y S L S S T L T L | |
| 601 | AGCAAAGCAGACTACGAGAAACACAAAGTCTACGCCTGCGAAGTTACCCATCAGGGCCTG | |
| 201 | S K A D Y E K H K V Y A C S V T H Q G L | |
| 661 | AGCTCGCCCGTCACAAAGAGCTTCAACAGGGGAGAGTGTTAGA | |
| 221 | S S P V T K S F N R G E C * | |

The human chimeric CTB007 heavy chain nucleic acid sequence is shown in Table 68 below.

TABLE 68

| Human chimeric CTB007 heavy chain nucleic acid sequence | |
|---|---|
| | SEQ ID NO.: 42 |
| 1 | ATGGAGTTGGGGCTGAGCTGGGTTTTCCTTGTTGTTATATTAGAAGGTGTCCAGTGTGAG |
| 61 | GTTCAGCTGCAGCAGTCTGGGGCAGAGCTTGTGAAGCCAGGGGCCTCAGTCAAGTTGTCC |
| 121 | TGCACAGCTTCGGGCTTCAACATTAAAGACACCTATATGCACTGGGTGAAGCAGAGGCCT |

TABLE 68-continued

Human chimeric CTB007 heavy chain nucleic acid sequence

```
 181  GAACAGGGCCTGGAGTGGATTGGAAGGATTGATCCTGCGAATGGTAATACTAAATATGAC
 241  CCGAAGTTCCAGGGCAAGGCCACTATAACAGCAGACACATCCTCCAACACAGCCTACCTG
 301  CAGCTCAGCAGCCTGACATCTGAGGACACTGCCGTCTATTACTGTGCCTATTACTACGTT
 361  AGTAACGCCTGGTTTACTTACTGGGGCCAAGGGACTCTGGTCACTGTCTCTGCAGCTAGC
 421  ACCAAGGGCCCATCGGTCTTCCCCCTGGCGCCCTGCTCCAGGAGCACCTCTGGGGGCACA
 481  GCGGCCCTGGGCTGCCTGGTCAAGGACTACTTCCCCGAACCGGTGACGGTGTCGTGGAAC
 541  TCAGGCGCCCTGACCAGCGGCGTGCACACCTTCCCGGCTGTCCTACAGTCCTCAGGACTC
 601  TACTCCCTCAGCAGCGTGGTGACCGTGCCCTCCAGCAGCTTGGGCACCCAGACCTACATC
 661  TGCAACGTGAATCACAAGCCCAGCAACACCAAGGTGGACAAGAGAGTTGAGCCCAAATCT
 721  TGTGACAAAACTCACACATGCCCACCGTGCCCAGCACCTGAACTCCTGGGGGGACCGTCA
 781  GTCTTCCTCTTCCCCCCAAAACCCAAGGACACCCTCATGATCTCCCGGACCCCTGAGGTC
 841  ACATGCGTGGTGGTGGACGTGAGCCACGAAGACCCTGAGGTCAAGTTCAACTGGTACGTG
 901  GACGGCGTGGAGGTGCATAATGCCAAGACAAAGCCGCGGGAGGAGCAGTACAACAGCACG
 961  TACCGTGTGGTCAGCGTCCTCACCGTCCTGCACCACGACTGGCTGAACGGCAAGGAGTAC
1021  AAGTGCAAGGTCTCCAACAAAGCCTCCCAGCCCCCATCGAGAAAACCATCTCCAAAGCC
1081  AAAGGGCAGCCCCGAGAACCACAGGTGTACACCCTGCCCCCATCCCGGGAGGAGATGACC
1141  AAGAACCAGGTCAGCCTGACCTGCCTGGTCAAAGGCTTCTATCCCAGCGACATCGCCGTG
1201  GAGTGGGAGAGCAATGGGCAGCCGGAGAACAACTACAAGACCACGCCTCCCGTGCTGGAC
1261  TCCGACGGCTCCTTCTTCCTCTATAGCAAGCTCACCATGGACAAGAGCAGGTGGCAGCAG
1321  GGGAACGTCTTCTCATGCTCCGTGATGCATGAGGCTCTGCACAACCACTACACGCAGAAG
1381  AGCCTCTCCCTGTCTCCGGGTAAATGA
```

The human chimeric CTB007 heavy chain amino acid sequence is shown in Table 69 below.

TABLE 69

Human chimeric CTB007 heavy chain amino acid sequence

SEQ ID NO.: 43

```
  1   M E L G L S W V F L V V I L E G V Q C E
 21   V Q L Q Q S G A E L V K P G A S V K L S
 41   C T A S G F N I K D T Y M H W V K Q R P
 61   E Q G L E W I G R I D P A N G N T K Y D
 81   P K F Q G K A T I T A D T S S N T A Y L
101   Q L S S L T S E D T A V Y Y C A Y Y Y V
121   S N A W F T Y W G Q G T L V T V S A A S
141   T K G P S V F P L A P C S R S T S G G T
161   A A L G C L V K D Y F P E P V T V S W N
181   S G A L T S G V H T F P A V L Q S S G L
201   Y S L S S V V T V P S S S L G T Q T Y I
221   C N V N H K P S N T K V D K R V E P K S
```

TABLE 69-continued

Human chimeric CTB007 heavy chain amino acid sequence

```
241   C D K T H T C P P C P A P E L L G G P S
261   V F L F P P K P K D T L M I S R T P E V
281   T C V V V D V S H E D P E V K F N W Y V
301   D G V E V H N A K T K P R E E Q Y N S T
321   Y R V V S V L T V L H Q D W L N G K E Y
341   K C K V S N K G L P A P I E K T I S K A
361   K G Q P R E P Q V Y T L P P S R E E M T
381   K N Q V S L T C L V K G F Y P S D I A V
401   E W E S N G Q P E N N Y K T T P P V L D
421   S D G S F F L Y S K L T N D K S R W Q Q
441   G N V F S C S V M H E A L H N H I T Q K
461   S L S L S P G K *
```

The human chimeric CTB007 heavy chain nucleic acid and amino acid sequence are shown in Table 70 below.

TABLE 70

| Human chimeric CTB007 heavy chain nucleic acid and amino acid sequence |
|---|
| 1    ATGGAGTTGGGGCTGAGCTGGGTTTTCCTTGTTGTTATATTAGAAGGTGTCCAGTGTGAG    SEQ ID NO.: 42<br>1     M   E   L   G   L   S   W   V   F   L   V   V   I   L   E   G   V   Q   C   E    SEQ ID NO.: 43 |
| 61   GTTCAGCTGCAGCAGTCTGGGGCAGAGCTTGTGAAGCCAGGGGCCTCAGTCAAGTTGTCC<br>21    V   Q   L   Q   Q   S   G   A   E   L   V   K   P   G   A   S   V   K   L   S |
| 121  TGCACAGCTTCGGGCTTCAACATTAAAGACACCTATATGCACTGGGTGAAGCAGAGGCCT<br>41    C   T   A   S   G   F   N   I   K   D   T   Y   M   H   W   V   K   Q   R   P |
| 181  GAACAGGGCCTGGAGTGGATTGGAAGGATTGATCCTGCGAATGGTAATACTAAATATGAC<br>61    E   Q   G   L   E   W   I   G   R   I   D   P   A   N   G   N   T   K   Y   D |
| 241  CCGAAGTTCCAGGGCAAGGCCACTATAACAGCAGACACATCCTCCAACACAGCCTACCTG<br>81    P   K   F   Q   G   K   A   T   I   T   A   D   T   S   S   N   T   A   Y   L |
| 301  CAGCTCAGCAGCCTGACATCTGAGGACACTGCCGTCTATTACTGTGCCTATTACTACGTT<br>101   Q   L   S   S   L   T   S   E   D   T   A   V   Y   Y   C   A   Y   Y   Y   V |
| 361  AGTAACGCCTGGTTTACTTACTGGGGCCAAGGGACTCTGGTCACTGTCTCTGCAGCTAGC<br>121   S   N   A   W   F   T   Y   W   G   Q   G   T   L   V   T   V   S   A   A   S |
| 421  ACCAAGGGCCCATCGGTCTTCCCCCTGGCGCCCTGCTGGAGGAGCACCTCTGGGGGCACA<br>141   T   K   G   P   S   V   F   P   L   A   P   C   S   R   S   T   S   G   G   T |
| 481  GCGGCCCTGGGCTGCCTGGTCAAGGACTACTTCCCCGAACCGGTGACGGTGTCGTGGAAC<br>161   A   A   L   G   C   L   V   K   D   Y   F   P   E   P   V   T   V   S   W   N |
| 541  TCAGGCGCCCTGACCAGCGGCGTGCACACCTTCCCGGCTGTCCTACAGTCCTCAGGACTC<br>181   S   G   A   L   T   S   G   V   H   T   F   P   A   V   L   Q   S   S   G   L |
| 601  TACTCCCTCAGCAGCGTGGTGACCGTGCCCTCCAGCAGCTTGGGCACCCAGACCTACATC<br>201   Y   S   L   S   S   V   V   T   V   P   S   S   S   L   G   T   Q   T   Y   I |
| 661  TGCAACGTGAATCACAAGCCCAGCAACACCAAGGTGGACAAGAGAGTTGAGCCCAAATCT<br>221   C   N   V   N   H   K   P   S   N   T   K   V   D   K   R   V   E   P   K   S |
| 721  TGTGACAAAACTCACACATGCCCACCGTGCCCAGCACCTGAACTCCTGGGGGGACCGTCA<br>241   C   D   K   T   H   T   C   P   P   C   P   A   P   E   L   L   G   G   P   S |
| 781  GTCTTCCTCTTCCCCCCAAAACCCAAGGACACCCTCATGATCTCCCGGACCCCTGAGGTC<br>261   V   F   L   F   P   P   K   P   K   D   T   L   M   I   S   R   T   P   E   V |
| 841  ACATGCGTGGTGGTGGACGTGAGCCACGAAGACCCTGAGGTCAAGTTCAACTGGTACGTG<br>281   T   C   V   V   V   D   V   S   H   E   D   P   E   V   K   F   N   W   Y   V |
| 901  GACGGCGTGGAGGTGCATAATGCCAAGACAAAGCCGCGGGAGGAGCAGTACAACAGCACG<br>301   D   G   V   E   V   H   N   A   K   T   K   P   R   E   E   Q   Y   N   S   T |
| 961  TACCGTGTGGTCAGCGTCCTCACCGTCCTGCACCAGGACTGGCTGAACGGCAAGGAGTAC<br>321   Y   R   V   V   S   V   L   T   V   L   H   Q   D   W   L   N   G   K   E   Y |
| 1021 AAGTGCAAGGTCTCCAACAAAGGCCTCCCAGCCCCCATCGAGAAAACCATCTCCAAAGCC<br>341   K   C   K   V   S   N   K   G   L   P   A   P   I   E   K   T   I   S   K   A |
| 1081 AAAGGGCAGCCCCGAGAACCACAGGTGTACACCCTGCCCCCATCCCGGGAGGAGATGACC<br>361   K   G   Q   P   R   E   P   Q   V   Y   T   L   P   P   S   R   E   E   M   T |
| 1141 AAGAACCAGGTCAGCCTGACCTGCCTGGTCAAAGGCTTCTATCCCAGCGACATCGCCGTG<br>381   K   N   Q   V   S   L   T   C   L   V   K   C   F   Y   P   S   D   I   A   V |
| 1201 GAGTGGGAGAGCAATGGGCAGCCGGAGAACAACTACAAGACCACGCCTCCCGTGCTGGAC<br>401   E   W   E   S   N   G   Q   P   E   N   N   Y   K   T   T   P   P   V   L   D |
| 1261 TCCGACGGCTCCTTCTTCCTCTATAGCAAGCTCACCATGGACAAGAGCAGGTGGCAGCAG<br>421   S   D   G   S   F   F   L   Y   S   K   L   T   M   D   K   S   R   W   Q   Q |
| 1321 GGGAACGTCTTCTCATGCTCCGTGATGCATGAGGCTCTGCACAACCACTACACGCAGAAG<br>441   G   N   V   F   S   C   S   V   M   H   E   A   L   H   N   H   Y   T   Q   K |
| 1381 AGCCTCTCCCTGTCTCCGGGTAAATGA<br>461   S   L   S   L   S   P   G   K   * |

Example 20

Analysis of Epitope Recognized by CTB003 and hCTB003

It is to be appreciated that the common epitope recognized by TRAIL receptor-binding agents Of the invention (e.g., CTB003 and hCTB003) may be further analyzed for subregions (fragments) or homologues of the amino acid sequence amino acid sequence VXDCTPWSDIECVHKE (SEQ ID NO.:44), wherein X is K or G as provided herein, which, when bound by TRAIL receptor-binding reagents of the invention can induce cell (e.g., cancer cell) apoptosis in TRAIL-R1 and/or TRAIL-R2 receptor polypeptide expressing cells in vitro and/or in vivo systems.

Select candidate peptides are prepared by methods known in the art which are fragments or homologues of the amino acid sequence VXDCTPWSDIECVHKE (SEQ ID NO.:44). These candidate peptides are tested for their ability to inhibit TRAIL receptor-binding agent binding to TRAIL receptors (e.g., TRAIL-R1 and TRAIL-R2) in a competitive ELISA as described below Competitive Inhibition ELISA.

ELISA plate is coated with 1 µg/ml TRAIL-R1 or TRAIL-R2-Fc fusion protein in PBS at 4° C. overnight. After washing three times with PBS, the plate is blocked with 3% BSA PBS at room temperature for one hour. 1 µg/ml CTB003 or hCTB003 (TRAIL receptor-binding agent) are added with various concentrations of candidate peptides, respectively, at 37° C. for 1 h. The unbound TRAIL receptor-binding agent) is removed by washing three time with PBS, and then HRP-conjugated goat anti-mouse IgG1 was added at 37° C. for 30 minutes. After washing three times with PBS, TMB substrate buffer is added for 10 minutes and then the reaction is stopped by adding 2N $H_2SO_4$. The values of optical density are recorded in a ELISA plate reader with a dual wavelength at 450 nm/650 nm. The OD value in the absence of a candidate peptide as a maximum binding of CTB003 (or hCTB003; TRAIL receptor-binding agent) to TRAIL-R1 or TRAIL-R2. The competitive inhibition of various concentrations of a candidate peptide to the binding of CTB003 to TRAIL-R2 is calculated as a percentage of maximum binding.

Results and Interpretation:

If the candidate peptide inhibits the binding of the TRAIL receptor-binding agent to both TRAIL-R1 and TRAIL-R2 in a concentration-dependent manner, then the candidate peptide represents a common region recognized by the TRAIL receptor-binding agent (e.g., CTB003 or hCTB003). Further, the candidate sequence can be targeted for generation of an agonistic antibody to induce apoptosis of cancer cells expressing either TRAIL-R1 or TRAIL-R2 or both. Further, the candidate peptide can be tested in the in vitro and in vivo models of the present invention to determine if the candidate peptide is capable of inhibiting TRAIL receptor-binding agent mediated inhibition of cell growth (e.g., tumor growth).

Example 21

Binding and Apoptosis-Inducing Activity of CTB003 to Tumor Cells that Differentially Express TRAIL-R1 and TRAIL-R2

Tumor cells may express differential levels of cell surface of TRAIL-R1 and TRAIL-R2, therefore a monospecific antibody directed against either TRAIL-R1 or TRAIL-R2 may not able to bind to and induce apoptosis of all tumor cells when administered alone. To determine whether CTB003 has a broader binding and apoptosis-inducing activity compared to monospecific TRAIL-R1 or TRAIL-R2 antibodies, studies were performed in two representative cell lines, human T leukaemia cells and human B lymphoma cells. Human T leukemia cells (Jurkat) only express TRAIL-R2 but not TRAIL-R1. Human B lymphoma cells (Ramos) express high levels of TRAIL-R1 but low levels of TRAIL-R2. They also exhibits a differential susceptibility to TRAIL-R1 or TRAIL-R2 monospecific antibody-induced apoptosis.

Flow Cytometry Analysis of Cell Surface Binding of CTB003.

$1\times10^6$ single cells were collected from cell culture medium and washed twice with FACS buffer (PBS containing 5% FCS, 0.1% $NaN_3$, pH7.4). Cells were incubated with 20 μl of 10 μg/ml CTB003, CTB006 or CTB007 on ice for 30 minutes. After washing twice with 1 ml FACS buffer, cells were further incubated with PE-conjugated goat anti-mouse IgG1 antibody on ice for 30 minutes. After washing twice with 1 ml FACS buffer, cells were suspended in 0.5 ml FACS buffer and 10,000 viable cells were analyzed by FACScan flow cytometer.

ATPLite Assay to Determine Cell Viability 1,000 target cells per well were cultured in 96-well plates in the presence of four concentrations of 10-fold diluted CTB003, CTB006 or CTB007 with the highest concentration at 1000 ng/ml and the lowest concentration at 10 ng/ml. After culture at 37° C. for 16 h, the cell viability of each culture was determined using the ATPLite kit according to the manufacturer's instructions (Packard Instruments, Meriden, Conn.): add 50 μl of cell lysis buffer and then 50 μl of substrate buffer. The reaction was counted in a luminescent reader. Cell viability was calculated as (cpm of treated cells/cmp of control cells)×100%.

Results:

Jurkat cells were positively stained with CTB006 but not CTB007 (FIG. 32, panel A) indicating that Jurkat cells only express TRAIL-R2 but not TRAIL-R1. Although Jurkat cells do not express TRAIL-R1, they were equally stained with CTB003. In contrast, Ramos cells were strongly stained with CTB007 or CTB003 but only weakly stained with CTB006 (FIG. 32, panel B), indicating that Ramos cells primarily express TRAIL-R1. These results demonstrate that CTB003 has an equal binding ability to the tumor cell surface regardless of their differential levels of TRAIL-R1 or TRAIL-R2.

Jurkat cells had a similar susceptibility to CTB006- and CTB003-induced apoptosis but were completely non-responsive to CTB007 over the antibody concentration range tested (FIG. 32, panel C). In contrast, Ramos cells were not susceptible to apoptosis induced by either CTB006 or CTB007 (FIG. 32, panel D) but were relatively sensitive to CTB003-induced apoptosis. These results indicate that CTB003 is useful in the induction of apoptosis of tumor cells that differentially express only one type of the death receptors. As such, TRAIL receptor-binding agents of the invention which bind to the TRAIL-R1 and/or TRAIL-R2 (e.g., CTB003 or hCTB003) may have the advantage of greater clinical utility in treatment of cancer patients than agents which bind to TRAIL-R1 or TRAIL-R2 alone, as the expression and function of the TRAIL receptors in primary tumor cells of patients are expected to vary largely.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

What we claim is:

1. An isolated antibody which binds TRAIL receptor 1 (TRAIL-R1) and TRAIL receptor 2 (TRAIL-R2), wherein said antibody, in its soluble form has in vivo and in vitro cell death-inducing activity in cancer cells that express TRAIL-R1 polypeptide or TRAIL-R2 polypeptide, and wherein said antibody binds a polypeptide region of at least about 90 percent amino acid homology to VXDCTPWSDIECVHKE (SEQ ID NO.:44), wherein X is K or G.

2. The antibody according to claim 1, wherein said antibody binds a TRAIL receptor 1 (TRAIL-R1) polypeptide and TRAIL receptor 2 (TRAIL-R2) polypeptide expressed on the surface of at least one cell.

3. The antibody according to claim 1, wherein said antibody has the same epitope specificity as produced by mouse-mouse hybridoma CTB003 having CGMCC Accession Number 1665.

4. The antibody according to claim 1 which is conjugated to a cancer therapeutic agent, wherein the therapeutic agent is selected from the group consisting of a tumor-activated prodrug, a radionuclide, a chemotherapeutic drug and a toxin.

5. A composition comprising the antibody of claim and a pharmaceutically acceptable carrier.

6. A commercial kit for treating a cancer comprising the antibody of claim 1 in a container and a chemotherapeutic agent wherein the chemotherapeutic agent and the antibody are optionally placed in separate containers.

7. A method selectively inducing cell death of cells expressing TRAIL-R1 and TRAIL-R2 polypeptide in a subject in need thereof, the method comprising administering to the subject an effective amount of the antibody of claim 1, thereby selectively inducing cell death of cells expressing TRAIL-R1 and TRAIL-R2 polypeptide.

8. The method according to claim 7, wherein the cells expressing TRAIL-R1 and TRAIL-R2 polypeptide are cancer cells.

9. The method according to claim 8, wherein the cancer cells are selected from the group consisting of: breast cancer cells; liver cancer cells; pancreatic cancer cells; and colorectal cancer cells.

* * * * *

UNITED STATES PATENT AND TRADEMARK OFFICE
CERTIFICATE OF CORRECTION

| | | |
|---|---|---|
| PATENT NO. | : 7,897,730 B2 | Page 1 of 1 |
| APPLICATION NO. | : 12/298001 | |
| DATED | : March 1, 2011 | |
| INVENTOR(S) | : Zheng Yu | |

It is certified that error appears in the above-identified patent and that said Letters Patent is hereby corrected as shown below:

ON THE FRONT FACE OF THE PATENT, UNDER ITEM (87)

PCT Pub. No.: WO2007/128321

Should read:

PCT Pub. No.: ~~WO2007/128321~~ WO2007/128231

Signed and Sealed this
Sixth Day of March, 2012

David J. Kappos
*Director of the United States Patent and Trademark Office*

SEQUENCE LISTING

```
<160> NUMBER OF SEQ ID NOS: 91

<210> SEQ ID NO 1
<211> LENGTH: 288
<212> TYPE: DNA
<213> ORGANISM: Mus sp.
<220> FEATURE:
<221> NAME/KEY: CDS
<222> LOCATION: (1)..(288)

<400> SEQUENCE: 1 gac atc cag atg acc caa tct tca tcc tcc ttt tct gta tct cta gga        48
Asp Ile Gln Met Thr Gln Ser Ser Ser Ser Phe Ser Val Ser Leu Gly
1               5                   10                  15 gac aga gtc acc att act tgc aag gca ggt gag gac ata tat aat cgg        96
Asp Arg Val Thr Ile Thr Cys Lys Ala Gly Glu Asp Ile Tyr Asn Arg
            20                  25                  30 tta gcc tgg tat cag cag aaa cca gga aat gct cct agg ctc tta ata       144
Leu Ala Trp Tyr Gln Gln Lys Pro Gly Asn Ala Pro Arg Leu Leu Ile
        35                  40                  45 tct ggt gca acc aat ttg gaa act ggg gtt cct tca aga ttc agt ggc       192
Ser Gly Ala Thr Asn Leu Glu Thr Gly Val Pro Ser Arg Phe Ser Gly
    50                  55                  60 agt gga tct gga aag gat tac act ctc agc att acc agt ctt cag act       240
Ser Gly Ser Gly Lys Asp Tyr Thr Leu Ser Ile Thr Ser Leu Gln Thr
65                  70                  75                  80 gaa gat gtt gct act tat tac tgt caa cag tat tgg agt act ccg ctc       288
Glu Asp Val Ala Thr Tyr Tyr Cys Gln Gln Tyr Trp Ser Thr Pro Leu
                85                  90                  95

<210> SEQ ID NO 2
<211> LENGTH: 96
<212> TYPE: PRT
<213> ORGANISM: Mus sp.

<400> SEQUENCE: 2

Asp Ile Gln Met Thr Gln Ser Ser Ser Ser Phe Ser Val Ser Leu Gly
1               5                   10                  15

Asp Arg Val Thr Ile Thr Cys Lys Ala Gly Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Asn Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Leu
                85                  90                  95

<210> SEQ ID NO 3
<211> LENGTH: 11
<212> TYPE: PRT
```

<213> ORGANISM: Mus sp.

<400> SEQUENCE: 3

Lys Ala Gly Glu Asp Ile Tyr Asn Arg Leu Ala
1               5                   10

<210> SEQ ID NO 4
<211> LENGTH: 7
<212> TYPE: PRT
<213> ORGANISM: Mus sp.

<400> SEQUENCE: 4

Gly Ala Thr Asn Leu Glu Thr
1               5

<210> SEQ ID NO 5
<211> LENGTH: 8
<212> TYPE: PRT
<213> ORGANISM: Mus sp.

<400> SEQUENCE: 5

Gln Gln Tyr Trp Ser Thr Pro Leu
1               5

<210> SEQ ID NO 6
<211> LENGTH: 30
<212> TYPE: PRT
<213> ORGANISM: Mus sp.

<400> SEQUENCE: 6

Glu Ser Ala Leu Ile Thr Gln Gln Asp Leu Ala Pro Gln Gln Arg Ala
1               5                   10                  15

Ala Pro Gln Gln Lys Arg Ser Ser Pro Ser Glu Gly Leu Cys
            20                  25                  30

<210> SEQ ID NO 7
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 7

| gag gtg cat ctc gtg gag tct ggg gga ggc tta gtg agg cct gga ggg | 48 |
| Glu Val His Leu Val Glu Ser Gly Gly Gly Leu Val Arg Pro Gly Gly | |
| 1               5                   10                  15 | |
| tcc ctg aaa ctc tcc tgt gcg gcc tct gga ttc gct ttc agt agc tat | 96 |
| Ser Leu Lys Leu Ser Cys Ala Ala Ser Gly Phe Ala Phe Ser Ser Tyr | |
|             20                  25                  30 | |
| gac atg tct tgg gtt cgc cag act ccg gag aag agg ctg gag tgg gtc | 144 |
| Asp Met Ser Trp Val Arg Gln Thr Pro Glu Lys Arg Leu Glu Trp Val | |
|         35                  40                  45 | |
| gca tac att agt gat ggt ggt ggt atc acc tac tat cca gac aca atg | 192 |
| Ala Tyr Ile Ser Asp Gly Gly Gly Ile Thr Tyr Tyr Pro Asp Thr Met | |
|     50                  55                  60 | |
| aag ggc cga ctc acc atc tcc aga gac aat gcc aag aat acc ctg tcc | 240 |
| Lys Gly Arg Leu Thr Ile Ser Arg Asp Asn Ala Lys Asn Thr Leu Ser | |
| 65                  70                  75                  80 | |
| ctg caa atg agc agt ctg aag tct gag gac aca gcc atg tat tac tgt | 288 |
| Leu Gln Met Ser Ser Leu Lys Ser Glu Asp Thr Ala Met Tyr Tyr Cys | |
|                 85                  90                  95 | |
| gca aga cat att act atg gtg gta gga ccc ttt gct | 324 |

Ala Arg His Ile Thr Met Val Val Gly Pro Phe Ala
            100                 105

<210> SEQ ID NO 8
<211> LENGTH: 108
<212> TYPE: PRT
<213> ORGANISM: Mus sp.

<400> SEQUENCE: 8

Glu Val His Leu Val Glu Ser Gly Gly Gly Leu Val Arg Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Tyr Ile Ser Asp Gly Gly Ile Thr Tyr Tyr Pro Asp Thr Met
    50                  55                  60

Lys Gly Arg Leu Thr Ile Ser Arg Asp Asn Ala Lys Asn Thr Leu Ser
65                  70                  75                  80

Leu Gln Met Ser Ser Leu Lys Ser Glu Asp Thr Ala Met Tyr Tyr Cys
                85                  90                  95

Ala Arg His Ile Thr Met Val Val Gly Pro Phe Ala
            100                 105

<210> SEQ ID NO 9
<211> LENGTH: 5
<212> TYPE: PRT
<213> ORGANISM: Mus sp.

<400> SEQUENCE: 9

Ser Tyr Asp Met Ser
1               5

<210> SEQ ID NO 10
<211> LENGTH: 17
<212> TYPE: PRT
<213> ORGANISM: Mus sp.

<400> SEQUENCE: 10

Tyr Ile Ser Asp Gly Gly Ile Thr Tyr Tyr Pro Asp Thr Met Lys
1               5                   10                  15

Gly

<210> SEQ ID NO 11
<211> LENGTH: 10
<212> TYPE: PRT
<213> ORGANISM: Mus sp.

<400> SEQUENCE: 11

His Ile Thr Met Val Val Gly Pro Phe Ala
1               5                   10

<210> SEQ ID NO 12
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(702)

```
<400> SEQUENCE: 12 atg agg ctc cct gct cag ctc ctg ggg ctg cta atg ctc tgg gtc tct      48
Met Arg Leu Pro Ala Gln Leu Leu Gly Leu Leu Met Leu Trp Val Ser
1               5                   10                  15 gga tcc agt ggt gac atc cag atg act cag tct tca tcc tcc ttt tct      96
Gly Ser Ser Gly Asp Ile Gln Met Thr Gln Ser Ser Ser Ser Phe Ser
            20                  25                  30 gta tct cta gga gac aga gtc acc att act tgc aag gca agt gag gac     144
Val Ser Leu Gly Asp Arg Val Thr Ile Thr Cys Lys Ala Ser Glu Asp
        35                  40                  45 ata tat aat cgg tta gcc tgg tat cag cag aaa cca gga aat gct cct     192
Ile Tyr Asn Arg Leu Ala Trp Tyr Gln Gln Lys Pro Gly Asn Ala Pro
    50                  55                  60 agg ctc tta ata tct ggt gca acc agt ttg gaa act ggg gtt cct tca     240
Arg Leu Leu Ile Ser Gly Ala Thr Ser Leu Glu Thr Gly Val Pro Ser
65                  70                  75                  80 aga ttc agt ggc agt gga tct gga aag gat tac act ctc agc att acc     288
Arg Phe Ser Gly Ser Gly Ser Gly Lys Asp Tyr Thr Leu Ser Ile Thr
                85                  90                  95 agt ctt cag act gaa gat gtt gct act tat tac tgt caa cag tat tgg     336
Ser Leu Gln Thr Glu Asp Val Ala Thr Tyr Tyr Cys Gln Gln Tyr Trp
            100                 105                 110 agt act ccg ctc acg ttc ggt gct ggg acc aag ctg gag ctg aaa cgg     384
Ser Thr Pro Leu Thr Phe Gly Ala Gly Thr Lys Leu Glu Leu Lys Arg
        115                 120                 125 gct gtg gct gca cca tct gtc gat atc ttc ccg cca tct gat gag cag     432
Ala Val Ala Ala Pro Ser Val Asp Ile Phe Pro Pro Ser Asp Glu Gln
    130                 135                 140 ttg aaa tct gga act gcc tct gtt gtg tgc ctg ctg aat aac ttc tac     480
Leu Lys Ser Gly Thr Ala Ser Val Val Cys Leu Leu Asn Asn Phe Tyr
145                 150                 155                 160 ccc aga gag gcc aaa gta cag tgg aag gtg gat aac gcc ctc caa tcg     528
Pro Arg Glu Ala Lys Val Gln Trp Lys Val Asp Asn Ala Leu Gln Ser
                165                 170                 175 ggt aac tcc cag gag agt gtc aca gag cag gac agc aag gac agc acc     576
Gly Asn Ser Gln Glu Ser Val Thr Glu Gln Asp Ser Lys Asp Ser Thr
            180                 185                 190 tac agc ctc agc agc acc ctg acg ctg agc aaa gca gac tac gag aaa     624
Tyr Ser Leu Ser Ser Thr Leu Thr Leu Ser Lys Ala Asp Tyr Glu Lys
        195                 200                 205 cac aaa gtc tac gcc tgc gaa gtt acc cat cag ggc ctg agc tcg ccc     672
His Lys Val Tyr Ala Cys Glu Val Thr His Gln Gly Leu Ser Ser Pro
    210                 215                 220 gtc aca aag agc ttc aac agg gga gag tgt tag                         705
Val Thr Lys Ser Phe Asn Arg Gly Glu Cys
225                 230

<210> SEQ ID NO 13
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Arg Leu Pro Ala Gln Leu Leu Gly Leu Leu Met Leu Trp Val Ser
1               5                   10                  15

Gly Ser Ser Gly Asp Ile Gln Met Thr Gln Ser Ser Ser Ser Phe Ser
            20                  25                  30
```

```
Val Ser Leu Gly Asp Arg Val Thr Ile Thr Cys Lys Ala Ser Glu Asp
            35                  40                  45
Ile Tyr Asn Arg Leu Ala Trp Tyr Gln Gln Lys Pro Gly Asn Ala Pro
 50                  55                  60
Arg Leu Leu Ile Ser Gly Ala Thr Ser Leu Glu Thr Gly Val Pro Ser
 65                  70                  75                  80
Arg Phe Ser Gly Ser Gly Ser Gly Lys Asp Tyr Thr Leu Ser Ile Thr
                 85                  90                  95
Ser Leu Gln Thr Glu Asp Val Ala Thr Tyr Tyr Cys Gln Gln Tyr Trp
            100                 105                 110
Ser Thr Pro Leu Thr Phe Gly Ala Gly Thr Lys Leu Glu Leu Lys Arg
        115                 120                 125
Ala Val Ala Ala Pro Ser Val Asp Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230

<210> SEQ ID NO 14
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1410)
<220> FEATURE:
<221> NAME/KEY: modified_base
<222> LOCATION: (8)..(9)
<223> OTHER INFORMATION: a, c, t, g, unknown or other

<400> SEQUENCE: 14 atg ggg ann ttg ggg ctg agc tgg gtt ttc ctt gtt gtt ata tta gaa      48
Met Gly Xaa Leu Gly Leu Ser Trp Val Phe Leu Val Val Ile Leu Glu
 1               5                  10                  15 ggt gtc cag tgt gag gtg cat ctc gtg gag tct ggg gga ggc tta gtg      96
Gly Val Gln Cys Glu Val His Leu Val Glu Ser Gly Gly Gly Leu Val
            20                  25                  30 agg cct gga ggg tcc ctg aaa ctc tcc tgt gcg gcc tct gga ttc gct     144
Arg Pro Gly Gly Ser Leu Lys Leu Ser Cys Ala Ala Ser Gly Phe Ala
        35                  40                  45 ttc agt agc tat gac atg tct tgg gtt cgc cag act ccg gag aag agg     192
Phe Ser Ser Tyr Asp Met Ser Trp Val Arg Gln Thr Pro Glu Lys Arg
    50                  55                  60 ctg gag tgg gtc gca tac att agt gat ggt ggt ggt atc acc tac tat     240
Leu Glu Trp Val Ala Tyr Ile Ser Asp Gly Gly Gly Ile Thr Tyr Tyr
 65                  70                  75                  80 cca gac aca atg aag ggc cga ttc acc atc tcc aga gac aat gcc aag     288
Pro Asp Thr Met Lys Gly Arg Phe Thr Ile Ser Arg Asp Asn Ala Lys
```

-continued

|  |  |  |  |  |  |  |  |  |  |  |  |  |  |  |  |
|---|---|---|---|---|---|---|---|---|---|---|---|---|---|---|---|
|  |  |  |  | 85 |  |  |  | 90 |  |  |  | 95 |  |  |  |

```
aat acc ctg tcc ctg caa atg agc agt ctg aag tct gag gac aca gcc      336
Asn Thr Leu Ser Leu Gln Met Ser Ser Leu Lys Ser Glu Asp Thr Ala
            100                 105                 110 atg tat tac tgt gca aga cat att act atg gtg gta gga ccc ttt gct      384
Met Tyr Tyr Cys Ala Arg His Ile Thr Met Val Val Gly Pro Phe Ala
        115                 120                 125 tac tgg ggc caa ggg act ctg gtc act gtc tct gca gct agc acc aag      432
Tyr Trp Gly Gln Gly Thr Leu Val Thr Val Ser Ala Ala Ser Thr Lys
130                 135                 140 ggc cca tcg gtc ttc ccc ctg gcg ccc tgc tcc agg agc acc tct ggg      480
Gly Pro Ser Val Phe Pro Leu Ala Pro Cys Ser Arg Ser Thr Ser Gly
145                 150                 155                 160 ggc aca gcg gcc ctg ggc tgc ctg gtc aag gac tac ttc ccc gaa ccg      528
Gly Thr Ala Ala Leu Gly Cys Leu Val Lys Asp Tyr Phe Pro Glu Pro
                165                 170                 175 gtg acg gtg tcg tgg aac tca ggc gcc ctg acc agc ggc gtg cac acc      576
Val Thr Val Ser Trp Asn Ser Gly Ala Leu Thr Ser Gly Val His Thr
            180                 185                 190 ttc ccg gct gtc cta cag tcc tca gga ctc tac tcc ctc agc agc gtg      624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac      672
Val Thr Val Pro Ser Ser Ser Leu Gly Thr Gln Thr Tyr Ile Cys Asn
    210                 215                 220 gtg aat cac aag ccc agc aac acc aag gtg gac aag aga gtt gag ccc      720
Val Asn His Lys Pro Ser Asn Thr Lys Val Asp Lys Arg Val Glu Pro
225                 230                 235                 240 aaa tct tgt gac aaa act cac aca tgc cca ccg tgc cca gca cct gaa      768
Lys Ser Cys Asp Lys Thr His Thr Cys Pro Pro Cys Pro Ala Pro Glu
                245                 250                 255 ctc ctg ggg gga ccg tca gtc ttc ctc ttc ccc cca aaa ccc aag gac      816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac      864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc      912
Val Ser His Glu Asp Pro Glu Val Lys Phe Asn Trp Tyr Val Asp Gly
    290                 295                 300 gtg gag gtg cat aat gcc aag aca aag ccg cgg gag gag cag tac aac      960
Val Glu Val His Asn Ala Lys Thr Lys Pro Arg Glu Glu Gln Tyr Asn
305                 310                 315                 320 agc acg tac cgt gtg gtc agc gtc ctc acc gtc ctg cac cag gac tgg     1008
Ser Thr Tyr Arg Val Val Ser Val Leu Thr Val Leu His Gln Asp Trp
                325                 330                 335 ctg aac ggc aag gag tac aag tgc aag gtc tcc aac aaa ggc ctc cca     1056
Leu Asn Gly Lys Glu Tyr Lys Cys Lys Val Ser Asn Lys Gly Leu Pro
            340                 345                 350 gcc ccc atc gag aaa acc atc tcc aaa gcc aaa ggg cag ccc cga gaa     1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac     1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tat ccc agc gac atc     1200
Gln Val Ser Leu Thr Cys Leu Val Lys Gly Phe Tyr Pro Ser Asp Ile
385                 390                 395                 400 gcc gtg gag tgg gag agc aat ggg cag ccg gag aac aac tac aag acc     1248
```

```
Ala Val Glu Trp Glu Ser Asn Gly Gln Pro Glu Asn Asn Tyr Lys Thr
            405                 410                 415 acg cct ccc gtg ctg gac tcc gac ggc tcc ttc ttc ctc tat agc aag    1296
Thr Pro Pro Val Leu Asp Ser Asp Gly Ser Phe Phe Leu Tyr Ser Lys
            420                 425                 430 ctc acc atg gac aag agc agg tgg cag cag ggg aac gtc ttc tca tgc    1344
Leu Thr Met Asp Lys Ser Arg Trp Gln Gln Gly Asn Val Phe Ser Cys
            435                 440                 445 tcc gtg atg cat gag gct ctg cac aac cac tac acg cag aag agc ctc    1392
Ser Val Met His Glu Ala Leu His Asn His Tyr Thr Gln Lys Ser Leu
450                 455                 460 tcc ctg tct ccg ggt aaa tga                                        1413
Ser Leu Ser Pro Gly Lys
465                 470

<210> SEQ ID NO 15
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Lys, Asn, Arg, Ser, Thr, Ile or Met

<400> SEQUENCE: 15

Met Gly Xaa Leu Gly Leu Ser Trp Val Phe Leu Val Val Ile Leu Glu
1               5                   10                  15

Gly Val Gln Cys Glu Val His Leu Val Glu Ser Gly Gly Gly Leu Val
            20                  25                  30

Arg Pro Gly Gly Ser Leu Lys Leu Ser Cys Ala Ala Ser Gly Phe Ala
        35                  40                  45

Phe Ser Ser Tyr Asp Met Ser Trp Val Arg Gln Thr Pro Glu Lys Arg
    50                  55                  60

Leu Glu Trp Val Ala Tyr Ile Ser Asp Gly Gly Gly Ile Thr Tyr Tyr
65                  70                  75                  80

Pro Asp Thr Met Lys Gly Arg Phe Thr Ile Ser Arg Asp Asn Ala Lys
                85                  90                  95

Asn Thr Leu Ser Leu Gln Met Ser Ser Leu Lys Ser Glu Asp Thr Ala
            100                 105                 110

Met Tyr Tyr Cys Ala Arg His Ile Thr Met Val Val Gly Pro Phe Ala
        115                 120                 125

Tyr Trp Gly Gln Gly Thr Leu Val Thr Val Ser Ala Ala Ser Thr Lys
    130                 135                 140

Gly Pro Ser Val Phe Pro Leu Ala Pro Cys Ser Arg Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240
```

-continued

```
Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Met Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 16
<211> LENGTH: 288
<212> TYPE: DNA
<213> ORGANISM: Mus sp.
<220> FEATURE:
<221> NAME/KEY: CDS
<222> LOCATION: (1)..(288)

<400> SEQUENCE: 16 gac atc gtc atg acc caa tct cac aaa ttc atg tcc act tca gta gga    48
Asp Ile Val Met Thr Gln Ser His Lys Phe Met Ser Thr Ser Val Gly
1               5                   10                  15 gac agg gtc agc atc acc tgc aag gcc agt cag gat gtg agt act gct    96
Asp Arg Val Ser Ile Thr Cys Lys Ala Ser Gln Asp Val Ser Thr Ala
            20                  25                  30 gta gcc tgg tat caa caa aaa cca ggg caa tct cct aga cta ctg att   144
Val Ala Trp Tyr Gln Gln Lys Pro Gly Gln Ser Pro Arg Leu Leu Ile
        35                  40                  45 tac tgg gca tcc acc cgg cac act gga gtc cct gat cgc ttc aca ggc   192
Tyr Trp Ala Ser Thr Arg His Thr Gly Val Pro Asp Arg Phe Thr Gly
    50                  55                  60 agt gga tct ggg aca gat tat act ctc acc atc agc agt gtg cag gct   240
Ser Gly Ser Gly Thr Asp Tyr Thr Leu Thr Ile Ser Ser Val Gln Ala
65                  70                  75                  80 gaa gac cag gca ctt tat tac tgt cag caa cat tat cgc act ccg tgg   288
Glu Asp Gln Ala Leu Tyr Tyr Cys Gln Gln His Tyr Arg Thr Pro Trp
                85                  90                  95
```

<210> SEQ ID NO 17
<211> LENGTH: 96
<212> TYPE: PRT
<213> ORGANISM: Mus sp.

<400> SEQUENCE: 17

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Arg Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Val Gln Ala
65                  70                  75                  80

Glu Asp Gln Ala Leu Tyr Tyr Cys Gln Gln His Tyr Arg Thr Pro Trp
                85                  90                  95

<210> SEQ ID NO 18
<211> LENGTH: 11
<212> TYPE: PRT
<213> ORGANISM: Mus sp.

<400> SEQUENCE: 18

Lys Ala Ser Gln Asp Val Ser Thr Ala Val Ala
1               5                   10

<210> SEQ ID NO 19
<211> LENGTH: 7
<212> TYPE: PRT
<213> ORGANISM: Mus sp.

<400> SEQUENCE: 19

Trp Ala Ser Thr Arg His Thr
1               5

<210> SEQ ID NO 20
<211> LENGTH: 8
<212> TYPE: PRT
<213> ORGANISM: Mus sp.

<400> SEQUENCE: 20

Gln Gln His Tyr Arg Thr Pro Trp
1               5

<210> SEQ ID NO 21
<211> LENGTH: 315
<212> TYPE: DNA
<213> ORGANISM: Mus sp.
<220> FEATURE:
<221> NAME/KEY: CDS
<222> LOCATION: (1)..(315)

<400> SEQUENCE: 21 cag gtc caa ctg cag cag cct gga cct gag ctg gtg aag cct ggg gct        48
Gln Val Gln Leu Gln Gln Pro Gly Pro Glu Leu Val Lys Pro Gly Ala
1               5                   10                  15 tca gtg agg atg tcc tgc aag gct tct ggc tac acc ttc aca agc tac        96
Ser Val Arg Met Ser Cys Lys Ala Ser Gly Tyr Thr Phe Thr Ser Tyr
            20                  25                  30

```
ttt ata cat tgg gtg aag cag agg cct gga cag gga ctt gag tgg att    144
Phe Ile His Trp Val Lys Gln Arg Pro Gly Gln Gly Leu Glu Trp Ile
         35                  40                  45 gga tgg att tat cct gga aat gtt aat act aag tac agt gag aag ttc    192
Gly Trp Ile Tyr Pro Gly Asn Val Asn Thr Lys Tyr Ser Glu Lys Phe
     50                  55                  60 aag ggt aag gcc aca ctg act gca gac aaa tcc tcc agc aca gcc tac    240
Lys Gly Lys Ala Thr Leu Thr Ala Asp Lys Ser Ser Ser Thr Ala Tyr
 65                  70                  75                  80 atg cag ttc agc agc ctg acc tct gag gac tct gcg gtc tat ttc tgt    288
Met Gln Phe Ser Ser Leu Thr Ser Glu Asp Ser Ala Val Tyr Phe Cys
                 85                  90                  95 gca aga ggg gag gct ggg tac ttt gac                                315
Ala Arg Gly Glu Ala Gly Tyr Phe Asp
                100             105

<210> SEQ ID NO 22
<211> LENGTH: 105
<212> TYPE: PRT
<213> ORGANISM: Mus sp.

<400> SEQUENCE: 22

Gln Val Gln Leu Gln Gln Pro Gly Pro Glu Leu Val Lys Pro Gly Ala
1               5                   10                  15

Ser Val Arg Met Ser Cys Lys Ala Ser Gly Tyr Thr Phe Thr Ser Tyr
            20                  25                  30

Phe Ile His Trp Val Lys Gln Arg Pro Gly Gln Gly Leu Glu Trp Ile
        35                  40                  45

Gly Trp Ile Tyr Pro Gly Asn Val Asn Thr Lys Tyr Ser Glu Lys Phe
    50                  55                  60

Lys Gly Lys Ala Thr Leu Thr Ala Asp Lys Ser Ser Ser Thr Ala Tyr
65                  70                  75                  80

Met Gln Phe Ser Ser Leu Thr Ser Glu Asp Ser Ala Val Tyr Phe Cys
                85                  90                  95

Ala Arg Gly Glu Ala Gly Tyr Phe Asp
                100             105

<210> SEQ ID NO 23
<211> LENGTH: 5
<212> TYPE: PRT
<213> ORGANISM: Mus sp.

<400> SEQUENCE: 23

Ser Tyr Phe Ile His
1               5

<210> SEQ ID NO 24
<211> LENGTH: 17
<212> TYPE: PRT
<213> ORGANISM: Mus sp.

<400> SEQUENCE: 24

Trp Ile Tyr Pro Gly Asn Val Asn Thr Lys Tyr Ser Glu Lys Phe Lys
1               5                   10                  15

Gly

<210> SEQ ID NO 25
<211> LENGTH: 7
<212> TYPE: PRT
<213> ORGANISM: Mus sp.
```

<400> SEQUENCE: 25

Gly Glu Ala Gly Tyr Phe Asp
1               5

<210> SEQ ID NO 26
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(702)

<400> SEQUENCE: 26

| | | |
|---|---|---|
| atg agg ctc cct gct cag ctc ctg ggg ctg cta atg ctc tgg gtc tct<br>Met Arg Leu Pro Ala Gln Leu Leu Gly Leu Leu Met Leu Trp Val Ser<br>1               5                   10                  15 | 48 |
| gga tcc agt ggt gac atc gtc atg acc caa tct cac aaa ttc atg tcc<br>Gly Ser Ser Gly Asp Ile Val Met Thr Gln Ser His Lys Phe Met Ser<br>            20                  25                  30 | 96 |
| act tca gta gga gac agg gtc agc atc acc tgc aag gcc agt cag gat<br>Thr Ser Val Gly Asp Arg Val Ser Ile Thr Cys Lys Ala Ser Gln Asp<br>        35                  40                  45 | 144 |
| gtg agt act gct gta gcc tgg tat caa caa aaa cca ggg caa tct cct<br>Val Ser Thr Ala Val Ala Trp Tyr Gln Gln Lys Pro Gly Gln Ser Pro<br>    50                  55                  60 | 192 |
| aga cta ctg att tac tgg gca tcc acc cgg cac act gga gtc cct gat<br>Arg Leu Leu Ile Tyr Trp Ala Ser Thr Arg His Thr Gly Val Pro Asp<br>65                  70                  75                  80 | 240 |
| cgc ttc aca ggc agt gga tct ggg aca gat tat act ctc acc atc agc<br>Arg Phe Thr Gly Ser Gly Ser Gly Thr Asp Tyr Thr Leu Thr Ile Ser<br>                85                  90                  95 | 288 |
| agt gtg cag gct gaa gac cag gca ctt tat tac tgt cag caa cat tat<br>Ser Val Gln Ala Glu Asp Gln Ala Leu Tyr Tyr Cys Gln Gln His Tyr<br>            100                 105                 110 | 336 |
| cgc act ccg tgg acg ttc ggt gga ggc acc aag ctg gaa atc aaa cgg<br>Arg Thr Pro Trp Thr Phe Gly Gly Gly Thr Lys Leu Glu Ile Lys Arg<br>        115                 120                 125 | 384 |
| gct gtg gct gca cca tct gtc gat atc ttc ccg cca tct gat gag cag<br>Ala Val Ala Ala Pro Ser Val Asp Ile Phe Pro Pro Ser Asp Glu Gln<br>    130                 135                 140 | 432 |
| ttg aaa tct gga act gcc tct gtt gtg tgc ctg ctg aat aac ttc tac<br>Leu Lys Ser Gly Thr Ala Ser Val Val Cys Leu Leu Asn Asn Phe Tyr<br>145                 150                 155                 160 | 480 |
| ccc aga gag gcc aaa gta cag tgg aag gtg gat aac gcc ctc caa tcg<br>Pro Arg Glu Ala Lys Val Gln Trp Lys Val Asp Asn Ala Leu Gln Ser<br>                165                 170                 175 | 528 |
| ggt aac tcc cag gag agt gtc aca gag cag gac agc aag gac agc acc<br>Gly Asn Ser Gln Glu Ser Val Thr Glu Gln Asp Ser Lys Asp Ser Thr<br>            180                 185                 190 | 576 |
| tac agc ctc agc agc acc ctg acg ctg agc aaa gca gac tac gag aaa<br>Tyr Ser Leu Ser Ser Thr Leu Thr Leu Ser Lys Ala Asp Tyr Glu Lys<br>        195                 200                 205 | 624 |
| cac aaa gtc tac gcc tgc gaa gtt acc cat cag ggc ctg agc tcg ccc<br>His Lys Val Tyr Ala Cys Glu Val Thr His Gln Gly Leu Ser Ser Pro<br>    210                 215                 220 | 672 |
| gtc aca aag agc ttc aac agg gga gag tgt tag<br>Val Thr Lys Ser Phe Asn Arg Gly Glu Cys<br>225                 230 | 705 |

```
<210> SEQ ID NO 27
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Arg Leu Pro Ala Gln Leu Leu Gly Leu Leu Met Leu Trp Val Ser
1               5                   10                  15

Gly Ser Ser Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Ser Thr Ala Val Ala Trp Tyr Gln Gln Lys Pro Gly Gln Ser Pro
    50                  55                  60

Arg Leu Leu Ile Tyr Trp Ala Ser Thr Arg His Thr Gly Val Pro Asp
65                  70                  75                  80

Arg Phe Thr Gly Ser Gly Ser Gly Thr Asp Tyr Thr Leu Thr Ile Ser
                85                  90                  95

Ser Val Gln Ala Glu Asp Gln Ala Leu Tyr Tyr Cys Gln Gln His Tyr
            100                 105                 110

Arg Thr Pro Trp Thr Phe Gly Gly Gly Thr Lys Leu Glu Ile Lys Arg
        115                 120                 125

Ala Val Ala Ala Pro Ser Val Asp Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 28
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1398)

<400> SEQUENCE: 28 atg gag ttg ggg ctg agc tgg gtt ttc ctt gtt gtt ata tta gaa ggt      48
Met Glu Leu Gly Leu Ser Trp Val Phe Leu Val Val Ile Leu Glu Gly
1               5                   10                  15 gtc cag tgt gag gtt cag ctg cag cag tct gga cct gag ctg gtg aag      96
Val Gln Cys Glu Val Gln Leu Gln Gln Ser Gly Pro Glu Leu Val Lys
            20                  25                  30 cct ggg gct tca gtg agg atg tcc tgc aag gct tct ggc tac acc ttc     144
```

```
                Pro Gly Ala Ser Val Arg Met Ser Cys Lys Ala Ser Gly Tyr Thr Phe
                            35                  40                  45 aca agc tac ttt ata cat tgg gtg aag cag agg cct gga cag gga ctt        192
Thr Ser Tyr Phe Ile His Trp Val Lys Gln Arg Pro Gly Gln Gly Leu
         50                  55                  60 gag tgg att gga tgg att tat cct gga aat gtt aat act aag tac agt        240
Glu Trp Ile Gly Trp Ile Tyr Pro Gly Asn Val Asn Thr Lys Tyr Ser
 65              70                  75                  80 gag aag ttc aag ggt aag gcc aca ctg act gca gac aaa tcc tcc agc        288
Glu Lys Phe Lys Gly Lys Ala Thr Leu Thr Ala Asp Lys Ser Ser Ser
                 85                  90                  95 aca gcc tac atg cag ttc agc agc ctg acc tct gag gac tct gcg gtc        336
Thr Ala Tyr Met Gln Phe Ser Ser Leu Thr Ser Glu Asp Ser Ala Val
             100                 105                 110 tat ttc tgt gca aga ggg gag gct ggg tac ttt gac tac tgg ggc caa        384
Tyr Phe Cys Ala Arg Gly Glu Ala Gly Tyr Phe Asp Tyr Trp Gly Gln
         115                 120                 125 ggc acc act ctc aca gtc tcc tca gct agc acc aag ggc cca tcg gtc        432
Gly Thr Thr Leu Thr Val Ser Ser Ala Ser Thr Lys Gly Pro Ser Val
     130                 135                 140 ttc ccc ctg gcg ccc tgc tcc agg agc acc tct ggg ggc aca gcg gcc        480
Phe Pro Leu Ala Pro Cys Ser Arg Ser Thr Ser Gly Gly Thr Ala Ala
145                 150                 155                 160 ctg ggc tgc ctg gtc aag gac tac ttc ccc gaa ccg gtg acg gtg tcg        528
Leu Gly Cys Leu Val Lys Asp Tyr Phe Pro Glu Pro Val Thr Val Ser
                 165                 170                 175 tgg aac tca ggc gcc ctg acc agc ggc gtg cac acc ttc ccg gct gtc        576
Trp Asn Ser Gly Ala Leu Thr Ser Gly Val His Thr Phe Pro Ala Val
             180                 185                 190 cta cag tcc tca gga ctc tac tcc ctc agc agc gtg gtg acc gtg ccc        624
Leu Gln Ser Ser Gly Leu Tyr Ser Leu Ser Ser Val Val Thr Val Pro
         195                 200                 205 tcc agc agc ttg ggc acc cag acc tac atc tgc aac gtg aat cac aag        672
Ser Ser Ser Leu Gly Thr Gln Thr Tyr Ile Cys Asn Val Asn His Lys
     210                 215                 220 ccc agc aac acc aag gtg gac aag aga gtt gag ccc aaa tct tgt gac        720
Pro Ser Asn Thr Lys Val Asp Lys Arg Val Glu Pro Lys Ser Cys Asp
225                 230                 235                 240 aaa act cac aca tgc cca ccg tgc cca gca cct gaa ctc ctg ggg gga        768
Lys Thr His Thr Cys Pro Pro Cys Pro Ala Pro Glu Leu Leu Gly Gly
                 245                 250                 255 ccg tca gtc ttc ctc ttc ccc cca aaa ccc aag gac acc ctc atg atc        816
Pro Ser Val Phe Leu Phe Pro Pro Lys Pro Lys Asp Thr Leu Met Ile
             260                 265                 270 tcc cgg acc cct gag gtc aca tgc gtg gtg gtg gac gtg agc cac gaa        864
Ser Arg Thr Pro Glu Val Thr Cys Val Val Val Asp Val Ser His Glu
         275                 280                 285 gac cct gag gtc aag ttc aac tgg tac gtg gac ggc gtg gag gtg cat        912
Asp Pro Glu Val Lys Phe Asn Trp Tyr Val Asp Gly Val Glu Val His
     290                 295                 300 aat gcc aag aca aag ccg cgg gag gag cag tac aac agc acg tac cgt        960
Asn Ala Lys Thr Lys Pro Arg Glu Glu Gln Tyr Asn Ser Thr Tyr Arg
305                 310                 315                 320 gtg gtc agc gtc ctc acc gtc ctg cac cag gac tgg ctg aac ggc aag       1008
Val Val Ser Val Leu Thr Val Leu His Gln Asp Trp Leu Asn Gly Lys
                 325                 330                 335 gag tac aag tgc aag gtc tcc aac aaa ggc ctc cca gcc ccc atc gag       1056
Glu Tyr Lys Cys Lys Val Ser Asn Lys Gly Leu Pro Ala Pro Ile Glu
             340                 345                 350
```

```
aaa acc atc tcc aaa gcc aaa ggg cag ccc cga gaa cca cag gtg tac    1104
Lys Thr Ile Ser Lys Ala Lys Gly Gln Pro Arg Glu Pro Gln Val Tyr
        355                 360                 365 acc ctg ccc cca tcc cgg gag gag atg acc aag aac cag gtc agc ctg    1152
Thr Leu Pro Pro Ser Arg Glu Glu Met Thr Lys Asn Gln Val Ser Leu
    370                 375                 380 acc tgc ctg gtc aaa ggc ttc tat ccc agc gac atc gcc gtg gag tgg    1200
Thr Cys Leu Val Lys Gly Phe Tyr Pro Ser Asp Ile Ala Val Glu Trp
385                 390                 395                 400 gag agc aat ggg cag ccg gag aac aac tac aag acc acg cct ccc gtg    1248
Glu Ser Asn Gly Gln Pro Glu Asn Asn Tyr Lys Thr Thr Pro Pro Val
                405                 410                 415 ctg gac tcc gac ggc tcc ttc ttc ctc tat agc aag ctc acc atg gac    1296
Leu Asp Ser Asp Gly Ser Phe Phe Leu Tyr Ser Lys Leu Thr Met Asp
            420                 425                 430 aag agc agg tgg cag cag ggg aac gtc ttc tca tgc tcc gtg atg cat    1344
Lys Ser Arg Trp Gln Gln Gly Asn Val Phe Ser Cys Ser Val Met His
        435                 440                 445 gag gct ctg cac aac cac tac acg cag aag agc ctc tcc ctg tct ccg    1392
Glu Ala Leu His Asn His Tyr Thr Gln Lys Ser Leu Ser Leu Ser Pro
    450                 455                 460 ggt aaa tga                                                         1401
Gly Lys
465

<210> SEQ ID NO 29
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Glu Leu Gly Leu Ser Trp Val Phe Leu Val Val Ile Leu Glu Gly
1               5                   10                  15

Val Gln Cys Glu Val Gln Leu Gln Gln Ser Gly Pro Glu Leu Val Lys
            20                  25                  30

Pro Gly Ala Ser Val Arg Met Ser Cys Lys Ala Ser Gly Tyr Thr Phe
        35                  40                  45

Thr Ser Tyr Phe Ile His Trp Val Lys Gln Arg Pro Gly Gln Gly Leu
    50                  55                  60

Glu Trp Ile Gly Trp Ile Tyr Pro Gly Asn Val Asn Thr Lys Tyr Ser
65                  70                  75                  80

Glu Lys Phe Lys Gly Lys Ala Thr Leu Thr Ala Asp Lys Ser Ser Ser
                85                  90                  95

Thr Ala Tyr Met Gln Phe Ser Ser Leu Thr Ser Glu Asp Ser Ala Val
            100                 105                 110

Tyr Phe Cys Ala Arg Gly Glu Ala Gly Tyr Phe Asp Tyr Trp Gly Gln
        115                 120                 125

Gly Thr Thr Leu Thr Val Ser Ser Ala Ser Thr Lys Gly Pro Ser Val
    130                 135                 140

Phe Pro Leu Ala Pro Cys Ser Arg Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190
```

```
Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Met Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465

<210> SEQ ID NO 30
<211> LENGTH: 285
<212> TYPE: DNA
<213> ORGANISM: Mus sp.
<220> FEATURE:
<221> NAME/KEY: CDS
<222> LOCATION: (1)..(285)

<400> SEQUENCE: 30 gac atc cag atg acc caa tct cca gcc tcc cta tct gta tct gtg gga    48
Asp Ile Gln Met Thr Gln Ser Pro Ala Ser Leu Ser Val Ser Val Gly
1               5                  10                  15 gaa act gtc acc atc aca tgt cga gca agt gag aat att tac agt aat    96
Glu Thr Val Thr Ile Thr Cys Arg Ala Ser Glu Asn Ile Tyr Ser Asn
            20                  25                  30 tta gaa tgg tat cag cag aaa cag gga aaa tct cct cag ctc ctg gtc   144
Leu Glu Trp Tyr Gln Gln Lys Gln Gly Lys Ser Pro Gln Leu Leu Val
        35                  40                  45 tat gct gca aca aac tta gca gat ggt gtg cca tca agg ttc agt ggc   192
Tyr Ala Ala Thr Asn Leu Ala Asp Gly Val Pro Ser Arg Phe Ser Gly
    50                  55                  60
```

```
                50                  55                  60
agt gga tca ggc aca cag tat tcc ctc aag atc aac agc ctg cag tct    240
Ser Gly Ser Gly Thr Gln Tyr Ser Leu Lys Ile Asn Ser Leu Gln Ser
 65                  70                  75                  80 gaa gat ttt ggg agt tat tac tgt caa cat ttt tgg ggt act tgg        285
Glu Asp Phe Gly Ser Tyr Tyr Cys Gln His Phe Trp Gly Thr Trp
                 85                  90                  95
```

<210> SEQ ID NO 31
<211> LENGTH: 95
<212> TYPE: PRT
<213> ORGANISM: Mus sp.

<400> SEQUENCE: 31

```
Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Asn Ile Tyr Ser Asn
                20                  25                  30

Leu Glu Trp Tyr Gln Gln Lys Gln Gly Lys Ser Pro Gln Leu Leu Val
            35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Trp
                85                  90                  95
```

<210> SEQ ID NO 32
<211> LENGTH: 11
<212> TYPE: PRT
<213> ORGANISM: Mus sp.

<400> SEQUENCE: 32

```
Arg Ala Ser Glu Asn Ile Tyr Ser Asn Leu Glu
 1               5                  10
```

<210> SEQ ID NO 33
<211> LENGTH: 7
<212> TYPE: PRT
<213> ORGANISM: Mus sp.

<400> SEQUENCE: 33

```
Ala Ala Thr Asn Leu Ala Asp
 1               5
```

<210> SEQ ID NO 34
<211> LENGTH: 7
<212> TYPE: PRT
<213> ORGANISM: Mus sp.

<400> SEQUENCE: 34

```
Gln His Phe Trp Gly Thr Trp
 1               5
```

<210> SEQ ID NO 35
<211> LENGTH: 321
<212> TYPE: DNA
<213> ORGANISM: Mus sp.
<220> FEATURE:
<221> NAME/KEY: CDS
<222> LOCATION: (1)..(321)

<400> SEQUENCE: 35

```
gag gtt cag ctg cag cag tct ggg gca gag ctt gtg aag cca ggg gcc       48
Glu Val Gln Leu Gln Gln Ser Gly Ala Glu Leu Val Lys Pro Gly Ala
1               5                   10                  15 tca gtc aag ttg tcc tgc aca gct tcg ggc ttc aac att aaa gac acc       96
Ser Val Lys Leu Ser Cys Thr Ala Ser Gly Phe Asn Ile Lys Asp Thr
            20                  25                  30 tat atg cac tgg gtg aag cag agg cct gaa cag ggc ctg gag tgg att     144
Tyr Met His Trp Val Lys Gln Arg Pro Glu Gln Gly Leu Glu Trp Ile
        35                  40                  45 gga agg att gat cct gcg aat ggt aat act aaa tat gac ccg aag ttc     192
Gly Arg Ile Asp Pro Ala Asn Gly Asn Thr Lys Tyr Asp Pro Lys Phe
50                  55                  60 cag ggc aag gcc act ata aca gca gac aca tcc tcc aac aca gcc tac     240
Gln Gly Lys Ala Thr Ile Thr Ala Asp Thr Ser Ser Asn Thr Ala Tyr
65                  70                  75                  80 ctg cag ctc agc agc ctg aca tct gag gac act gcc gtc tat tac tgt     288
Leu Gln Leu Ser Ser Leu Thr Ser Glu Asp Thr Ala Val Tyr Tyr Cys
                85                  90                  95 gcc tat tac tac gtt agt aac gcc tgg ttt act                         321
Ala Tyr Tyr Tyr Val Ser Asn Ala Trp Phe Thr
                100                 105

<210> SEQ ID NO 36
<211> LENGTH: 107
<212> TYPE: PRT
<213> ORGANISM: Mus sp.

<400> SEQUENCE: 36

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Tyr Tyr Tyr Val Ser Asn Ala Trp Phe Thr
                100                 105

<210> SEQ ID NO 37
<211> LENGTH: 5
<212> TYPE: PRT
<213> ORGANISM: Mus sp.

<400> SEQUENCE: 37

Asp Thr Tyr Met His
1               5

<210> SEQ ID NO 38
<211> LENGTH: 17
<212> TYPE: PRT
<213> ORGANISM: Mus sp.

<400> SEQUENCE: 38

Arg Ile Asp Pro Ala Asn Gly Asn Thr Lys Tyr Asp Pro Lys Phe Gln
1               5                   10                  15
```

<210> SEQ ID NO 39
<211> LENGTH: 9
<212> TYPE: PRT
<213> ORGANISM: Mus sp.

<400> SEQUENCE: 39

Tyr Tyr Val Ser Asn Ala Trp Phe Thr
1               5

<210> SEQ ID NO 40
<211> LENGTH: 703
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(699)

<400> SEQUENCE: 40

```
atg agg ctc cct gct cag ctc ctg ggg ctg cta atg ctc tgg gtc tct        48
Met Arg Leu Pro Ala Gln Leu Leu Gly Leu Leu Met Leu Trp Val Ser
1               5                   10                  15 gga tcc agt ggt gac atc cag atg acc caa tct cca gcc tcc cta tct        96
Gly Ser Ser Gly Asp Ile Gln Met Thr Gln Ser Pro Ala Ser Leu Ser
                20                  25                  30 gta tct gtg gga gaa act gtc acc atc aca tgt cga gca agt gag aat       144
Val Ser Val Gly Glu Thr Val Thr Ile Thr Cys Arg Ala Ser Glu Asn
            35                  40                  45 att tac agt aat tta gaa tgg tat cag cag aaa cag gga aaa tct cct       192
Ile Tyr Ser Asn Leu Glu Trp Tyr Gln Gln Lys Gln Gly Lys Ser Pro
        50                  55                  60 cag ctc ctg gtc tat gct gca aca aac tta gca gat ggt gtg cca tca       240
Gln Leu Leu Val Tyr Ala Ala Thr Asn Leu Ala Asp Gly Val Pro Ser
65                  70                  75                  80 agg ttc agt ggc agt gga tca ggc aca cag tat tcc ctc aag atc aac       288
Arg Phe Ser Gly Ser Gly Ser Gly Thr Gln Tyr Ser Leu Lys Ile Asn
                85                  90                  95 agc ctg cag tct gaa gat ttt ggg agt tat tac tgt caa cat ttt tgg       336
Ser Leu Gln Ser Glu Asp Phe Gly Ser Tyr Tyr Cys Gln His Phe Trp
            100                 105                 110 ggt act tgg acg ttc ggt gga ggc acc aag ctg gaa atc aaa cgg gct       384
Gly Thr Trp Thr Phe Gly Gly Gly Thr Lys Leu Glu Ile Lys Arg Ala
        115                 120                 125 gtg gct gca cca tct gtc gat atc ttc ccg cca tct gat gag cag ttg       432
Val Ala Ala Pro Ser Val Asp Ile Phe Pro Pro Ser Asp Glu Gln Leu
    130                 135                 140 aaa tct gga act gcc tct gtt gtg tgc ctg ctg aat aac ttc tac ccc       480
Lys Ser Gly Thr Ala Ser Val Val Cys Leu Leu Asn Asn Phe Tyr Pro
145                 150                 155                 160 aga gag gcc aaa gta cag tgg aag gtg gat aac gcc ctc caa tcg ggt       528
Arg Glu Ala Lys Val Gln Trp Lys Val Asp Asn Ala Leu Gln Ser Gly
                165                 170                 175 aac tcc cag gag agt gtc aca gag cag gac agc aag gac agc acc tac       576
Asn Ser Gln Glu Ser Val Thr Glu Gln Asp Ser Lys Asp Ser Thr Tyr
            180                 185                 190 agc ctc agc agc acc ctg acg ctg agc aaa gca gac tac gag aaa cac       624
Ser Leu Ser Ser Thr Leu Thr Leu Ser Lys Ala Asp Tyr Glu Lys His
        195                 200                 205
```

-continued

```
aaa gtc tac gcc tgc gaa gtt acc cat cag ggc ctg agc tcg ccc gtc      672
Lys Val Tyr Ala Cys Glu Val Thr His Gln Gly Leu Ser Ser Pro Val
    210                 215                 220 aca aag agc ttc aac agg gga gag tgt taga                             703
Thr Lys Ser Phe Asn Arg Gly Glu Cys
225                 230
```

<210> SEQ ID NO 41
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Met Arg Leu Pro Ala Gln Leu Leu Gly Leu Leu Met Leu Trp Val Ser
1               5                   10                  15

Gly Ser Ser Gly Asp Ile Gln Met Thr Gln Ser Pro Ala Ser Leu Ser
                20                  25                  30

Val Ser Val Gly Glu Thr Val Thr Ile Thr Cys Arg Ala Ser Glu Asn
            35                  40                  45

Ile Tyr Ser Asn Leu Glu Trp Tyr Gln Gln Lys Gln Gly Lys Ser Pro
        50                  55                  60

Gln Leu Leu Val Tyr Ala Ala Thr Asn Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Phe Gly Ser Tyr Tyr Cys Gln His Phe Trp
                100                 105                 110

Gly Thr Trp Thr Phe Gly Gly Gly Thr Lys Leu Glu Ile Lys Arg Ala
            115                 120                 125

Val Ala Ala Pro Ser Val Asp Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 42
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1404)

<400> SEQUENCE: 42

-continued

| | |
|---|---|
| atg gag ttg ggg ctg agc tgg gtt ttc ctt gtt gtt ata tta gaa ggt<br>Met Glu Leu Gly Leu Ser Trp Val Phe Leu Val Val Ile Leu Glu Gly<br>1               5                   10                  15 | 48 |
| gtc cag tgt gag gtt cag ctg cag cag tct ggg gca gag ctt gtg aag<br>Val Gln Cys Glu Val Gln Leu Gln Gln Ser Gly Ala Glu Leu Val Lys<br>            20                  25                  30 | 96 |
| cca ggg gcc tca gtc aag ttg tcc tgc aca gct tcg ggc ttc aac att<br>Pro Gly Ala Ser Val Lys Leu Ser Cys Thr Ala Ser Gly Phe Asn Ile<br>        35                  40                  45 | 144 |
| aaa gac acc tat atg cac tgg gtg aag cag agg cct gaa cag ggc ctg<br>Lys Asp Thr Tyr Met His Trp Val Lys Gln Arg Pro Glu Gln Gly Leu<br>    50                  55                  60 | 192 |
| gag tgg att gga agg att gat cct gcg aat ggt aat act aaa tat gac<br>Glu Trp Ile Gly Arg Ile Asp Pro Ala Asn Gly Asn Thr Lys Tyr Asp<br>65                  70                  75                  80 | 240 |
| ccg aag ttc cag ggc aag gcc act ata aca gca gac aca tcc tcc aac<br>Pro Lys Phe Gln Gly Lys Ala Thr Ile Thr Ala Asp Thr Ser Ser Asn<br>                85                  90                  95 | 288 |
| aca gcc tac ctg cag ctc agc agc ctg aca tct gag gac act gcc gtc<br>Thr Ala Tyr Leu Gln Leu Ser Ser Leu Thr Ser Glu Asp Thr Ala Val<br>            100                 105                 110 | 336 |
| tat tac tgt gcc tat tac tac gtt agt aac gcc tgg ttt act tac tgg<br>Tyr Tyr Cys Ala Tyr Tyr Tyr Val Ser Asn Ala Trp Phe Thr Tyr Trp<br>        115                 120                 125 | 384 |
| ggc caa ggg act ctg gtc act gtc tct gca gct agc acc aag ggc cca<br>Gly Gln Gly Thr Leu Val Thr Val Ser Ala Ala Ser Thr Lys Gly Pro<br>    130                 135                 140 | 432 |
| tcg gtc ttc ccc ctg gcg ccc tgc tcc agg agc acc tct ggg ggc aca<br>Ser Val Phe Pro Leu Ala Pro Cys Ser Arg Ser Thr Ser Gly Gly Thr<br>145                 150                 155                 160 | 480 |
| gcg gcc ctg ggc tgc ctg gtc aag gac tac ttc ccc gaa ccg gtg acg<br>Ala Ala Leu Gly Cys Leu Val Lys Asp Tyr Phe Pro Glu Pro Val Thr<br>                165                 170                 175 | 528 |
| gtg tcg tgg aac tca ggc gcc ctg acc agc ggc gtg cac acc ttc ccg<br>Val Ser Trp Asn Ser Gly Ala Leu Thr Ser Gly Val His Thr Phe Pro<br>            180                 185                 190 | 576 |
| gct gtc cta cag tcc tca gga ctc tac tcc ctc agc agc gtg gtg acc<br>Ala Val Leu Gln Ser Ser Gly Leu Tyr Ser Leu Ser Ser Val Val Thr<br>        195                 200                 205 | 624 |
| gtg ccc tcc agc agc ttg ggc acc cag acc tac atc tgc aac gtg aat<br>Val Pro Ser Ser Ser Leu Gly Thr Gln Thr Tyr Ile Cys Asn Val Asn<br>    210                 215                 220 | 672 |
| cac aag ccc agc aac acc aag gtg gac aag aga gtt gag ccc aaa tct<br>His Lys Pro Ser Asn Thr Lys Val Asp Lys Arg Val Glu Pro Lys Ser<br>225                 230                 235                 240 | 720 |
| tgt gac aaa act cac aca tgc cca ccg tgc cca gca cct gaa ctc ctg<br>Cys Asp Lys Thr His Thr Cys Pro Pro Cys Pro Ala Pro Glu Leu Leu<br>                245                 250                 255 | 768 |
| ggg gga ccg tca gtc ttc ctc ttc ccc cca aaa ccc aag gac acc ctc<br>Gly Gly Pro Ser Val Phe Leu Phe Pro Pro Lys Pro Lys Asp Thr Leu<br>            260                 265                 270 | 816 |
| atg atc tcc cgg acc cct gag gtc aca tgc gtg gtg gtg gac gtg agc<br>Met Ile Ser Arg Thr Pro Glu Val Thr Cys Val Val Val Asp Val Ser<br>        275                 280                 285 | 864 |
| cac gaa gac cct gag gtc aag ttc aac tgg tac gtg gac ggc gtg gag<br>His Glu Asp Pro Glu Val Lys Phe Asn Trp Tyr Val Asp Gly Val Glu<br>    290                 295                 300 | 912 |
| gtg cat aat gcc aag aca aag ccg cgg gag gag cag tac aac agc acg<br>Val His Asn Ala Lys Thr Lys Pro Arg Glu Glu Gln Tyr Asn Ser Thr<br>305                 310                 315                 320 | 960 |

-continued

```
tac cgt gtg gtc agc gtc ctc acc gtc ctg cac cag gac tgg ctg aac    1008
Tyr Arg Val Val Ser Val Leu Thr Val Leu His Gln Asp Trp Leu Asn
            325                 330                 335 ggc aag gag tac aag tgc aag gtc tcc aac aaa ggc ctc cca gcc ccc    1056
Gly Lys Glu Tyr Lys Cys Lys Val Ser Asn Lys Gly Leu Pro Ala Pro
            340                 345                 350 atc gag aaa acc atc tcc aaa gcc aaa ggg cag ccc cga gaa cca cag    1104
Ile Glu Lys Thr Ile Ser Lys Ala Lys Gly Gln Pro Arg Glu Pro Gln
            355                 360                 365 gtg tac acc ctg ccc cca tcc cgg gag gag atg acc aag aac cag gtc    1152
Val Tyr Thr Leu Pro Pro Ser Arg Glu Glu Met Thr Lys Asn Gln Val
    370                 375                 380 agc ctg acc tgc ctg gtc aaa ggc ttc tat ccc agc gac atc gcc gtg    1200
Ser Leu Thr Cys Leu Val Lys Gly Phe Tyr Pro Ser Asp Ile Ala Val
385                 390                 395                 400 gag tgg gag agc aat ggg cag ccg gag aac aac tac aag acc acg cct    1248
Glu Trp Glu Ser Asn Gly Gln Pro Glu Asn Asn Tyr Lys Thr Thr Pro
                405                 410                 415 ccc gtg ctg gac tcc gac ggc tcc ttc ttc ctc tat agc aag ctc acc    1296
Pro Val Leu Asp Ser Asp Gly Ser Phe Phe Leu Tyr Ser Lys Leu Thr
            420                 425                 430 atg gac aag agc agg tgg cag cag ggg aac gtc ttc tca tgc tcc gtg    1344
Met Asp Lys Ser Arg Trp Gln Gln Gly Asn Val Phe Ser Cys Ser Val
            435                 440                 445 atg cat gag gct ctg cac aac cac tac acg cag aag agc ctc tcc ctg    1392
Met His Glu Ala Leu His Asn His Tyr Thr Gln Lys Ser Leu Ser Leu
            450                 455                 460 tct ccg ggt aaa tga                                                 1407
Ser Pro Gly Lys
465
```

<210> SEQ ID NO 43
<211> LENGTH: 468
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Met Glu Leu Gly Leu Ser Trp Val Phe Leu Val Val Ile Leu Glu Gly
1               5                   10                  15

Val Gln Cys Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Lys Asp Thr Tyr Met His Trp Val Lys Gln Arg Pro Glu Gln Gly Leu
    50                  55                  60

Glu Trp Ile Gly Arg Ile Asp Pro Ala Asn Gly Asn Thr Lys Tyr Asp
65                  70                  75                  80

Pro Lys Phe Gln Gly Lys Ala Thr Ile Thr Ala Asp Thr Ser Ser Asn
            85                  90                  95

Thr Ala Tyr Leu Gln Leu Ser Ser Leu Thr Ser Glu Asp Thr Ala Val
                100                 105                 110

Tyr Tyr Cys Ala Tyr Tyr Val Ser Asn Ala Trp Phe Thr Tyr Trp
            115                 120                 125

Gly Gln Gly Thr Leu Val Thr Val Ser Ala Ala Ser Thr Lys Gly Pro
        130                 135                 140
```

```
Ser Val Phe Pro Leu Ala Pro Cys Ser Arg Ser Thr Ser Gly Gly Thr
145                 150                 155                 160

Ala Ala Leu Gly Cys Leu Val Lys Asp Tyr Phe Pro Glu Pro Val Thr
            165                 170                 175

Val Ser Trp Asn Ser Gly Ala Leu Thr Ser Gly Val His Thr Phe Pro
        180                 185                 190

Ala Val Leu Gln Ser Ser Gly Leu Tyr Ser Leu Ser Ser Val Val Thr
    195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Met Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys or Gly

<400> SEQUENCE: 44

Val Xaa Asp Cys Thr Pro Trp Ser Asp Ile Glu Cys Val His Lys Glu
```

<210> SEQ ID NO 45
<211> LENGTH: 16
<212> TYPE: PRT
<213> ORGANISM: Homo sapiens

<400> SEQUENCE: 45

Val Lys Asp Cys Thr Pro Trp Ser Asp Ile Glu Cys Val His Lys Glu
1               5                   10                  15

<210> SEQ ID NO 46
<211> LENGTH: 16
<212> TYPE: PRT
<213> ORGANISM: Homo sapiens

<400> SEQUENCE: 46

Val Gly Asp Cys Thr Pro Trp Ser Asp Ile Glu Cys Val His Lys Glu
1               5                   10                  15

<210> SEQ ID NO 47
<211> LENGTH: 16
<212> TYPE: PRT
<213> ORGANISM: Homo sapiens

<400> SEQUENCE: 47

Val Ser Asn Cys Thr Ser Trp Asp Asp Ile Gln Cys Val Glu Glu Phe
1               5                   10                  15

<210> SEQ ID NO 48
<211> LENGTH: 16
<212> TYPE: PRT
<213> ORGANISM: Homo sapiens

<400> SEQUENCE: 48

Val Ser Asn Cys Thr Pro Arg Ser Asp Ile Lys Cys Lys Asn Glu Ser
1               5                   10                  15

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gacgatgccc gatctacttt aaggg                                        25

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccactgggtg atgttggatg gg                                           22

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic

```
                         primer

<400> SEQUENCE: 51
gacgatgccc gatctacttt aaggg                                              25

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gacgatgccc gatctacttt aaggg                                              25

<210> SEQ ID NO 53
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggaacccttt ggcccagccg gccatggccs aggtycagct bcagcagtc                    49

<210> SEQ ID NO 54
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggaacccttt ggcccagccg gccatggccc aggttcacct gcagcartc                    49

<210> SEQ ID NO 55
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggaacccttt ggcccagccg gccatggccc aggtrcagct gaaggagtc                    49

<210> SEQ ID NO 56
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggaacccttt ggcccagccg gccatggccc aggtccaact vcagcarcc                    49

<210> SEQ ID NO 57
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 57
ggaacccttt ggcccagccg gccatggccc agatccagtt ggtvcagtc               49

<210> SEQ ID NO 58
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggaacccttt ggcccagccg gccatggccc aggtgcagct gaagsastc               49

<210> SEQ ID NO 59
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggaacccttt ggcccagccg gccatggccg aggtgcagsk ggtggagtc               49

<210> SEQ ID NO 60
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ggaacccttt ggcccagccg gccatggccg aagtgaarst tgaggagtc               49

<210> SEQ ID NO 61
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ggaacccttt ggcccagccg gccatggccg akgtsvagct tcaggagtc               49

<210> SEQ ID NO 62
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ggaacccttt ggcccagccg gccatggccg aggtgaasst ggtggaatc               49

<210> SEQ ID NO 63
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggaacccttt ggcccagccg gccatggccg aggtgaagct grtggartc        49

<210> SEQ ID NO 64
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggaacccttt ggcccagccg gccatggccg argtgaagct grtggagtc        49

<210> SEQ ID NO 65
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ggaacccttt ggcccagccg gccatggccg aagtgcagct gttggagac        49

<210> SEQ ID NO 66
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggaacccttt ggcccagccg gccatggccg argtgaagct tctcsagtc        49

<210> SEQ ID NO 67
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ggaacccttt ggcccagccg gccatggccc argttactct gaaagagt        48

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tarccyttga cmaggcatcc        20

<210> SEQ ID NO 69
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69

```
tattcgtcga cggatattgt gatgacbcag dc                                    32
```

<210> SEQ ID NO 70
<211> LENGTH: 32
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 70

```
tattcgtcga cggatrttkt gatgacccar ac                                    32
```

<210> SEQ ID NO 71
<211> LENGTH: 32
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 71

```
tattcgtcga cggaaaatgt gctcacccag tc                                    32
```

<210> SEQ ID NO 72
<211> LENGTH: 32
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 72

```
tattcgtcga cggayattgt gatgacacag tc                                    32
```

<210> SEQ ID NO 73
<211> LENGTH: 32
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 73

```
tattcgtcga cggacatcca gatgacacag ac                                    32
```

<210> SEQ ID NO 74
<211> LENGTH: 32
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 74

```
tattcgtcga cggayattgt gctsacycar tc                                    32
```

<210> SEQ ID NO 75
<211> LENGTH: 32
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 75

-continued tattcgtcga cggacatcca gatgacycar tc                              32

<210> SEQ ID NO 76
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tattcgtcga cgcaaattgt tctcacccag tc                              32

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cgttcactgc catcaatc                                              18

<210> SEQ ID NO 78
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Arg Ser Ser Pro Ser Glu Gly Leu Cys Pro Pro Gly His His Ile
1               5                   10                  15

Ser Glu Asp Gly Arg Asp Cys Ile Ser Cys Lys Tyr Gly Gln
            20                  25                  30

<210> SEQ ID NO 79
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Asp Cys Ile Ser Cys Lys Tyr Gly Gln Asp Tyr Ser Thr His Trp
1               5                   10                  15

Asn Asp Leu Leu Phe Cys Leu Arg Cys Thr Arg Cys Asp Ser
            20                  25                  30

<210> SEQ ID NO 80
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Phe Cys Leu Arg Cys Thr Arg Cys Asp Ser Gly Glu Val Glu Leu Ser
1               5                   10                  15

Pro Cys Thr Thr Thr Arg Asn Thr Val Cys Gln Cys Glu Glu
            20                  25                  30

<210> SEQ ID NO 81
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Arg Asn Thr Val Cys Gln Cys Glu Glu Gly Thr Phe Arg Glu Glu
1               5                   10                  15

Asp Ser Pro Glu Met Cys Arg Lys Cys Arg Thr Gly Cys Pro
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Lys Cys Arg Thr Gly Cys Pro Arg Gly Met Val Lys Val Gly Asp
1               5                   10                  15

Cys Thr Pro Trp Ser Asp Ile Glu Cys Val His Lys Glu Ser
            20                  25                  30

<210> SEQ ID NO 83
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Met Val Lys Val Gly Asp Cys Thr Pro Trp Ser Asp Ile Glu Cys Val
1               5                   10                  15

His Lys Glu Ser Gly Thr Lys His Ser Gly Glu Ala Pro Ala
            20                  25                  30

<210> SEQ ID NO 84
<211> LENGTH: 17
<212> TYPE: PRT
<213> ORGANISM: Mus sp.

<400> SEQUENCE: 84

Glu Val His Leu Val Glu Ser Gly Gly Gly Leu Val Arg Pro Gly Gly
1               5                   10                  15

Ser

<210> SEQ ID NO 85
<211> LENGTH: 18
<212> TYPE: PRT
<213> ORGANISM: Mus sp.

<400> SEQUENCE: 85

Ala Thr Met Arg Leu Pro Ala Gln Leu Leu Gly Leu Leu Met Leu Trp
1               5                   10                  15

Val Ser

<210> SEQ ID NO 86

```
<211> LENGTH: 17
<212> TYPE: PRT
<213> ORGANISM: Mus sp.

<400> SEQUENCE: 86

Gln Val Gln Leu Gln Gln Pro Gly Pro Glu Leu Val Lys Pro Gly Ala
1               5                   10                  15

Ser

<210> SEQ ID NO 87
<211> LENGTH: 16
<212> TYPE: PRT
<213> ORGANISM: Mus sp.

<400> SEQUENCE: 87

Asp Ile Val Met Thr Gln Ser His Lys Phe Met Ser Thr Ser Val Gly
1               5                   10                  15

<210> SEQ ID NO 88
<211> LENGTH: 17
<212> TYPE: PRT
<213> ORGANISM: Mus sp.

<400> SEQUENCE: 88

Glu Val Gln Leu Gln Gln Ser Gly Ala Glu Leu Val Lys Pro Gly Ala
1               5                   10                  15

Ser

<210> SEQ ID NO 89
<211> LENGTH: 15
<212> TYPE: PRT
<213> ORGANISM: Mus sp.

<400> SEQUENCE: 89

Asp Ile Gln Met Thr Gln Ser Pro Ala Ser Leu Ser Val Ser Val
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Val Gly Asp Cys Thr Pro Trp Ser Asp Ile Glu Cys Val His Lys Glu
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Val Lys Asp Cys Thr Pro Trp Ser Asp Ile Glu Cys Val His Lys Glu
1               5                   10                  15
```